(12) United States Patent
Verheesen et al.

US009803003B2

(10) Patent No.: US 9,803,003 B2
(45) Date of Patent: Oct. 31, 2017

(54) AGROCHEMICAL COMPOSITIONS COMPRISING ANTIBODIES BINDING TO SPHINGOLIPIDS

(71) Applicant: AGROSAVFE N.V., Ghent (BE)

(72) Inventors: Peter Verheesen, Mariakerke (BE); Chris De Jonghe, Mortsel (BE); Inge Elodie Van Daele, Melle (BE); Miguel Francesco Coleta De Bolle, Baarle-Nassau (NL); João Filipe Veloso Vieira, Didcot (GB); Karin Thevissen, Bierbeek (BE); Bruno Cammue, Alsemberg (DE)

(73) Assignee: AGROSAVFE N.V., Ghent (BE)

( * ) Notice: Subject to any disclaimer, the term of this patent is extended or adjusted under 35 U.S.C. 154(b) by 0 days.

(21) Appl. No.: 14/787,734

(22) PCT Filed: Apr. 29, 2014

(86) PCT No.: PCT/EP2014/058772
§ 371 (c)(1),
(2) Date: Oct. 28, 2015

(87) PCT Pub. No.: WO2014/191146
PCT Pub. Date: Dec. 4, 2014

(65) Prior Publication Data
US 2016/0075769 A1 Mar. 17, 2016

Related U.S. Application Data

(60) Provisional application No. 61/817,170, filed on Apr. 29, 2013.

(51) Int. Cl.
| | | |
|---|---|---|
| C07K 16/14 | (2006.01) |
| A01N 37/36 | (2006.01) |
| A01N 63/02 | (2006.01) |
| C12N 15/82 | (2006.01) |
| A01N 37/46 | (2006.01) |

(52) U.S. Cl.
CPC ........... *C07K 16/14* (2013.01); *A01N 37/46* (2013.01); *A01N 63/02* (2013.01); *C12N 15/8279* (2013.01); *C07K 2317/22* (2013.01); *C07K 2317/56* (2013.01); *C07K 2317/565* (2013.01); *C07K 2317/569* (2013.01); *C07K 2317/76* (2013.01)

(58) Field of Classification Search
CPC .......................... C07K 16/14; C07K 2317/56; C07K 2317/22; C07K 2317/565; C07K 2317/76; C07K 2317/569; C12N 15/8279; A01N 37/46; A01N 63/02
See application file for complete search history.

(56) References Cited

U.S. PATENT DOCUMENTS

| | | |
|---|---|---|
| 6,596,509 B1 | 7/2003 | Bauer et al. |
| 2012/0042416 A1 | 2/2012 | Schleker et al. |
| 2013/0224226 A1 | 8/2013 | Verheesen et al. |
| 2013/0225403 A1 | 8/2013 | Verheesen et al. |
| 2013/0227747 A1 | 8/2013 | Verheesen et al. |

FOREIGN PATENT DOCUMENTS

| | | |
|---|---|---|
| DE | 10234116 A1 | 2/2004 |
| EP | 368684 A1 | 3/1994 |
| EP | 1134231 A1 | 9/2001 |
| EP | 1198985 A1 | 4/2002 |
| WO | 9404678 A1 | 3/1994 |
| WO | 9425591 A1 | 11/1994 |
| WO | 9504079 A1 | 2/1995 |
| WO | 9609398 A1 | 3/1996 |
| WO | 9634103 A1 | 10/1996 |
| WO | 9749805 A2 | 12/1997 |
| WO | 9937681 A2 | 7/1999 |
| WO | 0040968 A1 | 7/2000 |
| WO | 0043507 A1 | 7/2000 |
| WO | 0065057 A1 | 11/2000 |
| WO | 0121817 A1 | 3/2001 |
| WO | 0140310 A2 | 6/2001 |
| WO | 0144301 A1 | 6/2001 |
| WO | 0190190 A2 | 11/2001 |
| WO | 03025020 A1 | 3/2003 |
| WO | 03035694 A2 | 5/2003 |
| WO | 03050531 A2 | 6/2003 |
| WO | 03054016 A2 | 7/2003 |
| WO | 03055527 A2 | 7/2003 |
| WO | 2004041862 A2 | 5/2004 |
| WO | 2004041863 A2 | 5/2004 |
| WO | 2004041865 A2 | 5/2004 |
| WO | 2004041867 A2 | 5/2004 |
| WO | 2004062551 A2 | 7/2004 |
| WO | 2006003388 A2 | 1/2006 |
| WO | 2006030220 A1 | 3/2006 |

(Continued)

OTHER PUBLICATIONS

Houghten et al. (Vaccines, 1986, Edited by Fred Brown: Cold Spring Harbor Laboratory).*

(Continued)

*Primary Examiner* — Padmavathi Baskar
(74) *Attorney, Agent, or Firm* — TraskBritt, P.C.

(57) ABSTRACT

The present invention relates to agrochemical and biological control compositions for combating pests, more specifically plant pests, comprising at least one polypeptide, which specifically binds to a pest. The invention further provides methods for protecting or treating a plant or a part of a plant from an infection or other biological interaction with a plant pathogen, at least comprising the step of applying directly or indirectly to a plant or to a part of a plant, an agrochemical composition, under conditions effective to protect or treat a plant or a part of a plant against a infection or biological interaction with a plant pathogen. Further provided are methods for producing such agrochemical compositions and formulations, to polypeptides with a specific pesticidal activity comprised within an agrochemical formulation, to nucleic acids encoding such polypeptide and to plants comprising chimeric genes comprising such nucleic acids.

7 Claims, 10 Drawing Sheets

(56) References Cited

FOREIGN PATENT DOCUMENTS

Figure 1:
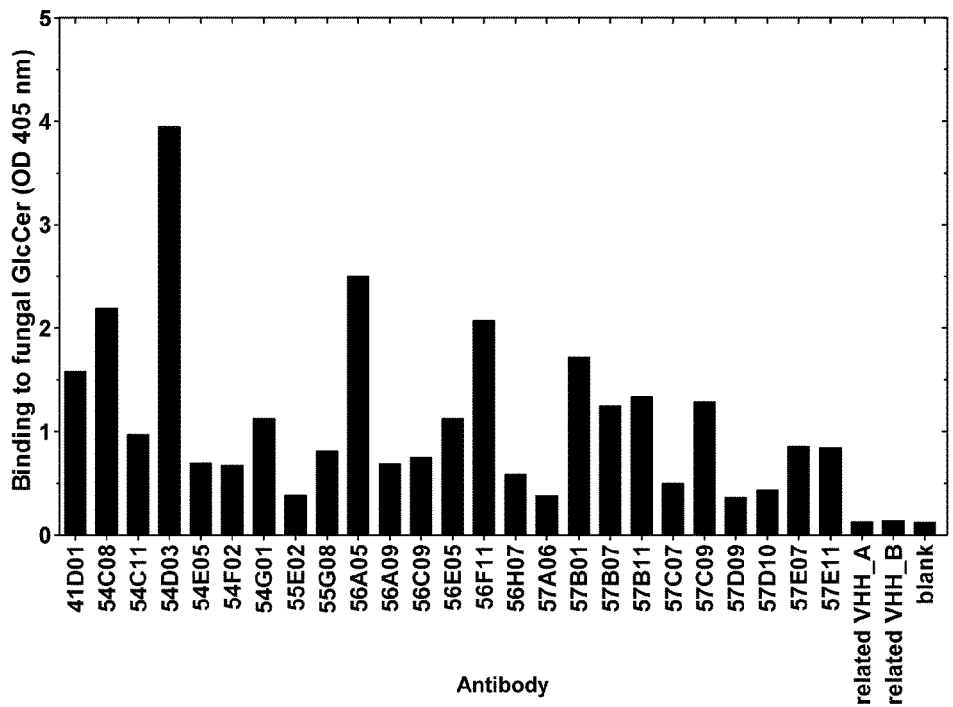

| WO | 2010019442 A1 | 2/2010 |
|---|---|---|
| WO | 2010066740 A1 | 6/2010 |
| WO | 2011023522 A1 | 3/2011 |
| WO | 2012025602 A1 | 3/2012 |
| WO | 2012025619 A1 | 3/2012 |
| WO | 2012025621 A1 | 3/2012 |
| WO | 2014177595 A1 | 11/2014 |
| WO | 2014191146 A1 | 12/2014 |

OTHER PUBLICATIONS

Nimrichter et al , vol. 6, Issue 7, Jun. 2004, pp. 657-665.*
Da Silva et al., Glucosylceramides in Collectotrichum gloeosporioides are involved in the differentiation of conidia into mycelial cells, Febs Letters, Mar. 12, 2004, pp. 137-143, vol. 561.
Nimrichter et al., Fungal Glucosylceramides: From Structural Components to Biologically Active Targets of New Antimicrobials, Frontiers in, Microbiology, Jan. 1, 2011, pp. 1-7.
PCT International Search Report, PCT/EP2014/058772, dated Aug. 16, 2013.
PCT International Search Report, PCT/EP2014/058771, dated Sep. 17, 2014.

* cited by examiner

Figure 7B

Figure 7C

SEQUENCE LISTING

```
<160> NUMBER OF SEQ ID NOS: 335

<210> SEQ ID NO 1
<211> LENGTH: 118
<212> TYPE: PRT
<213> ORGANISM: Artificial Sequence
<220> FEATURE:
<223> OTHER INFORMATION: VHH sequence 40F07

<400> SEQUENCE: 1
```

-continued

Gln Val Gln Leu Gln Glu Ser Gly Gly Gly Leu Val Gln Ala Gly Gly
1               5                   10                  15

Ser Leu Arg Leu Ser Cys Val Ala Ser Gly Thr Thr Phe Ser Ser Tyr
            20                  25                  30

Thr Met Gly Trp Tyr Arg Gln Ala Pro Gly Lys Gln Arg Glu Leu Leu
        35                  40                  45

Ala Ser Ile Glu Gly Gly Gly Asn Thr Asp Tyr Ala Asp Ser Val Lys
    50                  55                  60

Gly Arg Phe Thr Ile Ser Arg Asp Asn Ala Arg Asn Thr Val Tyr Leu
65              70                  75                  80

Gln Met Asn Ser Leu Lys Thr Glu Asp Thr Ala Val Tyr Tyr Cys Asn
            85                  90                  95

Ala Ala Arg Thr Trp Ser Ile Phe Arg Asn Tyr Trp Gly Gln Gly Thr
            100                 105                 110

Gln Val Thr Val Ser Ser
        115

<210> SEQ ID NO 2
<211> LENGTH: 115
<212> TYPE: PRT
<213> ORGANISM: Artificial Sequence
<220> FEATURE:
<223> OTHER INFORMATION: VHH sequence 41D01

<400> SEQUENCE: 2

Gln Val Gln Leu Gln Glu Ser Gly Gly Gly Leu Val Gln Ala Gly Gly
1               5                   10                  15

Ser Leu Arg Leu Ser Cys Ala Ala Ser Gly Arg Thr Phe Ser Arg Tyr
            20                  25                  30

Gly Met Gly Trp Phe Arg Gln Leu Pro Gly Lys Gln Arg Glu Leu Val
        35                  40                  45

Thr Ser Ile Thr Arg Gly Gly Thr Thr Thr Tyr Ala Asp Ser Val Lys
    50                  55                  60

Gly Arg Phe Thr Ile Ser Arg Asp Asn Ala Lys Asn Thr Val Tyr Leu
65              70                  75                  80

Gln Met Asn Ser Leu Lys Pro Glu Asp Thr Ala Val Tyr Tyr Cys Asn
            85                  90                  95

Ala Arg Ser Ile Trp Arg Asp Tyr Trp Gly Gln Gly Thr Gln Val Thr
            100                 105                 110

Val Ser Ser
    115

<210> SEQ ID NO 3
<211> LENGTH: 116
<212> TYPE: PRT
<213> ORGANISM: Artificial Sequence
<220> FEATURE:
<223> OTHER INFORMATION: VHH sequence 41D06

<400> SEQUENCE: 3

Gln Val Gln Leu Gln Glu Ser Gly Gly Gly Leu Val Gln Ala Gly Gly
1               5                   10                  15

Ser Leu Arg Leu Ser Cys Ala Ala Ser Gly Gly Ile Phe Gly Ile Asn
            20                  25                  30

Ala Met Arg Trp Tyr Arg Gln Ala Pro Gly Lys Gln Arg Glu Leu Val
        35                  40                  45

Ala Ser Ile Ser Ser Gly Gly Asn Thr Asn Tyr Ser Glu Ser Val Lys
    50                  55                  60

```
Gly Arg Phe Thr Ile Ser Arg Asp Asp Ala Asn Tyr Thr Val Tyr Leu
65                  70                  75                  80

Gln Met Asn Ser Leu Lys Pro Glu Asp Thr Ala Val Tyr Tyr Cys Asn
                85                  90                  95

Phe Val Arg Leu Trp Phe Pro Asp Tyr Trp Gly Gln Gly Thr Gln Val
            100                 105                 110

Thr Val Ser Ser
        115

<210> SEQ ID NO 4
<211> LENGTH: 121
<212> TYPE: PRT
<213> ORGANISM: Artificial Sequence
<220> FEATURE:
<223> OTHER INFORMATION: VHH sequence 41G10

<400> SEQUENCE: 4

Gln Val Gln Leu Gln Glu Ser Gly Gly Gly Leu Val Gln Pro Gly Gly
1               5                   10                  15

Ser Leu Thr Leu Ser Cys Ala Ala Thr Lys Thr Gly Phe Ser Ile Asn
            20                  25                  30

Ala Met Gly Trp Tyr Arg Gln Ala Pro Gly Lys Gln Arg Glu Met Val
        35                  40                  45

Ala Thr Ile Thr Ser Gly Gly Thr Thr Asn Tyr Ala Asp Ser Val Lys
    50                  55                  60

Gly Arg Phe Ala Ile Ser Arg Asp Asn Ala Lys Asn Thr Val Ser Leu
65                  70                  75                  80

Gln Met Asn Thr Leu Lys Pro Glu Asp Thr Ala Leu Tyr Tyr Cys Asn
                85                  90                  95

Thr Glu Ala Arg Arg Tyr Phe Thr Arg Ala Ser Gln Val Tyr Trp Gly
            100                 105                 110

Gln Gly Thr Gln Val Thr Val Ser Ser
        115                 120

<210> SEQ ID NO 5
<211> LENGTH: 120
<212> TYPE: PRT
<213> ORGANISM: Artificial Sequence
<220> FEATURE:
<223> OTHER INFORMATION: VHH sequence 41H05

<400> SEQUENCE: 5

Gln Val Gln Leu Gln Glu Ser Gly Gly Gly Leu Val Gln Pro Gly Gly
1               5                   10                  15

Ser Leu Arg Leu Ser Cys Ala Ala Ser Gly Gly Ile Phe Ser Ile Asn
            20                  25                  30

Ala Met Gly Trp Tyr Arg Gln Asp Pro Gly Lys Gln Arg Glu Met Val
        35                  40                  45

Ala Thr Ile Thr Ser Gly Ala Asn Thr Asn Tyr Thr Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Asn
                85                  90                  95

Ala Val Gly Arg Arg Trp Tyr Gly Gly Tyr Val Glu Leu Trp Gly Gln
            100                 105                 110

Gly Thr Gln Val Thr Val Ser Ser
```

115           120

<210> SEQ ID NO 6
<211> LENGTH: 119
<212> TYPE: PRT
<213> ORGANISM: Artificial Sequence
<220> FEATURE:
<223> OTHER INFORMATION: VHH sequence 42C11

<400> SEQUENCE: 6

Gln Val Gln Leu Gln Glu Ser Gly Gly Gly Leu Val Gln Pro Gly Gly
1               5                   10                  15

Ser Leu Arg Leu Ser Cys Ala Ala Ser Gly Ser Ile Phe Ser Thr Tyr
            20                  25                  30

Val Met Gly Trp Tyr Arg Gln Ala Ile Gly Lys Gln Arg Glu Leu Val
        35                  40                  45

Ala Thr Ile Thr Ser Ser Gly Lys Thr Asn Tyr Ala Ala Ser Val Lys
    50                  55                  60

Gly Arg Phe Thr Val Ser Arg Asp Ile Thr Lys Asn Thr Met Tyr Leu
65                  70                  75                  80

Gln Met Asn Ser Leu Lys Pro Glu Asp Thr Ala Val Tyr Tyr Cys Gly
                85                  90                  95

Ala Asp Arg Trp Val Leu Thr Arg Trp Ser Asn Tyr Trp Gly Gln Gly
            100                 105                 110

Thr Gln Val Thr Val Ser Ser
        115

<210> SEQ ID NO 7
<211> LENGTH: 116
<212> TYPE: PRT
<213> ORGANISM: Artificial Sequence
<220> FEATURE:
<223> OTHER INFORMATION: VHH sequence 42C12

<400> SEQUENCE: 7

Gln Val Gln Leu Gln Glu Ser Gly Gly Gly Leu Val Gln Pro Gly Gly
1               5                   10                  15

Ser Leu Arg Leu Ser Cys Ala Ala Ser Gly Ser Ile Ser Ser Leu Gly
            20                  25                  30

Trp Tyr Arg Gln Ala Pro Gly Lys Gln Arg Glu Phe Val Ala Ser Ala
        35                  40                  45

Thr Ser Gly Gly Asp Thr Thr Tyr Ala Asp Ser Val Lys Gly Arg Phe
    50                  55                  60

Thr Ile Ser Arg Asp Asn Ser Lys Asn Thr Val Tyr Leu Gln Met Asn
65                  70                  75                  80

Ser Leu Lys Pro Glu Asp Thr Ala Val Tyr Tyr Cys Lys Gly Gln Arg
                85                  90                  95

Gly Val Ala Trp Thr Arg Lys Glu Tyr Trp Gly Gln Gly Thr Gln Val
            100                 105                 110

Thr Val Ser Ser
        115

<210> SEQ ID NO 8
<211> LENGTH: 119
<212> TYPE: PRT
<213> ORGANISM: Artificial Sequence
<220> FEATURE:
<223> OTHER INFORMATION: VHH sequence 50D03

<400> SEQUENCE: 8

```
Gln Val Gln Leu Gln Glu Ser Gly Gly Gly Leu Val Gln Pro Gly Gly
1               5                   10                  15

Ser Leu Arg Leu Ser Cys Ala Ala Ser Gly Ser Ile Phe Ser Thr Tyr
            20                  25                  30

Ala Met Gly Trp Tyr Arg Gln Ala Ile Gly Lys Gln Arg Glu Leu Val
        35                  40                  45

Ala Thr Ile Thr Ser Ser Gly Lys Thr Asn Tyr Ala Ala Ser Val Lys
50                  55                  60

Gly Arg Phe Thr Ile Ser Arg Asp Ile Thr Lys Asn Thr Met Tyr Leu
65                  70                  75                  80

Gln Met Asn Ser Leu Lys Pro Glu Asp Thr Ala Val Tyr Tyr Cys Gly
                85                  90                  95

Ala Asp Arg Trp Val Leu Thr Arg Trp Ser Asn Tyr Trp Gly Gln Gly
            100                 105                 110

Thr Gln Val Thr Val Ser Ser
        115
```

<210> SEQ ID NO 9
<211> LENGTH: 120
<212> TYPE: PRT
<213> ORGANISM: Artificial Sequence
<220> FEATURE:
<223> OTHER INFORMATION: VHH sequence 50D07

<400> SEQUENCE: 9

```
Gln Val Gln Leu Gln Glu Ser Gly Gly Gly Leu Val Gln Pro Gly Gly
1               5                   10                  15

Ser Leu Arg Leu Ser Cys Thr Ala Ser Gly Asn Ile Val Asn Ile Arg
            20                  25                  30

Asp Met Gly Trp Tyr Arg Gln Val Pro Gly Lys Gln Arg Glu Leu Val
        35                  40                  45

Ala Thr Ile Thr Ser Asp Gln Ser Thr Asn Tyr Ala Asp Ser Val Lys
50                  55                  60

Gly Arg Phe Thr Thr Thr Arg Asp Asn Ala Lys Lys Thr Val Tyr Leu
65                  70                  75                  80

Gln Met Asp Ser Leu Lys Pro Glu Asp Thr Ala Gly Tyr Tyr Cys Asn
                85                  90                  95

Ala Arg Val Arg Thr Val Leu Arg Gly Trp Arg Asp Tyr Trp Gly Gln
            100                 105                 110

Gly Thr Gln Val Thr Val Ser Ser
        115                 120
```

<210> SEQ ID NO 10
<211> LENGTH: 119
<212> TYPE: PRT
<213> ORGANISM: Artificial Sequence
<220> FEATURE:
<223> OTHER INFORMATION: VHH sequence 50E02

<400> SEQUENCE: 10

```
Gln Val Gln Leu Gln Glu Ser Gly Gly Gly Leu Val Gln Pro Gly Gly
1               5                   10                  15

Ser Leu Arg Leu Ser Cys Ala Ala Ser Gly Ser Ile Phe Ser Ile Asn
            20                  25                  30

Ala Met Gly Trp Tyr Arg Gln Ala Pro Gly Lys Gln Arg Glu Leu Val
        35                  40                  45

Ala Ala Ile Thr Ser Asp Gly Ser Thr Asn Tyr Ala Asp Ser Val Lys
```

```
                    50                  55                  60
Gly Arg Phe Thr Ile Ser Arg Asp Asn Ala Lys Asn Thr Ala Tyr Leu
 65                  70                  75                  80

Gln Met Asn Ser Leu Lys Pro Glu Asp Thr Ala Val Tyr Tyr Cys Asn
                    85                  90                  95

Leu Arg Arg Arg Thr Phe Leu Lys Ser Ser Asp Tyr Trp Gly Gln Gly
                100                 105                 110

Thr Gln Val Thr Val Ser Ser
            115

<210> SEQ ID NO 11
<211> LENGTH: 123
<212> TYPE: PRT
<213> ORGANISM: Artificial Sequence
<220> FEATURE:
<223> OTHER INFORMATION: VHH sequence 51B08

<400> SEQUENCE: 11

Gln Val Gln Leu Gln Glu Ser Gly Gly Gly Leu Val Gln Ala Gly Asp
 1               5                  10                  15

Ser Leu Arg Leu Ser Cys Ala Ala Ser Gly Arg Arg Phe Gly Ser Tyr
                20                  25                  30

Ala Met Gly Trp Phe Arg Gln Val Pro Gly Lys Glu Arg Glu Leu Val
                35                  40                  45

Ala Gly Ile Ser Ser Gly Gly Ser Thr Lys Tyr Ala Asp Ser Val Arg
         50                  55                  60

Gly Arg Phe Thr Ile Ser Arg Asp Asn Ala Lys Asn Thr Val Ser Leu
 65                  70                  75                  80

Gln Met Lys Ser Leu Lys Pro Glu Asp Thr Ala Val Tyr Tyr Cys Asn
                85                  90                  95

Ala Lys Tyr Gly Arg Trp Thr Tyr Thr Gly Arg Pro Glu Tyr Asp Ser
                100                 105                 110

Trp Gly Gln Gly Thr Gln Val Thr Val Ser Ser
            115                 120

<210> SEQ ID NO 12
<211> LENGTH: 116
<212> TYPE: PRT
<213> ORGANISM: Artificial Sequence
<220> FEATURE:
<223> OTHER INFORMATION: VHH sequence 51C06

<400> SEQUENCE: 12

Gln Val Gln Leu Gln Glu Ser Gly Gly Gly Leu Val Gln Pro Gly Gly
 1               5                  10                  15

Ser Leu Arg Leu Ser Cys Ala Ala Ser Gly Ser Ile Phe Ser Ser Asp
                20                  25                  30

Thr Met Gly Trp Tyr Arg Arg Ala Pro Gly Lys Gln Arg Glu Leu Val
                35                  40                  45

Ala Ala Ile Thr Thr Gly Gly Asn Thr Asn Tyr Ala Asp Ser Val Lys
         50                  55                  60

Gly Arg Phe Thr Ile Ser Arg Asp Asn Ala Lys Asn Thr Val Tyr Leu
 65                  70                  75                  80

Gln Met Asn Ser Leu Gln Pro Glu Asp Thr Ala Val Tyr Tyr Cys Asn
                85                  90                  95

Cys Arg Arg Arg Trp Ser Arg Asp Phe Trp Gly Gln Gly Thr Gln Val
                100                 105                 110
```

```
Thr Val Ser Ser
        115

<210> SEQ ID NO 13
<211> LENGTH: 119
<212> TYPE: PRT
<213> ORGANISM: Artificial Sequence
<220> FEATURE:
<223> OTHER INFORMATION: VHH sequence 51C08

<400> SEQUENCE: 13

Gln Val Gln Leu Gln Glu Ser Gly Gly Gly Leu Val Gln Pro Gly Gly
1               5                   10                  15

Ser Leu Arg Leu Ser Cys Ala Ala Ser Gly Thr Ile Phe Ser Ile Lys
            20                  25                  30

Thr Met Gly Trp Tyr Arg Gln Ala Pro Gly Lys Gln Arg Glu Leu Val
        35                  40                  45

Ala Thr Ile Ser Asn Gly Gly Ser Thr Asn Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Asn
                85                  90                  95

Ala Arg Gln Gln Phe Ile Gly Ala Pro Tyr Glu Tyr Trp Gly Gln Gly
            100                 105                 110

Thr Gln Val Thr Val Ser Ser
        115

<210> SEQ ID NO 14
<211> LENGTH: 115
<212> TYPE: PRT
<213> ORGANISM: Artificial Sequence
<220> FEATURE:
<223> OTHER INFORMATION: VHH sequence 52A01

<400> SEQUENCE: 14

Gln Val Gln Leu Gln Glu Ser Gly Gly Gly Leu Val Gln Ala Gly Gly
1               5                   10                  15

Ser Leu Arg Leu Ser Cys Thr Ala Ser Gly Ala Ile Thr Phe Ser Leu
            20                  25                  30

Gly Thr Met Gly Trp Tyr Arg Gln Ala Pro Gly Lys Gln Arg Glu Leu
        35                  40                  45

Val Ala Ser Ile Ser Thr Gly Ser Thr Asn Tyr Ala Asp Ser Val Lys
    50                  55                  60

Gly Arg Phe Thr Ile Ser Arg Asp Ile Ile Lys Asn Ile Leu Tyr Leu
65                  70                  75                  80

Gln Met Asn Ser Leu Lys Pro Glu Asp Thr Ala Val Tyr Ser Cys Asn
                85                  90                  95

Ala Arg Leu Leu Trp Ser Asn Tyr Trp Gly Gln Gly Thr Gln Val Thr
            100                 105                 110

Val Ser Ser
    115

<210> SEQ ID NO 15
<211> LENGTH: 117
<212> TYPE: PRT
<213> ORGANISM: Artificial Sequence
<220> FEATURE:
<223> OTHER INFORMATION: VHH sequence 52B01
```

```
<400> SEQUENCE: 15

Gln Val Gln Leu Gln Glu Ser Gly Gly Gly Leu Val Gln Ala Gly Glu
1               5                   10                  15

Ser Leu Arg Leu Ser Cys Ala Ala Ser Gly Ser Thr Phe Ser Ile Asn
            20                  25                  30

Val Met Gly Trp Tyr Arg Gln Ala Pro Gly Glu Gln Arg Glu Leu Val
        35                  40                  45

Ala Thr Ile Ser Arg Gly Gly Ser Thr Asn Tyr Ala Asp Ser Val Lys
    50                  55                  60

Gly Arg Phe Thr Ile Ser Arg Asp Asn Ala Lys Val Thr Val Tyr Leu
65                  70                  75                  80

Gln Met Asp Ser Leu Lys Pro Glu Asp Thr Ala Val Tyr Tyr Cys Asn
                85                  90                  95

Ala Ala Gly Trp Val Gly Val Thr Asn Tyr Trp Gly Gln Gly Thr Gln
            100                 105                 110

Val Thr Val Ser Ser
        115

<210> SEQ ID NO 16
<211> LENGTH: 117
<212> TYPE: PRT
<213> ORGANISM: Artificial Sequence
<220> FEATURE:
<223> OTHER INFORMATION: VHH sequence 52G05

<400> SEQUENCE: 16

Gln Val Gln Leu Gln Glu Ser Gly Gly Gly Leu Val Gln Ala Gly Gly
1               5                   10                  15

Ser Leu Arg Leu Ser Cys Ala Ala Ser Gly Ser Thr Gly Ser Ile Ser
            20                  25                  30

Ala Met Gly Trp Tyr Arg Gln Ala Pro Gly Lys Gln Arg Glu Leu Val
        35                  40                  45

Ala Ser Ile Thr Arg Arg Gly Ser Thr Asn Tyr Ala Asp Ser Val Lys
    50                  55                  60

Asp Arg Phe Thr Ile Ser Arg Asp Asn Ala Trp Asn Thr Val Tyr Leu
65                  70                  75                  80

Gln Met Asn Ser Leu Lys Pro Glu Asp Thr Ala Val Tyr Tyr Cys Asn
                85                  90                  95

Ala Arg Arg Tyr Tyr Thr Arg Asn Asp Tyr Trp Gly Gln Gly Thr Gln
            100                 105                 110

Val Thr Val Ser Ser
        115

<210> SEQ ID NO 17
<211> LENGTH: 114
<212> TYPE: PRT
<213> ORGANISM: Artificial Sequence
<220> FEATURE:
<223> OTHER INFORMATION: VHH sequence 53A01

<400> SEQUENCE: 17

Gln Val Gln Leu Gln Glu Ser Gly Gly Gly Leu Gly Gln Ala Gly Gly
1               5                   10                  15

Ser Leu Arg Leu Ser Cys Glu Val Ser Gly Thr Thr Phe Ser Ile Asn
            20                  25                  30

Thr Met Gly Trp His Arg Gln Ala Pro Gly Lys Gln Arg Glu Leu Val
        35                  40                  45
```

```
Ala Ser Ile Ser Ser Gly Gly Trp Thr Asn Tyr Ala Asp Ser Val Lys
    50                  55                  60

Gly Arg Phe Thr Ile Ser Arg Asp Asn Ala Lys Lys Thr Val Tyr Leu
65                  70                  75                  80

Gln Met Asn Asn Leu Lys Pro Glu Asp Thr Ala Val Tyr Tyr Cys Arg
                85                  90                  95

Trp Gly Ala Ile Gly Asn Trp Tyr Gly Gln Gly Thr Gln Val Thr Val
                100                 105                 110

Ser Ser
```

<210> SEQ ID NO 18
<211> LENGTH: 117
<212> TYPE: PRT
<213> ORGANISM: Artificial Sequence
<220> FEATURE:
<223> OTHER INFORMATION: VHH sequence 53F05

<400> SEQUENCE: 18

```
Gln Val Gln Leu Gln Glu Ser Gly Gly Gly Leu Val Gln Pro Gly Gly
1               5                   10                  15

Ser Leu Arg Leu Ser Cys Ala Ala Ser Val Arg Ile Phe Gly Leu Asn
                20                  25                  30

Ala Met Gly Trp Tyr Arg Gln Gly Pro Gly Lys Gln Arg Glu Leu Val
            35                  40                  45

Ala Ser Ile Thr Thr Gly Gly Ser Thr Asn Tyr Ala Glu Pro Val Lys
    50                  55                  60

Gly Arg Phe Thr Ile Ser Arg Asp Asn Ala Asn Asn Thr Val Tyr Leu
65                  70                  75                  80

Gln Met Asn Asn Leu Lys Pro Glu Asp Thr Ala Val Tyr Tyr Cys Asn
                85                  90                  95

Ala Glu Arg Arg Trp Gly Leu Pro Asn Tyr Trp Gly Gln Gly Thr Gln
                100                 105                 110

Val Thr Val Ser Ser
            115
```

<210> SEQ ID NO 19
<211> LENGTH: 126
<212> TYPE: PRT
<213> ORGANISM: Artificial Sequence
<220> FEATURE:
<223> OTHER INFORMATION: VHH sequence 54A02

<400> SEQUENCE: 19

```
Gln Val Gln Leu Gln Glu Ser Gly Gly Gly Leu Val Glu Ala Gly Gly
1               5                   10                  15

Ser Leu Arg Leu Ser Cys Ala Ala Ser Gly Arg Thr Phe Ser Arg Tyr
                20                  25                  30

Gly Met Gly Trp Phe Arg Gln Ala Pro Gly Lys Glu Arg Glu Phe Val
            35                  40                  45

Ala Ala Asn Arg Trp Ser Gly Gly Ser Thr Tyr Tyr Ala Asp Ser Val
    50                  55                  60

Arg Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Tyr Ala His Ile Thr Ala Trp Gly Met Arg Asn Asp Tyr Glu
                100                 105                 110
```

```
Tyr Asp Tyr Trp Gly Gln Gly Thr Gln Val Thr Val Ser Ser
            115                 120                 125

<210> SEQ ID NO 20
<211> LENGTH: 125
<212> TYPE: PRT
<213> ORGANISM: Artificial Sequence
<220> FEATURE:
<223> OTHER INFORMATION: VHH sequence 54B01

<400> SEQUENCE: 20

Gln Val Gln Leu Gln Glu Ser Gly Gly Gly Leu Val Gln Ala Gly Gly
1               5                   10                  15

Ser Leu Arg Leu Ser Cys Ala Ala Thr Gly Arg Thr Phe Ser Arg Tyr
            20                  25                  30

Thr Met Gly Trp Phe Arg Gln Ala Pro Gly Lys Glu Arg Asp Phe Val
        35                  40                  45

Ala Gly Ile Thr Trp Thr Gly Gly Ser Thr Asp Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Gly Asn Leu Leu Arg Leu Ala Gly Gln Leu Arg Arg Gly Tyr
            100                 105                 110

Asp Ser Trp Gly Gln Gly Thr Gln Val Thr Val Ser Ser
            115                 120                 125

<210> SEQ ID NO 21
<211> LENGTH: 129
<212> TYPE: PRT
<213> ORGANISM: Artificial Sequence
<220> FEATURE:
<223> OTHER INFORMATION: VHH sequence 54C01

<400> SEQUENCE: 21

Gln Val Gln Leu Gln Glu Ser Gly Gly Gly Leu Val Gln Ala Gly Gly
1               5                   10                  15

Ser Leu Arg Leu Ser Cys Ala Ala Ser Gly Arg Thr Gly Ser Arg Tyr
            20                  25                  30

Ala Met Gly Trp Phe Arg Gln Ala Pro Gly Lys Glu Arg Glu Phe Val
        35                  40                  45

Ala Ala Ile Ser Trp Ser Gly Gly Ser Thr Tyr Tyr Ala Asp Ser Val
    50                  55                  60

Lys Asp Arg Phe Thr Ile Ser Arg Asp Asn Ala Lys Asn Thr Val Tyr
65                  70                  75                  80

Leu Gln Met His Ser Leu Lys Pro Glu Asp Thr Ala Val Tyr Tyr Cys
                85                  90                  95

Ala Thr Arg Asn Arg Ala Gly Pro His Tyr Ser Arg Gly Tyr Thr Ala
            100                 105                 110

Gly Gln Glu Tyr Asp Tyr Trp Gly Gln Gly Thr Gln Val Thr Val Ser
            115                 120                 125

Ser

<210> SEQ ID NO 22
<211> LENGTH: 121
<212> TYPE: PRT
<213> ORGANISM: Artificial Sequence
<220> FEATURE:
```

<223> OTHER INFORMATION: VHH sequence 54C04

<400> SEQUENCE: 22

```
Gln Val Gln Leu Gln Glu Ser Gly Gly Gly Leu Val Gln Pro Gly Gly
1               5                   10                  15

Ser Leu Arg Leu Ser Cys Ala Ala Ser Gly Arg Ile Phe Ser Ile Asn
            20                  25                  30

Ala Met Gly Trp Tyr Arg Gln Gly Pro Gly Lys Glu Arg Glu Leu Val
        35                  40                  45

Val Asp Met Thr Ser Gly Gly Ser Ile Asn Tyr Ala Asp Ser Val Ser
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys His
                85                  90                  95

Ala Asn Leu Arg Thr Ala Phe Trp Arg Asn Gly Asn Asp Tyr Trp Gly
            100                 105                 110

Gln Gly Thr Gln Val Thr Val Ser Ser
        115                 120
```

<210> SEQ ID NO 23
<211> LENGTH: 115
<212> TYPE: PRT
<213> ORGANISM: Artificial Sequence
<220> FEATURE:
<223> OTHER INFORMATION: VHH sequence 54C08

<400> SEQUENCE: 23

```
Gln Val Gln Leu Gln Glu Ser Gly Gly Gly Leu Val Gln Pro Gly Gly
1               5                   10                  15

Ser Leu Arg Leu Ser Cys Ala Ala Ser Gly Ser Ile Ser Ile Asn
            20                  25                  30

Ala Met Gly Trp Tyr Arg Gln Ala Pro Gly Lys Gln Arg Glu Leu Val
        35                  40                  45

Ala Ser Ile Thr Ser Gly Gly Ser Thr Asn Tyr Ala Asp Ser Val Lys
    50                  55                  60

Gly Arg Phe Thr Ile Ser Arg Asp Asn Ala Lys Asn Thr Val Asn Leu
65                  70                  75                  80

Gln Met Asn Ser Leu Lys Pro Glu Asp Thr Ala Val Tyr Tyr Cys Ser
                85                  90                  95

Ala Gly Pro Trp Tyr Arg Arg Ser Trp Gly Arg Gly Thr Gln Val Thr
            100                 105                 110

Val Ser Ser
        115
```

<210> SEQ ID NO 24
<211> LENGTH: 116
<212> TYPE: PRT
<213> ORGANISM: Artificial Sequence
<220> FEATURE:
<223> OTHER INFORMATION: VHH sequence 54C10

<400> SEQUENCE: 24

```
Gln Val Gln Leu Gln Glu Ser Gly Gly Gly Leu Val Gln Pro Gly Glu
1               5                   10                  15

Ser Leu Arg Leu Ser Cys Ala Ala Ser Ala Ser Ile Phe Trp Val Asn
            20                  25                  30

Asp Met Gly Trp Tyr Arg Gln Ala Pro Gly Lys Gln Arg Glu Leu Val
```

```
                    35                  40                  45

Ala Gln Ile Thr Arg Arg Gly Ser Thr Asn Tyr Ala Asp Ser Val Lys
            50                  55                  60

Gly Arg Phe Thr Ile Ser Arg Asp Asn Ala Lys Asp Glu Val Tyr Leu
65                  70                  75                  80

Gln Met Asn Ser Leu Lys Pro Glu Asp Thr Ala Val Tyr Tyr Cys Asn
                85                  90                  95

Ala Asp Leu Ala Val Arg Gly Arg Tyr Trp Gly Gln Gly Thr Gln Val
            100                 105                 110

Thr Val Ser Ser
        115

<210> SEQ ID NO 25
<211> LENGTH: 119
<212> TYPE: PRT
<213> ORGANISM: Artificial Sequence
<220> FEATURE:
<223> OTHER INFORMATION: VHH sequence 54C11

<400> SEQUENCE: 25

Gln Val Gln Leu Gln Glu Ser Gly Gly Gly Leu Val Gln Pro Gly Gly
1               5                   10                  15

Ser Leu Arg Leu Ser Cys Ala Ala Ser Gly Ser Phe Phe Pro Val Asn
            20                  25                  30

Asp Met Ala Trp Tyr Arg Gln Ala Leu Gly Asn Glu Arg Glu Leu Val
                35                  40                  45

Ala Asn Ile Thr Arg Gly Gly Ser Thr Asn Tyr Ala Asp Ser Val Lys
            50                  55                  60

Gly Arg Phe Thr Ile Ser Arg Asp Asn Ala Lys Asn Thr Val Tyr Leu
65                  70                  75                  80

Gln Met Asn Thr Leu Lys Pro Glu Asp Thr Ala Val Tyr Tyr Cys Asn
                85                  90                  95

Val Arg Ile Gly Phe Gly Trp Thr Ala Lys Ala Tyr Trp Gly Gln Gly
            100                 105                 110

Thr Gln Val Thr Val Ser Ser
        115

<210> SEQ ID NO 26
<211> LENGTH: 116
<212> TYPE: PRT
<213> ORGANISM: Artificial Sequence
<220> FEATURE:
<223> OTHER INFORMATION: VHH sequence 54D03

<400> SEQUENCE: 26

Gln Val Gln Leu Gln Glu Ser Gly Gly Gly Leu Val Gln Pro Gly Gly
1               5                   10                  15

Ser Leu Arg Leu Ser Cys Ala Ala Ser Gly Gly Ile Phe Gly Ile Asn
            20                  25                  30

Ala Met Arg Trp Tyr Arg Gln Ala Pro Gly Lys Gln Arg Glu Leu Val
                35                  40                  45

Ala Ser Ile Ser Ser Gly Gly Asn Thr Asn Tyr Ser Glu Ser Val Lys
            50                  55                  60

Gly Arg Phe Thr Ile Ser Arg Asp Asp Ala Asn Tyr Thr Val Tyr Leu
65                  70                  75                  80

Gln Met Asn Ser Leu Lys Pro Glu Asp Thr Ala Val Tyr Tyr Cys Asn
                85                  90                  95
```

Phe Val Arg Leu Trp Phe Pro Asp Tyr Trp Gly Gln Gly Thr Gln Val
            100                 105                 110

Thr Val Ser Ser
        115

<210> SEQ ID NO 27
<211> LENGTH: 116
<212> TYPE: PRT
<213> ORGANISM: Artificial Sequence
<220> FEATURE:
<223> OTHER INFORMATION: VHH sequence 54D06

<400> SEQUENCE: 27

Gln Val Gln Leu Gln Glu Ser Gly Gly Gly Leu Val Gln Pro Gly Gly
1               5                   10                  15

Ser Leu Arg Leu Ser Cys Ala Ala Ser Gly Ser Thr Ile Arg Ile Asn
            20                  25                  30

Ala Met Gly Trp Tyr Arg Gln Ala Pro Gly Lys Gln Arg Glu Leu Val
        35                  40                  45

Ala Thr Ile Thr Arg Gly Gly Ile Thr Asn Tyr Ala Asp Ser Val Lys
    50                  55                  60

Gly Arg Phe Thr Ile Ser Arg Asp Asn Ala Lys Phe Thr Val Tyr Leu
65                  70                  75                  80

Gln Met Asn Ser Leu Lys Pro Glu Asp Thr Ala Val Tyr Tyr Cys Asn
                85                  90                  95

Ala Arg Ser Trp Val Gly Pro Glu Tyr Trp Gly Gln Gly Thr Gln Val
            100                 105                 110

Thr Val Ser Ser
        115

<210> SEQ ID NO 28
<211> LENGTH: 120
<212> TYPE: PRT
<213> ORGANISM: Artificial Sequence
<220> FEATURE:
<223> OTHER INFORMATION: VHH sequence 54D10

<400> SEQUENCE: 28

Gln Val Gln Leu Gln Glu Ser Gly Gly Gly Leu Val Gln Pro Gly Gly
1               5                   10                  15

Ser Leu Arg Leu Ser Cys Ala Ala Ser Gly Met Thr Tyr Ser Ile His
            20                  25                  30

Ala Met Gly Trp Tyr Arg Gln Ala Pro Gly Lys Glu Arg Glu Leu Val
        35                  40                  45

Ala Ile Thr Ser Thr Ser Gly Thr Thr Asp Tyr Thr Asp Ser Val Lys
    50                  55                  60

Gly Arg Phe Thr Ile Ser Arg Asp Gly Ala Asn Asn Thr Val Tyr Leu
65                  70                  75                  80

Gln Met Asn Ser Leu Lys Ser Glu Asp Thr Ala Val Tyr Tyr Cys His
                85                  90                  95

Val Lys Thr Arg Thr Trp Tyr Asn Gly Lys Tyr Asp Tyr Trp Gly Gln
            100                 105                 110

Gly Thr Gln Val Thr Val Ser Ser
        115                 120

<210> SEQ ID NO 29
<211> LENGTH: 117
<212> TYPE: PRT
<213> ORGANISM: Artificial Sequence

```
<220> FEATURE:
<223> OTHER INFORMATION: VHH sequence 54E01

<400> SEQUENCE: 29

Gln Val Gln Leu Gln Glu Ser Gly Gly Gly Leu Val Gln Pro Gly Gly
1               5                   10                  15

Ser Leu Arg Leu Ser Cys Thr Ala Ser Gly Ser Ile Phe Ser Ile Asn
            20                  25                  30

Pro Met Gly Trp Tyr Arg Gln Ala Pro Gly Lys Gln Arg Glu Leu Val
        35                  40                  45

Ala Ala Ile Thr Ser Gly Gly Ser Thr Asn Tyr Ala Asp Tyr Val Lys
    50                  55                  60

Gly Arg Phe Thr Ile Ser Arg Asp Asn Ala Lys Asn Val Val Tyr Leu
65                  70                  75                  80

Gln Met Asn Ser Leu Lys Pro Glu Asp Thr Ala Val Tyr Tyr Cys Asn
                85                  90                  95

Gly Arg Ser Thr Leu Trp Arg Arg Asp Tyr Trp Gly Gln Gly Thr Gln
            100                 105                 110

Val Thr Val Ser Ser
        115

<210> SEQ ID NO 30
<211> LENGTH: 117
<212> TYPE: PRT
<213> ORGANISM: Artificial Sequence
<220> FEATURE:
<223> OTHER INFORMATION: VHH sequence 54E05

<400> SEQUENCE: 30

Gln Val Gln Leu Gln Glu Ser Gly Gly Gly Leu Val Gln Pro Gly Gly
1               5                   10                  15

Ser Leu Arg Leu Ser Cys Ala Ala Ser Gly Ser Ile Phe Ser Ile Asn
            20                  25                  30

Thr Met Gly Trp Tyr Arg Gln Ala Pro Gly Lys Gln Arg Glu Leu Val
        35                  40                  45

Ala Ala Ile Thr Asn Arg Gly Ser Thr Asn Tyr Ala Asp Phe Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Asp Asp Thr Ala Val Tyr Tyr Cys Asn
                85                  90                  95

Ala His Arg Ser Trp Pro Arg Tyr Asp Ser Trp Gly Gln Gly Thr Gln
            100                 105                 110

Val Thr Val Ser Ser
        115

<210> SEQ ID NO 31
<211> LENGTH: 118
<212> TYPE: PRT
<213> ORGANISM: Artificial Sequence
<220> FEATURE:
<223> OTHER INFORMATION: VHH sequence 54E10

<400> SEQUENCE: 31

Gln Val Gln Leu Gln Glu Ser Gly Gly Gly Leu Val Gln Pro Gly Gly
1               5                   10                  15

Ser Leu Arg Leu Ser Cys Ala Ser Gly Ser Ile Phe Ser Phe Asn
            20                  25                  30
```

Ala Met Gly Trp Tyr Arg Gln Ala Pro Gly Lys Gln Arg Glu Leu Val
        35                  40                  45

Ala Ala Ile Thr Arg Gly Gly Ser Thr Asn Tyr Ala Asp Ser Val Lys
 50                  55                  60

Gly Arg Phe Thr Ile Ser Arg Asp Asn Ala Asn Asn Thr Val Tyr Leu
 65                  70                  75                  80

Gln Met Asn Ser Leu Lys Pro Glu Asp Thr Ala Val Tyr Tyr Cys Asn
                 85                  90                  95

Ala Glu Ser Arg Ile Phe Arg Arg Tyr Asp Tyr Trp Gly Pro Gly Thr
                100                 105                 110

Gln Val Thr Val Ser Ser
            115

<210> SEQ ID NO 32
<211> LENGTH: 115
<212> TYPE: PRT
<213> ORGANISM: Artificial Sequence
<220> FEATURE:
<223> OTHER INFORMATION: VHH sequence 54F01

<400> SEQUENCE: 32

Gln Val Gln Leu Gln Glu Ser Gly Gly Gly Leu Val Gln Pro Gly Gly
 1               5                   10                  15

Ser Leu Arg Leu Ser Cys Val Thr Ser Gly Ser Ile Phe Gly Leu Asn
                 20                  25                  30

Leu Met Gly Trp Tyr Arg Gln Ala Pro Gly Lys Gln Arg Glu Leu Val
        35                  40                  45

Ala Thr Ile Thr Arg Gly Gly Ser Thr Asn Tyr Ala Asp Ser Val Lys
 50                  55                  60

Gly Arg Phe Thr Ile Ser Arg Asp Asn Ala Lys Lys Thr Val Tyr Leu
 65                  70                  75                  80

Gln Met Asn Ser Leu Lys Pro Glu Asp Thr Ala Val Tyr Tyr Cys Asn
                 85                  90                  95

Val Asp Arg Gly Trp Ser Ser Tyr Trp Gly Gln Gly Thr Gln Val Thr
                100                 105                 110

Val Ser Ser
        115

<210> SEQ ID NO 33
<211> LENGTH: 119
<212> TYPE: PRT
<213> ORGANISM: Artificial Sequence
<220> FEATURE:
<223> OTHER INFORMATION: VHH sequence 54F02

<400> SEQUENCE: 33

Gln Val Gln Leu Gln Glu Ser Gly Gly Gly Leu Val Gln Pro Gly Gly
 1               5                   10                  15

Ser Leu Arg Leu Ser Cys Val Thr Ser Gly Ser Ile Arg Ser Ile Asn
                 20                  25                  30

Thr Met Gly Trp Tyr Arg Gln Ala Pro Gly Asn Glu Arg Glu Leu Val
        35                  40                  45

Ala Thr Ile Thr Ser Gly Gly Thr Thr Asn Tyr Ala Asp Ser Val Lys
 50                  55                  60

Asn Arg Phe Thr Ile Ser Arg Asp Asn Ala Lys Asn Thr Val Tyr Leu
 65                  70                  75                  80

Gln Met Asn Ser Leu Lys Pro Glu Asp Thr Ala Val Tyr Tyr Cys Asn
                 85                  90                  95

Leu His Gln Arg Ala Trp Ala Arg Ser Tyr Val Tyr Trp Gly Gln Gly
                100                 105                 110

Thr Gln Val Thr Val Ser Ser
        115

<210> SEQ ID NO 34
<211> LENGTH: 117
<212> TYPE: PRT
<213> ORGANISM: Artificial Sequence
<220> FEATURE:
<223> OTHER INFORMATION: VHH sequence 54G01

<400> SEQUENCE: 34

Gln Val Gln Leu Gln Glu Ser Gly Gly Gly Ser Val Gln Pro Gly Gly
1               5                   10                  15

Ser Leu Arg Leu Ser Cys Ala Ala Ser Gly Ser Ile Phe Ala Val Asn
            20                  25                  30

Ala Met Gly Trp Tyr Arg Gln Ala Pro Gly His Gln Arg Glu Leu Val
        35                  40                  45

Ala Ile Ile Ser Ser Asn Ser Thr Ser Asn Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Phe Cys Tyr
                85                  90                  95

Ala Lys Arg Ser Trp Phe Ser Gln Glu Tyr Trp Gly Gln Gly Thr Gln
            100                 105                 110

Val Thr Val Ser Ser
        115

<210> SEQ ID NO 35
<211> LENGTH: 121
<212> TYPE: PRT
<213> ORGANISM: Artificial Sequence
<220> FEATURE:
<223> OTHER INFORMATION: VHH sequence 54G08

<400> SEQUENCE: 35

Gln Val Gln Leu Gln Glu Ser Gly Gly Gly Leu Val Gln Pro Gly Gly
1               5                   10                  15

Ser Leu Arg Leu Ser Cys Ala Ala Ser Gly Ser Ile Phe Ser Phe Asn
            20                  25                  30

Leu Met Gly Trp Tyr Arg Gln Ala Pro Gly Lys Gln Arg Glu Leu Val
        35                  40                  45

Ala Ala Ile Thr Ser Ser Asn Thr Asn Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Asn
                85                  90                  95

Ala Gln Tyr Thr Ile Thr Pro Trp Gly Ile Lys Lys Asp Tyr Trp Gly
            100                 105                 110

Gln Gly Thr Gln Val Thr Val Ser Ser
        115                 120

<210> SEQ ID NO 36
<211> LENGTH: 120
<212> TYPE: PRT

```
<213> ORGANISM: Artificial Sequence
<220> FEATURE:
<223> OTHER INFORMATION: VHH sequence 54G09

<400> SEQUENCE: 36

Gln Val Gln Leu Gln Glu Ser Gly Gly Gly Leu Met Gln Pro Gly Gly
1               5                   10                  15

Ser Leu Arg Leu Ser Cys Thr Ala Ser Gly Asn Ile Val Asn Ile Arg
            20                  25                  30

Asp Met Gly Trp Tyr Arg Gln Val Pro Gly Lys Gln Arg Glu Leu Val
        35                  40                  45

Ala Thr Ile Thr Ser Asp Gln Ser Thr Asn Tyr Ala Asp Ser Val Lys
    50                  55                  60

Gly Arg Phe Thr Thr Thr Arg Asp Asn Ala Lys Lys Thr Val Tyr Leu
65              70                  75                  80

Gln Met Asp Ser Leu Lys Pro Glu Asp Thr Ala Gly Tyr Tyr Cys Asn
            85                  90                  95

Ala Arg Val Arg Thr Val Leu Arg Gly Trp Arg Asp Tyr Trp Gly Gln
        100                 105                 110

Gly Thr Gln Val Thr Val Ser Ser
        115                 120

<210> SEQ ID NO 37
<211> LENGTH: 117
<212> TYPE: PRT
<213> ORGANISM: Artificial Sequence
<220> FEATURE:
<223> OTHER INFORMATION: VHH sequence 55B02

<400> SEQUENCE: 37

Gln Val Gln Leu Gln Glu Ser Gly Gly Gly Leu Val Gln Pro Gly Glu
1               5                   10                  15

Ser Leu Arg Leu Ser Cys Val Gly Ser Gly Ser Ile Phe Asn Ile Asn
            20                  25                  30

Ser Met Asn Trp Tyr Arg Gln Ala Ser Gly Lys Gln Arg Glu Leu Val
        35                  40                  45

Ala Asp Met Arg Ser Asp Gly Ser Thr Asn Tyr Ala Asp Ser Val Lys
    50                  55                  60

Gly Arg Phe Thr Ile Ser Arg Asp Asn Ala Arg Lys Thr Val Tyr Leu
65              70                  75                  80

Gln Met Asn Ser Leu Lys Pro Glu Asp Thr Ala Val Tyr Tyr Cys His
            85                  90                  95

Ala Asn Ser Ile Phe Arg Ser Arg Asp Tyr Trp Gly Gln Gly Thr Gln
        100                 105                 110

Val Thr Val Ser Ser
        115

<210> SEQ ID NO 38
<211> LENGTH: 125
<212> TYPE: PRT
<213> ORGANISM: Artificial Sequence
<220> FEATURE:
<223> OTHER INFORMATION: VHH sequence 55B05

<400> SEQUENCE: 38

Gln Val Gln Leu Gln Glu Ser Gly Gly Gly Val Val Gln Ala Gly Asp
1               5                   10                  15

Ser Leu Arg Leu Ser Cys Ala Ala Ser Gly Arg Thr Phe Gly Gly Tyr
            20                  25                  30
```

```
Thr Val Ala Trp Phe Arg Gln Ala Pro Gly Lys Glu Arg Glu Phe Val
        35                  40                  45

Ala Arg Ile Ser Trp Ser Gly Ile Met Ala Tyr Tyr Ala Glu Ser Val
        50                  55                  60

Lys Gly Arg Phe Thr Ile Ser Arg Asp Asn Ala Lys Asn Thr Val Tyr
 65                  70                  75                  80

Leu Gln Met Asn Ser Leu Lys Pro Glu Asp Thr Ala Val Tyr Tyr Cys
                 85                  90                  95

Ala Ser Arg Ser Gln Ile Arg Ser Pro Trp Ser Ser Leu Asp Asp Tyr
                100                 105                 110

Asp Arg Trp Gly Gln Gly Thr Gln Val Thr Val Ser Ser
        115                 120                 125

<210> SEQ ID NO 39
<211> LENGTH: 116
<212> TYPE: PRT
<213> ORGANISM: Artificial Sequence
<220> FEATURE:
<223> OTHER INFORMATION: VHH sequence 55C05

<400> SEQUENCE: 39

Gln Val Gln Leu Gln Glu Ser Gly Gly Gly Leu Val Gln Pro Gly Gly
 1               5                  10                  15

Ser Leu Arg Leu Ser Cys Val Val Ser Gly Ser Ile Ser Met Lys
        20                  25                  30

Ala Met Gly Trp His Arg Gln Ala Pro Gly Lys Glu Arg Glu Leu Val
        35                  40                  45

Ala Gln Ile Thr Arg Gly Asp Ser Thr Asn Tyr Ala Asp Ser Val Lys
        50                  55                  60

Gly Arg Phe Thr Ile Ser Arg Asp Asn Ala Lys Asn Thr Val Tyr Leu
 65                  70                  75                  80

Gln Met Asn Ser Leu Lys Pro Asp Asp Thr Gly Val Tyr Tyr Cys Asn
                 85                  90                  95

Ala Asp Arg Phe Phe Gly Arg Asp Tyr Trp Gly Lys Gly Thr Gln Val
                100                 105                 110

Thr Val Ser Ser
        115

<210> SEQ ID NO 40
<211> LENGTH: 120
<212> TYPE: PRT
<213> ORGANISM: Artificial Sequence
<220> FEATURE:
<223> OTHER INFORMATION: VHH sequence 55D08

<400> SEQUENCE: 40

Gln Val Gln Leu Gln Glu Ser Gly Gly Gly Leu Val Gln Pro Gly Gly
 1               5                  10                  15

Ser Leu Arg Leu Ser Cys Ala Ala Ser Arg Ser Ile Leu Ser Ile Ser
        20                  25                  30

Ala Met Gly Trp Tyr Arg Gln Gly Pro Gly Lys Gln Arg Glu Pro Val
        35                  40                  45

Ala Thr Ile Thr Ser Ala Gly Ser Ser Asn Tyr Ser Asp Ser Val Lys
        50                  55                  60

Gly Arg Phe Thr Ile Ser Arg Asp Asn Ala Lys Asn Thr Ala Tyr Leu
 65                  70                  75                  80

Gln Met Asn Ser Leu Lys Pro Glu Asp Thr Ala Val Tyr Tyr Cys Lys
```

```
                    85                  90                  95
Thr Val Tyr Ser Arg Pro Leu Leu Gly Pro Leu Glu Val Trp Gly Gln
                    100                 105                 110
Gly Thr Gln Val Thr Val Ser Ser
            115                 120

<210> SEQ ID NO 41
<211> LENGTH: 115
<212> TYPE: PRT
<213> ORGANISM: Artificial Sequence
<220> FEATURE:
<223> OTHER INFORMATION: VHH sequence 55E02

<400> SEQUENCE: 41

Gln Val Gln Leu Gln Glu Ser Gly Gly Gly Leu Val Gln Thr Gly Gly
1               5                   10                  15

Ser Leu Arg Leu Ser Cys Val Ala Ser Gly Ser Met Phe Ser Ser Asn
                20                  25                  30

Ala Met Ala Trp Tyr Arg Gln Ala Pro Gly Lys Gln Arg Glu Leu Val
            35                  40                  45

Ala Arg Ile Leu Ser Gly Gly Ser Thr Asn Tyr Ala Asp Ser Val Lys
50                  55                  60

Gly Arg Phe Thr Ile Ser Arg Gly Asn Ala Lys Asn Thr Val Tyr Leu
65                  70                  75                  80

Gln Met Asn Ser Leu Lys Pro Glu Asp Thr Ala Val Tyr Tyr Cys Asn
                85                  90                  95

Ala Val Arg Tyr Leu Val Asn Tyr Trp Gly Gln Gly Thr Gln Val Thr
            100                 105                 110

Val Ser Ser
        115

<210> SEQ ID NO 42
<211> LENGTH: 121
<212> TYPE: PRT
<213> ORGANISM: Artificial Sequence
<220> FEATURE:
<223> OTHER INFORMATION: VHH sequence 55E07

<400> SEQUENCE: 42

Gln Val Gln Leu Gln Glu Ser Gly Gly Gly Ser Val Gln Val Gly Asp
1               5                   10                  15

Ser Leu Thr Leu Ser Cys Val Ala Ser Gly Arg Ser Leu Asp Ile Tyr
                20                  25                  30

Gly Met Gly Trp Phe Arg Gln Ala Pro Gly Lys Glu Arg Glu Phe Val
            35                  40                  45

Ala Arg Ile Thr Ser Gly Gly Ser Thr Tyr Tyr Ala Asp Ser Val Lys
50                  55                  60

Gly Arg Phe Thr Leu Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Ala
                85                  90                  95

Ala Gly Val Val Val Ala Thr Ser Pro Lys Phe Tyr Ala Tyr Trp Gly
            100                 105                 110

Gln Gly Thr Gln Val Thr Val Ser Ser
        115                 120

<210> SEQ ID NO 43
<211> LENGTH: 116
```

```
<212> TYPE: PRT
<213> ORGANISM: Artificial Sequence
<220> FEATURE:
<223> OTHER INFORMATION: VHH sequence 55E09

<400> SEQUENCE: 43

Gln Val Gln Leu Gln Glu Ser Gly Gly Gly Leu Val Gln Ala Gly Gly
1               5                   10                  15

Ser Leu Arg Leu Ser Cys Ala Ala Ser Lys Arg Ile Phe Ser Thr Tyr
            20                  25                  30

Thr Met Gly Trp Phe Arg Gln Ala Pro Gly Lys Glu Arg Glu Phe Val
        35                  40                  45

Ala Ala Ile Ile Trp Ser Gly Arg Thr Arg Tyr Ala Asp Ser Val
    50                  55                  60

Lys Gly Arg Phe Thr Ile Ser Arg Asp Asn Ala Arg Asn Thr Val His
65                  70                  75                  80

Leu Gln Met Asn Ser Leu Glu Pro Glu Asp Thr Ala Val Tyr Tyr Cys
                85                  90                  95

Tyr Thr Arg Arg Leu Gly Thr Gly Tyr Trp Gly Gln Gly Thr Gln Val
            100                 105                 110

Thr Val Ser Ser
        115

<210> SEQ ID NO 44
<211> LENGTH: 115
<212> TYPE: PRT
<213> ORGANISM: Artificial Sequence
<220> FEATURE:
<223> OTHER INFORMATION: VHH sequence 55E10

<400> SEQUENCE: 44

Gln Val Gln Leu Gln Glu Ser Gly Gly Gly Leu Val Gln Ala Gly Gly
1               5                   10                  15

Ser Leu Arg Leu Ser Cys Ala Ala Ser Gly Ser Thr Phe Ser Ile Gln
            20                  25                  30

Thr Ile Gly Trp Tyr Arg Gln Ala Pro Gly Lys Gln Arg Asp Arg Val
        35                  40                  45

Ala Thr Ile Ser Ser Gly Gly Ser Thr Asn Tyr Ala Asp Ser Val Lys
    50                  55                  60

Gly Arg Phe Thr Ile Ser Arg Asp Asn Ala Lys Lys Thr Val Tyr Leu
65                  70                  75                  80

Gln Met Asn Asn Leu Lys Pro Glu Asp Thr Ala Val Tyr Tyr Cys Asn
                85                  90                  95

Leu Arg Tyr Trp Phe Arg Asp Tyr Trp Gly Gln Gly Thr Gln Val Thr
            100                 105                 110

Val Ser Ser
        115

<210> SEQ ID NO 45
<211> LENGTH: 115
<212> TYPE: PRT
<213> ORGANISM: Artificial Sequence
<220> FEATURE:
<223> OTHER INFORMATION: VHH sequence 55F04

<400> SEQUENCE: 45

Gln Val Gln Leu Gln Glu Ser Gly Gly Gly Leu Val Gln Pro Gly Gly
1               5                   10                  15

Ser Leu Arg Leu Ser Cys Ala Ala Ser Gly Ser Thr Phe Ser Ile Asn
```

-continued

```
                20                  25                  30
Val Arg Gly Trp Tyr Arg Gln Ala Pro Gly Lys Gln Arg Glu Leu Val
            35                  40                  45

Ala Thr Ile Thr Ser Asp Gly Ser Thr Asn Tyr Ala Asp Ser Val Lys
        50                  55                  60

Gly Arg Phe Thr Ile Ser Arg Asp Asn Ala Lys Asn Thr Ala Tyr Leu
65                  70                  75                  80

Gln Met Asn Ser Leu Lys Pro Glu Asp Thr Ala Val Tyr Tyr Cys Asn
                85                  90                  95

Ala Val Arg Leu Phe Arg Gln Tyr Trp Gly Gln Gly Thr Gln Val Thr
            100                 105                 110

Val Ser Ser
        115
```

<210> SEQ ID NO 46
<211> LENGTH: 125
<212> TYPE: PRT
<213> ORGANISM: Artificial Sequence
<220> FEATURE:
<223> OTHER INFORMATION: VHH sequence 55F09

<400> SEQUENCE: 46

```
Gln Val Gln Leu Gln Glu Ser Gly Gly Gly Leu Val Gln Pro Gly Gly
1               5                   10                  15

Ser Leu Arg Leu Ser Cys Ala Ala Ser Gly Ser Ile Phe Arg Leu Asn
            20                  25                  30

Ala Met Gly Trp Tyr Arg Gln Ala Pro Gly Lys Gln Arg Glu Leu Val
        35                  40                  45

Ala Ala Ile Thr Pro Gly Gly Gly Asn Thr Thr Tyr Ala Asp Ser Val
    50                  55                  60

Lys Gly Arg Phe Thr Ile Ser Arg Asp Asn Ala Leu Asn Thr Ile Tyr
65                  70                  75                  80

Leu Gln Met Asn Ser Leu Lys Pro Glu Asp Thr Ala Val Tyr Tyr Cys
                85                  90                  95

Asn Ala Gly Gly Ser Ser Arg Trp Tyr Ser Ser Arg Tyr Tyr Pro Gly
            100                 105                 110

Gly Tyr Trp Gly Gln Gly Thr Gln Val Thr Val Ser Ser
        115                 120                 125
```

<210> SEQ ID NO 47
<211> LENGTH: 126
<212> TYPE: PRT
<213> ORGANISM: Artificial Sequence
<220> FEATURE:
<223> OTHER INFORMATION: VHH sequence 55F10

<400> SEQUENCE: 47

```
Gln Val Gln Leu Gln Glu Ser Gly Gly Gly Leu Val Gln Ala Gly Gly
1               5                   10                  15

Ser Leu Arg Leu Ser Cys Ala Thr Ser Gly Gly Thr Phe Ser Arg Tyr
            20                  25                  30

Ala Met Gly Trp Phe Arg Gln Ala Pro Gly Lys Glu Arg Glu Leu Val
        35                  40                  45

Ala Thr Ile Arg Arg Ser Gly Ser Ser Thr Tyr Tyr Leu Asp Ser Thr
    50                  55                  60

Lys Gly Arg Phe Thr Ile Ser Arg Asp Asn Ala Lys Asn Thr Val Tyr
65                  70                  75                  80
```

```
Leu Gln Met Asn Ser Leu Lys Leu Glu Asp Thr Ala Val Tyr Tyr Cys
                85                  90                  95

Ala Ala Asp Ser Ser Ala Arg Ala Leu Val Gly Gly Pro Gly Asn Arg
            100                 105                 110

Trp Asp Tyr Trp Gly Gln Gly Thr Gln Val Thr Val Ser Ser
        115                 120                 125

<210> SEQ ID NO 48
<211> LENGTH: 118
<212> TYPE: PRT
<213> ORGANISM: Artificial Sequence
<220> FEATURE:
<223> OTHER INFORMATION: VHH sequence 55G02

<400> SEQUENCE: 48

Gln Val Gln Leu Gln Glu Ser Gly Gly Gly Leu Val Gln Pro Gly Gly
1               5                   10                  15

Ser Leu Arg Leu Ser Cys Ala Ala Ser Gly Ser Ile Gly Ser Ile Asn
            20                  25                  30

Val Met Gly Trp Tyr Arg Gln Tyr Pro Gly Lys Gln Arg Glu Leu Val
        35                  40                  45

Ala Phe Ile Thr Ser Gly Gly Ile Thr Asn Tyr Thr Asp Ser Val Lys
    50                  55                  60

Gly Arg Phe Ala Ile Ser Arg Asp Asn Ala Gln Asn Thr Val Tyr Leu
65                  70                  75                  80

Gln Met Asn Ser Leu Thr Pro Glu Asp Thr Ala Val Tyr Tyr Cys His
                85                  90                  95

Leu Lys Asn Ala Lys Asn Val Arg Pro Gly Tyr Trp Gly Gln Gly Thr
            100                 105                 110

Gln Val Thr Val Ser Ser
        115

<210> SEQ ID NO 49
<211> LENGTH: 116
<212> TYPE: PRT
<213> ORGANISM: Artificial Sequence
<220> FEATURE:
<223> OTHER INFORMATION: VHH sequence 55G08

<400> SEQUENCE: 49

Gln Val Gln Leu Gln Glu Ser Gly Gly Gly Leu Val Gln Pro Gly Gly
1               5                   10                  15

Ser Leu Arg Leu Ser Cys Arg Ala Ser Gly Gly Ile Phe Gly Ile Asn
            20                  25                  30

Ala Met Arg Trp Tyr Arg Gln Ala Pro Gly Lys Gln Arg Glu Leu Val
        35                  40                  45

Ala Ser Ile Ser Ser Gly Gly Thr Thr Asp Tyr Val Glu Ser Val Lys
    50                  55                  60

Gly Arg Phe Thr Ile Ser Arg Asp Asn Ala Thr Asn Thr Val Asp Leu
65                  70                  75                  80

Gln Met Ser Ala Leu Lys Pro Glu Asp Thr Ala Val Tyr Tyr Cys Asn
                85                  90                  95

Phe Val Arg Phe Trp Phe Pro Tyr Trp Gly Gln Gly Thr Gln Val
            100                 105                 110

Thr Val Ser Ser
        115

<210> SEQ ID NO 50
```

```
<211> LENGTH: 116
<212> TYPE: PRT
<213> ORGANISM: Artificial Sequence
<220> FEATURE:
<223> OTHER INFORMATION: VHH sequence 56A05

<400> SEQUENCE: 50
```

Gln Val Gln Leu Gln Glu Ser Gly Gly Gly Leu Val Gln Ala Gly Gly
1               5                   10                  15

Ser Leu Arg Leu Ser Cys Ala Ala Ser Gly Ile Thr Phe Met Ser Asn
            20                  25                  30

Thr Met Gly Trp Tyr Arg Gln Ala Pro Gly Lys Gln Arg Glu Leu Val
        35                  40                  45

Ala Ser Ile Ser Ser Gly Gly Ser Thr Asn Tyr Ala Asp Ser Val Lys
    50                  55                  60

Gly Arg Phe Thr Ile Ser Arg Asp Asn Ala Lys Lys Thr Val Tyr Leu
65                  70                  75                  80

Gln Met Asn Ser Leu Lys Pro Glu Asp Thr Ala Val Tyr Tyr Cys Asn
                85                  90                  95

Ala Arg Arg Asn Val Phe Ile Ser Ser Trp Gly Gln Gly Thr Gln Val
            100                 105                 110

Thr Val Ser Ser
            115

```
<210> SEQ ID NO 51
<211> LENGTH: 114
<212> TYPE: PRT
<213> ORGANISM: Artificial Sequence
<220> FEATURE:
<223> OTHER INFORMATION: VHH sequence 56A06

<400> SEQUENCE: 51
```

Gln Val Gln Leu Gln Glu Ser Gly Gly Gly Leu Val Gln Pro Gly Gly
1               5                   10                  15

Ser Leu Arg Leu Ser Cys Val Ala Ser Gly Ser Ile Ser Val Tyr Gly
            20                  25                  30

Met Gly Trp Tyr Arg Gln Ala Pro Gly Lys Gln Arg Glu Leu Val Ala
        35                  40                  45

Arg Ile Thr Asn Ile Gly Thr Thr Asn Tyr Ala Asp Ser Val Lys Gly
    50                  55                  60

Arg Phe Thr Ile Ser Arg Asp Asn Ala Lys Asn Thr Val Tyr Leu Gln
65                  70                  75                  80

Met Asn Ser Leu Gln Pro Glu Asp Thr Ala Val Tyr Tyr Cys Asn Leu
                85                  90                  95

Arg Arg Leu Gly Arg Asp Tyr Trp Gly Gln Gly Thr Gln Val Thr Val
            100                 105                 110

Ser Ser

```
<210> SEQ ID NO 52
<211> LENGTH: 118
<212> TYPE: PRT
<213> ORGANISM: Artificial Sequence
<220> FEATURE:
<223> OTHER INFORMATION: VHH sequence 56A09

<400> SEQUENCE: 52
```

Gln Val Gln Leu Gln Glu Ser Gly Gly Gly Leu Val Gln Pro Gly Gly
1               5                   10                  15

Ser Leu Arg Leu Ser Cys Ala Ala Ser Arg Thr Ala Leu Arg Leu Asn

```
                20                  25                  30
Ser Met Gly Trp Tyr Arg Gln Ala Pro Gly Ser Gln Arg Glu Leu Val
            35                  40                  45

Ala Thr Ile Thr Arg Gly Gly Thr Thr Asn Tyr Ala Asp Ser Val Lys
        50                  55                  60

Gly Arg Phe Thr Ile Ser Arg Glu Ile Gly Asn Asn Thr Val Tyr Leu
65                  70                  75                  80

Gln Met Asn Ser Leu Glu Pro Glu Asp Thr Ala Val Tyr Tyr Cys Asn
                85                  90                  95

Ala Asn Phe Gly Ile Leu Val Gly Arg Glu Tyr Trp Gly Lys Gly Thr
            100                 105                 110

Gln Val Thr Val Ser Ser
        115

<210> SEQ ID NO 53
<211> LENGTH: 116
<212> TYPE: PRT
<213> ORGANISM: Artificial Sequence
<220> FEATURE:
<223> OTHER INFORMATION: VHH sequence 56C09

<400> SEQUENCE: 53

Gln Val Gln Leu Gln Glu Ser Gly Gly Gly Leu Val Gln Ala Gly Gly
1               5                   10                  15

Ser Leu Arg Leu Ser Cys Ala Val Ser Gly Ser Ile Phe Ser Ile Leu
            20                  25                  30

Ser Met Ala Trp Tyr Arg Gln Thr Pro Gly Lys Gln Arg Glu Leu Val
            35                  40                  45

Ala Asn Ile Thr Ser Val Gly Ser Thr Asn Tyr Ala Asp Ser Val Lys
        50                  55                  60

Gly Arg Phe Thr Ile Ser Arg Asp Ile Ala Lys Lys Thr Leu Tyr Leu
65                  70                  75                  80

Gln Met Asn Asn Leu Lys Pro Glu Asp Thr Ala Ile Tyr Tyr Cys Asn
                85                  90                  95

Thr Arg Met Pro Phe Leu Gly Asp Ser Trp Gly Gln Gly Thr Gln Val
            100                 105                 110

Thr Val Ser Ser
        115

<210> SEQ ID NO 54
<211> LENGTH: 111
<212> TYPE: PRT
<213> ORGANISM: Artificial Sequence
<220> FEATURE:
<223> OTHER INFORMATION: VHH sequence 56C12

<400> SEQUENCE: 54

Gln Val Gln Leu Gln Glu Ser Gly Gly Gly Leu Val Gln Ala Gly Gly
1               5                   10                  15

Ser Leu Arg Leu Ser Cys Ala Val Ser Ala Phe Ser Phe Ser Asn Arg
            20                  25                  30

Ala Val Ser Trp Tyr Arg Gln Ala Pro Gly Lys Ser Arg Glu Trp Val
            35                  40                  45

Ala Ser Ile Ser Gly Ile Arg Ile Thr Thr Tyr Thr Asn Ser Val Lys
        50                  55                  60

Gly Arg Phe Ile Ile Ser Arg Asp Asn Ala Lys Lys Thr Val Tyr Leu
65                  70                  75                  80
```

Gln Met Asn Asp Leu Arg Pro Glu Asp Thr Gly Val Tyr Arg Cys Tyr
            85                  90                  95

Met Asn Arg Tyr Ser Gly Gln Gly Thr Gln Val Thr Val Ser Ser
            100                 105                 110

<210> SEQ ID NO 55
<211> LENGTH: 117
<212> TYPE: PRT
<213> ORGANISM: Artificial Sequence
<220> FEATURE:
<223> OTHER INFORMATION: VHH sequence 56D06

<400> SEQUENCE: 55

Gln Val Gln Leu Gln Glu Ser Gly Gly Gly Ser Val Gln Pro Gly Gly
1               5                   10                  15

Ser Leu Arg Leu Ser Cys Ala Ala Ser Gly Thr Val Phe Phe Ser Ile
            20                  25                  30

Ser Ala Met Gly Trp Tyr Arg Gln Ala Pro Gly Lys Gln Arg Glu Leu
        35                  40                  45

Val Ala Gly Ile Ser Arg Gly Gly Ser Thr Lys Tyr Gly Asp Phe Val
    50                  55                  60

Lys Gly Arg Phe Thr Ile Ser Arg Asp Asn Gly Lys Lys Thr Ile Trp
65                  70                  75                  80

Leu Gln Met Asn Asn Leu Gln Pro Glu Asp Thr Ala Ile Tyr Tyr Cys
                85                  90                  95

Arg Leu Thr Ser Ile Thr Gly Thr Tyr Leu Trp Gly Gln Gly Thr Gln
            100                 105                 110

Val Thr Val Ser Ser
        115

<210> SEQ ID NO 56
<211> LENGTH: 114
<212> TYPE: PRT
<213> ORGANISM: Artificial Sequence
<220> FEATURE:
<223> OTHER INFORMATION: VHH sequence 56D07

<400> SEQUENCE: 56

Gln Val Gln Leu Gln Glu Ser Gly Gly Gly Leu Val Gln Pro Gly Gly
1               5                   10                  15

Ser Leu Arg Leu Ser Cys Ala Ala Ser Gly Ser Ile Phe Ser Met Lys
            20                  25                  30

Val Met Gly Trp Tyr Arg Gln Gly Pro Gly Lys Leu Arg Glu Leu Val
        35                  40                  45

Ala Val Ile Thr Ser Gly Gly Arg Thr Asn Tyr Ala Glu Ser Val Lys
    50                  55                  60

Gly Arg Phe Thr Ile Ser Arg Asp Asn Ala Lys Asn Thr Val Ser Leu
65                  70                  75                  80

Gln Met Asn Ser Leu Gln Pro Glu Asp Thr Ala Val Tyr Tyr Cys Tyr
                85                  90                  95

Tyr Lys Thr Ile Arg Pro Tyr Trp Gly Gln Gly Thr Gln Val Thr Val
            100                 105                 110

Ser Ser

<210> SEQ ID NO 57
<211> LENGTH: 120
<212> TYPE: PRT
<213> ORGANISM: Artificial Sequence
<220> FEATURE:

<223> OTHER INFORMATION: VHH sequence 56D10

<400> SEQUENCE: 57

```
Gln Val Gln Leu Gln Glu Ser Gly Gly Gly Leu Val Gln Ala Gly Gly
1               5                   10                  15

Ser Leu Arg Leu Ser Cys Ala Ala Ser Gly Ile Thr Phe Arg Ile Thr
            20                  25                  30

Thr Met Gly Trp Tyr Arg Gln Ala Pro Gly Lys Gln Arg Glu Leu Val
        35                  40                  45

Ala Ser Ser Ser Gly Gly Thr Thr Asn Tyr Ala Ser Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Arg Pro Glu Asp Thr Ala Val Tyr Tyr Cys Asn
                85                  90                  95

Ala Arg Lys Phe Ile Thr Thr Pro Trp Ser Thr Asp Tyr Trp Gly Gln
            100                 105                 110

Gly Thr Gln Val Thr Val Ser Ser
        115                 120
```

<210> SEQ ID NO 58
<211> LENGTH: 116
<212> TYPE: PRT
<213> ORGANISM: Artificial Sequence
<220> FEATURE:
<223> OTHER INFORMATION: VHH sequence 56E04

<400> SEQUENCE: 58

```
Gln Val Gln Leu Gln Glu Ser Gly Gly Gly Leu Val Gln Pro Gly Asp
1               5                   10                  15

Ser Leu Arg Leu Ser Cys Thr Pro Ser Gly Ser Ile Phe Asn His Lys
            20                  25                  30

Ala Thr Gly Trp Tyr Arg Gln Ala Pro Gly Ser Gln Arg Glu Leu Val
        35                  40                  45

Ala Lys Ile Thr Thr Gly Gly Thr Thr Asn Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Ser Ser Leu Lys Pro Glu Asp Thr Ala Val Tyr Tyr Cys Asn
                85                  90                  95

Ala Glu Arg Tyr Phe Ala Thr Thr Leu Trp Gly Gln Gly Thr Gln Val
            100                 105                 110

Thr Val Ser Ser
        115
```

<210> SEQ ID NO 59
<211> LENGTH: 119
<212> TYPE: PRT
<213> ORGANISM: Artificial Sequence
<220> FEATURE:
<223> OTHER INFORMATION: VHH sequence 56E05

<400> SEQUENCE: 59

```
Gln Val Gln Leu Gln Glu Ser Gly Gly Gly Leu Val Gln Ala Gly Gly
1               5                   10                  15

Ser Leu Arg Leu Ser Cys Ala Ala Ser Gly Ile Thr Phe Ser Asn Asn
            20                  25                  30

Ala Gly Gly Trp Tyr Arg Gln Ala Pro Gly Gln Gln Arg Glu Leu Val
```

```
                35                  40                  45
Ala Arg Ile Ser Ser Gly Gly Asn Thr Asn Tyr Thr Asp Ser Val Lys
         50                  55                  60
Gly Arg Phe Thr Ile Ser Arg Asp Ile Thr Lys Asn Thr Leu Ser Leu
 65                  70                  75                  80
Gln Met Asn Asn Leu Lys Pro Glu Asp Ser Ala Val Tyr Tyr Cys Asn
                 85                  90                  95
Ala Gln Arg Arg Val Ile Leu Gly Pro Arg Asn Tyr Trp Gly Gln Gly
            100                 105                 110
Thr Gln Val Thr Val Ser Ser
            115

<210> SEQ ID NO 60
<211> LENGTH: 121
<212> TYPE: PRT
<213> ORGANISM: Artificial Sequence
<220> FEATURE:
<223> OTHER INFORMATION: VHH sequence 56E08

<400> SEQUENCE: 60

Gln Val Gln Leu Gln Glu Ser Gly Gly Gly Leu Val Gln Ala Gly Gly
 1               5                  10                  15
Ser Leu Arg Leu Ser Cys Ala Ala Ser Gly Asn Ile Phe Arg Ile Asn
            20                  25                  30
Asp Met Gly Trp Tyr Arg Gln Ala Pro Gly Asn Gln Arg Glu Leu Val
            35                  40                  45
Ala Thr Ile Thr Ser Ala Asn Ile Thr Asn Tyr Ala Asp Ser Val Lys
         50                  55                  60
Gly Arg Phe Thr Ile Ser Arg Asp Asn Ala Lys Asn Thr Val Tyr Leu
 65                  70                  75                  80
Gln Met Asn Ser Leu Asn Pro Glu Asp Thr Ala Val Tyr Tyr Cys Thr
                 85                  90                  95
Ala Gln Ala Lys Lys Trp Arg Ile Gly Pro Trp Ser Tyr Trp Gly
            100                 105                 110
Gln Gly Thr Gln Val Thr Val Ser Ser
            115                 120

<210> SEQ ID NO 61
<211> LENGTH: 119
<212> TYPE: PRT
<213> ORGANISM: Artificial Sequence
<220> FEATURE:
<223> OTHER INFORMATION: VHH sequence 56F07

<400> SEQUENCE: 61

Gln Val Gln Leu Gln Glu Ser Gly Gly Gly Leu Val Gln Pro Gly Gly
 1               5                  10                  15
Ser Leu Arg Leu Ser Cys Ala Ala Ser Gly Arg Ile Phe Ser Ile Asn
            20                  25                  30
Asp Met Ala Trp Tyr Arg Gln Ala Pro Gly Lys Gln Arg Glu Leu Val
            35                  40                  45
Ala Ile Ile Thr Asn Asp Asp Ser Thr Tyr Ala Asp Ser Val Lys
         50                  55                  60
Gly Arg Phe Thr Ile Ser Arg Asp Asn Ala Lys Asn Thr Val Tyr Leu
 65                  70                  75                  80
Gln Met Asn Ser Leu Lys Pro Glu Asp Thr Ala Val Tyr Tyr Cys Asn
                 85                  90                  95
```

```
Ala Asp Ile Asn Thr Ala Ile Trp Arg Arg Lys Tyr Trp Gly Gln Gly
            100                 105                 110

Thr Gln Val Thr Val Ser Ser
        115
```

<210> SEQ ID NO 62
<211> LENGTH: 121
<212> TYPE: PRT
<213> ORGANISM: Artificial Sequence
<220> FEATURE:
<223> OTHER INFORMATION: VHH sequence 56F11

<400> SEQUENCE: 62

```
Gln Val Gln Leu Gln Glu Ser Gly Gly Gly Leu Val Gln Ser Gly Gly
1               5                   10                  15

Ser Leu Arg Leu Ser Cys Val His Ser Lys Thr Thr Phe Thr Arg Asn
            20                  25                  30

Ala Met Gly Trp Tyr Arg Gln Ala Leu Gly Lys Glu Arg Glu Leu Val
        35                  40                  45

Ala Thr Ile Thr Ser Gly Gly Thr Thr Asn Tyr Ala Asp Ser Val Lys
    50                  55                  60

Gly Arg Phe Thr Ile Ser Met Asp Ser Ala Lys Asn Thr Val Tyr Leu
65                  70                  75                  80

Gln Met Asn Ser Leu Lys Pro Glu Asp Thr Ala Val Tyr Tyr Cys Asn
                85                  90                  95

Val Asn Thr Arg Arg Ile Phe Gly Gly Thr Val Arg Glu Tyr Trp Gly
            100                 105                 110

Gln Gly Thr Gln Val Thr Val Ser Ser
        115                 120
```

<210> SEQ ID NO 63
<211> LENGTH: 115
<212> TYPE: PRT
<213> ORGANISM: Artificial Sequence
<220> FEATURE:
<223> OTHER INFORMATION: VHH sequence 56G07

<400> SEQUENCE: 63

```
Gln Val Gln Leu Gln Glu Ser Gly Gly Gly Leu Val Gln Pro Gly Gly
1               5                   10                  15

Ser Leu Arg Leu Ser Cys Ala Val Ser Gly Ser Arg Ile Phe Ile His
            20                  25                  30

Asp Met Gly Trp His Arg Gln Ala Pro Gly Glu Pro Arg Glu Leu Val
        35                  40                  45

Ala Thr Ile Thr Pro Phe Gly Arg Arg Asn Tyr Ser Glu Tyr Val Lys
    50                  55                  60

Gly Arg Phe Thr Val Ser Arg Asp Ile Ala Arg Asn Thr Met Ser Leu
65                  70                  75                  80

Gln Met Ser Asn Leu Lys Ala Glu Asp Thr Gly Met Tyr Tyr Cys Asn
                85                  90                  95

Val Arg Val Asn Gly Val Asp Tyr Trp Gly Gln Gly Thr Gln Val Thr
            100                 105                 110

Val Ser Ser
        115
```

<210> SEQ ID NO 64
<211> LENGTH: 119
<212> TYPE: PRT
<213> ORGANISM: Artificial Sequence -continued

```
<220> FEATURE:
<223> OTHER INFORMATION: VHH sequence 56G08

<400> SEQUENCE: 64

Gln Val Gln Leu Gln Glu Ser Gly Gly Gly Leu Val Gln Ala Gly Gly
1               5                   10                  15

Ser Leu Arg Leu Ser Cys Ala Ile Ser Gly Ile Thr Phe Arg Arg Pro
            20                  25                  30

Phe Gly Ile Ser Arg Met Gly Trp Tyr Arg Gln Ala Pro Gly Lys Glu
        35                  40                  45

Arg Glu Leu Val Ala Thr Leu Ser Arg Ala Gly Thr Ser Arg Tyr Val
    50                  55                  60

Asp Ser Val Lys Gly Arg Phe Thr Ile Ser Arg Asp Asp Ala Lys Asn
65                  70                  75                  80

Thr Leu Tyr Leu Gln Met Val Ser Leu Asn Pro Glu Asp Thr Ala Val
                85                  90                  95

Tyr Tyr Cys Tyr Ile Ala Gln Leu Gly Thr Asp Tyr Trp Gly Gln Gly
            100                 105                 110

Thr Gln Val Thr Val Ser Ser
        115

<210> SEQ ID NO 65
<211> LENGTH: 117
<212> TYPE: PRT
<213> ORGANISM: Artificial Sequence
<220> FEATURE:
<223> OTHER INFORMATION: VHH sequence 56G10

<400> SEQUENCE: 65

Gln Val Gln Leu Gln Glu Ser Gly Gly Gly Leu Val Gln Ala Gly Gly
1               5                   10                  15

Ser Leu Arg Leu Ser Cys Val Ala Ser Gly Ile Thr Leu Arg Met Tyr
            20                  25                  30

Gln Val Gly Trp Tyr Arg Gln Ala Pro Gly Lys Gln Arg Glu Leu Val
        35                  40                  45

Ala Glu Ile Ser Ser Arg Gly Thr Thr Met Tyr Ala Asp Ser Val Lys
    50                  55                  60

Gly Arg Phe Thr Ile Ser Arg Asp Gly Ala Lys Asn Ile Val Tyr Leu
65                  70                  75                  80

Gln Met Asn Ser Leu Glu Pro Glu Asp Thr Ala Val Tyr Tyr Cys Asn
                85                  90                  95

Ala Arg Ala Phe Ala Phe Gly Arg Asn Ser Trp Gly Gln Gly Thr Gln
            100                 105                 110

Val Thr Val Ser Ser
        115

<210> SEQ ID NO 66
<211> LENGTH: 118
<212> TYPE: PRT
<213> ORGANISM: Artificial Sequence
<220> FEATURE:
<223> OTHER INFORMATION: VHH sequence 56H04

<400> SEQUENCE: 66

Gln Val Gln Leu Gln Glu Ser Gly Gly Gly Ser Val Gln Ala Gly Gly
1               5                   10                  15

Ser Leu Arg Leu Ser Cys Ala Val Ser Gly Gly Thr Phe Ser Asn Lys
            20                  25                  30
```

```
Ala Met Gly Trp Tyr Arg Gln Ser Gly Lys Gln Arg Ala Leu Val
            35                  40                  45

Ala Arg Ile Ser Thr Val Gly Thr Ala His Tyr Ala Asp Ser Val Lys
 50                  55                  60

Gly Arg Phe Thr Val Ser Lys Asp Asn Ala Gly Asn Thr Leu Tyr Leu
 65                  70                  75                  80

Gln Met Asn Ser Leu Lys Pro Glu Asp Thr Ala Val Tyr Tyr Cys Asn
                 85                  90                  95

Ala Gln Ala Gly Arg Leu Tyr Leu Arg Asn Tyr Trp Gly Gln Gly Thr
            100                 105                 110

Gln Val Thr Val Ser Ser
            115

<210> SEQ ID NO 67
<211> LENGTH: 119
<212> TYPE: PRT
<213> ORGANISM: Artificial Sequence
<220> FEATURE:
<223> OTHER INFORMATION: VHH sequence 56H05

<400> SEQUENCE: 67

Gln Val Gln Leu Gln Glu Ser Gly Gly Gly Leu Val Gln Pro Gly Glu
  1               5                  10                  15

Ser Leu Arg Leu Ser Cys Val Ala Ala Ser Thr Ser Ile Thr Thr
                 20                  25                  30

Phe Asn Thr Met Ala Trp Tyr Arg Gln Ala Pro Gly Lys Gln Arg Glu
             35                  40                  45

Leu Val Ala Gln Ile Asn Asn Arg Asp Asn Thr Glu Tyr Ala Asp Ser
 50                  55                  60

Val Lys Gly Arg Phe Ile Ile Ser Arg Gly Asn Ala Lys Asn Thr Ser
 65                  70                  75                  80

Asn Leu Gln Met Asn Asp Leu Lys Ser Glu Asp Thr Gly Ile Tyr Tyr
                 85                  90                  95

Cys Asn Ala Lys Arg Trp Ser Trp Ser Thr Gly Phe Trp Gly Gln Gly
            100                 105                 110

Thr Gln Val Thr Val Ser Ser
            115

<210> SEQ ID NO 68
<211> LENGTH: 114
<212> TYPE: PRT
<213> ORGANISM: Artificial Sequence
<220> FEATURE:
<223> OTHER INFORMATION: VHH sequence 56H07

<400> SEQUENCE: 68

Gln Val Gln Leu Gln Glu Ser Gly Gly Gly Leu Val Gln Ala Gly Gly
  1               5                  10                  15

Ser Leu Arg Leu Ser Cys Thr Ala Ser Gly Leu Thr Phe Ala Leu Gly
                 20                  25                  30

Thr Met Gly Trp Tyr Arg Gln Ala Pro Gly Lys Gln Arg Glu Leu Val
             35                  40                  45

Ala Ser Ile Ser Thr Gly Ser Thr Asn Tyr Ala Asp Ser Val Lys Gly
 50                  55                  60

Arg Phe Thr Ile Ser Arg Asp Ile Ile Lys Asn Ile Leu Tyr Leu Gln
 65                  70                  75                  80

Met Asn Ser Leu Lys Pro Glu Asp Thr Ala Val Tyr Ser Cys Asn Ala
                 85                  90                  95
```

Arg Leu Trp Trp Ser Asn Tyr Trp Gly Gln Gly Thr Gln Val Thr Val
            100                 105                 110

Ser Ser

<210> SEQ ID NO 69
<211> LENGTH: 118
<212> TYPE: PRT
<213> ORGANISM: Artificial Sequence
<220> FEATURE:
<223> OTHER INFORMATION: VHH sequence 56H08

<400> SEQUENCE: 69

Gln Val Gln Leu Gln Glu Ser Gly Gly Gly Leu Val Gln Ala Gly Gly
1               5                   10                  15

Ser Leu Arg Leu Ser Cys Thr Ala Ser Gly Arg Thr Ser Ser Val Asn
            20                  25                  30

Pro Met Gly Trp Tyr Arg Gln Ala Pro Gly Lys Gln Arg Glu Leu Val
            35                  40                  45

Ala Val Ile Ser Ser Asp Gly Ser Thr Asn Tyr Ala Asp Ser Val Lys
        50                  55                  60

Gly Arg Phe Thr Val Ser Arg Asp Asn Ala Lys Asn Thr Leu Tyr Leu
65                  70                  75                  80

Gln Met Asn Ser Leu Lys Pro Glu Asp Thr Ala Val Tyr Tyr Cys Asn
                85                  90                  95

Ala Asn Arg Arg Trp Ser Trp Gly Ser Glu Tyr Trp Gly Gln Gly Thr
            100                 105                 110

Gln Val Thr Val Ser Ser
        115

<210> SEQ ID NO 70
<211> LENGTH: 119
<212> TYPE: PRT
<213> ORGANISM: Artificial Sequence
<220> FEATURE:
<223> OTHER INFORMATION: VHH sequence 57A06

<400> SEQUENCE: 70

Gln Val Gln Leu Gln Glu Ser Gly Gly Gly Leu Val Gln Ala Gly Gly
1               5                   10                  15

Ser Leu Arg Leu Ser Cys Ala Ala Ser Gly Ile Thr Phe Thr Asn Asn
            20                  25                  30

Ala Gly Gly Trp Tyr Arg Gln Ala Pro Gly Gln Gln Arg Glu Leu Val
            35                  40                  45

Ala Arg Ile Ser Ser Gly Gly Asn Thr Asn Tyr Thr Asp Ser Val Lys
        50                  55                  60

Gly Arg Phe Thr Ile Ser Arg Asp Ile Thr Lys Asn Thr Leu Ser Leu
65                  70                  75                  80

Gln Met Asn Asn Leu Lys Pro Glu Asp Ser Ala Val Tyr Tyr Cys Asn
                85                  90                  95

Ala Gln Arg Arg Val Ile Leu Gly Pro Arg Asn Tyr Trp Gly Gln Gly
            100                 105                 110

Thr Gln Val Thr Val Ser Ser
        115

<210> SEQ ID NO 71
<211> LENGTH: 116
<212> TYPE: PRT
<213> ORGANISM: Artificial Sequence
<220> FEATURE:
<223> OTHER INFORMATION: VHH sequence 57B01

<400> SEQUENCE: 71

Gln Val Gln Leu Gln Glu Ser Gly Gly Gly Leu Val Gln Ala Gly Gly
1               5                   10                  15

Ser Leu Arg Leu Ser Cys Glu Ala Pro Val Ser Thr Phe Asn Ile Asn
            20                  25                  30

Ala Met Ala Trp Tyr Arg Gln Ala Pro Gly Lys Ser Arg Glu Leu Val
        35                  40                  45

Ala Arg Ile Ser Ser Gly Gly Ser Thr Asn Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Ile Cys Tyr
                85                  90                  95

Val Asn Arg His Trp Gly Trp Asp Tyr Trp Gly Gln Gly Thr Gln Val
            100                 105                 110

Thr Val Ser Ser
        115

<210> SEQ ID NO 72
<211> LENGTH: 122
<212> TYPE: PRT
<213> ORGANISM: Artificial Sequence
<220> FEATURE:
<223> OTHER INFORMATION: VHH sequence 57B07

<400> SEQUENCE: 72

Gln Val Gln Leu Gln Glu Ser Gly Gly Gly Leu Val Gln Pro Gly Gly
1               5                   10                  15

Thr Leu Arg Leu Ser Cys Val Ala Ser Gly Ser Phe Arg Ser Ile Asn
            20                  25                  30

Ala Met Gly Trp Tyr Arg Gln Ala Pro Gly Lys Gln Arg Glu Leu Val
        35                  40                  45

Ala Thr Val Asp Ser Gly Gly Tyr Thr Asn Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Ser Ser Leu Thr Pro Glu Asp Thr Ala Val Tyr Tyr Cys Tyr
                85                  90                  95

Ala Gly Ile Tyr Lys Trp Pro Trp Ser Val Asp Ala Arg Asp Tyr Trp
            100                 105                 110

Gly Gln Gly Thr Gln Val Thr Val Ser Ser
        115                 120

<210> SEQ ID NO 73
<211> LENGTH: 117
<212> TYPE: PRT
<213> ORGANISM: Artificial Sequence
<220> FEATURE:
<223> OTHER INFORMATION: VHH sequence 57B11

<400> SEQUENCE: 73

Gln Val Gln Leu Gln Glu Ser Gly Gly Gly Leu Val Gln Ala Gly Gly
1               5                   10                  15

Ser Leu Arg Leu Ser Cys Ala Ser Gly Ser Ser Ile Ser Met Asn
            20                  25                  30

```
Ser Met Gly Trp Tyr Arg Gln Ala Pro Gly Lys Glu Arg Glu Arg Val
        35                  40                  45

Ala Leu Ile Arg Ser Ser Gly Gly Thr Tyr Tyr Ala Asp Ser Val Lys
 50                  55                  60

Gly Arg Phe Thr Ile Ser Arg Asp Asn Ala Lys Asn Thr Val Tyr Leu
 65                  70                  75                  80

Gln Met Asn Asn Leu Lys Pro Glu Asp Thr Ala Val Tyr Tyr Cys Gln
                 85                  90                  95

Ala Arg Arg Thr Trp Leu Ser Ser Glu Ser Trp Gly Gln Gly Thr Gln
            100                 105                 110

Val Thr Val Ser Ser
            115
```

<210> SEQ ID NO 74
<211> LENGTH: 122
<212> TYPE: PRT
<213> ORGANISM: Artificial Sequence
<220> FEATURE:
<223> OTHER INFORMATION: VHH sequence 57C07

<400> SEQUENCE: 74

```
Gln Val Gln Leu Gln Glu Ser Gly Gly Gly Leu Val Gln Ala Gly Gly
 1               5                  10                  15

Ser Leu Arg Leu Ser Cys Ala Val Ser Gly Ser Thr Phe Gly Ile Asn
            20                  25                  30

Thr Met Gly Trp Tyr Arg Gln Ala Pro Glu Lys Gln Arg Glu Leu Val
        35                  40                  45

Ala Ser Ile Ser Arg Gly Gly Met Thr Asn Tyr Ala Asp Ser Val Lys
 50                  55                  60

Gly Arg Phe Ile Ile Ser Arg Asp Asn Ala Lys Asn Thr Val Tyr Leu
 65                  70                  75                  80

Gln Met Asn Ser Leu Lys Pro Glu Asp Thr Ala Val Tyr Val Cys Asn
                 85                  90                  95

Ala Gly Ile Arg Ser Arg Trp Tyr Gly Gly Pro Ile Thr Thr Tyr Trp
            100                 105                 110

Gly Gln Gly Thr Gln Val Thr Val Ser Ser
            115                 120
```

<210> SEQ ID NO 75
<211> LENGTH: 121
<212> TYPE: PRT
<213> ORGANISM: Artificial Sequence
<220> FEATURE:
<223> OTHER INFORMATION: VHH sequence 57C09

<400> SEQUENCE: 75

```
Gln Val Gln Leu Gln Glu Ser Gly Gly Gly Leu Val Gln Ala Gly Gly
 1               5                  10                  15

Ser Leu Arg Leu Ser Cys Ala Ala Ser Gly Ser Thr Gly Ser Ile Asn
            20                  25                  30

Ala Met Gly Trp Tyr Arg Gln Gly Pro Gly Lys Gln Arg Asp Leu Val
        35                  40                  45

Ala Ser Ile Ser Ser Gly Gly Ala Thr Asn Tyr Ala Asp Ser Val Lys
 50                  55                  60

Gly Arg Phe Thr Ile Ser Arg Asp Asn Ser Lys Asn Thr Val Tyr Leu
 65                  70                  75                  80

Gln Met Ser Ser Leu Lys Pro Glu Asp Thr Ala Val Tyr Tyr Cys Asn
                 85                  90                  95
```

```
Ala Lys Lys Ser Arg Trp Ser Trp Ser Ile Val His Asp Tyr Trp Gly
                100                 105                 110

Gln Gly Thr Gln Val Thr Val Ser Ser
        115                 120

<210> SEQ ID NO 76
<211> LENGTH: 118
<212> TYPE: PRT
<213> ORGANISM: Artificial Sequence
<220> FEATURE:
<223> OTHER INFORMATION: VHH sequence 57D02

<400> SEQUENCE: 76

Gln Val Gln Leu Gln Glu Ser Gly Gly Gly Ser Val Gln Thr Gly Gly
1               5                   10                  15

Ser Leu Thr Leu Ser Cys Thr Ser Gly Ser Ile Phe Gly Arg Ser
            20                  25                  30

Asp Met Gly Trp Tyr Arg Gln Ala Pro Gly Lys Gln Arg Glu Leu Val
            35                  40                  45

Ala Thr Ile Thr Arg Arg Ser Arg Thr Asn Tyr Ala Glu Phe Val Lys
        50                  55                  60

Gly Arg Phe Thr Ile Ser Arg Asp Ser Ala Lys Asn Leu Val Thr Leu
65                  70                  75                  80

Gln Met Asn Ser Leu Lys Pro Glu Asp Thr Asn Val Tyr Tyr Cys Asn
                85                  90                  95

Ala Arg Trp Gly Ala Gly Gly Ile Phe Ser Thr Trp Gly Gln Gly Thr
            100                 105                 110

Gln Val Thr Val Ser Ser
        115

<210> SEQ ID NO 77
<211> LENGTH: 120
<212> TYPE: PRT
<213> ORGANISM: Artificial Sequence
<220> FEATURE:
<223> OTHER INFORMATION: VHH sequence 57D09

<400> SEQUENCE: 77

Gln Val Gln Leu Gln Glu Ser Gly Gly Gly Leu Val Gln Pro Gly Glu
1               5                   10                  15

Ser Leu Arg Leu Ser Cys Ala Ala Ser Gly Ser Met Ser Ile Asp Ala
            20                  25                  30

Met Gly Trp Tyr Arg Gln Ala Pro Gly Asp Gln Arg Glu Leu Val Ala
            35                  40                  45

Ser Ile Thr Thr Gly Gly Ser Thr Asn Tyr Ala Asp Ser Val Lys Gly
        50                  55                  60

Arg Phe Thr Ile Ser Arg Asp Asn Ala Lys Asn Thr Val Trp Leu Gln
65                  70                  75                  80

Met Asn Ser Leu Lys Pro Glu Asp Thr Ala Val Tyr Tyr Cys Asn Ala
                85                  90                  95

Lys Val Arg Leu Arg Trp Phe Arg Pro Pro Ser Asp Tyr Trp Gly Gln
            100                 105                 110

Gly Thr Gln Val Thr Val Ser Ser
        115                 120

<210> SEQ ID NO 78
<211> LENGTH: 122
<212> TYPE: PRT
```

<213> ORGANISM: Artificial Sequence
<220> FEATURE:
<223> OTHER INFORMATION: VHH sequence 57D10

<400> SEQUENCE: 78

```
Gln Val Gln Leu Gln Glu Ser Gly Gly Gly Leu Val Gln Pro Gly Gly
1               5                   10                  15

Ser Leu Arg Leu Ser Cys Ala Ala Ser Gly Arg Leu Leu Ser Ile Ser
            20                  25                  30

Thr Met Gly Trp Tyr Arg Arg Thr Pro Glu Asp Gln Arg Glu Met Val
        35                  40                  45

Ala Ser Ile Thr Lys Asp Gly Thr Thr Asn Tyr Ala Asp Ser Val Lys
    50                  55                  60

Gly Arg Leu Thr Ile Ser Arg Asp Asn Ala Lys Asn Thr Val Tyr Leu
65                  70                  75                  80

Gln Met Asn Ser Leu Lys Pro Asp Asp Thr Ala Val Tyr Val Cys Asn
                85                  90                  95

Ala Arg Ala Thr Thr Trp Val Pro Tyr Arg Arg Asp Ala Glu Phe Trp
            100                 105                 110

Gly Gln Gly Thr Gln Val Thr Val Ser Ser
        115                 120
```

<210> SEQ ID NO 79
<211> LENGTH: 120
<212> TYPE: PRT
<213> ORGANISM: Artificial Sequence
<220> FEATURE:
<223> OTHER INFORMATION: VHH sequence 57E07

<400> SEQUENCE: 79

```
Gln Val Gln Leu Gln Glu Ser Gly Gly Gly Leu Val Gln Ala Gly Gly
1               5                   10                  15

Ser Leu Arg Leu Ser Cys Ala Ala Ser Gly Ser Ile Phe Gly Ile Asn
            20                  25                  30

Asp Met Gly Trp Tyr Arg Gln Ala Pro Gly Lys Gln Arg Asp Leu Val
        35                  40                  45

Ala Asp Ile Thr Arg Ser Gly Ser Thr His Tyr Val Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Asn
                85                  90                  95

Ala Asp Ser Gly Ser His Trp Trp Asn Arg Arg Asp Tyr Trp Gly Gln
            100                 105                 110

Gly Thr Gln Val Thr Val Ser Ser
        115                 120
```

<210> SEQ ID NO 80
<211> LENGTH: 118
<212> TYPE: PRT
<213> ORGANISM: Artificial Sequence
<220> FEATURE:
<223> OTHER INFORMATION: VHH sequence 57E11

<400> SEQUENCE: 80

```
Gln Val Gln Leu Gln Glu Ser Gly Gly Gly Leu Val Gln Pro Gly Gly
1               5                   10                  15

Ser Leu Lys Leu Ser Cys Ala Ala Ser Gly Phe Thr Phe Ser Ile Asn
            20                  25                  30
```

```
Thr Met Gly Trp Tyr Arg Gln Ala Pro Gly Lys Gln Arg Glu Leu Val
        35                  40                  45

Ala Arg Ile Ser Arg Leu Arg Val Thr Asn Tyr Ala Asp Ser Val Lys
 50                  55                  60

Gly Arg Phe Thr Ile Ser Arg Asp Asn Ala Lys Asn Thr Val Tyr Leu
 65                  70                  75                  80

Gln Met Asn Ser Leu Lys Pro Glu Asp Thr Ala Val Tyr Tyr Cys Asn
                 85                  90                  95

Ala Ala Asn Trp Gly Leu Ala Gly Asn Glu Tyr Trp Gly Gln Gly Thr
            100                 105                 110

Gln Val Thr Val Ser Ser
        115

<210> SEQ ID NO 81
<211> LENGTH: 116
<212> TYPE: PRT
<213> ORGANISM: Artificial Sequence
<220> FEATURE:
<223> OTHER INFORMATION: VHH sequence 57G01

<400> SEQUENCE: 81

Gln Val Gln Leu Gln Glu Ser Gly Gly Gly Leu Val Gln Ala Gly Gly
 1               5                  10                  15

Ser Leu Arg Pro Ser Cys Thr Ala Ser Gly Ser Thr Leu Leu Ile Asn
            20                  25                  30

Ser Met Gly Trp Tyr Arg Gln Ala Pro Gly Lys Gln Arg Glu Leu Val
        35                  40                  45

Ala Thr Ile Ser Asn Ser Gly Thr Thr Asn Tyr Val Asp Ala Val Lys
 50                  55                  60

Gly Arg Phe Ala Ile Ser Arg Asp Asn Ala Asn His Thr Val Tyr Leu
 65                  70                  75                  80

Gln Met Asn Ser Leu Glu Pro Glu Asp Thr Ala Val Tyr Tyr Cys Asn
                 85                  90                  95

Ala Gln Thr Phe Trp Arg Arg Asn Tyr Trp Gly Gln Gly Thr Gln Val
            100                 105                 110

Thr Val Ser Ser
        115

<210> SEQ ID NO 82
<211> LENGTH: 116
<212> TYPE: PRT
<213> ORGANISM: Artificial Sequence
<220> FEATURE:
<223> OTHER INFORMATION: VHH sequence 57G07

<400> SEQUENCE: 82

Gln Val Gln Leu Gln Glu Ser Gly Gly Gly Leu Val Gln Ala Gly Gly
 1               5                  10                  15

Ser Leu Arg Leu Ser Cys Ala Val Ser Gly Ser Thr Ser Arg Ile Asn
            20                  25                  30

Ala Met Gly Trp Tyr Arg Gln Ala Pro Gly Lys Lys Arg Glu Ser Val
        35                  40                  45

Ala Thr Ile Arg Arg Gly Gly Asn Thr Lys Tyr Ala Asp Ser Val Lys
 50                  55                  60

Gly Arg Phe Thr Ile Ser Arg Asp Asn Ala Asn Asn Thr Val Tyr Leu
 65                  70                  75                  80

Gln Leu Asn Ser Leu Lys Pro Glu Asp Thr Ala Val Tyr Tyr Cys Asn
```

-continued

```
                    85                  90                  95

Ala His Ser Trp Leu Asp Tyr Asp Tyr Trp Gly Arg Gly Thr Gln Val
                100                 105                 110

Thr Val Ser Ser
        115

<210> SEQ ID NO 83
<211> LENGTH: 114
<212> TYPE: PRT
<213> ORGANISM: Artificial Sequence
<220> FEATURE:
<223> OTHER INFORMATION: VHH sequence 57G08

<400> SEQUENCE: 83

Gln Val Gln Leu Gln Glu Ser Gly Gly Gly Leu Val Gln Ala Gly Gly
1               5                   10                  15

Ser Leu Arg Leu Ser Cys Ala Ser Arg Arg Ile Asn Gly Ile Thr
            20                  25                  30

Met Gly Trp Tyr Arg Gln Ala Pro Gly Lys Gln Arg Glu Leu Val Ala
        35                  40                  45

Thr Ile Asp Ile His Asn Ser Thr Lys Tyr Ala Asp Ser Val Lys Gly
    50                  55                  60

Arg Phe Ile Ile Ser Arg Asp Asn Gly Lys Ser Met Leu Tyr Leu Gln
65                  70                  75                  80

Met Asn Ser Leu Lys Pro Glu Asp Thr Ala Val Tyr Tyr Cys Asn Arg
                85                  90                  95

Ile Pro Thr Phe Gly Arg Tyr Trp Gly Gln Gly Thr Gln Val Thr Val
                100                 105                 110

Ser Ser

<210> SEQ ID NO 84
<211> LENGTH: 118
<212> TYPE: PRT
<213> ORGANISM: Artificial Sequence
<220> FEATURE:
<223> OTHER INFORMATION: VHH sequence 57H08

<400> SEQUENCE: 84

Gln Val Gln Leu Gln Glu Ser Gly Gly Gly Leu Val Gln Ala Gly Gly
1               5                   10                  15

Ser Leu Arg Leu Ser Cys Val Ala Ser Gly Ser Thr Phe Tyr Thr Phe
            20                  25                  30

Ser Thr Lys Asn Val Gly Trp Tyr Arg Gln Ala Pro Gly Lys Gln Arg
        35                  40                  45

Glu Leu Val Ala Gln Gln Arg Tyr Asp Gly Ser Thr Asn Tyr Ala Asp
    50                  55                  60

Ser Leu Gln Gly Arg Phe Thr Ile Ser Arg Asp Asn Ala Lys Arg Thr
65                  70                  75                  80

Val Tyr Leu Gln Met Asn Ser Leu Lys Pro Glu Asp Thr Ala Val Tyr
                85                  90                  95

Ile Cys Asn Val Asn Arg Gly Phe Ile Ser Tyr Trp Gly Gln Gly Thr
                100                 105                 110

Gln Val Thr Val Ser Ser
        115

<210> SEQ ID NO 85
<211> LENGTH: 5
<212> TYPE: PRT
```

```
<213> ORGANISM: Artificial Sequence
<220> FEATURE:
<223> OTHER INFORMATION: CDR1 of VHH sequence 40F07

<400> SEQUENCE: 85

Ser Tyr Thr Met Gly
1               5

<210> SEQ ID NO 86
<211> LENGTH: 5
<212> TYPE: PRT
<213> ORGANISM: Artificial Sequence
<220> FEATURE:
<223> OTHER INFORMATION: CDR1 of VHH sequence 41D01

<400> SEQUENCE: 86

Arg Tyr Gly Met Gly
1               5

<210> SEQ ID NO 87
<211> LENGTH: 5
<212> TYPE: PRT
<213> ORGANISM: Artificial Sequence
<220> FEATURE:
<223> OTHER INFORMATION: CDR1 of VHH sequence 41D06

<400> SEQUENCE: 87

Ile Asn Ala Met Arg
1               5

<210> SEQ ID NO 88
<211> LENGTH: 5
<212> TYPE: PRT
<213> ORGANISM: Artificial Sequence
<220> FEATURE:
<223> OTHER INFORMATION: CDR1 of VHH sequence 41G10

<400> SEQUENCE: 88

Ile Asn Ala Met Gly
1               5

<210> SEQ ID NO 89
<211> LENGTH: 5
<212> TYPE: PRT
<213> ORGANISM: Artificial Sequence
<220> FEATURE:
<223> OTHER INFORMATION: CDR1 of VHH sequence 41H05

<400> SEQUENCE: 89

Ile Asn Ala Met Gly
1               5

<210> SEQ ID NO 90
<211> LENGTH: 5
<212> TYPE: PRT
<213> ORGANISM: Artificial Sequence
<220> FEATURE:
<223> OTHER INFORMATION: CDR1 of VHH sequence 42C11

<400> SEQUENCE: 90

Thr Tyr Val Met Gly
1               5

<210> SEQ ID NO 91
<211> LENGTH: 5
<212> TYPE: PRT
<213> ORGANISM: Artificial Sequence
```

```
<220> FEATURE:
<223> OTHER INFORMATION: CDR1 of VHH sequence 42C12

<400> SEQUENCE: 91

Ile Ser Ser Leu Gly
1               5

<210> SEQ ID NO 92
<211> LENGTH: 5
<212> TYPE: PRT
<213> ORGANISM: Artificial Sequence
<220> FEATURE:
<223> OTHER INFORMATION: CDR1 of VHH sequence 50D03

<400> SEQUENCE: 92

Thr Tyr Ala Met Gly
1               5

<210> SEQ ID NO 93
<211> LENGTH: 5
<212> TYPE: PRT
<213> ORGANISM: Artificial Sequence
<220> FEATURE:
<223> OTHER INFORMATION: CDR1 of VHH sequence 50D07

<400> SEQUENCE: 93

Ile Arg Asp Met Gly
1               5

<210> SEQ ID NO 94
<211> LENGTH: 5
<212> TYPE: PRT
<213> ORGANISM: Artificial Sequence
<220> FEATURE:
<223> OTHER INFORMATION: CDR1 of VHH sequence 50E02

<400> SEQUENCE: 94

Ile Asn Ala Met Gly
1               5

<210> SEQ ID NO 95
<211> LENGTH: 5
<212> TYPE: PRT
<213> ORGANISM: Artificial Sequence
<220> FEATURE:
<223> OTHER INFORMATION: CDR1 of VHH sequence 51B08

<400> SEQUENCE: 95

Ser Tyr Ala Met Gly
1               5

<210> SEQ ID NO 96
<211> LENGTH: 5
<212> TYPE: PRT
<213> ORGANISM: Artificial Sequence
<220> FEATURE:
<223> OTHER INFORMATION: CDR1 of VHH sequence 51C06

<400> SEQUENCE: 96

Ser Asp Thr Met Gly
1               5

<210> SEQ ID NO 97
<211> LENGTH: 5
<212> TYPE: PRT
<213> ORGANISM: Artificial Sequence
<220> FEATURE:
```

<223> OTHER INFORMATION: CDR1 of VHH sequence 51C08

<400> SEQUENCE: 97

Ile Lys Thr Met Gly
1               5

<210> SEQ ID NO 98
<211> LENGTH: 5
<212> TYPE: PRT
<213> ORGANISM: Artificial Sequence
<220> FEATURE:
<223> OTHER INFORMATION: CDR1 of VHH sequence 52A01

<400> SEQUENCE: 98

Leu Gly Thr Met Gly
1               5

<210> SEQ ID NO 99
<211> LENGTH: 5
<212> TYPE: PRT
<213> ORGANISM: Artificial Sequence
<220> FEATURE:
<223> OTHER INFORMATION: CDR1 of VHH sequence 52B01

<400> SEQUENCE: 99

Ile Asn Val Met Gly
1               5

<210> SEQ ID NO 100
<211> LENGTH: 5
<212> TYPE: PRT
<213> ORGANISM: Artificial Sequence
<220> FEATURE:
<223> OTHER INFORMATION: CDR1 of VHH sequence 52G05

<400> SEQUENCE: 100

Ile Ser Ala Met Gly
1               5

<210> SEQ ID NO 101
<211> LENGTH: 5
<212> TYPE: PRT
<213> ORGANISM: Artificial Sequence
<220> FEATURE:
<223> OTHER INFORMATION: CDR1 of VHH sequence 53A01

<400> SEQUENCE: 101

Ile Asn Thr Met Gly
1               5

<210> SEQ ID NO 102
<211> LENGTH: 5
<212> TYPE: PRT
<213> ORGANISM: Artificial Sequence
<220> FEATURE:
<223> OTHER INFORMATION: CDR1 of VHH sequence 53F05

<400> SEQUENCE: 102

Leu Asn Ala Met Gly
1               5

<210> SEQ ID NO 103
<211> LENGTH: 5
<212> TYPE: PRT
<213> ORGANISM: Artificial Sequence
<220> FEATURE:
<223> OTHER INFORMATION: CDR1 of VHH sequence 54A02

-continued

```
<400> SEQUENCE: 103

Arg Tyr Gly Met Gly
1               5

<210> SEQ ID NO 104
<211> LENGTH: 5
<212> TYPE: PRT
<213> ORGANISM: Artificial Sequence
<220> FEATURE:
<223> OTHER INFORMATION: CDR1 of VHH sequence 54B01

<400> SEQUENCE: 104

Arg Tyr Thr Met Gly
1               5

<210> SEQ ID NO 105
<211> LENGTH: 5
<212> TYPE: PRT
<213> ORGANISM: Artificial Sequence
<220> FEATURE:
<223> OTHER INFORMATION: CDR1 of VHH sequence 54C01

<400> SEQUENCE: 105

Arg Tyr Ala Met Gly
1               5

<210> SEQ ID NO 106
<211> LENGTH: 5
<212> TYPE: PRT
<213> ORGANISM: Artificial Sequence
<220> FEATURE:
<223> OTHER INFORMATION: CDR1 of VHH sequence 54C04

<400> SEQUENCE: 106

Ile Asn Ala Met Gly
1               5

<210> SEQ ID NO 107
<211> LENGTH: 5
<212> TYPE: PRT
<213> ORGANISM: Artificial Sequence
<220> FEATURE:
<223> OTHER INFORMATION: CDR1 of VHH sequence 54C08

<400> SEQUENCE: 107

Ile Asn Ala Met Gly
1               5

<210> SEQ ID NO 108
<211> LENGTH: 5
<212> TYPE: PRT
<213> ORGANISM: Artificial Sequence
<220> FEATURE:
<223> OTHER INFORMATION: CDR1 of VHH sequence 54C10

<400> SEQUENCE: 108

Val Asn Asp Met Gly
1               5

<210> SEQ ID NO 109
<211> LENGTH: 5
<212> TYPE: PRT
<213> ORGANISM: Artificial Sequence
<220> FEATURE:
<223> OTHER INFORMATION: CDR1 of VHH sequence 54C11
```

```
<400> SEQUENCE: 109

Val Asn Asp Met Ala
1               5

<210> SEQ ID NO 110
<211> LENGTH: 5
<212> TYPE: PRT
<213> ORGANISM: Artificial Sequence
<220> FEATURE:
<223> OTHER INFORMATION: CDR1 of VHH sequence 54D03

<400> SEQUENCE: 110

Ile Asn Ala Met Arg
1               5

<210> SEQ ID NO 111
<211> LENGTH: 5
<212> TYPE: PRT
<213> ORGANISM: Artificial Sequence
<220> FEATURE:
<223> OTHER INFORMATION: CDR1 of VHH sequence 54D06

<400> SEQUENCE: 111

Ile Asn Ala Met Gly
1               5

<210> SEQ ID NO 112
<211> LENGTH: 5
<212> TYPE: PRT
<213> ORGANISM: Artificial Sequence
<220> FEATURE:
<223> OTHER INFORMATION: CDR1 of VHH sequence 54D10

<400> SEQUENCE: 112

Ile His Ala Met Gly
1               5

<210> SEQ ID NO 113
<211> LENGTH: 5
<212> TYPE: PRT
<213> ORGANISM: Artificial Sequence
<220> FEATURE:
<223> OTHER INFORMATION: CDR1 of VHH sequence 54E01

<400> SEQUENCE: 113

Ile Asn Pro Met Gly
1               5

<210> SEQ ID NO 114
<211> LENGTH: 5
<212> TYPE: PRT
<213> ORGANISM: Artificial Sequence
<220> FEATURE:
<223> OTHER INFORMATION: CDR1 of VHH sequence 54E05

<400> SEQUENCE: 114

Ile Asn Thr Met Gly
1               5

<210> SEQ ID NO 115
<211> LENGTH: 5
<212> TYPE: PRT
<213> ORGANISM: Artificial Sequence
<220> FEATURE:
<223> OTHER INFORMATION: CDR1 of VHH sequence 54E10

<400> SEQUENCE: 115
```

Phe Asn Ala Met Gly
1               5

<210> SEQ ID NO 116
<211> LENGTH: 5
<212> TYPE: PRT
<213> ORGANISM: Artificial Sequence
<220> FEATURE:
<223> OTHER INFORMATION: CDR1 of VHH sequence 54F01

<400> SEQUENCE: 116

Leu Asn Leu Met Gly
1               5

<210> SEQ ID NO 117
<211> LENGTH: 5
<212> TYPE: PRT
<213> ORGANISM: Artificial Sequence
<220> FEATURE:
<223> OTHER INFORMATION: CDR1 of VHH sequence 54F02

<400> SEQUENCE: 117

Ile Asn Thr Met Gly
1               5

<210> SEQ ID NO 118
<211> LENGTH: 5
<212> TYPE: PRT
<213> ORGANISM: Artificial Sequence
<220> FEATURE:
<223> OTHER INFORMATION: CDR1 of VHH sequence 54G01

<400> SEQUENCE: 118

Val Asn Ala Met Gly
1               5

<210> SEQ ID NO 119
<211> LENGTH: 5
<212> TYPE: PRT
<213> ORGANISM: Artificial Sequence
<220> FEATURE:
<223> OTHER INFORMATION: CDR1 of VHH sequence 54G08

<400> SEQUENCE: 119

Phe Asn Leu Met Gly
1               5

<210> SEQ ID NO 120
<211> LENGTH: 5
<212> TYPE: PRT
<213> ORGANISM: Artificial Sequence
<220> FEATURE:
<223> OTHER INFORMATION: CDR1 of VHH sequence 54G09

<400> SEQUENCE: 120

Ile Arg Asp Met Gly
1               5

<210> SEQ ID NO 121
<211> LENGTH: 5
<212> TYPE: PRT
<213> ORGANISM: Artificial Sequence
<220> FEATURE:
<223> OTHER INFORMATION: CDR1 of VHH sequence 55B02

<400> SEQUENCE: 121

Ile Asn Ser Met Asn
1               5

<210> SEQ ID NO 122
<211> LENGTH: 5
<212> TYPE: PRT
<213> ORGANISM: Artificial Sequence
<220> FEATURE:
<223> OTHER INFORMATION: CDR1 of VHH sequence 55B05

<400> SEQUENCE: 122

Gly Tyr Thr Val Ala
1               5

<210> SEQ ID NO 123
<211> LENGTH: 5
<212> TYPE: PRT
<213> ORGANISM: Artificial Sequence
<220> FEATURE:
<223> OTHER INFORMATION: CDR1 of VHH sequence 55C05

<400> SEQUENCE: 123

Met Lys Ala Met Gly
1               5

<210> SEQ ID NO 124
<211> LENGTH: 5
<212> TYPE: PRT
<213> ORGANISM: Artificial Sequence
<220> FEATURE:
<223> OTHER INFORMATION: CDR1 of VHH sequence 55D08

<400> SEQUENCE: 124

Ile Ser Ala Met Gly
1               5

<210> SEQ ID NO 125
<211> LENGTH: 5
<212> TYPE: PRT
<213> ORGANISM: Artificial Sequence
<220> FEATURE:
<223> OTHER INFORMATION: CDR1 of VHH sequence 55E02

<400> SEQUENCE: 125

Ser Asn Ala Met Ala
1               5

<210> SEQ ID NO 126
<211> LENGTH: 5
<212> TYPE: PRT
<213> ORGANISM: Artificial Sequence
<220> FEATURE:
<223> OTHER INFORMATION: CDR1 of VHH sequence 55E07

<400> SEQUENCE: 126

Ile Tyr Gly Met Gly
1               5

<210> SEQ ID NO 127
<211> LENGTH: 5
<212> TYPE: PRT
<213> ORGANISM: Artificial Sequence
<220> FEATURE:
<223> OTHER INFORMATION: CDR1 of VHH sequence 55E09

<400> SEQUENCE: 127

Thr Tyr Thr Met Gly

-continued

```
1               5

<210> SEQ ID NO 128
<211> LENGTH: 5
<212> TYPE: PRT
<213> ORGANISM: Artificial Sequence
<220> FEATURE:
<223> OTHER INFORMATION: CDR1 of VHH sequence 55E10

<400> SEQUENCE: 128

Ile Gln Thr Ile Gly
1               5

<210> SEQ ID NO 129
<211> LENGTH: 5
<212> TYPE: PRT
<213> ORGANISM: Artificial Sequence
<220> FEATURE:
<223> OTHER INFORMATION: CDR1 of VHH sequence 55F04

<400> SEQUENCE: 129

Ile Asn Val Arg Gly
1               5

<210> SEQ ID NO 130
<211> LENGTH: 5
<212> TYPE: PRT
<213> ORGANISM: Artificial Sequence
<220> FEATURE:
<223> OTHER INFORMATION: CDR1 of VHH sequence 55F09

<400> SEQUENCE: 130

Leu Asn Ala Met Gly
1               5

<210> SEQ ID NO 131
<211> LENGTH: 5
<212> TYPE: PRT
<213> ORGANISM: Artificial Sequence
<220> FEATURE:
<223> OTHER INFORMATION: CDR1 of VHH sequence 55F10

<400> SEQUENCE: 131

Arg Tyr Ala Met Gly
1               5

<210> SEQ ID NO 132
<211> LENGTH: 5
<212> TYPE: PRT
<213> ORGANISM: Artificial Sequence
<220> FEATURE:
<223> OTHER INFORMATION: CDR1 of VHH sequence 55G02

<400> SEQUENCE: 132

Ile Asn Val Met Gly
1               5

<210> SEQ ID NO 133
<211> LENGTH: 5
<212> TYPE: PRT
<213> ORGANISM: Artificial Sequence
<220> FEATURE:
<223> OTHER INFORMATION: CDR1 of VHH sequence 55G08

<400> SEQUENCE: 133

Ile Asn Ala Met Arg
1               5
```

-continued

<210> SEQ ID NO 134
<211> LENGTH: 5
<212> TYPE: PRT
<213> ORGANISM: Artificial Sequence
<220> FEATURE:
<223> OTHER INFORMATION: CDR1 of VHH sequence 56A05

<400> SEQUENCE: 134

Ser Asn Thr Met Gly
1               5

<210> SEQ ID NO 135
<211> LENGTH: 5
<212> TYPE: PRT
<213> ORGANISM: Artificial Sequence
<220> FEATURE:
<223> OTHER INFORMATION: CDR1 of VHH sequence 56A06

<400> SEQUENCE: 135

Val Tyr Gly Met Gly
1               5

<210> SEQ ID NO 136
<211> LENGTH: 5
<212> TYPE: PRT
<213> ORGANISM: Artificial Sequence
<220> FEATURE:
<223> OTHER INFORMATION: CDR1 of VHH sequence 56A09

<400> SEQUENCE: 136

Leu Asn Ser Met Gly
1               5

<210> SEQ ID NO 137
<211> LENGTH: 5
<212> TYPE: PRT
<213> ORGANISM: Artificial Sequence
<220> FEATURE:
<223> OTHER INFORMATION: CDR1 of VHH sequence 56C09

<400> SEQUENCE: 137

Ile Leu Ser Met Ala
1               5

<210> SEQ ID NO 138
<211> LENGTH: 5
<212> TYPE: PRT
<213> ORGANISM: Artificial Sequence
<220> FEATURE:
<223> OTHER INFORMATION: CDR1 of VHH sequence 56C12

<400> SEQUENCE: 138

Asn Arg Ala Val Ser
1               5

<210> SEQ ID NO 139
<211> LENGTH: 5
<212> TYPE: PRT
<213> ORGANISM: Artificial Sequence
<220> FEATURE:
<223> OTHER INFORMATION: CDR1 of VHH sequence 56D06

<400> SEQUENCE: 139

Ile Ser Ala Met Gly
1               5

<210> SEQ ID NO 140
<211> LENGTH: 5
<212> TYPE: PRT
<213> ORGANISM: Artificial Sequence
<220> FEATURE:
<223> OTHER INFORMATION: CDR1 of VHH sequence 56D07

<400> SEQUENCE: 140

Met Lys Val Met Gly
1               5

<210> SEQ ID NO 141
<211> LENGTH: 5
<212> TYPE: PRT
<213> ORGANISM: Artificial Sequence
<220> FEATURE:
<223> OTHER INFORMATION: CDR1 of VHH sequence 56D10

<400> SEQUENCE: 141

Ile Thr Thr Met Gly
1               5

<210> SEQ ID NO 142
<211> LENGTH: 5
<212> TYPE: PRT
<213> ORGANISM: Artificial Sequence
<220> FEATURE:
<223> OTHER INFORMATION: CDR1 of VHH sequence 56E04

<400> SEQUENCE: 142

His Lys Ala Thr Gly
1               5

<210> SEQ ID NO 143
<211> LENGTH: 5
<212> TYPE: PRT
<213> ORGANISM: Artificial Sequence
<220> FEATURE:
<223> OTHER INFORMATION: CDR1 of VHH sequence 56E05

<400> SEQUENCE: 143

Asn Asn Ala Gly Gly
1               5

<210> SEQ ID NO 144
<211> LENGTH: 5
<212> TYPE: PRT
<213> ORGANISM: Artificial Sequence
<220> FEATURE:
<223> OTHER INFORMATION: CDR1 of VHH sequence 56E08

<400> SEQUENCE: 144

Ile Asn Asp Met Gly
1               5

<210> SEQ ID NO 145
<211> LENGTH: 5
<212> TYPE: PRT
<213> ORGANISM: Artificial Sequence
<220> FEATURE:
<223> OTHER INFORMATION: CDR1 of VHH sequence 56F07

<400> SEQUENCE: 145

Ile Asn Asp Met Ala
1               5

-continued

```
<210> SEQ ID NO 146
<211> LENGTH: 5
<212> TYPE: PRT
<213> ORGANISM: Artificial Sequence
<220> FEATURE:
<223> OTHER INFORMATION: CDR1 of VHH sequence 56F11

<400> SEQUENCE: 146

Arg Asn Ala Met Gly
1               5

<210> SEQ ID NO 147
<211> LENGTH: 5
<212> TYPE: PRT
<213> ORGANISM: Artificial Sequence
<220> FEATURE:
<223> OTHER INFORMATION: CDR1 of VHH sequence 56G07

<400> SEQUENCE: 147

Ile His Asp Met Gly
1               5

<210> SEQ ID NO 148
<211> LENGTH: 5
<212> TYPE: PRT
<213> ORGANISM: Artificial Sequence
<220> FEATURE:
<223> OTHER INFORMATION: CDR1 of VHH sequence 56G08

<400> SEQUENCE: 148

Ile Ser Arg Met Gly
1               5

<210> SEQ ID NO 149
<211> LENGTH: 5
<212> TYPE: PRT
<213> ORGANISM: Artificial Sequence
<220> FEATURE:
<223> OTHER INFORMATION: CDR1 of VHH sequence 56G10

<400> SEQUENCE: 149

Met Tyr Gln Val Gly
1               5

<210> SEQ ID NO 150
<211> LENGTH: 5
<212> TYPE: PRT
<213> ORGANISM: Artificial Sequence
<220> FEATURE:
<223> OTHER INFORMATION: CDR1 of VHH sequence 56H04

<400> SEQUENCE: 150

Asn Lys Ala Met Gly
1               5

<210> SEQ ID NO 151
<211> LENGTH: 5
<212> TYPE: PRT
<213> ORGANISM: Artificial Sequence
<220> FEATURE:
<223> OTHER INFORMATION: CDR1 of VHH sequence 56H05

<400> SEQUENCE: 151

Phe Asn Thr Met Ala
1               5

<210> SEQ ID NO 152
```

-continued

```
<211> LENGTH: 5
<212> TYPE: PRT
<213> ORGANISM: Artificial Sequence
<220> FEATURE:
<223> OTHER INFORMATION: CDR1 of VHH sequence 56H07

<400> SEQUENCE: 152

Leu Gly Thr Met Gly
1               5

<210> SEQ ID NO 153
<211> LENGTH: 5
<212> TYPE: PRT
<213> ORGANISM: Artificial Sequence
<220> FEATURE:
<223> OTHER INFORMATION: CDR1 of VHH sequence 56H08

<400> SEQUENCE: 153

Val Asn Pro Met Gly
1               5

<210> SEQ ID NO 154
<211> LENGTH: 5
<212> TYPE: PRT
<213> ORGANISM: Artificial Sequence
<220> FEATURE:
<223> OTHER INFORMATION: CDR1 of VHH sequence 57A06

<400> SEQUENCE: 154

Asn Asn Ala Gly Gly
1               5

<210> SEQ ID NO 155
<211> LENGTH: 5
<212> TYPE: PRT
<213> ORGANISM: Artificial Sequence
<220> FEATURE:
<223> OTHER INFORMATION: CDR1 of VHH sequence 57B01

<400> SEQUENCE: 155

Ile Asn Ala Met Ala
1               5

<210> SEQ ID NO 156
<211> LENGTH: 5
<212> TYPE: PRT
<213> ORGANISM: Artificial Sequence
<220> FEATURE:
<223> OTHER INFORMATION: CDR1 of VHH sequence 57B07

<400> SEQUENCE: 156

Ile Asn Ala Met Gly
1               5

<210> SEQ ID NO 157
<211> LENGTH: 5
<212> TYPE: PRT
<213> ORGANISM: Artificial Sequence
<220> FEATURE:
<223> OTHER INFORMATION: CDR1 of VHH sequence 57B11

<400> SEQUENCE: 157

Met Asn Ser Met Gly
1               5

<210> SEQ ID NO 158
<211> LENGTH: 5
```

-continued

```
<212> TYPE: PRT
<213> ORGANISM: Artificial Sequence
<220> FEATURE:
<223> OTHER INFORMATION: CDR1 of VHH sequence 57C07

<400> SEQUENCE: 158

Ile Asn Thr Met Gly
1               5

<210> SEQ ID NO 159
<211> LENGTH: 5
<212> TYPE: PRT
<213> ORGANISM: Artificial Sequence
<220> FEATURE:
<223> OTHER INFORMATION: CDR1 of VHH sequence 57C09

<400> SEQUENCE: 159

Ile Asn Ala Met Gly
1               5

<210> SEQ ID NO 160
<211> LENGTH: 5
<212> TYPE: PRT
<213> ORGANISM: Artificial Sequence
<220> FEATURE:
<223> OTHER INFORMATION: CDR1 of VHH sequence 57D02

<400> SEQUENCE: 160

Arg Ser Asp Met Gly
1               5

<210> SEQ ID NO 161
<211> LENGTH: 5
<212> TYPE: PRT
<213> ORGANISM: Artificial Sequence
<220> FEATURE:
<223> OTHER INFORMATION: CDR1 of VHH sequence 57D09

<400> SEQUENCE: 161

Ile Asp Ala Met Gly
1               5

<210> SEQ ID NO 162
<211> LENGTH: 5
<212> TYPE: PRT
<213> ORGANISM: Artificial Sequence
<220> FEATURE:
<223> OTHER INFORMATION: CDR1 of VHH sequence 57D10

<400> SEQUENCE: 162

Ile Ser Thr Met Gly
1               5

<210> SEQ ID NO 163
<211> LENGTH: 5
<212> TYPE: PRT
<213> ORGANISM: Artificial Sequence
<220> FEATURE:
<223> OTHER INFORMATION: CDR1 of VHH sequence 57E07

<400> SEQUENCE: 163

Ile Asn Asp Met Gly
1               5

<210> SEQ ID NO 164
<211> LENGTH: 5
<212> TYPE: PRT
```

```
<213> ORGANISM: Artificial Sequence
<220> FEATURE:
<223> OTHER INFORMATION: CDR1 of VHH sequence 57E11

<400> SEQUENCE: 164

Ile Asn Thr Met Gly
1               5

<210> SEQ ID NO 165
<211> LENGTH: 5
<212> TYPE: PRT
<213> ORGANISM: Artificial Sequence
<220> FEATURE:
<223> OTHER INFORMATION: CDR1 of VHH sequence 57G01

<400> SEQUENCE: 165

Ile Asn Ser Met Gly
1               5

<210> SEQ ID NO 166
<211> LENGTH: 5
<212> TYPE: PRT
<213> ORGANISM: Artificial Sequence
<220> FEATURE:
<223> OTHER INFORMATION: CDR1 of VHH sequence 57G07

<400> SEQUENCE: 166

Ile Asn Ala Met Gly
1               5

<210> SEQ ID NO 167
<211> LENGTH: 5
<212> TYPE: PRT
<213> ORGANISM: Artificial Sequence
<220> FEATURE:
<223> OTHER INFORMATION: CDR1 of VHH sequence 57G08

<400> SEQUENCE: 167

Gly Ile Thr Met Gly
1               5

<210> SEQ ID NO 168
<211> LENGTH: 5
<212> TYPE: PRT
<213> ORGANISM: Artificial Sequence
<220> FEATURE:
<223> OTHER INFORMATION: CDR1 of VHH sequence 57H08

<400> SEQUENCE: 168

Thr Lys Asn Val Gly
1               5

<210> SEQ ID NO 169
<211> LENGTH: 16
<212> TYPE: PRT
<213> ORGANISM: Artificial Sequence
<220> FEATURE:
<223> OTHER INFORMATION: CDR2 of VHH sequence 40F07

<400> SEQUENCE: 169

Ser Ile Glu Gly Gly Gly Asn Thr Asp Tyr Ala Asp Ser Val Lys Gly
1               5                   10                  15

<210> SEQ ID NO 170
<211> LENGTH: 16
<212> TYPE: PRT
<213> ORGANISM: Artificial Sequence
```

```
<220> FEATURE:
<223> OTHER INFORMATION: CDR2 of VHH sequence 41D01

<400> SEQUENCE: 170

Ser Ile Thr Arg Gly Gly Thr Thr Thr Tyr Ala Asp Ser Val Lys Gly
1               5                   10                  15

<210> SEQ ID NO 171
<211> LENGTH: 16
<212> TYPE: PRT
<213> ORGANISM: Artificial Sequence
<220> FEATURE:
<223> OTHER INFORMATION: CDR2 of VHH sequence 41D06

<400> SEQUENCE: 171

Ser Ile Ser Ser Gly Gly Asn Thr Asn Tyr Ser Glu Ser Val Lys Gly
1               5                   10                  15

<210> SEQ ID NO 172
<211> LENGTH: 16
<212> TYPE: PRT
<213> ORGANISM: Artificial Sequence
<220> FEATURE:
<223> OTHER INFORMATION: CDR2 of VHH sequence 41G10

<400> SEQUENCE: 172

Thr Ile Thr Ser Gly Gly Thr Thr Asn Tyr Ala Asp Ser Val Lys Gly
1               5                   10                  15

<210> SEQ ID NO 173
<211> LENGTH: 16
<212> TYPE: PRT
<213> ORGANISM: Artificial Sequence
<220> FEATURE:
<223> OTHER INFORMATION: CDR2 of VHH sequence 41H05

<400> SEQUENCE: 173

Thr Ile Thr Ser Gly Ala Asn Thr Asn Tyr Thr Asp Ser Val Lys Gly
1               5                   10                  15

<210> SEQ ID NO 174
<211> LENGTH: 16
<212> TYPE: PRT
<213> ORGANISM: Artificial Sequence
<220> FEATURE:
<223> OTHER INFORMATION: CDR2 of VHH sequence 42C11

<400> SEQUENCE: 174

Thr Ile Thr Ser Ser Gly Lys Thr Asn Tyr Ala Ala Ser Val Lys Gly
1               5                   10                  15

<210> SEQ ID NO 175
<211> LENGTH: 16
<212> TYPE: PRT
<213> ORGANISM: Artificial Sequence
<220> FEATURE:
<223> OTHER INFORMATION: CDR2 of VHH sequence 42C12

<400> SEQUENCE: 175

Ser Ala Thr Ser Gly Gly Asp Thr Thr Tyr Ala Asp Ser Val Lys Gly
1               5                   10                  15

<210> SEQ ID NO 176
<211> LENGTH: 16
<212> TYPE: PRT
<213> ORGANISM: Artificial Sequence
<220> FEATURE:
```

<223> OTHER INFORMATION: CDR2 of VHH sequence 50D03

<400> SEQUENCE: 176

Thr Ile Thr Ser Ser Gly Lys Thr Asn Tyr Ala Ala Ser Val Lys Gly
1               5                   10                  15

<210> SEQ ID NO 177
<211> LENGTH: 16
<212> TYPE: PRT
<213> ORGANISM: Artificial Sequence
<220> FEATURE:
<223> OTHER INFORMATION: CDR2 of VHH sequence 50D07

<400> SEQUENCE: 177

Thr Ile Thr Ser Asp Gln Ser Thr Asn Tyr Ala Asp Ser Val Lys Gly
1               5                   10                  15

<210> SEQ ID NO 178
<211> LENGTH: 16
<212> TYPE: PRT
<213> ORGANISM: Artificial Sequence
<220> FEATURE:
<223> OTHER INFORMATION: CDR2 of VHH sequence 50E02

<400> SEQUENCE: 178

Ala Ile Thr Ser Asp Gly Ser Thr Asn Tyr Ala Asp Ser Val Lys Gly
1               5                   10                  15

<210> SEQ ID NO 179
<211> LENGTH: 16
<212> TYPE: PRT
<213> ORGANISM: Artificial Sequence
<220> FEATURE:
<223> OTHER INFORMATION: CDR2 of VHH sequence 51B08

<400> SEQUENCE: 179

Gly Ile Ser Ser Gly Gly Ser Thr Lys Tyr Ala Asp Ser Val Arg Gly
1               5                   10                  15

<210> SEQ ID NO 180
<211> LENGTH: 16
<212> TYPE: PRT
<213> ORGANISM: Artificial Sequence
<220> FEATURE:
<223> OTHER INFORMATION: CDR2 of VHH sequence 51C06

<400> SEQUENCE: 180

Ala Ile Thr Thr Gly Gly Asn Thr Asn Tyr Ala Asp Ser Val Lys Gly
1               5                   10                  15

<210> SEQ ID NO 181
<211> LENGTH: 16
<212> TYPE: PRT
<213> ORGANISM: Artificial Sequence
<220> FEATURE:
<223> OTHER INFORMATION: CDR2 of VHH sequence 51C08

<400> SEQUENCE: 181

Thr Ile Ser Asn Gly Gly Ser Thr Asn Tyr Ala Asp Ser Val Lys Gly
1               5                   10                  15

<210> SEQ ID NO 182
<211> LENGTH: 15
<212> TYPE: PRT
<213> ORGANISM: Artificial Sequence
<220> FEATURE:
<223> OTHER INFORMATION: CDR2 of VHH sequence 52A01

```
<400> SEQUENCE: 182

Ser Ile Ser Thr Gly Ser Thr Asn Tyr Ala Asp Ser Val Lys Gly
1               5                   10                  15

<210> SEQ ID NO 183
<211> LENGTH: 16
<212> TYPE: PRT
<213> ORGANISM: Artificial Sequence
<220> FEATURE:
<223> OTHER INFORMATION: CDR2 of VHH sequence 52B01

<400> SEQUENCE: 183

Thr Ile Ser Arg Gly Gly Ser Thr Asn Tyr Ala Asp Ser Val Lys Gly
1               5                   10                  15

<210> SEQ ID NO 184
<211> LENGTH: 16
<212> TYPE: PRT
<213> ORGANISM: Artificial Sequence
<220> FEATURE:
<223> OTHER INFORMATION: CDR2 of VHH sequence 52G05

<400> SEQUENCE: 184

Ser Ile Thr Arg Arg Gly Ser Thr Asn Tyr Ala Asp Ser Val Lys Asp
1               5                   10                  15

<210> SEQ ID NO 185
<211> LENGTH: 16
<212> TYPE: PRT
<213> ORGANISM: Artificial Sequence
<220> FEATURE:
<223> OTHER INFORMATION: CDR2 of VHH sequence 53A01

<400> SEQUENCE: 185

Ser Ile Ser Ser Gly Gly Trp Thr Asn Tyr Ala Asp Ser Val Lys Gly
1               5                   10                  15

<210> SEQ ID NO 186
<211> LENGTH: 16
<212> TYPE: PRT
<213> ORGANISM: Artificial Sequence
<220> FEATURE:
<223> OTHER INFORMATION: CDR2 of VHH sequence 53F05

<400> SEQUENCE: 186

Ser Ile Thr Thr Gly Gly Ser Thr Asn Tyr Ala Glu Pro Val Lys Gly
1               5                   10                  15

<210> SEQ ID NO 187
<211> LENGTH: 17
<212> TYPE: PRT
<213> ORGANISM: Artificial Sequence
<220> FEATURE:
<223> OTHER INFORMATION: CDR2 of VHH sequence 54A02

<400> SEQUENCE: 187

Ala Asn Arg Trp Ser Gly Gly Ser Thr Tyr Tyr Ala Asp Ser Val Arg
1               5                   10                  15
Gly

<210> SEQ ID NO 188
<211> LENGTH: 17
<212> TYPE: PRT
<213> ORGANISM: Artificial Sequence
<220> FEATURE:
```

<223> OTHER INFORMATION: CDR2 of VHH sequence 54B01

<400> SEQUENCE: 188

Gly Ile Thr Trp Thr Gly Gly Ser Thr Asp Tyr Ala Asp Ser Val Lys
1               5                   10                  15
Gly

<210> SEQ ID NO 189
<211> LENGTH: 17
<212> TYPE: PRT
<213> ORGANISM: Artificial Sequence
<220> FEATURE:
<223> OTHER INFORMATION: CDR2 of VHH sequence 54C01

<400> SEQUENCE: 189

Ala Ile Ser Trp Ser Gly Gly Ser Thr Tyr Tyr Ala Asp Ser Val Lys
1               5                   10                  15
Asp

<210> SEQ ID NO 190
<211> LENGTH: 16
<212> TYPE: PRT
<213> ORGANISM: Artificial Sequence
<220> FEATURE:
<223> OTHER INFORMATION: CDR2 of VHH sequence 54C04

<400> SEQUENCE: 190

Asp Met Thr Ser Gly Gly Ser Ile Asn Tyr Ala Asp Ser Val Ser Gly
1               5                   10                  15

<210> SEQ ID NO 191
<211> LENGTH: 16
<212> TYPE: PRT
<213> ORGANISM: Artificial Sequence
<220> FEATURE:
<223> OTHER INFORMATION: CDR2 of VHH sequence 54C08

<400> SEQUENCE: 191

Ser Ile Thr Ser Gly Gly Ser Thr Asn Tyr Ala Asp Ser Val Lys Gly
1               5                   10                  15

<210> SEQ ID NO 192
<211> LENGTH: 16
<212> TYPE: PRT
<213> ORGANISM: Artificial Sequence
<220> FEATURE:
<223> OTHER INFORMATION: CDR2 of VHH sequence 54C10

<400> SEQUENCE: 192

Gln Ile Thr Arg Arg Gly Ser Thr Asn Tyr Ala Asp Ser Val Lys Gly
1               5                   10                  15

<210> SEQ ID NO 193
<211> LENGTH: 16
<212> TYPE: PRT
<213> ORGANISM: Artificial Sequence
<220> FEATURE:
<223> OTHER INFORMATION: CDR2 of VHH sequence 54C11

<400> SEQUENCE: 193

Asn Ile Thr Arg Gly Gly Ser Thr Asn Tyr Ala Asp Ser Val Lys Gly
1               5                   10                  15

<210> SEQ ID NO 194
<211> LENGTH: 16

```
<212> TYPE: PRT
<213> ORGANISM: Artificial Sequence
<220> FEATURE:
<223> OTHER INFORMATION: CDR2 of VHH sequence 54D03

<400> SEQUENCE: 194

Ser Ile Ser Ser Gly Gly Asn Thr Asn Tyr Ser Glu Ser Val Lys Gly
1               5                   10                  15

<210> SEQ ID NO 195
<211> LENGTH: 16
<212> TYPE: PRT
<213> ORGANISM: Artificial Sequence
<220> FEATURE:
<223> OTHER INFORMATION: CDR2 of VHH sequence 54D06

<400> SEQUENCE: 195

Thr Ile Thr Arg Gly Gly Ile Thr Asn Tyr Ala Asp Ser Val Lys Gly
1               5                   10                  15

<210> SEQ ID NO 196
<211> LENGTH: 16
<212> TYPE: PRT
<213> ORGANISM: Artificial Sequence
<220> FEATURE:
<223> OTHER INFORMATION: CDR2 of VHH sequence 54D10

<400> SEQUENCE: 196

Ile Thr Ser Thr Ser Gly Thr Thr Asp Tyr Thr Asp Ser Val Lys Gly
1               5                   10                  15

<210> SEQ ID NO 197
<211> LENGTH: 16
<212> TYPE: PRT
<213> ORGANISM: Artificial Sequence
<220> FEATURE:
<223> OTHER INFORMATION: CDR2 of VHH sequence 54E01

<400> SEQUENCE: 197

Ala Ile Thr Ser Gly Gly Ser Thr Asn Tyr Ala Asp Tyr Val Lys Gly
1               5                   10                  15

<210> SEQ ID NO 198
<211> LENGTH: 16
<212> TYPE: PRT
<213> ORGANISM: Artificial Sequence
<220> FEATURE:
<223> OTHER INFORMATION: CDR2 of VHH sequence 54E05

<400> SEQUENCE: 198

Ala Ile Thr Asn Arg Gly Ser Thr Asn Tyr Ala Asp Phe Val Lys Gly
1               5                   10                  15

<210> SEQ ID NO 199
<211> LENGTH: 16
<212> TYPE: PRT
<213> ORGANISM: Artificial Sequence
<220> FEATURE:
<223> OTHER INFORMATION: CDR2 of VHH sequence 54E10

<400> SEQUENCE: 199

Ala Ile Thr Arg Gly Gly Ser Thr Asn Tyr Ala Asp Ser Val Lys Gly
1               5                   10                  15

<210> SEQ ID NO 200
<211> LENGTH: 16
<212> TYPE: PRT
```

<213> ORGANISM: Artificial Sequence
<220> FEATURE:
<223> OTHER INFORMATION: CDR2 of VHH sequence 54F01

<400> SEQUENCE: 200

Thr Ile Thr Arg Gly Gly Ser Thr Asn Tyr Ala Asp Ser Val Lys Gly
1               5                   10                  15

<210> SEQ ID NO 201
<211> LENGTH: 16
<212> TYPE: PRT
<213> ORGANISM: Artificial Sequence
<220> FEATURE:
<223> OTHER INFORMATION: CDR2 of VHH sequence 54F02

<400> SEQUENCE: 201

Thr Ile Thr Ser Gly Gly Thr Thr Asn Tyr Ala Asp Ser Val Lys Asn
1               5                   10                  15

<210> SEQ ID NO 202
<211> LENGTH: 16
<212> TYPE: PRT
<213> ORGANISM: Artificial Sequence
<220> FEATURE:
<223> OTHER INFORMATION: CDR2 of VHH sequence 54G01

<400> SEQUENCE: 202

Ile Ile Ser Ser Asn Ser Thr Ser Asn Tyr Ala Asp Ser Val Lys Gly
1               5                   10                  15

<210> SEQ ID NO 203
<211> LENGTH: 16
<212> TYPE: PRT
<213> ORGANISM: Artificial Sequence
<220> FEATURE:
<223> OTHER INFORMATION: CDR2 of VHH sequence 54G08

<400> SEQUENCE: 203

Ala Ile Thr Ser Ser Ser Asn Thr Asn Tyr Ala Asp Ser Val Lys Gly
1               5                   10                  15

<210> SEQ ID NO 204
<211> LENGTH: 16
<212> TYPE: PRT
<213> ORGANISM: Artificial Sequence
<220> FEATURE:
<223> OTHER INFORMATION: CDR2 of VHH sequence 54G09

<400> SEQUENCE: 204

Thr Ile Thr Ser Asp Gln Ser Thr Asn Tyr Ala Asp Ser Val Lys Gly
1               5                   10                  15

<210> SEQ ID NO 205
<211> LENGTH: 16
<212> TYPE: PRT
<213> ORGANISM: Artificial Sequence
<220> FEATURE:
<223> OTHER INFORMATION: CDR2 of VHH sequence 55B02

<400> SEQUENCE: 205

Asp Met Arg Ser Asp Gly Ser Thr Asn Tyr Ala Asp Ser Val Lys Gly
1               5                   10                  15

<210> SEQ ID NO 206
<211> LENGTH: 17
<212> TYPE: PRT
<213> ORGANISM: Artificial Sequence

```
<220> FEATURE:
<223> OTHER INFORMATION: CDR2 of VHH sequence 55B05

<400> SEQUENCE: 206

Arg Ile Ser Trp Ser Gly Ile Met Ala Tyr Tyr Ala Glu Ser Val Lys
1               5                   10                  15
Gly

<210> SEQ ID NO 207
<211> LENGTH: 16
<212> TYPE: PRT
<213> ORGANISM: Artificial Sequence
<220> FEATURE:
<223> OTHER INFORMATION: CDR2 of VHH sequence 55C05

<400> SEQUENCE: 207

Gln Ile Thr Arg Gly Asp Ser Thr Asn Tyr Ala Asp Ser Val Lys Gly
1               5                   10                  15

<210> SEQ ID NO 208
<211> LENGTH: 16
<212> TYPE: PRT
<213> ORGANISM: Artificial Sequence
<220> FEATURE:
<223> OTHER INFORMATION: CDR2 of VHH sequence 55D08

<400> SEQUENCE: 208

Thr Ile Thr Ser Ala Gly Ser Ser Asn Tyr Ser Asp Ser Val Lys Gly
1               5                   10                  15

<210> SEQ ID NO 209
<211> LENGTH: 16
<212> TYPE: PRT
<213> ORGANISM: Artificial Sequence
<220> FEATURE:
<223> OTHER INFORMATION: CDR2 of VHH sequence 55E02

<400> SEQUENCE: 209

Arg Ile Leu Ser Gly Gly Ser Thr Asn Tyr Ala Asp Ser Val Lys Gly
1               5                   10                  15

<210> SEQ ID NO 210
<211> LENGTH: 16
<212> TYPE: PRT
<213> ORGANISM: Artificial Sequence
<220> FEATURE:
<223> OTHER INFORMATION: CDR2 of VHH sequence 55E07

<400> SEQUENCE: 210

Arg Ile Thr Ser Gly Gly Ser Thr Tyr Tyr Ala Asp Ser Val Lys Gly
1               5                   10                  15

<210> SEQ ID NO 211
<211> LENGTH: 17
<212> TYPE: PRT
<213> ORGANISM: Artificial Sequence
<220> FEATURE:
<223> OTHER INFORMATION: CDR2 of VHH sequence 55E09

<400> SEQUENCE: 211

Ala Ile Ile Trp Ser Gly Gly Arg Thr Arg Tyr Ala Asp Ser Val Lys
1               5                   10                  15
Gly

<210> SEQ ID NO 212
```

```
<211> LENGTH: 16
<212> TYPE: PRT
<213> ORGANISM: Artificial Sequence
<220> FEATURE:
<223> OTHER INFORMATION: CDR2 of VHH sequence 55E10

<400> SEQUENCE: 212

Thr Ile Ser Ser Gly Gly Ser Thr Asn Tyr Ala Asp Ser Val Lys Gly
1               5                   10                  15

<210> SEQ ID NO 213
<211> LENGTH: 16
<212> TYPE: PRT
<213> ORGANISM: Artificial Sequence
<220> FEATURE:
<223> OTHER INFORMATION: CDR2 of VHH sequence 55F04

<400> SEQUENCE: 213

Thr Ile Thr Ser Asp Gly Ser Thr Asn Tyr Ala Asp Ser Val Lys Gly
1               5                   10                  15

<210> SEQ ID NO 214
<211> LENGTH: 17
<212> TYPE: PRT
<213> ORGANISM: Artificial Sequence
<220> FEATURE:
<223> OTHER INFORMATION: CDR2 of VHH sequence 55F09

<400> SEQUENCE: 214

Ala Ile Thr Pro Gly Gly Gly Asn Thr Thr Tyr Ala Asp Ser Val Lys
1               5                   10                  15

Gly

<210> SEQ ID NO 215
<211> LENGTH: 17
<212> TYPE: PRT
<213> ORGANISM: Artificial Sequence
<220> FEATURE:
<223> OTHER INFORMATION: CDR2 of VHH sequence 55F10

<400> SEQUENCE: 215

Thr Ile Arg Arg Ser Gly Ser Ser Thr Tyr Tyr Leu Asp Ser Thr Lys
1               5                   10                  15

Gly

<210> SEQ ID NO 216
<211> LENGTH: 16
<212> TYPE: PRT
<213> ORGANISM: Artificial Sequence
<220> FEATURE:
<223> OTHER INFORMATION: CDR2 of VHH sequence 55G02

<400> SEQUENCE: 216

Phe Ile Thr Ser Gly Gly Ile Thr Asn Tyr Thr Asp Ser Val Lys Gly
1               5                   10                  15

<210> SEQ ID NO 217
<211> LENGTH: 16
<212> TYPE: PRT
<213> ORGANISM: Artificial Sequence
<220> FEATURE:
<223> OTHER INFORMATION: CDR2 of VHH sequence 55G08

<400> SEQUENCE: 217

Ser Ile Ser Ser Gly Gly Thr Thr Asp Tyr Val Glu Ser Val Lys Gly
1               5                   10                  15
```

<210> SEQ ID NO 218
<211> LENGTH: 16
<212> TYPE: PRT
<213> ORGANISM: Artificial Sequence
<220> FEATURE:
<223> OTHER INFORMATION: CDR2 of VHH sequence 56A05

<400> SEQUENCE: 218

Ser Ile Ser Ser Gly Gly Ser Thr Asn Tyr Ala Asp Ser Val Lys Gly
1               5                   10                  15

<210> SEQ ID NO 219
<211> LENGTH: 16
<212> TYPE: PRT
<213> ORGANISM: Artificial Sequence
<220> FEATURE:
<223> OTHER INFORMATION: CDR2 of VHH sequence 56A06

<400> SEQUENCE: 219

Arg Ile Thr Asn Ile Gly Thr Thr Asn Tyr Ala Asp Ser Val Lys Gly
1               5                   10                  15

<210> SEQ ID NO 220
<211> LENGTH: 16
<212> TYPE: PRT
<213> ORGANISM: Artificial Sequence
<220> FEATURE:
<223> OTHER INFORMATION: CDR2 of VHH sequence 56A09

<400> SEQUENCE: 220

Thr Ile Thr Arg Gly Gly Thr Thr Asn Tyr Ala Asp Ser Val Lys Gly
1               5                   10                  15

<210> SEQ ID NO 221
<211> LENGTH: 16
<212> TYPE: PRT
<213> ORGANISM: Artificial Sequence
<220> FEATURE:
<223> OTHER INFORMATION: CDR2 of VHH sequence 56C09

<400> SEQUENCE: 221

Asn Ile Thr Ser Val Gly Ser Thr Asn Tyr Ala Asp Ser Val Lys Gly
1               5                   10                  15

<210> SEQ ID NO 222
<211> LENGTH: 16
<212> TYPE: PRT
<213> ORGANISM: Artificial Sequence
<220> FEATURE:
<223> OTHER INFORMATION: CDR2 of VHH sequence 56C12

<400> SEQUENCE: 222

Ser Ile Ser Gly Ile Arg Ile Thr Thr Tyr Thr Asn Ser Val Lys Gly
1               5                   10                  15

<210> SEQ ID NO 223
<211> LENGTH: 16
<212> TYPE: PRT
<213> ORGANISM: Artificial Sequence
<220> FEATURE:
<223> OTHER INFORMATION: CDR2 of VHH sequence 56D07

<400> SEQUENCE: 223

Val Ile Thr Ser Gly Gly Arg Thr Asn Tyr Ala Glu Ser Val Lys Gly
1               5                   10                  15

<210> SEQ ID NO 224
<211> LENGTH: 16
<212> TYPE: PRT
<213> ORGANISM: Artificial Sequence
<220> FEATURE:
<223> OTHER INFORMATION: CDR2 of VHH sequence 56D07

<400> SEQUENCE: 224

Val Ile Thr Ser Gly Gly Arg Thr Asn Tyr Ala Glu Ser Val Lys Gly
1               5                   10                  15

<210> SEQ ID NO 225
<211> LENGTH: 16
<212> TYPE: PRT
<213> ORGANISM: Artificial Sequence
<220> FEATURE:
<223> OTHER INFORMATION: CDR2 of VHH sequence 56D10

<400> SEQUENCE: 225

Ser Ser Ser Ser Gly Gly Thr Thr Asn Tyr Ala Ser Ser Val Lys Gly
1               5                   10                  15

<210> SEQ ID NO 226
<211> LENGTH: 16
<212> TYPE: PRT
<213> ORGANISM: Artificial Sequence
<220> FEATURE:
<223> OTHER INFORMATION: CDR2 of VHH sequence 56E04

<400> SEQUENCE: 226

Lys Ile Thr Thr Gly Gly Thr Thr Asn Tyr Ala Asp Ser Val Lys Gly
1               5                   10                  15

<210> SEQ ID NO 227
<211> LENGTH: 16
<212> TYPE: PRT
<213> ORGANISM: Artificial Sequence
<220> FEATURE:
<223> OTHER INFORMATION: CDR2 of VHH sequence 56E05

<400> SEQUENCE: 227

Arg Ile Ser Ser Gly Gly Asn Thr Asn Tyr Thr Asp Ser Val Lys Gly
1               5                   10                  15

<210> SEQ ID NO 228
<211> LENGTH: 16
<212> TYPE: PRT
<213> ORGANISM: Artificial Sequence
<220> FEATURE:
<223> OTHER INFORMATION: CDR2 of VHH sequence 56E08

<400> SEQUENCE: 228

Thr Ile Thr Ser Ala Asn Ile Thr Asn Tyr Ala Asp Ser Val Lys Gly
1               5                   10                  15

<210> SEQ ID NO 229
<211> LENGTH: 16
<212> TYPE: PRT
<213> ORGANISM: Artificial Sequence
<220> FEATURE:
<223> OTHER INFORMATION: CDR2 of VHH sequence 56F07

<400> SEQUENCE: 229

Ile Ile Thr Asn Asp Asp Ser Thr Thr Tyr Ala Asp Ser Val Lys Gly
1               5                   10                  15

-continued

```
<210> SEQ ID NO 230
<211> LENGTH: 16
<212> TYPE: PRT
<213> ORGANISM: Artificial Sequence
<220> FEATURE:
<223> OTHER INFORMATION: CDR2 of VHH sequence 56F11

<400> SEQUENCE: 230

Thr Ile Thr Ser Gly Gly Thr Thr Asn Tyr Ala Asp Ser Val Lys Gly
1               5                   10                  15

<210> SEQ ID NO 231
<211> LENGTH: 16
<212> TYPE: PRT
<213> ORGANISM: Artificial Sequence
<220> FEATURE:
<223> OTHER INFORMATION: CDR2 of VHH sequence 56G07

<400> SEQUENCE: 231

Thr Ile Thr Pro Phe Gly Arg Arg Asn Tyr Ser Glu Tyr Val Lys Gly
1               5                   10                  15

<210> SEQ ID NO 232
<211> LENGTH: 16
<212> TYPE: PRT
<213> ORGANISM: Artificial Sequence
<220> FEATURE:
<223> OTHER INFORMATION: CDR2 of VHH sequence 56G08

<400> SEQUENCE: 232

Thr Leu Ser Arg Ala Gly Thr Ser Arg Tyr Val Asp Ser Val Lys Gly
1               5                   10                  15

<210> SEQ ID NO 233
<211> LENGTH: 16
<212> TYPE: PRT
<213> ORGANISM: Artificial Sequence
<220> FEATURE:
<223> OTHER INFORMATION: CDR2 of VHH sequence 56G10

<400> SEQUENCE: 233

Glu Ile Ser Ser Arg Gly Thr Thr Met Tyr Ala Asp Ser Val Lys Gly
1               5                   10                  15

<210> SEQ ID NO 234
<211> LENGTH: 16
<212> TYPE: PRT
<213> ORGANISM: Artificial Sequence
<220> FEATURE:
<223> OTHER INFORMATION: CDR2 of VHH sequence 56H04

<400> SEQUENCE: 234

Arg Ile Ser Thr Val Gly Thr Ala His Tyr Ala Asp Ser Val Lys Gly
1               5                   10                  15

<210> SEQ ID NO 235
<211> LENGTH: 16
<212> TYPE: PRT
<213> ORGANISM: Artificial Sequence
<220> FEATURE:
<223> OTHER INFORMATION: CDR2 of VHH sequence 56H05

<400> SEQUENCE: 235

Gln Ile Asn Asn Arg Asp Asn Thr Glu Tyr Ala Asp Ser Val Lys Gly
1               5                   10                  15

<210> SEQ ID NO 236
```

```
<211> LENGTH: 15
<212> TYPE: PRT
<213> ORGANISM: Artificial Sequence
<220> FEATURE:
<223> OTHER INFORMATION: CDR2 of VHH sequence 56H07

<400> SEQUENCE: 236

Ser Ile Ser Thr Gly Ser Thr Asn Tyr Ala Asp Ser Val Lys Gly
1               5                   10                  15

<210> SEQ ID NO 237
<211> LENGTH: 16
<212> TYPE: PRT
<213> ORGANISM: Artificial Sequence
<220> FEATURE:
<223> OTHER INFORMATION: CDR2 of VHH sequence 56H08

<400> SEQUENCE: 237

Val Ile Ser Ser Asp Gly Ser Thr Asn Tyr Ala Asp Ser Val Lys Gly
1               5                   10                  15

<210> SEQ ID NO 238
<211> LENGTH: 16
<212> TYPE: PRT
<213> ORGANISM: Artificial Sequence
<220> FEATURE:
<223> OTHER INFORMATION: CDR2 of VHH sequence 57A06

<400> SEQUENCE: 238

Arg Ile Ser Ser Gly Gly Asn Thr Asn Tyr Thr Asp Ser Val Lys Gly
1               5                   10                  15

<210> SEQ ID NO 239
<211> LENGTH: 16
<212> TYPE: PRT
<213> ORGANISM: Artificial Sequence
<220> FEATURE:
<223> OTHER INFORMATION: CDR2 of VHH sequence 57B01

<400> SEQUENCE: 239

Arg Ile Ser Ser Gly Gly Ser Thr Asn Tyr Ala Asp Ser Val Lys Gly
1               5                   10                  15

<210> SEQ ID NO 240
<211> LENGTH: 16
<212> TYPE: PRT
<213> ORGANISM: Artificial Sequence
<220> FEATURE:
<223> OTHER INFORMATION: CDR2 of VHH sequence 57B07

<400> SEQUENCE: 240

Thr Val Asp Ser Gly Gly Tyr Thr Asn Tyr Ala Asp Ser Val Lys Gly
1               5                   10                  15

<210> SEQ ID NO 241
<211> LENGTH: 16
<212> TYPE: PRT
<213> ORGANISM: Artificial Sequence
<220> FEATURE:
<223> OTHER INFORMATION: CDR2 of VHH sequence 57B11

<400> SEQUENCE: 241

Leu Ile Arg Ser Ser Gly Gly Thr Tyr Tyr Ala Asp Ser Val Lys Gly
1               5                   10                  15

<210> SEQ ID NO 242
<211> LENGTH: 16
```

```
<212> TYPE: PRT
<213> ORGANISM: Artificial Sequence
<220> FEATURE:
<223> OTHER INFORMATION: CDR2 of VHH sequence 57C07

<400> SEQUENCE: 242

Ser Ile Ser Arg Gly Gly Met Thr Asn Tyr Ala Asp Ser Val Lys Gly
1               5                   10                  15

<210> SEQ ID NO 243
<211> LENGTH: 16
<212> TYPE: PRT
<213> ORGANISM: Artificial Sequence
<220> FEATURE:
<223> OTHER INFORMATION: CDR2 of VHH sequence 57C09

<400> SEQUENCE: 243

Ser Ile Ser Ser Gly Gly Ala Thr Asn Tyr Ala Asp Ser Val Lys Gly
1               5                   10                  15

<210> SEQ ID NO 244
<211> LENGTH: 16
<212> TYPE: PRT
<213> ORGANISM: Artificial Sequence
<220> FEATURE:
<223> OTHER INFORMATION: CDR2 of VHH sequence 57D02

<400> SEQUENCE: 244

Thr Ile Thr Arg Arg Ser Arg Thr Asn Tyr Ala Glu Phe Val Lys Gly
1               5                   10                  15

<210> SEQ ID NO 245
<211> LENGTH: 16
<212> TYPE: PRT
<213> ORGANISM: Artificial Sequence
<220> FEATURE:
<223> OTHER INFORMATION: CDR2 of VHH sequence 57D09

<400> SEQUENCE: 245

Ser Ile Thr Thr Gly Gly Ser Thr Asn Tyr Ala Asp Ser Val Lys Gly
1               5                   10                  15

<210> SEQ ID NO 246
<211> LENGTH: 16
<212> TYPE: PRT
<213> ORGANISM: Artificial Sequence
<220> FEATURE:
<223> OTHER INFORMATION: CDR2 of VHH sequence 57D10

<400> SEQUENCE: 246

Ser Ile Thr Lys Asp Gly Thr Thr Asn Tyr Ala Asp Ser Val Lys Gly
1               5                   10                  15

<210> SEQ ID NO 247
<211> LENGTH: 16
<212> TYPE: PRT
<213> ORGANISM: Artificial Sequence
<220> FEATURE:
<223> OTHER INFORMATION: CDR2 of VHH sequence 57E07

<400> SEQUENCE: 247

Asp Ile Thr Arg Ser Gly Ser Thr His Tyr Val Asp Ser Val Lys Gly
1               5                   10                  15

<210> SEQ ID NO 248
<211> LENGTH: 16
<212> TYPE: PRT
```

<213> ORGANISM: Artificial Sequence
<220> FEATURE:
<223> OTHER INFORMATION: CDR2 of VHH sequence 57E11

<400> SEQUENCE: 248

Arg Ile Ser Arg Leu Arg Val Thr Asn Tyr Ala Asp Ser Val Lys Gly
1               5                   10                  15

<210> SEQ ID NO 249
<211> LENGTH: 16
<212> TYPE: PRT
<213> ORGANISM: Artificial Sequence
<220> FEATURE:
<223> OTHER INFORMATION: CDR2 of VHH sequence 57G01

<400> SEQUENCE: 249

Thr Ile Ser Asn Ser Gly Thr Thr Asn Tyr Val Asp Ala Val Lys Gly
1               5                   10                  15

<210> SEQ ID NO 250
<211> LENGTH: 16
<212> TYPE: PRT
<213> ORGANISM: Artificial Sequence
<220> FEATURE:
<223> OTHER INFORMATION: CDR2 of VHH sequence 57G07

<400> SEQUENCE: 250

Thr Ile Arg Arg Gly Gly Asn Thr Lys Tyr Ala Asp Ser Val Lys Gly
1               5                   10                  15

<210> SEQ ID NO 251
<211> LENGTH: 16
<212> TYPE: PRT
<213> ORGANISM: Artificial Sequence
<220> FEATURE:
<223> OTHER INFORMATION: CDR2 of VHH sequence 57G08

<400> SEQUENCE: 251

Thr Ile Asp Ile His Asn Ser Thr Lys Tyr Ala Asp Ser Val Lys Gly
1               5                   10                  15

<210> SEQ ID NO 252
<211> LENGTH: 16
<212> TYPE: PRT
<213> ORGANISM: Artificial Sequence
<220> FEATURE:
<223> OTHER INFORMATION: CDR2 of VHH sequence 57H08

<400> SEQUENCE: 252

Gln Gln Arg Tyr Asp Gly Ser Thr Asn Tyr Ala Asp Ser Leu Gln Gly
1               5                   10                  15

<210> SEQ ID NO 253
<211> LENGTH: 10
<212> TYPE: PRT
<213> ORGANISM: Artificial Sequence
<220> FEATURE:
<223> OTHER INFORMATION: CDR3 of VHH sequence 40F07

<400> SEQUENCE: 253

Ala Arg Thr Trp Ser Ile Phe Arg Asn Tyr
1               5                   10

<210> SEQ ID NO 254
<211> LENGTH: 7
<212> TYPE: PRT
<213> ORGANISM: Artificial Sequence

```
<220> FEATURE:
<223> OTHER INFORMATION: CDR3 of VHH sequence 41D01

<400> SEQUENCE: 254

Arg Ser Ile Trp Arg Asp Tyr
1               5

<210> SEQ ID NO 255
<211> LENGTH: 8
<212> TYPE: PRT
<213> ORGANISM: Artificial Sequence
<220> FEATURE:
<223> OTHER INFORMATION: CDR3 of VHH sequence 41D06

<400> SEQUENCE: 255

Val Arg Leu Trp Phe Pro Asp Tyr
1               5

<210> SEQ ID NO 256
<211> LENGTH: 13
<212> TYPE: PRT
<213> ORGANISM: Artificial Sequence
<220> FEATURE:
<223> OTHER INFORMATION: CDR3 of VHH sequence 41G10

<400> SEQUENCE: 256

Glu Ala Arg Arg Tyr Phe Thr Arg Ala Ser Gln Val Tyr
1               5                   10

<210> SEQ ID NO 257
<211> LENGTH: 12
<212> TYPE: PRT
<213> ORGANISM: Artificial Sequence
<220> FEATURE:
<223> OTHER INFORMATION: CDR3 of VHH sequence 41H05

<400> SEQUENCE: 257

Val Gly Arg Arg Trp Tyr Gly Gly Tyr Val Glu Leu
1               5                   10

<210> SEQ ID NO 258
<211> LENGTH: 11
<212> TYPE: PRT
<213> ORGANISM: Artificial Sequence
<220> FEATURE:
<223> OTHER INFORMATION: CDR3 of VHH sequence 42C11

<400> SEQUENCE: 258

Asp Arg Trp Val Leu Thr Arg Trp Ser Asn Tyr
1               5                   10

<210> SEQ ID NO 259
<211> LENGTH: 11
<212> TYPE: PRT
<213> ORGANISM: Artificial Sequence
<220> FEATURE:
<223> OTHER INFORMATION: CDR3 of VHH sequence 42C12

<400> SEQUENCE: 259

Gln Arg Gly Val Ala Trp Thr Arg Lys Glu Tyr
1               5                   10

<210> SEQ ID NO 260
<211> LENGTH: 11
<212> TYPE: PRT
<213> ORGANISM: Artificial Sequence
<220> FEATURE:
```

<223> OTHER INFORMATION: CDR3 of VHH sequence 50D03

<400> SEQUENCE: 260

Asp Arg Trp Val Leu Thr Arg Trp Ser Asn Tyr
1               5                   10

<210> SEQ ID NO 261
<211> LENGTH: 12
<212> TYPE: PRT
<213> ORGANISM: Artificial Sequence
<220> FEATURE:
<223> OTHER INFORMATION: CDR3 of VHH sequence 50D07

<400> SEQUENCE: 261

Arg Val Arg Thr Val Leu Arg Gly Trp Arg Asp Tyr
1               5                   10

<210> SEQ ID NO 262
<211> LENGTH: 11
<212> TYPE: PRT
<213> ORGANISM: Artificial Sequence
<220> FEATURE:
<223> OTHER INFORMATION: CDR3 of VHH sequence 50E02

<400> SEQUENCE: 262

Arg Arg Arg Thr Phe Leu Lys Ser Ser Asp Tyr
1               5                   10

<210> SEQ ID NO 263
<211> LENGTH: 15
<212> TYPE: PRT
<213> ORGANISM: Artificial Sequence
<220> FEATURE:
<223> OTHER INFORMATION: CDR3 of VHH sequence 51B08

<400> SEQUENCE: 263

Lys Tyr Gly Arg Trp Thr Tyr Thr Gly Arg Pro Glu Tyr Asp Ser
1               5                   10                  15

<210> SEQ ID NO 264
<211> LENGTH: 8
<212> TYPE: PRT
<213> ORGANISM: Artificial Sequence
<220> FEATURE:
<223> OTHER INFORMATION: CDR3 of VHH sequence 51C06

<400> SEQUENCE: 264

Arg Arg Arg Trp Ser Arg Asp Phe
1               5

<210> SEQ ID NO 265
<211> LENGTH: 11
<212> TYPE: PRT
<213> ORGANISM: Artificial Sequence
<220> FEATURE:
<223> OTHER INFORMATION: CDR3 of VHH sequence 51C08

<400> SEQUENCE: 265

Arg Gln Gln Phe Ile Gly Ala Pro Tyr Glu Tyr
1               5                   10

<210> SEQ ID NO 266
<211> LENGTH: 7
<212> TYPE: PRT
<213> ORGANISM: Artificial Sequence
<220> FEATURE:
<223> OTHER INFORMATION: CDR3 of VHH sequence 52A01

```
<400> SEQUENCE: 266

Arg Leu Leu Trp Ser Asn Tyr
1               5

<210> SEQ ID NO 267
<211> LENGTH: 9
<212> TYPE: PRT
<213> ORGANISM: Artificial Sequence
<220> FEATURE:
<223> OTHER INFORMATION: CDR3 of VHH sequence 52B01

<400> SEQUENCE: 267

Ala Gly Trp Val Gly Val Thr Asn Tyr
1               5

<210> SEQ ID NO 268
<211> LENGTH: 9
<212> TYPE: PRT
<213> ORGANISM: Artificial Sequence
<220> FEATURE:
<223> OTHER INFORMATION: CDR3 of VHH sequence 52G05

<400> SEQUENCE: 268

Arg Arg Tyr Tyr Thr Arg Asn Asp Tyr
1               5

<210> SEQ ID NO 269
<211> LENGTH: 6
<212> TYPE: PRT
<213> ORGANISM: Artificial Sequence
<220> FEATURE:
<223> OTHER INFORMATION: CDR3 of VHH sequence 53A01

<400> SEQUENCE: 269

Gly Ala Ile Gly Asn Trp
1               5

<210> SEQ ID NO 270
<211> LENGTH: 9
<212> TYPE: PRT
<213> ORGANISM: Artificial Sequence
<220> FEATURE:
<223> OTHER INFORMATION: CDR3 of VHH sequence 53F05

<400> SEQUENCE: 270

Glu Arg Arg Trp Gly Leu Pro Asn Tyr
1               5

<210> SEQ ID NO 271
<211> LENGTH: 17
<212> TYPE: PRT
<213> ORGANISM: Artificial Sequence
<220> FEATURE:
<223> OTHER INFORMATION: CDR3 of VHH sequence 54A02

<400> SEQUENCE: 271

Tyr Ala His Ile Thr Ala Trp Gly Met Arg Asn Asp Tyr Glu Tyr Asp
1               5                   10                  15

Tyr

<210> SEQ ID NO 272
<211> LENGTH: 16
<212> TYPE: PRT
<213> ORGANISM: Artificial Sequence
<220> FEATURE:
```

<223> OTHER INFORMATION: CDR3 of VHH sequence 54B01

<400> SEQUENCE: 272

Gly Asn Leu Leu Arg Leu Ala Gly Gln Leu Arg Arg Gly Tyr Asp Ser
1               5                   10                  15

<210> SEQ ID NO 273
<211> LENGTH: 20
<212> TYPE: PRT
<213> ORGANISM: Artificial Sequence
<220> FEATURE:
<223> OTHER INFORMATION: CDR3 of VHH sequence 54C01

<400> SEQUENCE: 273

Arg Asn Arg Ala Gly Pro His Tyr Ser Arg Gly Tyr Thr Ala Gly Gln
1               5                   10                  15

Glu Tyr Asp Tyr
            20

<210> SEQ ID NO 274
<211> LENGTH: 13
<212> TYPE: PRT
<213> ORGANISM: Artificial Sequence
<220> FEATURE:
<223> OTHER INFORMATION: CDR3 of VHH sequence 54C04

<400> SEQUENCE: 274

Asn Leu Arg Thr Ala Phe Trp Arg Asn Gly Asn Asp Tyr
1               5                   10

<210> SEQ ID NO 275
<211> LENGTH: 7
<212> TYPE: PRT
<213> ORGANISM: Artificial Sequence
<220> FEATURE:
<223> OTHER INFORMATION: CDR3 of VHH sequence 54C08

<400> SEQUENCE: 275

Gly Pro Trp Tyr Arg Arg Ser
1               5

<210> SEQ ID NO 276
<211> LENGTH: 8
<212> TYPE: PRT
<213> ORGANISM: Artificial Sequence
<220> FEATURE:
<223> OTHER INFORMATION: CDR3 of VHH sequence 54C10

<400> SEQUENCE: 276

Asp Leu Ala Val Arg Gly Arg Tyr
1               5

<210> SEQ ID NO 277
<211> LENGTH: 11
<212> TYPE: PRT
<213> ORGANISM: Artificial Sequence
<220> FEATURE:
<223> OTHER INFORMATION: CDR3 of VHH sequence 54C11

<400> SEQUENCE: 277

Arg Ile Gly Phe Gly Trp Thr Ala Lys Ala Tyr
1               5                   10

<210> SEQ ID NO 278
<211> LENGTH: 8
<212> TYPE: PRT

-continued

```
<213> ORGANISM: Artificial Sequence
<220> FEATURE:
<223> OTHER INFORMATION: CDR3 of VHH sequence 54D03

<400> SEQUENCE: 278

Val Arg Leu Trp Phe Pro Asp Tyr
1               5

<210> SEQ ID NO 279
<211> LENGTH: 8
<212> TYPE: PRT
<213> ORGANISM: Artificial Sequence
<220> FEATURE:
<223> OTHER INFORMATION: CDR3 of VHH sequence 54D06

<400> SEQUENCE: 279

Arg Ser Trp Val Gly Pro Glu Tyr
1               5

<210> SEQ ID NO 280
<211> LENGTH: 12
<212> TYPE: PRT
<213> ORGANISM: Artificial Sequence
<220> FEATURE:
<223> OTHER INFORMATION: CDR3 of VHH sequence 54D10

<400> SEQUENCE: 280

Lys Thr Arg Thr Trp Tyr Asn Gly Lys Tyr Asp Tyr
1               5                   10

<210> SEQ ID NO 281
<211> LENGTH: 9
<212> TYPE: PRT
<213> ORGANISM: Artificial Sequence
<220> FEATURE:
<223> OTHER INFORMATION: CDR3 of VHH sequence 54E01

<400> SEQUENCE: 281

Arg Ser Thr Leu Trp Arg Arg Asp Tyr
1               5

<210> SEQ ID NO 282
<211> LENGTH: 9
<212> TYPE: PRT
<213> ORGANISM: Artificial Sequence
<220> FEATURE:
<223> OTHER INFORMATION: CDR3 of VHH sequence 54E05

<400> SEQUENCE: 282

His Arg Ser Trp Pro Arg Tyr Asp Ser
1               5

<210> SEQ ID NO 283
<211> LENGTH: 10
<212> TYPE: PRT
<213> ORGANISM: Artificial Sequence
<220> FEATURE:
<223> OTHER INFORMATION: CDR3 of VHH sequence 54E10

<400> SEQUENCE: 283

Glu Ser Arg Ile Phe Arg Arg Tyr Asp Tyr
1               5                   10

<210> SEQ ID NO 284
<211> LENGTH: 7
<212> TYPE: PRT
<213> ORGANISM: Artificial Sequence
```

-continued

```
<220> FEATURE:
<223> OTHER INFORMATION: CDR3 of VHH sequence 54F01

<400> SEQUENCE: 284

Asp Arg Gly Trp Ser Ser Tyr
1               5

<210> SEQ ID NO 285
<211> LENGTH: 11
<212> TYPE: PRT
<213> ORGANISM: Artificial Sequence
<220> FEATURE:
<223> OTHER INFORMATION: CDR3 of VHH sequence 54F02

<400> SEQUENCE: 285

His Gln Arg Ala Trp Ala Arg Ser Tyr Val Tyr
1               5                   10

<210> SEQ ID NO 286
<211> LENGTH: 9
<212> TYPE: PRT
<213> ORGANISM: Artificial Sequence
<220> FEATURE:
<223> OTHER INFORMATION: CDR3 of VHH sequence 54G01

<400> SEQUENCE: 286

Lys Arg Ser Trp Phe Ser Gln Glu Tyr
1               5

<210> SEQ ID NO 287
<211> LENGTH: 13
<212> TYPE: PRT
<213> ORGANISM: Artificial Sequence
<220> FEATURE:
<223> OTHER INFORMATION: CDR3 of VHH sequence 54G08

<400> SEQUENCE: 287

Gln Tyr Thr Ile Thr Pro Trp Gly Ile Lys Lys Asp Tyr
1               5                   10

<210> SEQ ID NO 288
<211> LENGTH: 12
<212> TYPE: PRT
<213> ORGANISM: Artificial Sequence
<220> FEATURE:
<223> OTHER INFORMATION: CDR3 of VHH sequence 54G09

<400> SEQUENCE: 288

Arg Val Arg Thr Val Leu Arg Gly Trp Arg Asp Tyr
1               5                   10

<210> SEQ ID NO 289
<211> LENGTH: 9
<212> TYPE: PRT
<213> ORGANISM: Artificial Sequence
<220> FEATURE:
<223> OTHER INFORMATION: CDR3 of VHH sequence 55B02

<400> SEQUENCE: 289

Asn Ser Ile Phe Arg Ser Arg Asp Tyr
1               5

<210> SEQ ID NO 290
<211> LENGTH: 16
<212> TYPE: PRT
<213> ORGANISM: Artificial Sequence
<220> FEATURE:
```

-continued

<223> OTHER INFORMATION: CDR3 of VHH sequence 55B05

<400> SEQUENCE: 290

Arg Ser Gln Ile Arg Ser Pro Trp Ser Ser Leu Asp Asp Tyr Asp Arg
1               5                   10                  15

<210> SEQ ID NO 291
<211> LENGTH: 8
<212> TYPE: PRT
<213> ORGANISM: Artificial Sequence
<220> FEATURE:
<223> OTHER INFORMATION: CDR3 of VHH sequence 55C05

<400> SEQUENCE: 291

Asp Arg Phe Phe Gly Arg Asp Tyr
1               5

<210> SEQ ID NO 292
<211> LENGTH: 12
<212> TYPE: PRT
<213> ORGANISM: Artificial Sequence
<220> FEATURE:
<223> OTHER INFORMATION: CDR3 of VHH sequence 55D08

<400> SEQUENCE: 292

Val Tyr Ser Arg Pro Leu Leu Gly Pro Leu Glu Val
1               5                   10

<210> SEQ ID NO 293
<211> LENGTH: 7
<212> TYPE: PRT
<213> ORGANISM: Artificial Sequence
<220> FEATURE:
<223> OTHER INFORMATION: CDR3 of VHH sequence 55E02

<400> SEQUENCE: 293

Val Arg Tyr Leu Val Asn Tyr
1               5

<210> SEQ ID NO 294
<211> LENGTH: 13
<212> TYPE: PRT
<213> ORGANISM: Artificial Sequence
<220> FEATURE:
<223> OTHER INFORMATION: CDR3 of VHH sequence 55E07

<400> SEQUENCE: 294

Gly Val Val Val Ala Thr Ser Pro Lys Phe Tyr Ala Tyr
1               5                   10

<210> SEQ ID NO 295
<211> LENGTH: 7
<212> TYPE: PRT
<213> ORGANISM: Artificial Sequence
<220> FEATURE:
<223> OTHER INFORMATION: CDR3 of VHH sequence 55E09

<400> SEQUENCE: 295

Arg Arg Leu Gly Thr Gly Tyr
1               5

<210> SEQ ID NO 296
<211> LENGTH: 7
<212> TYPE: PRT
<213> ORGANISM: Artificial Sequence
<220> FEATURE:
<223> OTHER INFORMATION: CDR3 of VHH sequence 55E10

-continued

<400> SEQUENCE: 296

Arg Tyr Trp Phe Arg Asp Tyr
1               5

<210> SEQ ID NO 297
<211> LENGTH: 7
<212> TYPE: PRT
<213> ORGANISM: Artificial Sequence
<220> FEATURE:
<223> OTHER INFORMATION: CDR3 of VHH sequence 55F04

<400> SEQUENCE: 297

Val Arg Leu Phe Arg Gln Tyr
1               5

<210> SEQ ID NO 298
<211> LENGTH: 16
<212> TYPE: PRT
<213> ORGANISM: Artificial Sequence
<220> FEATURE:
<223> OTHER INFORMATION: CDR3 of VHH sequence 55F09

<400> SEQUENCE: 298

Gly Gly Ser Ser Arg Trp Tyr Ser Ser Arg Tyr Tyr Pro Gly Gly Tyr
1               5                   10                  15

<210> SEQ ID NO 299
<211> LENGTH: 17
<212> TYPE: PRT
<213> ORGANISM: Artificial Sequence
<220> FEATURE:
<223> OTHER INFORMATION: CDR3 of VHH sequence 55F10

<400> SEQUENCE: 299

Asp Ser Ser Ala Arg Ala Leu Val Gly Gly Pro Gly Asn Arg Trp Asp
1               5                   10                  15

Tyr

<210> SEQ ID NO 300
<211> LENGTH: 10
<212> TYPE: PRT
<213> ORGANISM: Artificial Sequence
<220> FEATURE:
<223> OTHER INFORMATION: CDR3 of VHH sequence 55G02

<400> SEQUENCE: 300

Lys Asn Ala Lys Asn Val Arg Pro Gly Tyr
1               5                   10

<210> SEQ ID NO 301
<211> LENGTH: 8
<212> TYPE: PRT
<213> ORGANISM: Artificial Sequence
<220> FEATURE:
<223> OTHER INFORMATION: CDR3 of VHH sequence 55G08

<400> SEQUENCE: 301

Val Arg Phe Trp Phe Pro Asp Tyr
1               5

<210> SEQ ID NO 302
<211> LENGTH: 8
<212> TYPE: PRT
<213> ORGANISM: Artificial Sequence
<220> FEATURE:

```
<223> OTHER INFORMATION: CDR3 of VHH sequence 56A05

<400> SEQUENCE: 302

Arg Arg Asn Val Phe Ile Ser Ser
1               5

<210> SEQ ID NO 303
<211> LENGTH: 7
<212> TYPE: PRT
<213> ORGANISM: Artificial Sequence
<220> FEATURE:
<223> OTHER INFORMATION: CDR3 of VHH sequence 56A06

<400> SEQUENCE: 303

Arg Arg Leu Gly Arg Asp Tyr
1               5

<210> SEQ ID NO 304
<211> LENGTH: 10
<212> TYPE: PRT
<213> ORGANISM: Artificial Sequence
<220> FEATURE:
<223> OTHER INFORMATION: CDR3 of VHH sequence 56A09

<400> SEQUENCE: 304

Asn Phe Gly Ile Leu Val Gly Arg Glu Tyr
1               5                   10

<210> SEQ ID NO 305
<211> LENGTH: 8
<212> TYPE: PRT
<213> ORGANISM: Artificial Sequence
<220> FEATURE:
<223> OTHER INFORMATION: CDR3 of VHH sequence 56C09

<400> SEQUENCE: 305

Arg Met Pro Phe Leu Gly Asp Ser
1               5

<210> SEQ ID NO 306
<211> LENGTH: 8
<212> TYPE: PRT
<213> ORGANISM: Artificial Sequence
<220> FEATURE:
<223> OTHER INFORMATION: CDR3 of VHH sequence 56D06

<400> SEQUENCE: 306

Thr Ser Ile Thr Gly Thr Tyr Leu
1               5

<210> SEQ ID NO 307
<211> LENGTH: 6
<212> TYPE: PRT
<213> ORGANISM: Artificial Sequence
<220> FEATURE:
<223> OTHER INFORMATION: CDR3 of VHH sequence 56D07

<400> SEQUENCE: 307

Lys Thr Ile Arg Pro Tyr
1               5

<210> SEQ ID NO 308
<211> LENGTH: 12
<212> TYPE: PRT
<213> ORGANISM: Artificial Sequence
<220> FEATURE:
<223> OTHER INFORMATION: CDR3 of VHH sequence 56D10
```

```
<400> SEQUENCE: 308

Arg Lys Phe Ile Thr Thr Pro Trp Ser Thr Asp Tyr
1               5                   10

<210> SEQ ID NO 309
<211> LENGTH: 8
<212> TYPE: PRT
<213> ORGANISM: Artificial Sequence
<220> FEATURE:
<223> OTHER INFORMATION: CDR3 of VHH sequence 56E04

<400> SEQUENCE: 309

Glu Arg Tyr Phe Ala Thr Thr Leu
1               5

<210> SEQ ID NO 310
<211> LENGTH: 11
<212> TYPE: PRT
<213> ORGANISM: Artificial Sequence
<220> FEATURE:
<223> OTHER INFORMATION: CDR3 of VHH sequence 56E05

<400> SEQUENCE: 310

Gln Arg Arg Val Ile Leu Gly Pro Arg Asn Tyr
1               5                   10

<210> SEQ ID NO 311
<211> LENGTH: 13
<212> TYPE: PRT
<213> ORGANISM: Artificial Sequence
<220> FEATURE:
<223> OTHER INFORMATION: CDR3 of VHH sequence 56E08

<400> SEQUENCE: 311

Gln Ala Lys Lys Trp Arg Ile Gly Pro Trp Ser Asp Tyr
1               5                   10

<210> SEQ ID NO 312
<211> LENGTH: 11
<212> TYPE: PRT
<213> ORGANISM: Artificial Sequence
<220> FEATURE:
<223> OTHER INFORMATION: CDR3 of VHH sequence 56F07

<400> SEQUENCE: 312

Asp Ile Asn Thr Ala Ile Trp Arg Arg Lys Tyr
1               5                   10

<210> SEQ ID NO 313
<211> LENGTH: 13
<212> TYPE: PRT
<213> ORGANISM: Artificial Sequence
<220> FEATURE:
<223> OTHER INFORMATION: CDR3 of VHH sequence 56F11

<400> SEQUENCE: 313

Asn Thr Arg Arg Ile Phe Gly Gly Thr Val Arg Glu Tyr
1               5                   10

<210> SEQ ID NO 314
<211> LENGTH: 7
<212> TYPE: PRT
<213> ORGANISM: Artificial Sequence
<220> FEATURE:
<223> OTHER INFORMATION: CDR3 of VHH sequence 56G07
```

```
<400> SEQUENCE: 314

Arg Val Asn Gly Val Asp Tyr
1               5

<210> SEQ ID NO 315
<211> LENGTH: 7
<212> TYPE: PRT
<213> ORGANISM: Artificial Sequence
<220> FEATURE:
<223> OTHER INFORMATION: CDR3 of VHH sequence 56G08

<400> SEQUENCE: 315

Ala Gln Leu Gly Thr Asp Tyr
1               5

<210> SEQ ID NO 316
<211> LENGTH: 9
<212> TYPE: PRT
<213> ORGANISM: Artificial Sequence
<220> FEATURE:
<223> OTHER INFORMATION: CDR3 of VHH sequence 56G10

<400> SEQUENCE: 316

Arg Ala Phe Ala Phe Gly Arg Asn Ser
1               5

<210> SEQ ID NO 317
<211> LENGTH: 10
<212> TYPE: PRT
<213> ORGANISM: Artificial Sequence
<220> FEATURE:
<223> OTHER INFORMATION: CDR3 of VHH sequence 56H04

<400> SEQUENCE: 317

Gln Ala Gly Arg Leu Tyr Leu Arg Asn Tyr
1               5                   10

<210> SEQ ID NO 318
<211> LENGTH: 9
<212> TYPE: PRT
<213> ORGANISM: Artificial Sequence
<220> FEATURE:
<223> OTHER INFORMATION: CDR3 of VHH sequence 56H05

<400> SEQUENCE: 318

Lys Arg Trp Ser Trp Ser Thr Gly Phe
1               5

<210> SEQ ID NO 319
<211> LENGTH: 7
<212> TYPE: PRT
<213> ORGANISM: Artificial Sequence
<220> FEATURE:
<223> OTHER INFORMATION: CDR3 of VHH sequence 56H07

<400> SEQUENCE: 319

Arg Leu Trp Trp Ser Asn Tyr
1               5

<210> SEQ ID NO 320
<211> LENGTH: 10
<212> TYPE: PRT
<213> ORGANISM: Artificial Sequence
<220> FEATURE:
<223> OTHER INFORMATION: CDR3 of VHH sequence 56H08

<400> SEQUENCE: 320
```

Asn Arg Arg Trp Ser Trp Gly Ser Glu Tyr
1               5                   10

<210> SEQ ID NO 321
<211> LENGTH: 11
<212> TYPE: PRT
<213> ORGANISM: Artificial Sequence
<220> FEATURE:
<223> OTHER INFORMATION: CDR3 of VHH sequence 57A06

<400> SEQUENCE: 321

Gln Arg Arg Val Ile Leu Gly Pro Arg Asn Tyr
1               5                   10

<210> SEQ ID NO 322
<211> LENGTH: 8
<212> TYPE: PRT
<213> ORGANISM: Artificial Sequence
<220> FEATURE:
<223> OTHER INFORMATION: CDR3 of VHH sequence 57B01

<400> SEQUENCE: 322

Asn Arg His Trp Gly Trp Asp Tyr
1               5

<210> SEQ ID NO 323
<211> LENGTH: 14
<212> TYPE: PRT
<213> ORGANISM: Artificial Sequence
<220> FEATURE:
<223> OTHER INFORMATION: CDR3 of VHH sequence 57B07

<400> SEQUENCE: 323

Gly Ile Tyr Lys Trp Pro Trp Ser Val Asp Ala Arg Asp Tyr
1               5                   10

<210> SEQ ID NO 324
<211> LENGTH: 9
<212> TYPE: PRT
<213> ORGANISM: Artificial Sequence
<220> FEATURE:
<223> OTHER INFORMATION: CDR3 of VHH sequence 57B11

<400> SEQUENCE: 324

Arg Arg Thr Trp Leu Ser Ser Glu Ser
1               5

<210> SEQ ID NO 325
<211> LENGTH: 14
<212> TYPE: PRT
<213> ORGANISM: Artificial Sequence
<220> FEATURE:
<223> OTHER INFORMATION: CDR3 of VHH sequence 57C07

<400> SEQUENCE: 325

Gly Ile Arg Ser Arg Trp Tyr Gly Gly Pro Ile Thr Thr Tyr
1               5                   10

<210> SEQ ID NO 326
<211> LENGTH: 13
<212> TYPE: PRT
<213> ORGANISM: Artificial Sequence
<220> FEATURE:
<223> OTHER INFORMATION: CDR3 of VHH sequence 57C09

<400> SEQUENCE: 326

```
Lys Lys Ser Arg Trp Ser Trp Ser Ile Val His Asp Tyr
1               5                   10

<210> SEQ ID NO 327
<211> LENGTH: 10
<212> TYPE: PRT
<213> ORGANISM: Artificial Sequence
<220> FEATURE:
<223> OTHER INFORMATION: CDR3 of VHH sequence 57D02

<400> SEQUENCE: 327

Arg Trp Gly Ala Gly Gly Ile Phe Ser Thr
1               5                   10

<210> SEQ ID NO 328
<211> LENGTH: 13
<212> TYPE: PRT
<213> ORGANISM: Artificial Sequence
<220> FEATURE:
<223> OTHER INFORMATION: CDR3 of VHH sequence 57D09

<400> SEQUENCE: 328

Lys Val Arg Leu Arg Trp Phe Arg Pro Pro Ser Asp Tyr
1               5                   10

<210> SEQ ID NO 329
<211> LENGTH: 14
<212> TYPE: PRT
<213> ORGANISM: Artificial Sequence
<220> FEATURE:
<223> OTHER INFORMATION: CDR3 of VHH sequence 57D10

<400> SEQUENCE: 329

Arg Ala Thr Thr Trp Val Pro Tyr Arg Arg Asp Ala Glu Phe
1               5                   10

<210> SEQ ID NO 330
<211> LENGTH: 12
<212> TYPE: PRT
<213> ORGANISM: Artificial Sequence
<220> FEATURE:
<223> OTHER INFORMATION: CDR3 of VHH sequence 57E07

<400> SEQUENCE: 330

Asp Ser Gly Ser His Trp Trp Asn Arg Arg Asp Tyr
1               5                   10

<210> SEQ ID NO 331
<211> LENGTH: 10
<212> TYPE: PRT
<213> ORGANISM: Artificial Sequence
<220> FEATURE:
<223> OTHER INFORMATION: CDR3 of VHH sequence 57E11

<400> SEQUENCE: 331

Ala Asn Trp Gly Leu Ala Gly Asn Glu Tyr
1               5                   10

<210> SEQ ID NO 332
<211> LENGTH: 8
<212> TYPE: PRT
<213> ORGANISM: Artificial Sequence
<220> FEATURE:
<223> OTHER INFORMATION: CDR3 of VHH sequence 57G01

<400> SEQUENCE: 332

Gln Thr Phe Trp Arg Arg Asn Tyr
```

```
<210> SEQ ID NO 333
<211> LENGTH: 8
<212> TYPE: PRT
<213> ORGANISM: Artificial Sequence
<220> FEATURE:
<223> OTHER INFORMATION: CDR3 of VHH sequence 57G07

<400> SEQUENCE: 333

His Ser Trp Leu Asp Tyr Asp Tyr
1               5

<210> SEQ ID NO 334
<211> LENGTH: 7
<212> TYPE: PRT
<213> ORGANISM: Artificial Sequence
<220> FEATURE:
<223> OTHER INFORMATION: CDR3 of VHH sequence 57G08

<400> SEQUENCE: 334

Ile Pro Thr Phe Gly Arg Tyr
1               5

<210> SEQ ID NO 335
<211> LENGTH: 7
<212> TYPE: PRT
<213> ORGANISM: Artificial Sequence
<220> FEATURE:
<223> OTHER INFORMATION: CDR3 of VHH sequence 57H08

<400> SEQUENCE: 335

Asn Arg Gly Phe Ile Ser Tyr
1               5
```

AGROCHEMICAL COMPOSITIONS COMPRISING ANTIBODIES BINDING TO SPHINGOLIPIDS

CROSS-REFERENCE TO RELATED APPLICATIONS

This application is a national phase entry under 35 U.S.C. §371 of International Patent Application PCT/EP2014/058772, filed Apr. 29, 2014, designating the United States of America and published in English as International Patent Publication WO 2014/191146 A1 on Dec. 4, 2014. which claims the benefit under Article 8 of the Patent Cooperation Treaty and under 35 U.S.C. §119(e) to U.S. Provisional Patent Application Ser. No. 61/817,170, filed Apr. 29, 2013, the disclosure of each of which is hereby incorporated herein in its entirety by this reference.

STATEMENT ACCORDING TO 37 C.F.R. §1.821(c) or (e)—SEQUENCE LISTING SUBMITTED AS A TXT AND PDF FILES

Pursuant to 37 C.F.R. §1.821(c) or (e), files containing a TXT version and a PDF version of the Sequence Listing have been submitted concomitant with this application, the contents of which are hereby incorporated by reference.

FIELD OF THE INVENTION

The present invention relates to effecting control of plant pests. More specifically the invention provides agrochemical compositions comprising polypeptide compositions of a specific length and concentration which are useful to combat crop pests such as insects, fungi, nematodes, bacteria and the like.

BACKGROUND

The presence and persistence of pathogenic fungal infections seen in patients and animals but also in plant crops can be mainly attributed to the selective pressure of broad-spectrum anti-fungals and the general lack of efficacy of anti-fungal agents, which are available at present. In humans and animals, systemic fungal infections such as invasive candidiasis and invasive aspergillosis may be caused by a variety of fungal pathogens, for example the virulent *Candida* species *C. albicans, C. tropicalis* and *C. krusei* and the less virulent species *C. parapsilosis* and *Torulopsis glabrata* (the latter sometimes referred to as *Candida glabrata*). Although *C. albicans* was once the most common fungal isolate obtained from intensive care units, later studies have indicated that *C. tropicalis, C. glabrata, C. parapsilosis* and *C. krusei* now account for about half of such isolates. The rise of non-*albicans* species implies the emergence of *Candida* species resistant to conventional antifungal therapy.

Traditionally, *C. albicans, C. tropicalis* and *C. parapsilosis* have been treated by the antifungal agent amphotericin B, regarded as the "gold standard" of systemic antifungal therapy. Unfortunately, amphotericin B is itself highly toxic and its use is tempered by side effects including chills, fever, myalgia or thrombophlebitis. Other anti-fungal agents include the oral azole drugs (miconazole, ketoconazole, itraconazole, fluconazole) and 5-fluorocytosine. However, fungal species such as *C. krusei* and *T. glabrata* are resistant to fluconazole, and these species often occur in patients where this drug has been administered prophylactically. Furthermore, fluconazole-resistant strains of *C. albicans* have also been reported. Thus, despite the advances made in therapeutic anti-fungal drugs, the need for effective agents for treatment of fungal infections remains acute.

In agriculture, crop protection relies heavily on the use of pesticides, which are applied to the crops by spraying them onto the crop, applying during watering of the crops or incorporating them into the soil. Pesticides are often organic chemical molecules and their repeated application to crops poses toxicity threats to both agricultural workers during handling and to the environment, due to spray drift, persistence in the soil or washing off into surface or ground water. It would be advantageous to be able to use alternative compounds that are less toxic to humans and the environment, but that at the same time provide effective control of plant pests.

Proteinaceous pesticides with specificity against a certain plant pest target may be very advantageous in this respect, as they are expected to be short-lived in the environment and to have less toxic off-target effects. However, there are only a few proteinaceous or peptidergic pesticides known. Some examples are Bt toxins, lectins, defensins, fabatins, tachyplesin, magainin, harpin (see WO2010019442), pea albumin 1-subunit b (PA1b). However, these proteinaceous pesticides are either small peptides with compact structures, stabilized by several disulphide bridges, or are larger proteins (>300 amino acids) which occur in crystalline form (cry toxins). It is indeed known in the field of agriculture that biologicals, and in particular proteins, are challenging structures for developing pesticides, as they generally have far too little stability to maintain their pesticidal function in an agrochemical formulation, in particular for applications in the field.

SUMMARY OF THE INVENTION

The present inventors have successfully developed polypeptides with surprisingly high specificity, affinity and potency against targets of pests, in particular plant, animal or human pathogenic pests, such as but not limited to plant, animal or human pathogenic fungi. Moreover, it is shown that these polypeptides retain their integrity, stability and activity in a composition and that efficacious pest or pathogenic control can surprisingly be achieved by applying compositions, comprising the polypeptides as disclosed in the present application, to crops, animals or humans.

The efficacy and potency of the polypeptides as disclosed herein suggests a potential for either a lower treatment dosage and/or a more effective treatment at the same dose. This can imply a reduction of unwanted side-effects and reduced toxicity in both agrochemical and medical applications. Moreover, this allows the application of lower amounts or dosages of the polypeptides or compositions disclosed herein.

More particularly, the present inventors have found that targeting a molecular structure of a pest or pathogen with the polypeptides envisaged herein allows for efficient control of that pathogen. In particular, the present inventors have developed polypeptides that are capable of preventing, protecting, treating or curing a plant, animal or human from (developing) an infection by a pathogen or from any other biological interaction with a pathogen. Therefore, the present invention demonstrates for the first time that biological molecules, such as polypeptides or amino acid sequences, can be used to effectively protect or treat a plant, animal or human from being damaged in any way by or from suffering from a biological interaction between the plant, animal or human and a pathogen, such as for instance through a pathogen infection.

In a first aspect, the present invention provides agrochemical compositions comprising at least one polypeptide, which specifically binds to a pest.

In particular embodiments, the agrochemical compositions as disclosed herein, comprise at least one antibody or a functional fragment thereof, such as but not limited to a heavy chain antibody or a functional fragment thereof.

In particular embodiments, the agrochemical compositions as disclosed herein, comprise at least one heavy chain variable domain of a heavy chain antibody ($V_{HH}$), which is naturally devoid of light chains or a functional fragment thereof, such as but not limited to a heavy chain variable domain of a camelid heavy chain antibody (camelid $V_{HH}$) or a functional fragment thereof.

In particular embodiments, the agrochemical compositions as disclosed herein, comprise at least one camelized heavy chain variable domain of a conventional four-chain antibody (camelized $V_H$), or a functional fragment thereof.

In certain particular embodiments, the agrochemical compositions as disclosed herein, comprise at least one heavy chain variable domain of an antibody or a functional fragment thereof, which do not have an amino acid sequence that is exactly the same as (i.e. as in a degree of sequence identity of 100% with) the amino acid sequence of a naturally occurring $V_H$ domain, such as the amino acid sequence of a naturally occurring $V_H$ domain from a mammal, and in particular from a human being.

In further particular embodiments, the agrochemical compositions as disclosed herein at least comprise a polypeptide, which specifically binds to at least one plasma membrane component of a pest.

In certain specific embodiments, the at least one plasma membrane component of the pest to which the polypeptides comprised in the compositions as disclosed herein bind, is not a protein.

In certain specific embodiments, the at least one plasma membrane component of the pest to which the polypeptides comprised in the compositions as disclosed herein bind, is a sphingolipid, such as but not limited to a ceramide, for instance a glucosylceramide.

In certain specific embodiments, the at least polypeptide in the agrochemical compositions disclosed herein is present in an amount effective to protect or treat a plant or a part of the plant from an infection or other biological interaction with the plant pathogen, such as for example but not limited to the concentration of the polypeptide in the agrochemical composition ranging from 0.0001% to 50% by weight.

In further particular embodiments, the at least polypeptide in the agrochemical compositions disclosed herein is formulated in an aqueous solution, optionally but without limitation together with an agrochemically suitable carrier and/or one or more suitable adjuvants.

In specific embodiments, the agrochemical compositions comprise at least one polypeptide, which specifically binds to a pathogenic fungus.

In further specific embodiments, the agrochemical compositions comprise at least one polypeptide, which specifically binds to a plant pest, such as but not limited to a plant pathogenic fungus.

In certain particular embodiments, the agrochemical compositions as disclosed herein at least comprise a polypeptide, which specifically binds to a plant pathogenic fungus, such as but not limited to a plant pathogenic fungus of a genus chosen from the group comprising *Alternaria, Ascochyta, Botrytis, Cercospora, Colletotrichum, Diplodia, Erysiphe, Fusarium, Leptosphaeria, Gaeumanomyces, Helminthosporium, Macrophomina, Nectria, Penicillium, Peronospora, Phoma, Phymatotrichum, Phytophthora, Plasmopara, Podosphaera, Puccinia, Pyrenophora, Pyricularia, Pythium, Rhizoctonia, Scerotium, Sclerotinia, Septoria, Thielaviopsis, Uncinula, Venturia, Verticillium, Magnaporthe, Blumeria, Mycosphaerella, Ustilago, Melampsora, Phakospora, Monilinia, Mucor, Rhizopus*, and *Aspergillus*.

In particular embodiments, the agrochemical compositions as disclosed herein at least comprise a polypeptide, which specifically binds to a pest, which is a pest for a plant chosen from the group comprising cereals, sorghum, rice, sugar beet, fodder beet, fruit, nuts, the plantain family or grapevines, leguminous crops, oil crops, cucurbits, fibre plants, fuel crops, vegetables, ornamentals, shrubs, broad-leaved trees, evergreens, grasses, coffee, tea, tobacco, hops, pepper, rubber and latex plants.

In still further particular embodiments, the at least one polypeptide in the agrochemical compositions disclosed herein, at least comprises any one of the combinations:

a CDR1 region having SEQ ID NO: 85, a CDR2 region having has SEQ ID NO: 169, and a CDR3 region having SEQ ID NO: 253, and/or a CDR1 region having SEQ ID NO: 86, a CDR2 region having has SEQ ID NO: 170, and a CDR3 region having SEQ ID NO: 254, and/or a CDR1 region having SEQ ID NO: 87, a CDR2 region having has SEQ ID NO: 171, and a CDR3 region having SEQ ID NO: 255, and/or a CDR1 region having SEQ ID NO: 88, a CDR2 region having has SEQ ID NO: 172, and a CDR3 region having SEQ ID NO: 256, and/or a CDR1 region having SEQ ID NO: 89, a CDR2 region having has SEQ ID NO: 173, and a CDR3 region having SEQ ID NO: 257, and/or a CDR1 region having SEQ ID NO: 90, a CDR2 region having has SEQ ID NO: 174, and a CDR3 region having SEQ ID NO: 258, and/or a CDR1 region having SEQ ID NO: 91, a CDR2 region having has SEQ ID NO: 175, and a CDR3 region having SEQ ID NO: 259, and/or a CDR1 region having SEQ ID NO: 92, a CDR2 region having has SEQ ID NO: 176, and a CDR3 region having SEQ ID NO: 260, and/or a CDR1 region having SEQ ID NO: 93, a CDR2 region having has SEQ ID NO: 177, and a CDR3 region having SEQ ID NO: 261, and/or a CDR1 region having SEQ ID NO: 94, a CDR2 region having has SEQ ID NO: 178, and a CDR3 region having SEQ ID NO: 262, and/or a CDR1 region having SEQ ID NO: 95, a CDR2 region having has SEQ ID NO: 179, and a CDR3 region having SEQ ID NO: 263, and/or a CDR1 region having SEQ ID NO: 96, a CDR2 region having has SEQ ID NO: 180, and a CDR3 region having SEQ ID NO: 264, and/or a CDR1 region having SEQ ID NO: 97, a CDR2 region having has SEQ ID NO: 181, and a CDR3 region having SEQ ID NO: 265, and/or a CDR1 region having SEQ ID NO: 98, a CDR2 region having has SEQ ID NO: 182, and a CDR3 region having SEQ ID NO: 266, and/or a CDR1 region having SEQ ID NO: 99, a CDR2 region having has SEQ ID NO: 183, and a CDR3 region having SEQ ID NO: 267, and/or a CDR1 region having SEQ ID NO: 100, a CDR2 region having has SEQ ID NO: 184, and a CDR3 region having SEQ ID NO: 268, and/or a CDR1 region having SEQ ID NO: 101, a CDR2 region having has SEQ ID NO: 185, and a CDR3 region having SEQ ID NO: 269, and/or a CDR1 region having SEQ ID NO: 102, a CDR2 region having has SEQ ID NO: 186, and a CDR3 region having SEQ ID NO: 270, and/or a CDR1 region having SEQ ID NO: 103, a CDR2 region having has SEQ ID NO: 187, and a CDR3 region having SEQ ID NO: 271, and/or a CDR1 region having SEQ ID NO: 104, a CDR2 region having has SEQ ID NO: 188, and a CDR3 region having SEQ ID NO: 272, and/or a CDR1 region having SEQ ID NO: 105, a CDR2 region having has SEQ ID NO: 189, and a CDR3 region having SEQ ID NO: 273, and/or a CDR1 region having SEQ ID NO: 106, a CDR2 region having has SEQ ID NO: 190, and a CDR3 region having SEQ ID NO: 274, and/or a CDR1 region having SEQ ID NO: 107, a CDR2 region having has SEQ ID NO: 191, and a CDR3 region having SEQ ID NO: 275, and/or a CDR1 region having SEQ ID NO: 108, a CDR2 region having has SEQ ID NO: 192, and a CDR3 region having SEQ ID NO: 276, and/or a CDR1 region having SEQ ID NO: 109, a CDR2 region having has SEQ ID NO: 193, and a CDR3 region having SEQ ID NO: 277, and/or a CDR1 region having SEQ ID NO: 110, a CDR2 region having has SEQ ID NO: 194, and a CDR3 region having SEQ ID NO: 278, and/or a CDR1 region having SEQ ID NO: 111, a CDR2 region having has SEQ ID NO: 195, and a CDR3 region having SEQ ID NO: 279, and/or a CDR1 region having SEQ ID NO: 112, a CDR2 region having has SEQ ID NO: 196, and a CDR3 region having SEQ ID NO: 280, and/or a CDR1 region having SEQ ID NO: 113, a CDR2 region having has SEQ ID NO: 197, and a CDR3 region having SEQ ID NO: 281, and/or a CDR1 region having SEQ ID NO: 114, a CDR2 region having has SEQ ID NO: 198, and a CDR3 region having SEQ ID NO: 282, and/or a CDR1 region having SEQ ID NO: 115, a CDR2 region having has SEQ ID NO: 199, and a CDR3 region having SEQ ID NO: 283, and/or a CDR1 region having SEQ ID NO: 116, a CDR2 region having has SEQ ID NO: 200, and a CDR3 region having SEQ ID NO: 284, and/or a CDR1 region having SEQ ID NO: 117, a CDR2 region having has SEQ ID NO: 201, and a CDR3 region having SEQ ID NO: 285, and/or a CDR1 region having SEQ ID NO: 118, a CDR2 region having has SEQ ID NO: 202, and a CDR3 region having SEQ ID NO: 286, and/or a CDR1 region having SEQ ID NO: 119, a CDR2 region having has SEQ ID NO: 203, and a CDR3 region having SEQ ID NO: 287, and/or a CDR1 region having SEQ ID NO: 120, a CDR2 region having has SEQ ID NO: 204, and a CDR3 region having SEQ ID NO: 288, and/or a CDR1 region having SEQ ID NO: 121, a CDR2 region having has SEQ ID NO: 205, and a CDR3 region having SEQ ID NO: 289, and/or a CDR1 region having SEQ ID NO: 122, a CDR2 region having has SEQ ID NO: 206, and a CDR3 region having SEQ ID NO: 290, and/or a CDR1 region having SEQ ID NO: 123, a CDR2 region having has SEQ ID NO: 207, and a CDR3 region having SEQ ID NO: 291, and/or a CDR1 region having SEQ ID NO: 124, a CDR2 region having has SEQ ID NO: 208, and a CDR3 region having SEQ ID NO: 292, and/or a CDR1 region having SEQ ID NO: 125, a CDR2 region having has SEQ ID NO: 209, and a CDR3 region having SEQ ID NO: 293, and/or a CDR1 region having SEQ ID NO: 126, a CDR2 region having has SEQ ID NO: 210, and a CDR3 region having SEQ ID NO: 294, and/or a CDR1 region having SEQ ID NO: 127, a CDR2 region having has SEQ ID NO: 211, and a CDR3 region having SEQ ID NO: 295, and/or a CDR1 region having SEQ ID NO: 128, a CDR2 region having has SEQ ID NO: 212, and a CDR3 region having SEQ ID NO: 296, and/or a CDR1 region having SEQ ID NO: 129, a CDR2 region having has SEQ ID NO: 213, and a CDR3 region having SEQ ID NO: 297, and/or a CDR1 region having SEQ ID NO: 130, a CDR2 region having has SEQ ID NO: 214, and a CDR3 region having SEQ ID NO: 298, and/or a CDR1 region having SEQ ID NO: 131, a CDR2 region having has SEQ ID NO: 215, and a CDR3 region having SEQ ID NO: 299, and/or a CDR1 region having SEQ ID NO: 132, a CDR2 region having has SEQ ID NO: 216, and a CDR3 region having SEQ ID NO: 300, and/or a CDR1 region having SEQ ID NO: 133, a CDR2 region having has SEQ ID NO: 217, and a CDR3 region having SEQ ID NO: 301, and/or a CDR1 region having SEQ ID NO: 134, a CDR2 region having has SEQ ID NO: 218, and a CDR3 region having SEQ ID NO: 302, and/or a CDR1 region having SEQ ID NO: 135, a CDR2 region having has SEQ ID NO: 219, and a CDR3 region having SEQ ID NO: 303, and/or a CDR1 region having SEQ ID NO: 136, a CDR2 region having has SEQ ID NO: 220, and a CDR3 region having SEQ ID NO: 304, and/or a CDR1 region having SEQ ID NO: 137, a CDR2 region having has SEQ ID NO: 221, and a CDR3 region having SEQ ID NO: 305, and/or a CDR1 region having SEQ ID NO: 138, a CDR2 region having has SEQ ID NO: 222, and a CDR3 region having the amino acid sequence NRY, and/or a CDR1 region having SEQ ID NO: 139, a CDR2 region having has SEQ ID NO: 223, and a CDR3 region having SEQ ID NO: 306, and/or a CDR1 region having SEQ ID NO: 140, a CDR2 region having has SEQ ID NO: 224, and a CDR3 region having SEQ ID NO: 307, and/or a CDR1 region having SEQ ID NO: 141, a CDR2 region having has SEQ ID NO: 225, and a CDR3 region having SEQ ID NO: 308, and/or a CDR1 region having SEQ ID NO: 142, a CDR2 region having has SEQ ID NO: 226, and a CDR3 region having SEQ ID NO: 309, and/or a CDR1 region having SEQ ID NO: 143, a CDR2 region having has SEQ ID NO: 227, and a CDR3 region having SEQ ID NO: 310, and/or a CDR1 region having SEQ ID NO: 144, a CDR2 region having has SEQ ID NO: 228, and a CDR3 region having SEQ ID NO: 311, and/or a CDR1 region having SEQ ID NO: 145, a CDR2 region having has SEQ ID NO: 229, and a CDR3 region having SEQ ID NO: 312, and/or a CDR1 region having SEQ ID NO: 146, a CDR2 region having has SEQ ID NO: 230, and a CDR3 region having SEQ ID NO: 313, and/or a CDR1 region having SEQ ID NO: 147, a CDR2 region having has SEQ ID NO: 231, and a CDR3 region having SEQ ID NO: 314, and/or a CDR1 region having SEQ ID NO: 148, a CDR2 region having has SEQ ID NO: 232, and a CDR3 region having SEQ ID NO: 315, and/or a CDR1 region having SEQ ID NO: 149, a CDR2 region having has SEQ ID NO: 233, and a CDR3 region having SEQ ID NO: 316, and/or a CDR1 region having SEQ ID NO: 150, a CDR2 region having has SEQ ID NO: 234, and a CDR3 region having SEQ ID NO: 317, and/or a CDR1 region having SEQ ID NO: 151, a CDR2 region having has SEQ ID NO: 235, and a CDR3 region having SEQ ID NO: 318, and/or a CDR1 region having SEQ ID NO: 152, a CDR2 region having has SEQ ID NO: 236, and a CDR3 region having SEQ ID NO: 319, and/or a CDR1 region having SEQ ID NO: 153, a CDR2 region having has SEQ ID NO: 237, and a CDR3 region having SEQ ID NO: 320, and/or a CDR1 region having SEQ ID NO: 154, a CDR2 region having has SEQ ID NO: 238, and a CDR3 region having SEQ ID NO: 321, and/or a CDR1 region having SEQ ID NO: 155, a CDR2 region having has SEQ ID NO: 239, and a CDR3 region having SEQ ID NO: 322, and/or a CDR1 region having SEQ ID NO: 156, a CDR2 region having has SEQ ID NO: 240, and a CDR3 region having SEQ ID NO: 323, and/or a CDR1 region having SEQ ID NO: 157, a CDR2 region having has SEQ ID NO: 241, and a CDR3 region having SEQ ID NO: 324, and/or a CDR1 region having SEQ ID NO: 158, a CDR2 region having has SEQ ID NO: 242, and a CDR3 region having SEQ ID NO: 325, and/or a CDR1 region having SEQ ID NO: 159, a CDR2 region having has SEQ ID NO: 243, and a CDR3 region having SEQ ID NO: 326, and/or a CDR1 region having SEQ ID NO: 160, a CDR2 region having has SEQ ID NO: 244, and a CDR3 region having SEQ ID NO: 327, and/or a CDR1 region having SEQ ID NO: 161, a CDR2 region having has SEQ ID NO: 245, and a CDR3 region having SEQ ID NO: 328, and/or a CDR1 region having SEQ ID NO: 162, a CDR2 region having has SEQ ID NO: 246, and a CDR3 region having SEQ ID NO: 329, and/or a CDR1 region having SEQ ID NO: 163, a CDR2 region having has SEQ ID NO: 247, and a CDR3 region having SEQ ID NO: 330, and/or a CDR1 region having SEQ ID NO: 164, a CDR2 region having has SEQ ID NO: 248, and a CDR3 region having SEQ ID NO: 331, and/or a CDR1 region having SEQ ID NO: 165, a CDR2 region having has SEQ ID NO: 249, and a CDR3 region having SEQ ID NO: 332, and/or a CDR1 region having SEQ ID NO: 166, a CDR2 region having has SEQ ID NO: 250, and a CDR3 region having SEQ ID NO: 333, and/or a CDR1 region having SEQ ID NO: 167, a CDR2 region having has SEQ ID NO: 251, and a CDR3 region having SEQ ID NO: 334, and/or a CDR1 region having SEQ ID NO: 168, a CDR2 region having has SEQ ID NO: 252, and a CDR3 region having SEQ ID NO: 335.

In further embodiments, the at least one polypeptide in the agrochemical compositions disclosed herein, at least comprises an amino acid sequence chosen from the group consisting of SEQ ID NO's: 1 to 84.

In a further aspect, the present invention provides compositions comprising at least one polypeptide, which specifically binds to a pest, for use as an anti-pest agent.

In yet a further aspect, the present invention provides uses of agrochemical compositions comprising at least one polypeptide, which specifically binds to a pest, as an anti-pest agent on plants.

In specific embodiments, the anti-pest agent is a biostatic agent or a pesticidal agent, such as but not limited to a fungistatic agent or fungicidal agent.

In a further aspect, the present invention provides methods for protecting or treating a plant or a part of a plant from an infection or other biological interaction with a plant pest, wherein the methods at least comprise the step of applying directly or indirectly to the plant or to a part of the plant, an agrochemical composition as disclosed herein, under conditions effective to protect or treat the plant or a part of the plant against infection or biological interaction with the plant pathogen.

In particular embodiments, these methods comprise applying directly or indirectly to the plant or to a part of the plant an agrochemical composition as disclosed herein at an application rate higher than 50 g of the agrochemical composition per hectare, such as but not limited to an application rate higher than 75 g of the agrochemical composition per hectare, such as an application rate higher than 100 g of the agrochemical composition per hectare, or in particular an application rate higher than 200 g of the agrochemical composition per hectare.

In particular embodiments, these methods comprise applying directly or indirectly to the plant or to a part of the plant an agrochemical composition as disclosed herein at an application rate between 50 g and 100 g of the agrochemical composition per hectare, such as but not limited to an application rate of between 50 g and 200 g of the agrochemical composition per hectare, in particular an application rate of between 75 g and 175 g of the agrochemical composition per hectare, such as between 75 g and 150 g of the agrochemical composition per hectare or between 75 g and 125 g per hectare.

In particular embodiments, the agrochemical compositions as disclosed herein are directly or indirectly applied to the plant or to a part of the plant by spraying, atomizing, foaming, fogging, culturing in hydroculture, culturing in hydroponics, coating, submerging, and/or encrusting, optionally post-harvest.

In still a further aspect, the present invention provides post-harvest treatment methods for protecting or treating a harvested plant or a harvested part of the plant from an infection or other biological interaction with a plant pathogen, at least comprising the step of applying directly or indirectly to the harvested plant or to a harvested part of the plant, an agrochemical composition as disclosed herein, under conditions effective to protect or treat the harvested plant or a harvested part of the plant against infection or biological interaction with the plant pathogen.

In yet a further aspect, the present invention provides methods of inhibiting the growth of a plant pathogen or methods of killing a plant pathogen, the methods comprising at least the step of applying directly or indirectly to a plant or to a part of the plant, an agrochemical composition as disclosed herein.

In particular embodiments of these methods, the agrochemical compositions as disclosed herein are directly or indirectly applied to the plant or to a part of the plant by spraying, atomizing, foaming, fogging, culturing in hydroculture, culturing in hydroponics, coating, submerging, and/or encrusting, optionally post-harvest.

In yet another aspect, the present invention provides methods for producing an agrochemical composition as disclosed herein, the methods at least comprising the steps of:
  obtaining at least one polypeptide, which specifically binds to a pest, and
  formulating the polypeptide in an agrochemical composition.

In particular embodiments of these methods, the step of obtaining at least one polypeptide, which specifically binds to a pest comprises:
  (a) expressing a nucleotide sequence encoding a polypeptide, which specifically binds to a pest, and optionally
  (b) isolating and/or purifying the polypeptide.

In particular embodiments of these methods, the step of obtaining at least one polypeptide, which specifically binds to a pest comprises:
a) providing a set, collection or library of polypeptide sequences;
b) screening the set, collection or library of polypeptide sequences for sequences that specifically bind to and/or have affinity for a pest, and optionally
c) isolating the polypeptide sequences that specifically bind to and/or have affinity for a pest.

DETAILED DESCRIPTION OF THE INVENTION

The present invention will be described with respect to particular embodiments but the invention is not limited thereto.

Statements (features) and embodiments of the polypeptides, compositions and methods as disclosed herein are set herebelow. Each of the statements and embodiments as disclosed by the invention so defined may be combined with any other statement and/or embodiment unless clearly indicated to the contrary. In particular, any feature indicated as being preferred or advantageous may be combined with any other feature or features indicated as being preferred or advantageous.

Numbered statements as disclosed in the present application are:

1. An agrochemical composition for combating plant pests, which composition comprises at least one polypeptide of between 80 and 200 amino acids as the active substance.

2. An agrochemical composition for combating plant pests, which composition comprises at least one polypeptide of between 80 and 200 amino acids as the active substance, wherein the polypeptide is present in a concentration of 0.01 to 50% (w/w) of the total weight of the agrochemical composition.

3. The agrochemical composition according to statements 1 or 2, wherein the polypeptide is obtained by affinity selection to a specific plant pest target.

4. The agrochemical composition according to statement 3, wherein the polypeptide has an affinity for the target with a dissociation constant below $10^{-6}$M.

5. The agrochemical composition according to any of the statements 1 to 4, wherein the polypeptide comprises 3 CDRs and 4 FRs.

6. The agrochemical composition according to any of the statements 1 to 5, wherein the polypeptide is derived from a camelid antibody.

7. The agrochemical composition according to any of the statements 1 to 6, wherein the polypeptide is a VHH.

8. The agrochemical composition according to any one of the statements 1 to 7 wherein the plant pest is a fungal pathogen.

9. A method for combating plant pests, which method comprises applying the composition according to any of the statements 1 to 8 to a crop at an application rate higher than 50 g per hectare of the polypeptide comprised in the agrochemical composition.

10. The method for producing an agrochemical composition according to any of the statements 1 to 8, comprising formulating a polypeptide of between 80 and 200 amino acids with pesticidal activity together with at least one customary agrochemical auxiliary agent.

11. A polypeptide of between 80 and 200 amino acids, obtained by affinity selection to a specific plant pest target, which is able to inhibit the growth and/or the activity of a crop pest at a minimum inhibitory concentration of about 0.00001 to 1 µM.

12. A nucleic acid sequence encoding a polypeptide according to statement 11.

13. A chimeric gene comprising a plant expressible promoter, a nucleic acid sequence according to statement 12 and a terminator sequence.

14. A recombinant vector comprising a chimeric gene of statement 13.

15. A plant comprising a chimeric gene as defined in statement 14.

16. An agrochemical composition comprising at least one polypeptide, which specifically binds to a pest.

17. The agrochemical composition according to any of the statements 1 to 8, which comprises at least one polypeptide, which specifically binds to a pest.

18. The agrochemical composition according to any of the statements 1 to 8 and 17, wherein the at least one polypeptide is an antibody or a functional fragment thereof.

19. The agrochemical composition according any of the statements 1 to 8, 17 and 18, wherein the at least one polypeptide is a heavy chain antibody or a functional fragment thereof.

20. The agrochemical composition according to any of the statements 1 to 8 and 17 to 19, which comprises at least one heavy chain variable domain of a heavy chain antibody ($V_{HH}$) or a functional fragment thereof, which specifically binds to a pest.

21. The agrochemical composition according to any of the statements 1 to 8 and 17 to 20, which comprises at least one camelid heavy chain variable domain of a heavy chain antibody (camelid $V_{HH}$) or a functional fragment thereof, which specifically binds to a sphingolipid of a plant pathogen.

22. The agrochemical composition according to any of the statements 1 to 8 and 17 to 21, which comprises at least one camelized heavy chain variable domain of a conventional four-chain antibody (camelized $V_H$) or a functional fragment thereof, which specifically binds to a sphingolipid of a plant pathogen.

23. The agrochemical composition according to any of the statements 1 to 8 and 17 to 22, wherein said at least one polypeptide specifically binds to at least one plasma membrane component of a pest.

24. The agrochemical composition according to statement 23, wherein the at least one plasma membrane component of the pest is not a protein.

25. The agrochemical composition according to statements 23 or 24, wherein the at least one plasma membrane component of the pest is a sphingolipid.

26. The agrochemical composition according to statement 25, wherein the sphingolipid is a ceramide.

27. The agrochemical composition according to any of the statements 25 or 26, wherein the sphingolipid is glucosylceramide.

28. The agrochemical composition according to any of the statements 1 to 8 and 17 to 27, wherein the at least one heavy chain variable domain is present in an amount effective to protect or treat a plant or a part of the plant from an infection or other biological interaction with the plant pathogen.

29. The agrochemical composition according to any of the statements 1 to 8 and 17 to 28, wherein the concentration of the at least one heavy chain variable domain in the agrochemical composition ranges from 0.0001% to 50% by weight.

30. The agrochemical composition according to any of the statements 1 to 8 and 17 to 29, wherein the at least one heavy chain variable domain is formulated in an aqueous solution.

31. The agrochemical composition according to any of the statements 1 to 8 and 17 to 30, which further comprises an agrochemically suitable carrier and/or one or more suitable adjuvants.

32. The agrochemical composition according to any of the statements 1 to 8 and 17 to 31, wherein the pest is a pathogenic fungus.

33. The agrochemical composition according to any of the statements 1 to 8 and 17 to 32, wherein the pest is a plant pest.

34. The agrochemical composition according to any of the statements 1 to 8 and 17 to 33, wherein the plant pest is a plant pathogenic fungus.

35. The agrochemical composition according to any of the statements 1 to 8 and 34, wherein the genus of the plant pathogenic fungus is chosen from the group comprising *Alternaria, Ascochyta, Botrytis, Cercospora, Colletotrichum, Diplodia, Erysiphe, Fusarium, Leptosphaeria, Gaeumanomyces, Helminthosporium, Macrophomina, Nectria, Penicillium, Peronospora, Phoma, Phymatotrichum, Phytophthora, Plasmopara, Podosphaera, Puccinia, Pyrenophora, Pyricularia, Pythium, Rhizoctonia, Scerotium, Sclerotinia, Septoria, Thielaviopsis, Uncinula, Venturia, Verticillium, Magnaporthe, Blumeria, Mycosphaerella, Ustilago, Melampsora, Phakospora, Monilinia, Mucor, Rhizopus*, and *Aspergillus*.

36. The agrochemical composition according to any of the statements 1 to 8 and 33 to 35, wherein the plant pest is a plant pathogen for a plant chosen from the group comprising cereals, sorghum, rice, sugar beet, fodder beet, fruit, nuts, the plantain family or grapevines, leguminous crops, oil crops, cucurbits, fibre plants, fuel crops, vegetables, ornamentals, shrubs, broad-leaved trees, evergreens, grasses, coffee, tea, tobacco, hops, pepper, rubber and latex plants.

37. The agrochemical composition according to any of the statements 1 to 8 and 17 to 36, wherein the at least one polypeptide at least comprises one or more of the following combinations:

a CDR1 region having SEQ ID NO: 85, a CDR2 region having has SEQ ID NO: 169, and a CDR3 region having SEQ ID NO: 253, and/or a CDR1 region having SEQ ID NO: 86, a CDR2 region having has SEQ ID NO: 170, and a CDR3 region having SEQ ID NO: 254, and/or a CDR1 region having SEQ ID NO: 87, a CDR2 region having has SEQ ID NO: 171, and a CDR3 region having SEQ ID NO: 255, and/or a CDR1 region having SEQ ID NO: 88, a CDR2 region having has SEQ ID NO: 172, and a CDR3 region having SEQ ID NO: 256, and/or a CDR1 region having SEQ ID NO: 89, a CDR2 region having has SEQ ID NO: 173, and a CDR3 region having SEQ ID NO: 257, and/or a CDR1 region having SEQ ID NO: 90, a CDR2 region having has SEQ ID NO: 174, and a CDR3 region having SEQ ID NO: 258, and/or a CDR1 region having SEQ ID NO: 91, a CDR2 region having has SEQ ID NO: 175, and a CDR3 region having SEQ ID NO: 259, and/or a CDR1 region having SEQ ID NO: 92, a CDR2 region having has SEQ ID NO: 176, and a CDR3 region having SEQ ID NO: 260, and/or a CDR1 region having SEQ ID NO: 93, a CDR2 region having has SEQ ID NO: 177, and a CDR3 region having SEQ ID NO: 261, and/or a CDR1 region having SEQ ID NO: 94, a CDR2 region having has SEQ ID NO: 178, and a CDR3 region having SEQ ID NO: 262, and/or a CDR1 region having SEQ ID NO: 95, a CDR2 region having has SEQ ID NO: 179, and a CDR3 region having SEQ ID NO: 263, and/or a CDR1 region having SEQ ID NO: 96, a CDR2 region having has SEQ ID NO: 180, and a CDR3 region having SEQ ID NO: 264, and/or a CDR1 region having SEQ ID NO: 97, a CDR2 region having has SEQ ID NO: 181, and a CDR3 region having SEQ ID NO: 265, and/or a CDR1 region having SEQ ID NO: 98, a CDR2 region having has SEQ ID NO: 182, and a CDR3 region having SEQ ID NO: 266, and/or a CDR1 region having SEQ ID NO: 99, a CDR2 region having has SEQ ID NO: 183, and a CDR3 region having SEQ ID NO: 267, and/or a CDR1 region having SEQ ID NO: 100, a CDR2 region having has SEQ ID NO: 184, and a CDR3 region having SEQ ID NO: 268, and/or a CDR1 region having SEQ ID NO: 101, a CDR2 region having has SEQ ID NO: 185, and a CDR3 region having SEQ ID NO: 269, and/or a CDR1 region having SEQ ID NO: 102, a CDR2 region having has SEQ ID NO: 186, and a CDR3 region having SEQ ID NO: 270, and/or a CDR1 region having SEQ ID NO: 103, a CDR2 region having has SEQ ID NO: 187, and a CDR3 region having SEQ ID NO: 271, and/or a CDR1 region having SEQ ID NO: 104, a CDR2 region having has SEQ ID NO: 188, and a CDR3 region having SEQ ID NO: 272, and/or a CDR1 region having SEQ ID NO: 105, a CDR2 region having has SEQ ID NO: 189, and a CDR3 region having SEQ ID NO: 273, and/or a CDR1 region having SEQ ID NO: 106, a CDR2 region having has SEQ ID NO: 190, and a CDR3 region having SEQ ID NO: 274, and/or a CDR1 region having SEQ ID NO: 107, a CDR2 region having has SEQ ID NO: 191, and a CDR3 region having SEQ ID NO: 275, and/or a CDR1 region having SEQ ID NO: 108, a CDR2 region having has SEQ ID NO: 192, and a CDR3 region having SEQ ID NO: 276, and/or a CDR1 region having SEQ ID NO: 109, a CDR2 region having has SEQ ID NO: 193, and a CDR3 region having SEQ ID NO: 277, and/or a CDR1 region having SEQ ID NO: 110, a CDR2 region having has SEQ ID NO: 194, and a CDR3 region having SEQ ID NO: 278, and/or a CDR1 region having SEQ ID NO: 111, a CDR2 region having has SEQ ID NO: 195, and a CDR3 region having SEQ ID NO: 279, and/or a CDR1 region having SEQ ID NO: 112, a CDR2 region having has SEQ ID NO: 196, and a CDR3 region having SEQ ID NO: 280, and/or a CDR1 region having SEQ ID NO: 113, a CDR2 region having has SEQ ID NO: 197, and a CDR3 region having SEQ ID NO: 281, and/or a CDR1 region having SEQ ID NO: 114, a CDR2 region having has SEQ ID NO: 198, and a CDR3 region having SEQ ID NO: 282, and/or a CDR1 region having SEQ ID NO: 115, a CDR2 region having has SEQ ID NO: 199, and a CDR3 region having SEQ ID NO: 283, and/or a CDR1 region having SEQ ID NO: 116, a CDR2 region having has SEQ ID NO: 200, and a CDR3 region having SEQ ID NO: 284, and/or a CDR1 region having SEQ ID NO: 117, a CDR2 region having has SEQ ID NO: 201, and a CDR3 region having SEQ ID NO: 285, and/or a CDR1 region having SEQ ID NO: 118, a CDR2 region having has SEQ ID NO: 202, and a CDR3 region having SEQ ID NO: 286, and/or a CDR1 region having SEQ ID NO: 119, a CDR2 region having has SEQ ID NO: 203, and a CDR3 region having SEQ ID NO: 287, and/or a CDR1 region having SEQ ID NO: 120, a CDR2 region having has SEQ ID NO: 204, and a CDR3 region having SEQ ID NO: 288, and/or a CDR1 region having SEQ ID NO: 121, a CDR2 region having has SEQ ID NO: 205, and a CDR3 region having SEQ ID NO: 289, and/or a CDR1 region having SEQ ID NO: 122, a CDR2 region having has SEQ ID NO: 206, and a CDR3 region having SEQ ID NO: 290, and/or a CDR1 region having SEQ ID NO: 123, a CDR2 region having has SEQ ID NO: 207, and a CDR3 region having SEQ ID NO: 291, and/or a CDR1 region having SEQ ID NO: 124, a CDR2 region having has SEQ ID NO: 208, and a CDR3 region having SEQ ID NO: 292, and/or a CDR1 region having SEQ ID NO: 125, a CDR2 region having has SEQ ID NO: 209, and a CDR3 region having SEQ ID NO: 293, and/or a CDR1 region having SEQ ID NO: 126, a CDR2 region having has SEQ ID NO: 210, and a CDR3 region having SEQ ID NO: 294, and/or a CDR1 region having SEQ ID NO: 127, a CDR2 region having has SEQ ID NO: 211, and a CDR3 region having SEQ ID NO: 295, and/or a CDR1 region having SEQ ID NO: 128, a CDR2 region having has SEQ ID NO: 212, and a CDR3 region having SEQ ID NO: 296, and/or a CDR1 region having SEQ ID NO: 129, a CDR2 region having has SEQ ID NO: 213, and a CDR3 region having SEQ ID NO: 297, and/or a CDR1 region having SEQ ID NO: 130, a CDR2 region having has SEQ ID NO: 214, and a CDR3 region having SEQ ID NO: 298, and/or a CDR1 region having SEQ ID NO: 131, a CDR2 region having has SEQ ID NO: 215, and a CDR3 region having SEQ ID NO: 299, and/or a CDR1 region having SEQ ID NO: 132, a CDR2 region having has SEQ ID NO: 216, and a CDR3 region having SEQ ID NO: 300, and/or a CDR1 region having SEQ ID NO: 133, a CDR2 region having has SEQ ID NO: 217, and a CDR3 region having SEQ ID NO: 301, and/or a CDR1 region having SEQ ID NO: 134, a CDR2 region having has SEQ ID NO: 218, and a CDR3 region having SEQ ID NO: 302, and/or a CDR1 region having SEQ ID NO: 135, a CDR2 region having has SEQ ID NO: 219, and a CDR3 region having SEQ ID NO: 303, and/or a CDR1 region having SEQ ID NO: 136, a CDR2 region having has SEQ ID NO: 220, and a CDR3 region having SEQ ID NO: 304, and/or a CDR1 region having SEQ ID NO: 137, a CDR2 region having has SEQ ID NO: 221, and a CDR3 region having SEQ ID NO: 305, and/or a CDR1 region having SEQ ID NO: 138, a CDR2 region having has SEQ ID NO: 222, and a CDR3 region having the amino acid sequence NRY, and/or a CDR1 region having SEQ ID NO: 139, a CDR2 region having has SEQ ID NO: 223, and a CDR3 region having SEQ ID NO: 306, and/or a CDR1 region having SEQ ID NO: 140, a CDR2 region having has SEQ ID NO: 224, and a CDR3 region having SEQ ID NO: 307, and/or a CDR1 region having SEQ ID NO: 141, a CDR2 region having has SEQ ID NO: 225, and a CDR3 region having SEQ ID NO: 308, and/or a CDR1 region having SEQ ID NO: 142, a CDR2 region having has SEQ ID NO: 226, and a CDR3 region having SEQ ID NO: 309, and/or a CDR1 region having SEQ ID NO: 143, a CDR2 region having has SEQ ID NO: 227, and a CDR3 region having SEQ ID NO: 310, and/or a CDR1 region having SEQ ID NO: 144, a CDR2 region having has SEQ ID NO: 228, and a CDR3 region having SEQ ID NO: 311, and/or a CDR1 region having SEQ ID NO: 145, a CDR2 region having has SEQ ID NO: 229, and a CDR3 region having SEQ ID NO: 312, and/or a CDR1 region having SEQ ID NO: 146, a CDR2 region having has SEQ ID NO: 230, and a CDR3 region having SEQ ID NO: 313, and/or a CDR1 region having SEQ ID NO: 147, a CDR2 region having has SEQ ID NO: 231, and a CDR3 region having SEQ ID NO: 314, and/or a CDR1 region having SEQ ID NO: 148, a CDR2 region having has SEQ ID NO: 232, and a CDR3 region having SEQ ID NO: 315, and/or a CDR1 region having SEQ ID NO: 149, a CDR2 region having has SEQ ID NO: 233, and a CDR3 region having SEQ ID NO: 316, and/or a CDR1 region having SEQ ID NO: 150, a CDR2 region having has SEQ ID NO: 234, and a CDR3 region having SEQ ID NO: 317, and/or
a CDR1 region having SEQ ID NO: 151, a CDR2 region having has SEQ ID NO: 235, and a CDR3 region having SEQ ID NO: 318, and/or
a CDR1 region having SEQ ID NO: 152, a CDR2 region having has SEQ ID NO: 236, and a CDR3 region having SEQ ID NO: 319, and/or
a CDR1 region having SEQ ID NO: 153, a CDR2 region having has SEQ ID NO: 237, and a CDR3 region having SEQ ID NO: 320, and/or
a CDR1 region having SEQ ID NO: 154, a CDR2 region having has SEQ ID NO: 238, and a CDR3 region having SEQ ID NO: 321, and/or
a CDR1 region having SEQ ID NO: 155, a CDR2 region having has SEQ ID NO: 239, and a CDR3 region having SEQ ID NO: 322, and/or
a CDR1 region having SEQ ID NO: 156, a CDR2 region having has SEQ ID NO: 240, and a CDR3 region having SEQ ID NO: 323, and/or
a CDR1 region having SEQ ID NO: 157, a CDR2 region having has SEQ ID NO: 241, and a CDR3 region having SEQ ID NO: 324, and/or
a CDR1 region having SEQ ID NO: 158, a CDR2 region having has SEQ ID NO: 242, and a CDR3 region having SEQ ID NO: 325, and/or
a CDR1 region having SEQ ID NO: 159, a CDR2 region having has SEQ ID NO: 243, and a CDR3 region having SEQ ID NO: 326, and/or
a CDR1 region having SEQ ID NO: 160, a CDR2 region having has SEQ ID NO: 244, and a CDR3 region having SEQ ID NO: 327, and/or
a CDR1 region having SEQ ID NO: 161, a CDR2 region having has SEQ ID NO: 245, and a CDR3 region having SEQ ID NO: 328, and/or
a CDR1 region having SEQ ID NO: 162, a CDR2 region having has SEQ ID NO: 246, and a CDR3 region having SEQ ID NO: 329, and/or
a CDR1 region having SEQ ID NO: 163, a CDR2 region having has SEQ ID NO: 247, and a CDR3 region having SEQ ID NO: 330, and/or
a CDR1 region having SEQ ID NO: 164, a CDR2 region having has SEQ ID NO: 248, and a CDR3 region having SEQ ID NO: 331, and/or
a CDR1 region having SEQ ID NO: 165, a CDR2 region having has SEQ ID NO: 249, and a CDR3 region having SEQ ID NO: 332, and/or
a CDR1 region having SEQ ID NO: 166, a CDR2 region having has SEQ ID NO: 250, and a CDR3 region having SEQ ID NO: 333, and/or
a CDR1 region having SEQ ID NO: 167, a CDR2 region having has SEQ ID NO: 251, and a CDR3 region having SEQ ID NO: 334, and/or
a CDR1 region having SEQ ID NO: 168, a CDR2 region having has SEQ ID NO: 252, and a CDR3 region having SEQ ID NO: 335.

38. The agrochemical composition according to any of the statements 1 to 8 and 17 to 37, wherein the at least one polypeptide comprises an amino acid sequence chosen from the group consisting of SEQ ID NO's: 1 to 84.

39. A composition comprising at least one polypeptide, which specifically binds to a pest, for use as an anti-pest agent.

40. Use of an agrochemical composition according to any of statements 1 to 8 and 17 to 38 as an anti-pest agent on plants.

41. The composition according to statement 39 or the use according to statement 40, wherein the anti-pest agent is a biostatic agent.

42. The composition according to statement 39 or the use according to statement 40, wherein the anti-pest agent is a fungistatic agent.

43. The composition according to statement 39 or the use according to statement 40, wherein the anti-pest agent is a pesticidal agent.

44. The composition according to statement 39 or the use according to statement 40, wherein the anti-pest agent is a fungicidal agent.

45. A method for protecting or treating a plant or a part of the plant from an infection or other biological interaction with a plant pathogen, at least comprising the step of applying directly or indirectly to the plant or to a part of the plant, an agrochemical composition according to any of the statements 1 to 8 and 17 to 38, under conditions effective to protect or treat the plant or a part of the plant against the infection or biological interaction with the plant pathogen.

46. A method according to statement 9 for protecting or treating a plant or a part of the plant from an infection or other biological interaction with a plant pathogen, at least comprising the step of applying directly or indirectly to the plant or to a part of the plant, an agrochemical composition according to any of the statements 1 to 8 and 17 to 38, under conditions effective to protect or treat the plant or a part of the plant against the infection or biological interaction with the plant pathogen.

47. The method according to any of the statements 9, 45 or 46, comprising applying directly or indirectly to the plant or to a part of the plant an agrochemical composition according to any one of statements 1 to 8 and 17 to 38 at an application rate higher than 50 g of the agrochemical composition per hectare.

48. The method according to any of the statements 9 or 45 to 47, wherein the agrochemical composition is directly or indirectly applied to the plant or to a part of the plant by spraying, atomizing, foaming, fogging, culturing in hydroculture, culturing in hydroponics, coating, submerging, and/or encrusting.

49. The method according to any of the statements 9 or 45 to 48, wherein the agrochemical composition is directly or indirectly applied to the plant or to a part of the plant, optionally post-harvest.

50. A post-harvest treatment method for protecting or treating a harvested plant or a harvested part of the plant from an infection or other biological interaction with a plant pathogen, at least comprising the step of applying directly or indirectly to the harvested plant or to a harvested part of the plant, an agrochemical composition according to any one of statements 1 to 8 and 17 to 38, under conditions effective to protect or treat the harvested plant or a harvested part of the plant against the infection or biological interaction with the plant pathogen.

51. A method of inhibiting the growth of a plant pathogen, comprising at least the step of applying directly or indirectly to a plant or to a part of the plant, an agrochemical composition according to any one of statements 1 to 8 and 17 to 38.

52. A method of killing a plant pathogen, comprising at least the step of applying directly or indirectly to a plant or to a part of the plant, an agrochemical composition according to any one of statements 1 to 8 and 17 to 38.

53. The method according to statements 51 or 52, wherein the agrochemical composition is directly or indirectly applied to the plant or to a part of the plant by spraying, atomizing, foaming, fogging, culturing in hydroculture, culturing in hydroponics, coating, submerging, and/or encrusting.

54. The method according to any one of statements 51 to 53, wherein the agrochemical composition is directly or indirectly applied to the plant or to a part of the plant, optionally post-harvest.

55. A method for producing an agrochemical composition according to any one of statements 1 to 8 and 17 to 38, at least comprising the steps of:
   obtaining at least one polypeptide, which specifically binds to a pest, and
   formulating the polypeptide in an agrochemical composition according to any one of statements 1 to 8 and 17 to 38.

56. A method according to statement 10 for producing an agrochemical composition according to any one of statements 1 to 8 and 17 to 38, at least comprising the steps of:
   obtaining at least one polypeptide, which specifically binds to a pest, and
   formulating the polypeptide in an agrochemical composition according to any one of statements 1 to 8 and 17 to 38.

57. The method according to statements 10 or 56, wherein the step of obtaining at least one polypeptide, which specifically binds to a pest comprises:
   (a) expressing a nucleotide sequence encoding a polypeptide, which specifically binds to a pest, and optionally
   (b) isolating and/or purifying the polypeptide.

58. The method according to statements 10, 56 or 57, wherein the step of obtaining at least one polypeptide, which specifically binds to a pest comprises:
   a) providing a set, collection or library of polypeptide sequences;
   b) screening the set, collection or library of polypeptide sequences for sequences that specifically bind to and/or have affinity for a pest, and optionally
   c) isolating the polypeptide sequences that specifically bind to and/or have affinity for a pest.

DEFINITIONS

The present invention will be described with respect to particular embodiments but the invention is not limited thereto but only by the claims. Any reference signs in the claims shall not be construed as limiting the scope.

Where the term "comprising" is used in the present description and claims, it does not exclude other elements or steps.

Where an indefinite or definite article is used when referring to a singular noun e.g. "a" or "an", "the", this includes a plural of that noun unless something else is specifically stated.

The term "about" as used herein when referring to a measurable value such as a parameter, an amount, a temporal duration, and the like, is meant to encompass variations of +/−10% or less, preferably +/−5% or less, more preferably +/−1% or less, and still more preferably +/−0.1% or less of and from the specified value, insofar such variations are appropriate to perform in the disclosed invention. It is to be understood that the value to which the modifier 'about' refers is itself also specifically, and preferably, disclosed.

The following terms or definitions are provided solely to aid in the understanding of the invention. Unless specifically defined herein, all terms used herein have the same meaning as they would to one skilled in the art of the present invention. Practitioners are particularly directed to Sambrook et al., Molecular Cloning: A Laboratory Manual, $2^{nd}$ ed., Cold Spring Harbor Press, Plainsview, N.Y. (1989); and Ausubel et al., Current Protocols in Molecular Biology (Supplement 47), John Wiley & Sons, New York (1999), for definitions and terms of the art. The definitions provided herein should not be construed to have a scope less than understood by a person of ordinary skill in the art.

Unless indicated otherwise, all methods, steps, techniques and manipulations that are not specifically described in detail can be performed and have been performed in a manner known per se, as will be clear to the skilled person. Reference is for example again made to the standard handbooks, to the general background art referred to above and to the further references cited therein.

As used herein, the terms "polypeptide", "protein", "peptide", and "amino acid sequence" are used interchangeably, and refer to a polymeric form of amino acids of any length, which can include coded and non-coded amino acids, chemically or biochemically modified or derivatized amino acids, and polypeptides having modified peptide backbones.

As used herein, amino acid residues will be indicated either by their full name or according to the standard three-letter or one-letter amino acid code.

As used herein, the terms "nucleic acid molecule", "polynucleotide", "polynucleic acid", "nucleic acid" are used interchangeably and refer to a polymeric form of nucleotides of any length, either deoxyribonucleotides or ribonucleotides, or analogs thereof. Polynucleotides may have any three-dimensional structure, and may perform any function, known or unknown. Non-limiting examples of polynucleotides include a gene, a gene fragment, exons, introns, messenger RNA (mRNA), transfer RNA, ribosomal RNA, ribozymes, cDNA, recombinant polynucleotides, branched polynucleotides, plasmids, vectors, isolated DNA of any sequence, control regions, isolated RNA of any sequence, nucleic acid probes, and primers. The nucleic acid molecule may be linear or circular.

As used herein, the term "homology" denotes at least secondary structural similarity between two macromolecules, particularly between two polypeptides or polynucleotides, from same or different taxons, wherein said similarity is due to shared ancestry. Hence, the term "homologues" denotes so-related macromolecules having said secondary and optionally tertiary structural similarity. For comparing two or more nucleotide sequences, the '(percentage of) sequence identity' between a first nucleotide sequence and a second nucleotide sequence may be calculated using methods known by the person skilled in the art, e.g. by dividing the number of nucleotides in the first nucleotide sequence that are identical to the nucleotides at the corresponding positions in the second nucleotide sequence by the total number of nucleotides in the first nucleotide sequence and multiplying by 100% or by using a known computer algorithm for sequence alignment such as NCBI Blast. In determining the degree of sequence identity between two amino acid sequences, the skilled person may take into account so-called 'conservative' amino acid substitutions, which can generally be described as amino acid substitutions in which an amino acid residue is replaced with another amino acid residue of similar chemical structure and which has little or essentially no influence on the function, activity or other biological properties of the polypeptide. Possible conservative amino acid substitutions will be clear to the person skilled in the art. Amino acid sequences and nucleic acid sequences are said to be "exactly the same" if they have 100% sequence identity over their entire length.

As used herein, the terms "complementarity determining region" or "CDR" within the context of antibodies refer to variable regions of either the H (heavy) or the L (light) chains (also abbreviated as VH and VL, respectively) and contain the amino acid sequences capable of specifically binding to antigenic targets. These CDR regions account for the basic specificity of the antibody for a particular antigenic determinant structure. Such regions are also referred to as "hypervariable regions." The CDRs represent non-contiguous stretches of amino acids within the variable regions but, regardless of species, the positional locations of these critical amino acid sequences within the variable heavy and light chain regions have been found to have similar locations within the amino acid sequences of the variable chains. The variable heavy and light chains of all canonical antibodies each have 3 CDR regions, each non-contiguous with the others (termed L1, L2, L3, H1, H2, H3) for the respective light (L) and heavy (H) chains.

The term "affinity", as used herein, refers to the degree to which a polypeptide, in particular an immunoglobulin, such as an antibody, or an immunoglobulin fragment, such as a VHH, binds to an antigen so as to shift the equilibrium of antigen and polypeptide toward the presence of a complex formed by their binding. Thus, for example, where an antigen and antibody (fragment) are combined in relatively equal concentration, an antibody (fragment) of high affinity will bind to the available antigen so as to shift the equilibrium toward high concentration of the resulting complex. The dissociation constant is commonly used to describe the affinity between the protein binding domain and the antigenic target. Typically, the dissociation constant is lower than $10^{-5}$ M. Preferably, the dissociation constant is lower than $10^{-6}$ M, more preferably, lower than $10^{-7}$ M. Most preferably, the dissociation constant is lower than $10^{-8}$ M.

The terms "specifically bind" and "specific binding", as used herein, generally refers to the ability of a polypeptide, in particular an immunoglobulin, such as an antibody, or an immunoglobulin fragment, such as a VHH, to preferentially bind to a particular antigen that is present in a homogeneous mixture of different antigens. In certain embodiments, a specific binding interaction will discriminate between desirable and undesirable antigens in a sample, in some embodiments more than about 10 to 100-fold or more (e.g., more than about 1000- or 10,000-fold).

Accordingly, an amino acid sequence as disclosed herein is said to "specifically bind to" a particular target when that amino acid sequence has affinity for, specificity for and/or is specifically directed against that target (or for at least one part or fragment thereof).

The "specificity" of an amino acid sequence as disclosed herein can be determined based on affinity and/or avidity.

An amino acid sequence as disclosed herein is said to be "specific for a first target antigen of interest as opposed to a second target antigen of interest" when it binds to the first target antigen of interest with an affinity that is at least 5 times, such as at least 10 times, such as at least 100 times, and preferably at least 1000 times higher than the affinity with which that amino acid sequence as disclosed herein binds to the second target antigen of interest. Accordingly, in certain embodiments, when an amino acid sequence as disclosed herein is said to be "specific for" a first target antigen of interest as opposed to a second target antigen of interest, it may specifically bind to (as defined herein) the first target antigen of interest, but not to the second target antigen of interest.

As used herein, the terms "inhibiting", "reducing" and/or "preventing" may refer to (the use of) an amino acid sequence as disclosed herein that specifically binds to a target antigen of interest and inhibits, reduces and/or prevents the interaction between that target antigen of interest, and its natural binding partner. The terms "inhibiting", "reducing" and/or "preventing" may also refer to (the use of) an amino acid sequence as disclosed herein that specifically binds to a target antigen of interest and inhibits, reduces and/or prevents a biological activity of that target antigen of interest, as measured using a suitable in vitro, cellular or in vivo assay. Accordingly, "inhibiting", "reducing" and/or "preventing" may also refer to (the use of) an amino acid sequence as disclosed herein that specifically binds to a target antigen of interest and inhibits, reduces and/or prevents one or more biological or physiological mechanisms, effects, responses, functions pathways or activities in which the target antigen of interest is involved. Such an action of the amino acid sequence as disclosed herein as an antagonist may be determined in any suitable manner and/or using any suitable (in vitro and usually cellular or in vivo) assay known in the art, depending on the target antigen of interest.

Thus, more particularly, "inhibiting", "reducing" and/or "preventing" using amino acid sequence as disclosed herein may mean either inhibiting, reducing and/or preventing the interaction between a target antigen of interest and its natural binding partner, or, inhibiting, reducing and/or preventing the activity of a target antigen of interest, or, inhibiting, reducing and/or preventing one or more biological or physiological mechanisms, effects, responses, functions pathways or activities in which the target antigen of interest is involved, such as by at least 10%, but preferably at least 20%, for example by at least 50%, at least 60%, at least 70%, at least 80%, at least 90%, at least 95% or more, as measured using a suitable in vitro, cellular or in vivo assay, compared to the activity of the target antigen of interest in the same assay under the same conditions but without using the amino acid sequence as disclosed herein. In addition, "inhibiting", "reducing" and/or "preventing" may also mean inducing a decrease in affinity, avidity, specificity and/or selectivity of a target antigen of interest for one or more of its natural binding partners and/or inducing a decrease in the sensitivity of the target antigen of interest for one or more conditions in the medium or surroundings in which the target antigen of interest is present (such as pH, ion strength, the presence of co-factors, etc.), compared to the same conditions but without the presence of the amino acid sequence as disclosed herein. In the context of the present invention, "inhibiting", "reducing" and/or "preventing" may also involve allosteric inhibition, reduction and/or prevention of the activity of a target antigen of interest.

The inhibiting or antagonizing activity or the enhancing or agonizing activity of an amino acid sequence as disclosed herein may be reversible or irreversible, but for agrochemical, pharmaceutical and pharmacological applications will typically occur reversibly.

An amino acid sequence as disclosed herein is considered to be "(in) essentially isolated (form)" as used herein, when it has been extracted or purified from the host cell and/or medium in which it is produced.

In respect of the amino acid sequences as disclosed herein, the terms "binding region", "binding site" or "interaction site" present on the amino acid sequences as disclosed herein shall herein have the meaning of a particular site, region, locus, part, or domain present on the target molecule, which particular site, region, locus, part, or domain is responsible for binding to that target molecule. Such binding region thus essentially consists of that particular site, region, locus, part, or domain of the target molecule, which is in contact with the amino acid sequence when bound to that target molecule.

"Plant" as used herein, means live plants and live plant parts, including fresh fruit, vegetables and seeds. Also, the term "plant" as used herein encompasses whole plants, ancestors and progeny of the plants and plant parts, including seeds, shoots, stems, leaves, roots (including tubers), flowers, and tissues and organs, wherein each of the aforementioned comprise the gene/nucleic acid of interest. The term "plant" also encompasses plant cells, suspension cultures, callus tissue, embryos, meristematic regions, gametophytes, sporophytes, pollen and microspores, again wherein each of the aforementioned comprises the gene/nucleic acid of interest.

The choice of suitable control plants is a routine part of an experimental setup and may include corresponding wild type plants or corresponding plants without the gene of interest. The control plant is typically of the same plant species or even of the same variety as the plant to be assessed. The control plant may also be a nullizygote of the plant to be assessed. Nullizygotes are individuals missing the transgene by segregation. A "control plant" as used herein refers not only to whole plants, but also to plant parts, including seeds and seed parts.

"Crop" as used herein means a plant species or variety that is grown to be harvested as food, livestock fodder, fuel raw material, or for any other economic purpose. As a non-limiting example, said crops can be maize, cereals, such as wheat, rye, barley and oats, sorghum, rice, sugar beet and fodder beet, fruit, such as pome fruit (e.g. apples and pears), citrus fruit (e.g. oranges, lemons, limes, grapefruit, or mandarins), stone fruit (e.g. peaches, nectarines or plums), nuts (e.g. almonds or walnuts), soft fruit (e.g. cherries, strawberries, blackberries or raspberries), the plantain family or grapevines, leguminous crops, such as beans, lentils, peas and soya, oil crops, such as sunflower, safflower, rapeseed, canola, castor or olives, cucurbits, such as cucumbers, melons or pumpkins, fibre plants, such as cotton, flax or hemp, fuel crops, such as sugarcane, miscanthus or switchgrass, vegetables, such as potatoes, tomatoes, peppers, lettuce, spinach, onions, carrots, egg-plants, asparagus or cabage, ornamentals, such as flowers (e.g. petunias, pelargoniums, roses, tulips, lilies, or chrysanthemums), shrubs, broad-leaved trees (e.g. poplars or willows) and evergreens (e.g. conifers), grasses, such as lawn, turf or forage grass or other useful plants, such as coffee, tea, tobacco, hops, pepper, rubber or latex plants.

A "pest", as used here, is an organism that is harmful to plants, animals, humans or human concerns, and includes, but is not limited to crop pests (as later defined), household pests, such as cockroaches, ants, etc., and disease vectors, such as malaria mosquitoes.

A "plant pest", "plant pathogen" or "crop pest", as used in the application interchangeably, refers to organisms that specifically cause damage to plants, plant parts or plant products, particularly plants, plant parts or plant products, used in agriculture. Note that the term "plant pest" or "crop pest" is used in the meaning that the pest targets and harms plants. Pests particularly belong to invertebrate animals (e.g. insects (including agricultural pest insects, insect pests of ornamental plants, insect pests of forests). Relevant crop pest examples include, but are not limited to, aphids, caterpillars, flies, wasps, and the like, nematodes (living freely in soil or particularly species that parasitize plant roots, such as root-knot nematode and cyst nematodes such as soybean cyst nematode and potato cyst nematode), mites (such as spider mites, thread-footed mites and gall mites) and gastropods (including slugs such as *Deroceras* spp., *Milax* spp., *Tandonia* sp., *Limax* spp., *Arion* spp. and *Veronicella* spp. and snails such as *Helix* spp., *Cernuella* spp., *Theba* spp., *Cochlicella* spp., *Achatina* spp., *Succinea* spp., Ovachlamys spp., *Amphibulima* spp., *Zachrysia* spp., *Bradybaena* spp., and *Pomacea* spp.), pathogenic fungi (including *Ascomycetes* (such as *Fusarium* spp., *Thielaviopsis* spp., *Verticillium* spp., *Magnaporthe* spp.), *Basidiomycetes* (such as *Rhizoctonia* spp., *Phakospora* spp., *Puccinia* spp.), and fungal-like *Oomycetes* (such as *Pythium* spp. and *Phytophthora* spp.), bacteria (such as *Burkholderia* spp. and Proteobacteria such as *Xanthomonas* spp. and *Pseudomonas* spp.), Phytoplasma, Spiroplasma, viruses (such as tobacco mosaic virus and cauliflower mosaic virus), and protozoa.

"Microbe", as used herein, means bacterium, virus, fungus, yeast and the like and "microbial" means derived from a microbe.

"Fungus", as used herein, means a eukaryotic organism, belonging to the group of Eumycota. The term fungus in the present invention also includes fungal-like organisms such as the Oomycota. Oomycota (or *oomycetes*) form a distinct phylogenetic lineage of fungus-like eukaryotic microorganisms. This group was originally classified among the fungi but modern insights support a relatively close relationship with the photosynthetic organisms such as brown algae and diatoms, within the group of heterokonts.

"Pest infection" or "pest disease" as used herein refers to any inflammatory condition, disease or disorder in a living organism, such as a plant, animal or human, which is caused by a pest.

"Fungal infection" or "fungal disease" as used herein refers to any inflammatory condition, disease or disorder in a living organism, such as a plant, animal or human, which is caused by a fungus.

"Active substance", "active ingredient" or "active principle", as used interchangeably herein, means any biological, biochemical or chemical element and its derivatives, fragments or compounds based thereon, including microorganisms, having general or specific action against harmful organisms on a subject, and in particular on plants, parts of plants or on plant products, as they occur naturally or by manufacture, including any impurity inevitably resulting from the manufacturing process.

"Agrochemical", as used herein, means suitable for use in the agrochemical industry (including agriculture, horticulture, floriculture and home and garden uses, but also products intended for non-crop related uses such as public health/pest control operator uses to control undesirable insects and rodents, household uses, such as household fungicides and insecticides and agents, for protecting plants or parts of plants, crops, bulbs, tubers, fruits (e.g. from harmful organisms, diseases or pests); for controlling, preferably promoting or increasing, the growth of plants; and/or for promoting the yield of plants, crops or the parts of plants that are harvested (e.g. its fruits, flowers, seeds etc.). Examples of such substances will be clear to the skilled person and may for example include compounds that are active as insecticides (e.g. contact insecticides or systemic insecticides, including insecticides for household use), herbicides (e.g. contact herbicides or systemic herbicides, including herbicides for household use), fungicides (e.g. contact fungicides or systemic fungicides, including fungicides for household use), nematicides (e.g. contact nematicides or systemic nematicides, including nematicides for household use) and other pesticides or biocides (for example agents for killing insects or snails); as well as fertilizers;

growth regulators such as plant hormones; micro-nutrients, safeners, pheromones; repellants; insect baits; and/or active principles that are used to modulate (i.e. increase, decrease, inhibit, enhance and/or trigger) gene expression (and/or other biological or biochemical processes) in or by the targeted plant (e.g. the plant to be protected or the plant to be controlled), such as nucleic acids (e.g., single stranded or double stranded RNA, as for example used in the context of RNAi technology) and other factors, proteins, chemicals, etc. known per se for this purpose, etc. Examples of such agrochemicals will be clear to the skilled person; and for example include, without limitation: glyphosate, paraquat, metolachlor, acetochlor, mesotrione, 2,4-D, atrazine, glufosinate, sulfosate, fenoxaprop, pendimethalin, picloram, trifluralin, bromoxynil, clodinafop, fluroxypyr, nicosulfuron, bensulfuron, imazetapyr, dicamba, imidacloprid, thiamethoxam, fipronil, chlorpyrifos, deltamethrin, lambda-cyhalotrin, endosulfan, methamidophos, carbofuran, clothianidin, cypermethrin, abamectin, diflufenican, spinosad, indoxacarb, bifenthrin, tefluthrin, azoxystrobin, thiamethoxam, tebuconazole, mancozeb, cyazofamid, fluazinam, pyraclostrobin, epoxiconazole, chlorothalonil, copper fungicides, trifloxystrobin, prothioconazole, difenoconazole, carbendazim, propiconazole, thiophanate, sulphur, boscalid and other known agrochemicals or any suitable combination(s) thereof.

An "agrochemical composition" as used herein means a composition for agrochemical use, as further defined, comprising at least one active substance, optionally with one or more additives favoring optimal dispersion, atomization, deposition, leaf wetting, distribution, retention and/or uptake of agrochemicals. It will become clear from the further description herein that an agrochemical composition as used herein includes biological control agents or biological pesticides (including but not limited to biological biocidal, biostatic, fungistatic and fungicidal agents) and these terms will be interchangeably used in the present application. Accordingly, an agrochemical composition as used herein includes compositions comprising at least one biological molecule as an active ingredient, substance or principle for controlling pests in plants or in other agro-related settings (such for example in soil). Non-limiting examples of biological molecules being used as active principles in the agrochemical compositions disclosed herein are proteins (including antibodies and fragments thereof, such as but not limited to heavy chain variable domain fragments of antibodies, including VHH's), nucleic acid sequences, (poly-) saccharides, lipids, vitamins, hormones glycolipids, sterols, and glycerolipids.

As a non-limiting example, the additives in the agrochemical compositions disclosed herein may include but are not limited to diluents, solvents, adjuvants, surfactants, wetting agents, spreading agents, oils, stickers, thickeners, penetrants, buffering agents, acidifiers, anti-settling agents, anti-freeze agents, photo-protectors, defoaming agents, biocides and/or drift control agents.

A "biostatic composition" or a "biostatic agent" as used herein means any active ingredient, substance or principle or a composition comprising any active ingredient, substance or principle for biostatic use (as further defined herein) comprising at least one active biostatic substance or ingredient, optionally combined with one or more additives favoring optimal dispersion, atomization, deposition, leaf wetting, distribution, retention and/or uptake of the active substance or ingredient. As a non-limiting examples such additives are diluents, solvents, adjuvants, (ionic) surfactants, wetting agents, spreading agents, oils, stickers, thickeners, penetrants, buffering agents, acidifiers, anti-settling agents, anti-freeze agents, photo-protectors, defoaming agents, biocides, protease inhibitors and/or drift control agents.

A "biocidal composition" or a "biocidal agent" as used herein means any active ingredient, substance or principle or a composition comprising any active ingredient, substance or principle for biocidal use (as further defined herein) comprising at least one active biocidal substance or ingredient, optionally combined with one or more additives favoring optimal dispersion, atomization, deposition, leaf wetting, distribution, retention and/or uptake of the active substance or ingredient. As a non-limiting examples such additives are diluents, solvents, adjuvants, (ionic) surfactants, wetting agents, spreading agents, oils, stickers, thickeners, penetrants, buffering agents, acidifiers, anti-settling agents, anti-freeze agents, photo-protectors, defoaming agents, biocides, protease inhibitors and/or drift control agents.

A "fungistatic composition" or a "fungistatic agent" as used herein means any active ingredient, substance or principle or a composition comprising any active ingredient, substance or principle for fungistatic use (as further defined herein) comprising at least one active fungistatic substance or ingredient, optionally combined with one or more additives favoring optimal dispersion, atomization, deposition, leaf wetting, distribution, retention and/or uptake of the active substance or ingredient. As a non-limiting examples such additives are diluents, solvents, adjuvants, (ionic) surfactants, wetting agents, spreading agents, oils, stickers, thickeners, penetrants, buffering agents, acidifiers, anti-settling agents, anti-freeze agents, photo-protectors, defoaming agents, biocides, protease inhibitors and/or drift control agents.

A "fungicidal composition" or a "fungicidal agent" as used herein means any active ingredient, substance or principle or a composition comprising any active ingredient, substance or principle for fungicidal use (as further defined herein) comprising at least one active fungicidal substance or ingredient, optionally combined with one or more additives favoring optimal dispersion, atomization, deposition, leaf wetting, distribution, retention and/or uptake of the active substance or ingredient. As a non-limiting examples such additives are diluents, solvents, adjuvants, (ionic) surfactants, wetting agents, spreading agents, oils, stickers, thickeners, penetrants, buffering agents, acidifiers, anti-settling agents, anti-freeze agents, photo-protectors, defoaming agents, biocides, protease inhibitors and/or drift control agents.

"Agrochemical use", as used herein, not only includes the use of agrochemicals as defined above (for example, pesticides, growth regulators, nutrients/fertilizers, repellants, defoliants etc.) that are suitable and/or intended for use in field grown crops (e.g., agriculture), but also includes the use of agrochemicals as defined above (for example, pesticides, growth regulators, nutrients/fertilizers, repellants, defoliants etc.) that are meant for use in greenhouse grown crops (e.g. horticulture/floriculture) or hydroponic culture systems and even the use of agrochemicals as defined above that are suitable and/or intended for non-crop uses such as uses in private gardens, household uses (for example, herbicides or insecticides for household use), or uses by pest control operators (for example, weed control etc.).

"Biostatic (effect)" or "biostatic use", as used herein, includes any effect or use of an active substance (optionally comprised in a biostatic, biocidal, fungicidal or fungistatic composition as defined herein) for controlling, modulating or interfering with the harmful activity of a pest, such as a plant pest or a plant pathogen, including but not limited to inhibiting the growth or activity of the pest, altering the behavior of the pest, and repelling or attracting the pest in plants, plant parts or in other agro-related settings, such as for example for household uses or in soil.

"Biocidal (effect)" or "biocidal use", as used herein, includes any effect or use of an active substance (optionally comprised in a biocidal or fungicidal composition as defined herein) for controlling, modulating or interfering with the harmful activity of a pest, such as a plant pest or a plant pathogen, including but not limited to killing the pest, inhibiting the growth or activity of the pest, altering the behavior of the pest, and repelling or attracting the pest in plants, plant parts or in other agro-related settings, such as for example for household uses or in soil.

"Fungistatic (effect)" or "Fungistatic use", as used herein, includes any effect or use of an active substance (optionally comprised in a fungicidal or fungistatic composition as defined herein) for controlling, modulating or interfering with the harmful activity of a fungus, including but not limited to inhibiting the growth or activity of the fungus, altering the behavior of the fungus, and repelling or attracting the fungus in plants, plant parts or in other agro-related settings, such as for example for household uses or in soil.

"Fungicidal (effect)" or "Fungicidal use", as used herein, includes any effect or use of an active substance (optionally comprised in a fungicidal composition as defined herein) for controlling, modulating or interfering with the harmful activity of a fungus, including but not limited to killing the fungus, inhibiting the growth or activity of the fungus, altering the behavior of the fungus, and repelling or attracting the fungus in plants, plant parts or in other agro-related settings, such as for example for household uses or in soil.

"Pesticidal activity" or "biocidal activity", as used interchangeably herein, means to interfere with the harmful activity of a pest, including but not limited to killing the pest, inhibiting the growth or activity of the pest, altering the behavior of the pest, repelling or attracting the pest.

"Biostatic activity", as used herein, means to interfere with the harmful activity of a pest, including but not limited to inhibiting the growth or activity of the pest, altering the behavior of the pest, repelling or attracting the pest.

Pesticidal, biocidal, or biostatic activity of an active ingredient, substance or principle or a composition or agent comprising a pesticidal, biocidal, or biostatic active ingredient, substance or principle, can be expressed as the minimum inhibitory activity (MIC) of an agent (expressed in units of concentration such as e.g. mg/mL), without however being restricted thereto.

"Fungicidal activity", as used herein, means to interfere with the harmful activity of a fungus, including but not limited to killing the fungus, inhibiting the growth or activity of the fungus, altering the behavior of the fungus, and repelling or attracting the fungus.

"Fungistatic activity", as used herein, means to interfere with the harmful activity of a fungus, including but not limited to inhibiting the growth or activity of the fungus, altering the behavior of the fungus, and repelling or attracting the fungus.

Fungicidal or fungistatic activity of an active ingredient, substance or principle or a composition or agent comprising a pesticidal, biocidal, or biostatic active ingredient, substance or principle, can be expressed as the minimum inhibitory activity (MIC) of an agent (expressed in units of concentration such as e.g. mg/mL), without however being restricted thereto.

A "carrier", as used herein, means any solid, semi-solid or liquid carrier in or on(to) which an active substance can be suitably incorporated, included, immobilized, adsorbed, absorbed, bound, encapsulated, embedded, attached, or comprised. Non-limiting examples of such carriers include nanocapsules, microcapsules, nanospheres, microspheres, nanoparticles, microparticles, liposomes, vesicles, beads, a gel, weak ionic resin particles, liposomes, cochleate delivery vehicles, small granules, granulates, nano-tubes, buckyballs, water droplets that are part of an water-in-oil emulsion, oil droplets that are part of an oil-in-water emulsion, organic materials such as cork, wood or other plant-derived materials (e.g. in the form of seed shells, wood chips, pulp, spheres, beads, sheets or any other suitable form), paper or cardboard, inorganic materials such as talc, clay, microcrystalline cellulose, silica, alumina, silicates and zeolites, or even microbial cells (such as yeast cells) or suitable fractions or fragments thereof.

As used herein, the term "antibody" refers to polyclonal antibodies, monoclonal antibodies, humanized antibodies, single-chain antibodies, and fragments thereof such as Fab F(ab)2, Fv, and other fragments that retain the antigen binding function of the parent antibody. As such, an antibody may refer to an immunoglobulin or glycoprotein, or fragment or portion thereof, or to a construct comprising an antigen-binding portion comprised within a modified immunoglobulin-like framework, or to an antigen-binding portion comprised within a construct comprising a non-immunoglobulin-like framework or scaffold.

As used herein, the term "monoclonal antibody" refers to an antibody composition having a homogeneous antibody population. The term is not limited regarding the species or source of the antibody, nor is it intended to be limited by the manner in which it is made. The term encompasses whole immunoglobulins as well as fragments such as Fab, Fab)2, Fv, and others that retain the antigen binding function of the antibody. Monoclonal antibodies of any mammalian species can be used in this invention. In practice, however, the antibodies will typically be of rat or murine origin because of the availability of rat or murine cell lines for use in making the required hybrid cell lines or hybridomas to produce monoclonal antibodies.

As used herein, the term "polyclonal antibody" refers to an antibody composition having a heterogeneous antibody population. Polyclonal antibodies are often derived from the pooled serum from immunized animals or from selected humans.

"Heavy chain variable domain of an antibody or a functional fragment thereof", as used herein, means (i) the variable domain of the heavy chain of a heavy chain antibody, which is naturally devoid of light chains (also indicated hereafter as $V_{HH}$), including but not limited to the variable domain of the heavy chain of heavy chain antibodies of camelids or sharks or (ii) the variable domain of the heavy chain of a conventional four-chain antibody (also indicated hereafter as $V_H$), including but not limited to a camelized (as further defined herein) variable domain of the heavy chain of a conventional four-chain antibody (also indicated hereafter as camelized $V_H$). As further described hereinbelow, the amino acid sequence and structure of a heavy chain variable domain of an antibody can be considered, without however being limited thereto, to be comprised of four framework regions or "FR's", which are referred to in the art and hereinbelow as "framework region 1" or "FR1"; as "framework region 2" or "FR2"; as "framework region 3" or "FR3"; and as "framework region 4" or "FR4", respectively, which framework regions are interrupted by three complementary determining regions or "CDR's", which are referred to in the art as "complementarity determining region 1" or "CDR1"; as "complementarity determining region 2" or "CDR2"; and as "complementarity determining region 3" or "CDR3", respectively.

As also further described hereinbelow, the total number of amino acid residues in a heavy chain variable domain of an antibody (including a $V_{HH}$ or a $V_H$) can be in the region of 110-130, is preferably 112-115, and is most preferably 113. It should however be noted that parts, fragments or analogs of a heavy chain variable domain of an antibody are not particularly limited as to their length and/or size, as long as such parts, fragments or analogs retain (at least part of) the functional activity, such as the pesticidal, biocidal, biostatic activity, fungicidal or fungistatic activity (as defined herein) and/or retain (at least part of) the binding specificity of the original a heavy chain variable domain of an antibody from which these parts, fragments or analogs are derived from. Parts, fragments or analogs retaining (at least part of) the functional activity, such as the pesticidal, biocidal, biostatic activity, fungicidal or fungistatic activity (as defined herein) and/or retaining (at least part of) the binding specificity of the original heavy chain variable domain of an antibody from which these parts, fragments or analogs are derived from are also further referred to herein as "functional fragments" of a heavy chain variable domain.

The amino acid residues of a variable domain of a heavy chain variable domain of an antibody (including a $V_{HH}$ or a $V_H$) are numbered according to the general numbering for heavy chain variable domains given by Kabat et al. ("*Sequence of proteins of immunological interest*", US Public Health Services, NIH Bethesda, Md., Publication No. 91), as applied to $V_{HH}$ domains from Camelids in the article of Riechmann and Muyldermans, referred to above (see for example FIG. 2 of said reference). According to this numbering, FR1 of a heavy chain variable domain comprises the amino acid residues at positions 1-30, CDR1 of a heavy chain variable domain comprises the amino acid residues at positions 31-35, FR2 of a heavy chain variable domain comprises the amino acids at positions 36-49, CDR2 of a heavy chain variable domain comprises the amino acid residues at positions 50-65, FR3 of a heavy chain variable domain comprises the amino acid residues at positions 66-94, CDR3 of a heavy chain variable domain comprises the amino acid residues at positions 95-102, and FR4 of a heavy chain variable domain comprises the amino acid residues at positions 103-113. [In this respect, it should be noted that—as is well known in the art for $V_{HH}$ domains—the total number of amino acid residues in each of the CDR's may vary and may not correspond to the total number of amino acid residues indicated by the Kabat numbering (that is, one or more positions according to the Kabat numbering may not be occupied in the actual sequence, or the actual sequence may contain more amino acid residues than the number allowed for by the Kabat numbering). This means that, generally, the numbering according to Kabat may or may not correspond to the actual numbering of the amino acid residues in the actual sequence. Generally, however, it can be said that, according to the numbering of Kabat and irrespective of the number of amino acid residues in the CDR's, position 1 according to the Kabat numbering corresponds to the start of FR1 and visa versa, position 36 according to the Kabat numbering corresponds to the start of FR2 and visa versa, position 66 according to the Kabat numbering corresponds to the start of FR3 and visa versa, and position 103 according to the Kabat numbering corresponds to the start of FR4 and visa versa.].

Alternative methods for numbering the amino acid residues of heavy chain variable domains are the method described by Chothia et al. (Nature 342, 877-883 (1989)), the so-called "AbM definition" and the so-called "contact definition". However, in the present description, claims and figures, the numbering according to Kabat as applied to $V_{HH}$ domains by Riechmann and Muyldermans will be followed, unless indicated otherwise.

For a general description of heavy chain antibodies and the variable domains thereof, reference is inter alia made to the following references, which are mentioned as general background art: WO 94/04678, WO 95/04079 and WO 96/34103 of the Vrije Universiteit Brussel; WO 94/25591, WO 99/37681, WO 00/40968, WO 00/43507, WO 00/65057, WO 01/40310, WO 01/44301, EP 1134231 and WO 02/48193 of Unilever; WO 97/49805, WO 01/21817, WO 03/035694, WO 03/054016 and WO 03/055527 of the Vlaams Instituut voor Biotechnologie (VIB); WO 03/050531 of Algonomics N.V. and Ablynx N V; WO 01/90190 by the National Research Council of Canada; WO 03/025020 (=EP 1 433 793) by the Institute of Antibodies; as well as WO 04/041867, WO 04/041862, WO 04/041865, WO 04/041863, WO 04/062551 by Ablynx N V and the further published patent applications by Ablynx N V; Hamers-Casterman et al., Nature 1993 Jun. 3; 363 (6428): 446-8; Davies and Riechmann, FEBS Lett. 1994 Feb. 21; 339(3): 285-90; Muyldermans et al., Protein Eng. 1994 September; 7(9): 1129-3; Davies and Riechmann, Biotechnology (NY) 1995 May; 13(5): 475-9; Gharoudi et al., 9th Forum of Applied Biotechnology, Med. Fac. Landbouw Univ. Gent. 1995; 60/4a part I: 2097-2100; Davies and Riechmann, Protein Eng. 1996 June; 9(6): 531-7; Desmyter et al., Nat Struct Biol. 1996 September; 3(9): 803-11; Sheriff et al., Nat Struct Biol. 1996 September; 3(9): 733-6; Spinelli et al., Nat Struct Biol. 1996 September; 3(9): 752-7; Arbabi Ghahroudi et al., FEBS Lett. 1997 Sep. 15; 414(3): 521-6; Vu et al., Mol. Immunol. 1997 November-December; 34(16-17): 1121-31; Atarhouch et al., Journal of Carnel Practice and Research 1997; 4: 177-182; Nguyen et al., J. Mol. Biol. 1998 Jan. 23; 275(3): 413-8; Lauwereys et al., EMBO J. 1998 Jul. 1; 17(13): 3512-20; Frenken et al., Res Immunol. 1998 July-August; 149(6):589-99; Transue et al., Proteins 1998 Sep. 1; 32(4): 515-22; Muyldermans and Lauwereys, J. Mol. Recognit. 1999 March-April; 12 (2): 131-40; van der Linden et al., Biochim. Biophys. Acta 1999 Apr. 12; 1431(1): 37-46; Decanniere et al., Structure Fold. Des. 1999 Apr. 15; 7(4): 361-70; Ngyuen et al., Mol. Immunol. 1999 June; 36(8): 515-24; Woolven et al., Immunogenetics 1999 October; 50 (1-2): 98-101; Riechmann and Muyldermans, J. Immunol. Methods 1999 Dec. 10; 231 (1-2): 25-38; Spinelli et al., Biochemistry 2000 Feb. 15; 39(6): 1217-22; Frenken et al., J. Biotechnol. 2000 Feb. 28; 78(1): 11-21; Nguyen et al., EMBO J. 2000 Mar. 1; 19(5): 921-30; van der Linden et al., J. Immunol. Methods 2000 Jun. 23; 240 (1-2): 185-95; Decanniere et al., J. Mol. Biol. 2000 Jun. 30; 300 (1): 83-91; van der Linden et al., J. Biotechnol. 2000 Jul. 14; 80(3): 261-70; Harmsen et al., Mol. Immunol. 2000 August; 37(10): 579-90; Perez et al., Biochemistry 2001 Jan. 9; 40(1): 74-83; Conrath et al., J. Biol. Chem. 2001 Mar. 9; 276 (10): 7346-50; Muyldermans et al., Trends Biochem Sci. 2001 April; 26(4):230-5; Muyldermans S., J. Biotechnol. 2001 June; 74 (4): 277-302; Desmyter et al., J. Biol. Chem. 2001 Jul. 13; 276 (28): 26285-90; Spinelli et al., J. Mol. Biol. 2001 Aug. 3; 311 (1): 123-9; Conrath et al., Antimicrob Agents Chemother. 2001 October; 45 (10): 2807-12; Decanniere et al., J. Mol. Biol. 2001 Oct. 26; 313(3): 473-8; Nguyen et al., Adv Immunol. 2001; 79: 261-96; Muruganandam et al., FASEB J. 2002 February; 16 (2): 240-2; Ewert et al., Biochemistry 2002 Mar. 19; 41 (11): 3628-36; Dumoulin et al., Protein Sci. 2002 March; 11 (3): 500-15; Cortez-Retamozo et al., Int. J. Cancer. 2002 Mar. 20; 98 (3): 456-62; Su et al., Mol. Biol. Evol. 2002 March; 19 (3): 205-15; van der Vaart J M., Methods Mol. Biol. 2002; 178: 359-66; Vranken et al., Biochemistry 2002 Jul. 9; 41 (27): 8570-9; Nguyen et al., Immunogenetics 2002 April; 54 (1): 39-47; Renisio et al., Proteins 2002 Jun. 1; 47 (4): 546-55; Desmyter et al., J. Biol. Chem. 2002 Jun. 28; 277 (26): 23645-50; Ledeboer et al., J. Dairy Sci. 2002 June; 85 (6): 1376-82; De Genst et al., J. Biol. Chem. 2002 Aug. 16; 277 (33): 29897-907; Ferrat et al., Biochem. J. 2002 Sep. 1; 366 (Pt 2): 415-22; Thomassen et al., Enzyme and Microbial Technol. 2002; 30: 273-8; Harmsen et al., Appl. Microbiol. Biotechnol. 2002 December; 60 (4): 449-54; Jobling et al., Nat. Biotechnol. 2003 January; 21 (1): 77-80; Conrath et al., Dev. Comp. Immunol. 2003 February; 27 (2): 87-103; Pleschberger et al., Bioconjug. Chem. 2003 March-April; 14 (2): 440-8; Lah et al., J. Biol. Chem. 2003 Apr. 18; 278 (16): 14101-11; Nguyen et al., Immunology. 2003 May; 109 (1): 93-101; Joosten et al., Microb. Cell Fact. 2003 Jan. 30; 2 (1): 1; Li et al., Proteins 2003 Jul. 1; 52 (1): 47-50; Loris et al., Biol. Chem. 2003 Jul. 25; 278 (30): 28252-7; van Koningsbruggen et al., J. Immunol. Methods. 2003 August; 279 (1-2): 149-61; Dumoulin et al., Nature. 2003 Aug. 14; 424 (6950): 783-8; Bond et al., J. Mol. Biol. 2003 Sep. 19; 332 (3): 643-55; Yau et al., J. Immunol. Methods. 2003 Oct. 1; 281 (1-2): 161-75; Dekker et al., J. Virol. 2003 November; 77 (22): 12132-9; Meddeb-Mouelhi et al., Toxicon. 2003 December; 42 (7): 785-91; Verheesen et al., Biochim. Biophys. Acta 2003 Dec. 5; 1624 (1-3): 21-8; Zhang et al., J Mol Biol. 2004 Jan. 2; 335 (1): 49-56; Stijlemans et al., J Biol. Chem. 2004 Jan. 9; 279 (2): 1256-61; Cortez-Retamozo et al., Cancer Res. 2004 Apr. 15; 64 (8): 2853-7; Spinelli et al., FEBS Lett. 2004 Apr. 23; 564 (1-2): 35-40; Pleschberger et al., Bioconjug. Chem. 2004 May-June; 15 (3): 664-71; Nicaise et al., Protein Sci. 2004 July; 13 (7): 1882-91; Omidfar et al., Tumour Biol. 2004 July-August; 25 (4): 179-87; Omidfar et al., Tumour Biol. 2004 September-December; 25(5-6): 296-305; Szynol et al., Antimicrob Agents Chemother. 2004 September; 48(9):3390-5; Saerens et al., J. Biol. Chem. 2004 Dec. 10; 279 (50): 51965-72; De Genst et al., J. Biol. Chem. 2004 Dec. 17; 279 (51): 53593-601; Dolk et al., Appl. Environ. Microbiol. 2005 January; 71(1): 442-50; Joosten et al., Appl Microbiol Biotechnol. 2005 January; 66(4): 384-92; Dumoulin et al., J. Mol. Biol. 2005 Feb. 25; 346 (3): 773-88; Yau et al., J Immunol Methods. 2005 February; 297 (1-2): 213-24; De Genst et al., J. Biol. Chem. 2005 Apr. 8; 280 (14): 14114-21; Huang et al., Eur. J. Hum. Genet. 2005 Apr. 13; Dolk et al., Proteins. 2005 May 15; 59 (3): 555-64; Bond et al., J. Mol. Biol. 2005 May 6; 348(3):699-709; Zarebski et al., J. Mol. Biol. 2005 Apr. 21; [E-publication ahead of print].

Generally, it should be noted that the term "heavy chain variable domain" as used herein in its broadest sense is not limited to a specific biological source or to a specific method of preparation. For example, as will be discussed in more detail below, the heavy chain variable domains of the invention can be obtained (1) by isolating the $V_{HH}$ domain of a naturally occurring heavy chain antibody; (2) by isolating the $V_H$ domain of a naturally occurring four-chain antibody (3) by expression of a nucleotide sequence encoding a naturally occurring $V_{HH}$ domain; (4) by expression of a nucleotide sequence encoding a naturally occurring $V_H$ domain (5) by "camelization" (as described below) of a naturally occurring $V_H$ domain from any animal species, in particular a species of mammal, such as from a human being, or by expression of a nucleic acid encoding such a camelized $V_H$ domain; (6) by "camelisation" of a "domain antibody" or "Dab" as described by Ward et al (supra), or by expression of a nucleic acid encoding such a camelized $V_H$ domain (7) using synthetic or semi-synthetic techniques for preparing proteins, polypeptides or other amino acid sequences; (8) by preparing a nucleic acid encoding a $V_{HH}$ or a $V_H$ using techniques for nucleic acid synthesis, followed by expression of the nucleic acid thus obtained; and/or (9) by any combination of the foregoing. Suitable methods and techniques for performing the foregoing will be clear to the skilled person based on the disclosure herein and for example include the methods and techniques described in more detail hereinbelow.

However, according to a specific embodiment, the heavy chain variable domains as disclosed herein do not have an amino acid sequence that is exactly the same as (i.e. as a degree of sequence identity of 100% with) the amino acid sequence of a naturally occurring $V_H$ domain, such as the amino acid sequence of a naturally occurring $V_H$ domain from a mammal, and in particular from a human being.

The terms "effective amount" and "effective dose", as used herein, mean the amount needed to achieve the desired result or results.

As used herein, the terms "determining", "measuring", "assessing", "monitoring" and "assaying" are used interchangeably and include both quantitative and qualitative determinations.

All documents cited in the present specification are hereby incorporated by reference in their entirety. Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

[Compositions Comprising at Least One Polypeptide]

In one aspect, the present inventors have identified agrochemical compositions comprising at least one polypeptide, which can specifically bind to a pest. Importantly, through this interaction with a specific molecular structure of the pest, the compositions disclosed herein are capable of controlling, modulating, inhibiting, preventing or reducing one or more biological activities of the plant pathogen, such that the growth of the plant pathogen is controlled, modulated, inhibited, prevented or reduced. In certain embodiments, the agrochemical compositions as disclosed herein are capable of killing a plant pest through the specific interaction of at least one polypeptide, which can specifically bind to a pest and which is comprised in the compositions. Accordingly, the agrochemical compositions as disclosed herein can be used to modulate, such as to change, decrease or inhibit, the biological function of a plant pest by binding to a binding site present on a target of that plant pest thereby affecting the natural biological activities (such as, but not limited to, growth) of the pest and/or one or more biological pathways in which the structural target of that pest is involved.

Furthermore, the compositions comprising at least one polypeptide as disclosed herein have several additional advantages over the traditional immunoglobulin and non-immunoglobulin binding agents known in the art. Indeed, in certain embodiments, the amino acid sequences as disclosed herein are isolated heavy chain immunoglobulin variable domains, which are more potent and more stable than conventional four-chain antibodies, leading to (1) lower dosage forms, less frequent dosage and thus less side effects;

and (2) improved stability resulting in a broader choice of administration routes. Because of their small size, heavy chain immunoglobulin variable domains have the ability to cross membranes and penetrate into physiological compartments, tissues and organs not accessible to other, larger polypeptides and proteins.

In one specific, but non-limiting embodiment, the at least one polypeptide comprised in the compositions as disclosed herein may be a polypeptide comprising or, under suitable conditions (such as physiological conditions) capable of forming an immunoglobulin fold (i.e. by folding). Reference is inter alia made to the review by Halaby et al., J. (1999) Protein Eng. 12, 563-71. Preferably, when properly folded so as to form an immunoglobulin fold, such a polypeptide sequence is capable of specific binding (as defined herein) to a target or an antigen; and more preferably capable of binding to a pest target or a pest antigen with an affinity (suitably measured and/or expressed as a $K_D$-value (actual or apparent), a $K_A$-value (actual or apparent), a $k_{on}$-rate and/or a $k_{off}$-rate, or alternatively as an $IC_{50}$ value, as further described herein) that is as defined herein. Also, parts, fragments, analogs, mutants, variants, alleles and/or derivatives of such polypeptide sequences are preferably such that they comprise an immunoglobulin fold or are capable for forming, under suitable conditions, an immunoglobulin fold.

In particular embodiments, the invention provides an agrochemical composition or a biological pesticide composition for combating plant pests, more particularly a plant fungus, which composition comprises at least one polypeptide or amino acid sequence of between 80 and 200 amino acids as the active substance.

In certain further embodiments, the invention provides an agrochemical composition for combating plant pests, which composition comprises at least two polypeptides or at least two amino acid sequences of between 80 and 200 amino acids as the active substance.

In still further embodiments, the invention provides an agrochemical composition for combating plant pests, which composition comprises at least three polypeptides or at least three amino acid sequences of between 80 and 200 amino acids as the active substance.

The agrochemical composition according to the invention is an agrochemical composition, as defined herein, for combating plant pests, as defined before, meaning that the agrochemical composition, more in particular the active substance, as defined before, comprised in the agrochemical composition, is able to interfere with, preferably to reduce or to arrest, the harmful effects of one or more plantpests on one or more plants, preferably crops.

Thus, in one embodiment, the agrochemical composition comprises a polypeptide of between 80 and 200 amino acids as the active substance.

In more specific embodiments the agrochemical composition comprises a polypeptide of between 80-100 amino acids, 800-120 amino acids, 80-140 amino acids, 80-160 amino acids or 80-180 amino acids.

In yet another embodiment the agrochemical composition comprises a polypeptide of between 100-200 amino acids, 100-180 amino acids, 100-160 amino acids, 100-150 amino acids, 100-140 amino acids or 100-120 amino acids.

In yet another embodiment the agrochemical composition comprises a polypeptide of between 110-200 amino acids, 110-180 amino acids, 110-160 amino acids, 110-140 amino acids or 110-130 amino acids.

In yet another embodiment, the agrochemical composition comprises a polypeptide of between 120-200 amino acids, 120-180 amino acids, 120-160 amino acids, or 120-140 amino acids.

In yet another embodiment, the agrochemical composition comprises a polypeptide of between 140-200 amino acids, 140-180 amino acids, or 140-160 amino acids.

In yet another embodiment, the agrochemical composition comprises a polypeptide of between 160-200 amino acids or 160-180 amino acids.

The polypeptides or amino acid sequences comprised in the compositions disclosed herein can be a naturally occurring polypeptides or amino acid sequences, they can be derived from a naturally occurring polypeptide, or alternatively they can be entirely artificially designed. The polypeptides or amino acid sequences can be immunoglobulin-based or they can be based on domains present in proteins, including but not limited to microbial proteins, protease inhibitors, toxins, fibronectin, lipocalins, single chain antiparallel coiled coil proteins or repeat motif proteins. Non-limiting examples of such polypeptides, with the herein described ranges of amino acid lengths, include carbohydrate binding domains (CBD) (Blake et al (2006) J. Biol. Chem. 281, 29321-29329), heavy chain antibodies (hcAb), single domain antibodies (sdAb), minibodies (Tramontano et al (1994) J. Mol. Recognition 7, 9-24), the variable domain of camelid heavy chain antibodies (VHH), the variable domain of the new antigen receptors (VNAR), affibodies (Nygren P. A. (2008) FEBS J. 275, 2668-2676), alphabodies (see WO2010066740), designed ankyrin-repeat domains (DARPins) (Stumpp et al (2008) Drug Discovery Today 13, 695-701), anticalins (Skerra et al (2008) FEBS J. 275, 2677-2683), knottins (Kolmar et al (2008) FEBS J. 275, 2684-2690) and engineered CH2 domains (nanoantibodies, see Dimitrov D S (2009) mAbs 1, 26-28). In particular, the polypeptides or amino acid sequences as disclosed herein consist of a single polypeptide chain and are not post-translationally modified. More particularly, the polypeptides or amino acid sequences as disclosed are derived from an innate or adaptive immune system, preferably from a protein of an innate or adaptive immune system. Still more particularly, the polypeptides or amino acid sequences as disclosed herein are derived from an immunoglobulin. Most particularly, the polypeptides or amino acid sequences as disclosed herein comprise 4 framework regions and 3 complementary determining regions, or any suitable fragment thereof (which will then usually contain at least some of the amino acid residues that form at least one of the complementary determining regions). In particular, the polypeptides or amino acid sequences as disclosed herein are easy to produce at high yield, preferably in a microbial recombinant expression system, and convenient to isolate and/or purify subsequently. Particularly, the polypeptides or amino acid sequences as disclosed herein are selected from the group consisting of DARPins, knottins, alphabodies and $V_{HH}$'s. More particularly, the polypeptides or amino acid sequences as disclosed herein are selected from the group consisting of Alphabodies and $V_{HH}$'s. Most particularly, the polypeptides or amino acid sequences as disclosed herein are $V_{HH}$'s.

In particular, the at least one polypeptide comprised in the compositions disclosed herein consists of a single polypeptide chain and is not post-translationally modified. More particularly, the at least one polypeptide comprised in the compositions disclosed herein are derived from an innate or adaptive immune system, preferably from a protein of an innate or adaptive immune system. Still more particularly, the at least one polypeptide comprised in the compositions disclosed herein as disclosed herein are derived from an immunoglobulin. Most particularly, the at least one polypeptide comprised in the compositions disclosed herein comprise 4 framework regions and 3 complementary determining regions, or any suitable fragment thereof (which will then usually contain at least some of the amino acid residues that form at least one of the complementary determining regions). In particular, the at least one polypeptide comprised in the compositions disclosed herein are easy to produce at high yield, preferably in a microbial recombinant expression system, and convenient to isolate and/or purify subsequently.

According to particular embodiments, the invention provides a number of stretches of amino acid residues (i.e. small peptides) that are particularly suited for binding to a pest antigen or a pest target, such as but not limited to a fungal antigen or a fungal target.

These stretches of amino acid residues may be present in, and/or may be incorporated into, the polypeptides as disclosed herein, in particular in such a way that they form (part of) the antigen binding site of that polypeptide. As these stretches of amino acid residues were first generated as CDR sequences of antibodies, such as heavy chain antibodies, or of $V_H$ or $V_{HH}$ sequences that were raised against a pest target (or may be based on and/or derived from such CDR sequences, as further described herein), they will also generally be referred to herein as "CDR sequences" (i.e. as CDR1 sequences, CDR2 sequences and CDR3 sequences, respectively). It should however be noted that the invention in its broadest sense is not limited to a specific structural role or function that these stretches of amino acid residues may have in the polypeptides as disclosed herein, as long as these stretches of amino acid residues allow the polypeptides as disclosed herein to specifically bind to a pest target. Thus, generally, the invention in its broadest sense relates to agrochemical compositions comprising a polypeptide that is capable of binding to a pest target and that comprises a combination of CDR sequences as described herein.

Thus, in particular, but non-limiting embodiments, the polypeptides as disclosed herein may be polypeptides that comprise at least one amino acid sequence that is chosen from the group consisting of the CDR1 sequences, CDR2 sequences and CDR3 sequences that are described herein. In particular, a polypeptide as disclosed herein may comprise at least one antigen binding site, wherein said antigen binding site comprises at least one combination of a CDR1 sequence, a CDR2 sequence and a CDR3 sequence that are described herein.

Any polypeptide comprised in the agrochemical compositions as disclosed herein and having one these CDR sequence combinations is preferably such that it can specifically bind (as defined herein) to a pest target or a pest antigen, and more in particular such that it specifically binds to a target of a plant pathogen, in particular with dissociation constant (Kd) of $10^{-8}$ moles/liter or less of said polypeptide in solution.

Specific binding of a polypeptide to a pest target can be determined in any suitable manner known per se, including, for example biopanning, Scatchard analysis and/or competitive binding assays, such as radioimmunoassays (RIA), enzyme immunoassays (EIA) and sandwich competition assays, and the different variants thereof known in the art.

In a preferred embodiment, the polypeptide of between 80 and 200 amino acids, is obtained by affinity selection against a particular pest target molecule and said polypeptide has a high affinity for said pest target molecule: typically, the dissociation constant of the binding between the polypeptide and its pest target molecule is lower than $10^{-5}$ M, more preferably, the dissociation constant is lower than $10^{-6}$ M, even more preferably, the dissociation constant is lower than $10^{-7}$ M, most preferably, the dissociation constant is lower than $10^{-8}$ M.

In particular embodiments, the at least one polypeptide comprised in the compositions disclosed herein has a minimum inhibitory concentration (MIC) value for said plant pathogenic fungus of 1.0 μg/mL or less of said variable domain in solution.

Also disclosed herein are polypeptides of between 80 and 200 amino acids or a sub-range as disclosed herein before, obtained by affinity selection to a specific plant pest target, which is able to inhibit the growth and/or the activity of a crop pest at a minimum inhibitory concentration of about 0.00001 to 1 μM. In specific embodiments the minimum inhibitory concentrations are between 0.0001 to 1 μM, are between 0.001 to 1 μM, between 0.01 to 1 μM, between 0.1 to 1 μM, between 0.0001 to 0.1 μM, between 0.001 to 0.1 μM, between 0.01 to 0.1 μM, between 0.00001 to 0.01 μM, between 0.0001 to 0.01 μM, between 0.001 to 0.01 μM.

The Minimal Inhibitory Concentration or the MIC value is the lowest concentration of an agent such as a polypeptide that inhibits the visible growth of the crop or plant pest after incubation. For example the minimum fungicidal concentration (MFC) is considered as the lowest concentration of polypeptide which prevents growth and reduces the fungal inoculum by a 99.90% within 24 h. MFCs (Minimal Fungal Concentrations) can be determined on agar plates but can also be conveniently determined in fluids (e.g. in microwell plates) depending on the type of the fungus and the assay conditions.

In further particular embodiments, the compositions as disclosed herein at least comprise a polypeptide comprising one or more of the combinations chosen from the group comprising:
 a CDR1 region having SEQ ID NO: 85, a CDR2 region having has SEQ ID NO: 169, and a CDR3 region having SEQ ID NO: 253, and/or
 a CDR1 region having SEQ ID NO: 86, a CDR2 region having has SEQ ID NO: 170, and a CDR3 region having SEQ ID NO: 254, and/or
 a CDR1 region having SEQ ID NO: 87, a CDR2 region having has SEQ ID NO: 171, and a CDR3 region having SEQ ID NO: 255, and/or
 a CDR1 region having SEQ ID NO: 88, a CDR2 region having has SEQ ID NO: 172, and a CDR3 region having SEQ ID NO: 256, and/or
 a CDR1 region having SEQ ID NO: 89, a CDR2 region having has SEQ ID NO: 173, and a CDR3 region having SEQ ID NO: 257, and/or
 a CDR1 region having SEQ ID NO: 90, a CDR2 region having has SEQ ID NO: 174, and a CDR3 region having SEQ ID NO: 258, and/or
 a CDR1 region having SEQ ID NO: 91, a CDR2 region having has SEQ ID NO: 175, and a CDR3 region having SEQ ID NO: 259, and/or
 a CDR1 region having SEQ ID NO: 92, a CDR2 region having has SEQ ID NO: 176, and a CDR3 region having SEQ ID NO: 260, and/or
 a CDR1 region having SEQ ID NO: 93, a CDR2 region having has SEQ ID NO: 177, and a CDR3 region having SEQ ID NO: 261, and/or
 a CDR1 region having SEQ ID NO: 94, a CDR2 region having has SEQ ID NO: 178, and a CDR3 region having SEQ ID NO: 262, and/or a CDR1 region having SEQ ID NO: 95, a CDR2 region having has SEQ ID NO: 179, and a CDR3 region having SEQ ID NO: 263, and/or a CDR1 region having SEQ ID NO: 96, a CDR2 region having has SEQ ID NO: 180, and a CDR3 region having SEQ ID NO: 264, and/or a CDR1 region having SEQ ID NO: 97, a CDR2 region having has SEQ ID NO: 181, and a CDR3 region having SEQ ID NO: 265, and/or a CDR1 region having SEQ ID NO: 98, a CDR2 region having has SEQ ID NO: 182, and a CDR3 region having SEQ ID NO: 266, and/or a CDR1 region having SEQ ID NO: 99, a CDR2 region having has SEQ ID NO: 183, and a CDR3 region having SEQ ID NO: 267, and/or a CDR1 region having SEQ ID NO: 100, a CDR2 region having has SEQ ID NO: 184, and a CDR3 region having SEQ ID NO: 268, and/or a CDR1 region having SEQ ID NO: 101, a CDR2 region having has SEQ ID NO: 185, and a CDR3 region having SEQ ID NO: 269, and/or a CDR1 region having SEQ ID NO: 102, a CDR2 region having has SEQ ID NO: 186, and a CDR3 region having SEQ ID NO: 270, and/or a CDR1 region having SEQ ID NO: 103, a CDR2 region having has SEQ ID NO: 187, and a CDR3 region having SEQ ID NO: 271, and/or a CDR1 region having SEQ ID NO: 104, a CDR2 region having has SEQ ID NO: 188, and a CDR3 region having SEQ ID NO: 272, and/or a CDR1 region having SEQ ID NO: 105, a CDR2 region having has SEQ ID NO: 189, and a CDR3 region having SEQ ID NO: 273, and/or a CDR1 region having SEQ ID NO: 106, a CDR2 region having has SEQ ID NO: 190, and a CDR3 region having SEQ ID NO: 274, and/or a CDR1 region having SEQ ID NO: 107, a CDR2 region having has SEQ ID NO: 191, and a CDR3 region having SEQ ID NO: 275, and/or a CDR1 region having SEQ ID NO: 108, a CDR2 region having has SEQ ID NO: 192, and a CDR3 region having SEQ ID NO: 276, and/or a CDR1 region having SEQ ID NO: 109, a CDR2 region having has SEQ ID NO: 193, and a CDR3 region having SEQ ID NO: 277, and/or a CDR1 region having SEQ ID NO: 110, a CDR2 region having has SEQ ID NO: 194, and a CDR3 region having SEQ ID NO: 278, and/or a CDR1 region having SEQ ID NO: 111, a CDR2 region having has SEQ ID NO: 195, and a CDR3 region having SEQ ID NO: 279, and/or a CDR1 region having SEQ ID NO: 112, a CDR2 region having has SEQ ID NO: 196, and a CDR3 region having SEQ ID NO: 280, and/or a CDR1 region having SEQ ID NO: 113, a CDR2 region having has SEQ ID NO: 197, and a CDR3 region having SEQ ID NO: 281, and/or a CDR1 region having SEQ ID NO: 114, a CDR2 region having has SEQ ID NO: 198, and a CDR3 region having SEQ ID NO: 282, and/or a CDR1 region having SEQ ID NO: 115, a CDR2 region having has SEQ ID NO: 199, and a CDR3 region having SEQ ID NO: 283, and/or a CDR1 region having SEQ ID NO: 116, a CDR2 region having has SEQ ID NO: 200, and a CDR3 region having SEQ ID NO: 284, and/or a CDR1 region having SEQ ID NO: 117, a CDR2 region having has SEQ ID NO: 201, and a CDR3 region having SEQ ID NO: 285, and/or a CDR1 region having SEQ ID NO: 118, a CDR2 region having has SEQ ID NO: 202, and a CDR3 region having SEQ ID NO: 286, and/or a CDR1 region having SEQ ID NO: 119, a CDR2 region having has SEQ ID NO: 203, and a CDR3 region having SEQ ID NO: 287, and/or a CDR1 region having SEQ ID NO: 120, a CDR2 region having has SEQ ID NO: 204, and a CDR3 region having SEQ ID NO: 288, and/or a CDR1 region having SEQ ID NO: 121, a CDR2 region having has SEQ ID NO: 205, and a CDR3 region having SEQ ID NO: 289, and/or a CDR1 region having SEQ ID NO: 122, a CDR2 region having has SEQ ID NO: 206, and a CDR3 region having SEQ ID NO: 290, and/or a CDR1 region having SEQ ID NO: 123, a CDR2 region having has SEQ ID NO: 207, and a CDR3 region having SEQ ID NO: 291, and/or a CDR1 region having SEQ ID NO: 124, a CDR2 region having has SEQ ID NO: 208, and a CDR3 region having SEQ ID NO: 292, and/or a CDR1 region having SEQ ID NO: 125, a CDR2 region having has SEQ ID NO: 209, and a CDR3 region having SEQ ID NO: 293, and/or a CDR1 region having SEQ ID NO: 126, a CDR2 region having has SEQ ID NO: 210, and a CDR3 region having SEQ ID NO: 294, and/or a CDR1 region having SEQ ID NO: 127, a CDR2 region having has SEQ ID NO: 211, and a CDR3 region having SEQ ID NO: 295, and/or a CDR1 region having SEQ ID NO: 128, a CDR2 region having has SEQ ID NO: 212, and a CDR3 region having SEQ ID NO: 296, and/or a CDR1 region having SEQ ID NO: 129, a CDR2 region having has SEQ ID NO: 213, and a CDR3 region having SEQ ID NO: 297, and/or a CDR1 region having SEQ ID NO: 130, a CDR2 region having has SEQ ID NO: 214, and a CDR3 region having SEQ ID NO: 298, and/or a CDR1 region having SEQ ID NO: 131, a CDR2 region having has SEQ ID NO: 215, and a CDR3 region having SEQ ID NO: 299, and/or a CDR1 region having SEQ ID NO: 132, a CDR2 region having has SEQ ID NO: 216, and a CDR3 region having SEQ ID NO: 300, and/or a CDR1 region having SEQ ID NO: 133, a CDR2 region having has SEQ ID NO: 217, and a CDR3 region having SEQ ID NO: 301, and/or a CDR1 region having SEQ ID NO: 134, a CDR2 region having has SEQ ID NO: 218, and a CDR3 region having SEQ ID NO: 302, and/or a CDR1 region having SEQ ID NO: 135, a CDR2 region having has SEQ ID NO: 219, and a CDR3 region having SEQ ID NO: 303, and/or a CDR1 region having SEQ ID NO: 136, a CDR2 region having has SEQ ID NO: 220, and a CDR3 region having SEQ ID NO: 304, and/or a CDR1 region having SEQ ID NO: 137, a CDR2 region having has SEQ ID NO: 221, and a CDR3 region having SEQ ID NO: 305, and/or a CDR1 region having SEQ ID NO: 138, a CDR2 region having has SEQ ID NO: 222, and a CDR3 region having the amino acid sequence NRY, and/or a CDR1 region having SEQ ID NO: 139, a CDR2 region having has SEQ ID NO: 223, and a CDR3 region having SEQ ID NO: 306, and/or a CDR1 region having SEQ ID NO: 140, a CDR2 region having has SEQ ID NO: 224, and a CDR3 region having SEQ ID NO: 307, and/or a CDR1 region having SEQ ID NO: 141, a CDR2 region having has SEQ ID NO: 225, and a CDR3 region having SEQ ID NO: 308, and/or a CDR1 region having SEQ ID NO: 142, a CDR2 region having has SEQ ID NO: 226, and a CDR3 region having SEQ ID NO: 309, and/or a CDR1 region having SEQ ID NO: 143, a CDR2 region having has SEQ ID NO: 227, and a CDR3 region having SEQ ID NO: 310, and/or a CDR1 region having SEQ ID NO: 144, a CDR2 region having has SEQ ID NO: 228, and a CDR3 region having SEQ ID NO: 311, and/or a CDR1 region having SEQ ID NO: 145, a CDR2 region having has SEQ ID NO: 229, and a CDR3 region having SEQ ID NO: 312, and/or a CDR1 region having SEQ ID NO: 146, a CDR2 region having has SEQ ID NO: 230, and a CDR3 region having SEQ ID NO: 313, and/or a CDR1 region having SEQ ID NO: 147, a CDR2 region having has SEQ ID NO: 231, and a CDR3 region having SEQ ID NO: 314, and/or a CDR1 region having SEQ ID NO: 148, a CDR2 region having has SEQ ID NO: 232, and a CDR3 region having SEQ ID NO: 315, and/or a CDR1 region having SEQ ID NO: 149, a CDR2 region having has SEQ ID NO: 233, and a CDR3 region having SEQ ID NO: 316, and/or a CDR1 region having SEQ ID NO: 150, a CDR2 region having has SEQ ID NO: 234, and a CDR3 region having SEQ ID NO: 317, and/or a CDR1 region having SEQ ID NO: 151, a CDR2 region having has SEQ ID NO: 235, and a CDR3 region having SEQ ID NO: 318, and/or a CDR1 region having SEQ ID NO: 152, a CDR2 region having has SEQ ID NO: 236, and a CDR3 region having SEQ ID NO: 319, and/or a CDR1 region having SEQ ID NO: 153, a CDR2 region having has SEQ ID NO: 237, and a CDR3 region having SEQ ID NO: 320, and/or a CDR1 region having SEQ ID NO: 154, a CDR2 region having has SEQ ID NO: 238, and a CDR3 region having SEQ ID NO: 321, and/or a CDR1 region having SEQ ID NO: 155, a CDR2 region having has SEQ ID NO: 239, and a CDR3 region having SEQ ID NO: 322, and/or a CDR1 region having SEQ ID NO: 156, a CDR2 region having has SEQ ID NO: 240, and a CDR3 region having SEQ ID NO: 323, and/or a CDR1 region having SEQ ID NO: 157, a CDR2 region having has SEQ ID NO: 241, and a CDR3 region having SEQ ID NO: 324, and/or a CDR1 region having SEQ ID NO: 158, a CDR2 region having has SEQ ID NO: 242, and a CDR3 region having SEQ ID NO: 325, and/or a CDR1 region having SEQ ID NO: 159, a CDR2 region having has SEQ ID NO: 243, and a CDR3 region having SEQ ID NO: 326, and/or a CDR1 region having SEQ ID NO: 160, a CDR2 region having has SEQ ID NO: 244, and a CDR3 region having SEQ ID NO: 327, and/or a CDR1 region having SEQ ID NO: 161, a CDR2 region having has SEQ ID NO: 245, and a CDR3 region having SEQ ID NO: 328, and/or a CDR1 region having SEQ ID NO: 162, a CDR2 region having has SEQ ID NO: 246, and a CDR3 region having SEQ ID NO: 329, and/or a CDR1 region having SEQ ID NO: 163, a CDR2 region having has SEQ ID NO: 247, and a CDR3 region having SEQ ID NO: 330, and/or a CDR1 region having SEQ ID NO: 164, a CDR2 region having has SEQ ID NO: 248, and a CDR3 region having SEQ ID NO: 331, and/or a CDR1 region having SEQ ID NO: 165, a CDR2 region having has SEQ ID NO: 249, and a CDR3 region having SEQ ID NO: 332, and/or a CDR1 region having SEQ ID NO: 166, a CDR2 region having has SEQ ID NO: 250, and a CDR3 region having SEQ ID NO: 333, and/or a CDR1 region having SEQ ID NO: 167, a CDR2 region having has SEQ ID NO: 251, and a CDR3 region having SEQ ID NO: 334, and/or a CDR1 region having SEQ ID NO: 168, a CDR2 region having has SEQ ID NO: 252, and a CDR3 region having SEQ ID NO: 335.

In particular embodiments, the polypeptides in the compositions as disclosed herein are heavy chain variable domains that essentially consist of four framework regions (FR1 to FR4 respectively) and three complementarity determining regions (CDR1 to CDR3 respectively); or any suitable fragment of such an heavy chain variable domain (which will then usually contain at least some of the amino acid residues that form at least one of the CDR's, as further described herein).

The polypeptides as disclosed herein may in particular be an antibody, such as for instance a heavy chain antibody. In further particular embodiments, the polypeptides as disclosed herein may be a heavy chain variable domain sequence of an antibody that is derived from a conventional four-chain antibody (such as, without limitation, a $V_H$ sequence that is derived from a human antibody) or be a so-called $V_{HH}$-sequence (as defined herein) that is derived from a so-called "heavy chain antibody" (as defined herein).

In particular embodiments, the compositions as disclosed herein, at least comprise a heavy chain variable domain sequence derived of an antibody or a functional fragment thereof, such as but not limited to a camelid heavy chain antibody or a functional fragment thereof, which variable domain sequence thus may be for instance a heavy chain variable domain of a camelid heavy chain antibody ($V_{HH}$).

However, it should be noted that the invention is not limited as to the origin of the polypeptides comprised in the compositions disclosed herein (or of the nucleotide sequence of the invention used to express it), nor as to the way that the polypeptides or nucleotide sequences thereof is (or has been) generated or obtained. Thus, the polypeptides in the compositions disclosed herein may be naturally occurring polypeptides (from any suitable species) or synthetic or semi-synthetic polypeptides. In a specific but non-limiting embodiment of the invention, the polypeptide is a naturally occurring immunoglobulin sequence (from any suitable species) or a synthetic or semi-synthetic immunoglobulin sequence, including but not limited to "camelized" immunoglobulin sequences, as well as immunoglobulin sequences that have been obtained by techniques such as affinity maturation (for example, starting from synthetic, random or naturally occurring immunoglobulin sequences), CDR grafting, veneering, combining fragments derived from different immunoglobulin sequences, PCR assembly using overlapping primers, and similar techniques for engineering immunoglobulin sequences well known to the skilled person; or any suitable combination of any of the foregoing.

The polypeptide sequences of the compositions disclosed herein may in particular be a domain antibody (or an heavy chain variable domain that is suitable for use as a domain antibody), a single domain antibody (or an heavy chain variable domain that is suitable for use as a single domain antibody), or a "dAb" (or an heavy chain variable domain that is suitable for use as a dAb); other single variable domains, or any suitable fragment of any one thereof. For a general description of (single) domain antibodies, reference is also made to the prior art cited above, as well as to EP 0 368 684. For the term "dAb's", reference is for example made to Ward et al. (Nature 1989 Oct. 12; 341 (6242): 544-6), to Holt et al., Trends Biotechnol., 2003, 21(11):484-490; as well as to for example WO 06/030220, WO 06/003388 and other published patent applications of Domantis Ltd.

Thus, in particular embodiments, the present invention provides polypeptides with the (general) structure

FR1-CDR1-FR2-CDR2-FR3-CDR3-FR4 in which FR1 to FR4 refer to framework regions 1 to 4, respectively, and in which CDR1 to CDR3 refer to the complementarity determining regions 1 to 3, respectively, and are as further defined herein.

SEQ ID NO's: 1 to 84 (see Table 1) give the amino acid sequences of a number of polypeptides that have been raised against a pest target, in particular against fungal glucosylceramide.

TABLE 1

VHH sequences

| Name | SEQ ID | VHH Amino acid sequence |
|---|---|---|
| 40F07 | 1 | QVQLQESGGGLVQAGGSLRLSCVASGTTFSSY<br>TMGWYRQAPGKQRELLASIEGGGNTDYADSVK<br>GRFTISRDNARNTVYLQMNSLKTEDTAVYYCN<br>AARTWSIFRNYWGQGTQVTVSS |
| 41D01 | 2 | QVQLQESGGGLVQAGGSLRLSCAASGRTFSRY<br>GMGWFRQLPGKQRELVTSITRGGTTTYADSVK<br>GRFTISRDNAKNTVYLQMNSLKPEDTAVYYCN<br>ARSIWRDYWGQGTQVTVSS |
| 41D06 | 3 | QVQLQESGGGLVQAGGSLRLSCAASGGIFGIN<br>AMRWYRQAPGKQRELVASISSGGNTNYSESVK<br>GRFTISRDDANYTVYLQMNSLKPEDTAVYYCN<br>FVRLWFPDYWGQGTQVTVSS |
| 41G10 | 4 | QVQLQESGGGLVQPGGSLTLSCAATKTGFSIN<br>AMGWYRQAPGKQREMVATITSGGTTNYADSVK<br>GRFAISRDNAKNTVSLQMNTLKPEDTALYYCN<br>TEARRYFTRASQVYWGQGTQVTVSS |
| 41H05 | 5 | QVQLQESGGGLVQPGGSLRLSCAASGGIFSIN<br>AMGWYRQDPGKQREMVATITSGANTNYTDSVK<br>GRFTISRDNAKNTVYLQMNSLKPEDTAVYYCN<br>AVGRRWYGGYVELWGQGTQVTVSS |
| 42C11 | 6 | QVQLQESGGGLVQPGGSLRLSCAASGSIFSTY<br>VMGWYRQAIGKQRELVATITSSGKTNYAASVK<br>GRFTVSRDITKNTMYLQMNSLKPEDTAVYYCG<br>ADRWVLTRWSNYWGQGTQVTVSS |
| 42C12 | 7 | QVQLQESGGGLVQPGGSLRLSCAASGSISSLG<br>WYRQAPGKQREFVASATSGGDTTYADSVKGRF<br>TISRDNSKNTVYLQMNSLKPEDTAVYYCKGQR<br>GVAWTRKEYWGQGTQVTVSS |

TABLE 1-continued

VHH sequences

| Name | SEQ ID | VHH Amino acid sequence |
|---|---|---|
| 50D03 | 8 | QVQLQESGGGLVQPGGSLRLSCAASGSIFSTY<br>AMGWYRQAIGKQRELVATITSSGKTNYAASVK<br>GRFTISRDITKNTMYLQMNSLKPEDTAVYYCG<br>ADRWVLTRWSNYWGQGTQVTVSS |
| 50D07 | 9 | QVQLQESGGGLVQPGGSLRLSCTASGNIVNIR<br>DMGWYRQVPGKQRELVATITSDQSTNYADSVK<br>GRFTTTRDNAKKTVYLQMDSLKPEDTAGYYCN<br>ARVRTVLRGWRDYWGQGTQVTVSS |
| 50E02 | 10 | QVQLQESGGGLVQPGGSLRLSCAASGSIFSIN<br>AMGWYRQAPGKQRELVAAITSDGSTNYADSVK<br>GRFTISRDNAKNTAYLQMNSLKPEDTAVYYCN<br>LRRRTFLKSSDYWGQGTQVTVSS |
| 51B08 | 11 | QVQLQESGGGLVQAGDSLRLSCAASGRRFGSY<br>AMGWFRQVPGKERELVAGISSGGSTKYADSVR<br>GRFTISRDNAKNTVSLQMKSLKPEDTAVYYCN<br>AKYGRWTYTGRPEYDSWGQGTQVTVSS |
| 51C06 | 12 | QVQLQESGGGLVQPGGSLRLSCAASGSIFSSD<br>TMGWYRRAPGKQRELVAAITTGGNTNYADSVK<br>GRFTISRDNAKNTVYLQMNSLQPEDTAVYYCN<br>CRRRWSRDFWGQGTQVTVSS |
| 51C08 | 13 | QVQLQESGGGLVQPGGSLRLSCAASGTIFSIK<br>TMGWYRQAPGKQRELVATISNGGSTNYADSVK<br>GRFTISRDNAKNTVYLQMNSLKPEDTAVYYCN<br>ARQQFIGAPYEYWGQGTQVTVSS |
| 52A01 | 14 | QVQLQESGGGLVQAGGSLRLSCTASGAITFSL<br>GTMGWYRQAPGKQRELVASISTGSTNYADSVK<br>GRFTISRDIIKNILYLQMNSLKPEDTAVYSCN<br>ARLLWSNYWGQGTQVTVSS |
| 52B01 | 15 | QVQLQESGGGLVQAGESLRLSCAASGSTFSIN<br>VMGWYRQAPGEQRELVATISRGGSTNYADSVK<br>GRFTISRDNAKVTVYLQMDSLKPEDTAVYYCN<br>AAGWVGVTNYWGQGTQVTVSS |
| 52G05 | 16 | QVQLQESGGGLVQAGGSLRLSCAASGSTGSIS<br>AMGWYRQAPGKQRELVASITRRGSTNYADSVK<br>DRFTISRDNAWNTVYLQMNSLKPEDTAVYYCN<br>ARRYYTRNDYWGQGTQVTVSS |
| 53A01 | 17 | QVQLQESGGGLGQAGGSLRLSCEVSGTTFSIN<br>TMGWHRQAPGKQRELVASISSGGWTNYADSVK<br>GRFTISRDNAKKTVYLQMNNLKPEDTAVYYCR<br>WGAIGNWYGQGTQVTVSS |
| 53F05 | 18 | QVQLQESGGGLVQPGGSLRLSCAASVRIFGLN<br>AMGWYRQGPGKQRELVASITTGGSTNYAEPVK<br>GRFTISRDNANNTVYLQMNNLKPEDTAVYYCN<br>AERRWGLPNYWGQGTQVTVSS |
| 54A02 | 19 | QVQLQESGGGLVEAGGSLRLSCAASGRTFSRY<br>GMGWFRQAPGKEREFVAANRWSGGSTYYADSV<br>RGRFTISRDNAKNTVYLQMNSLKPEDTAVYYC<br>AAYAHITAWGMRNDYEYDYWGQGTQVTVSS |
| 54B01 | 20 | QVQLQESGGGLVQAGGSLRLSCAATGRTFSRY<br>TMGWFRQAPGKERDFVAGITWTGGSTDYADSV<br>KGRFTISRDNAKNTVYLQMNSLKPEDTAVYYC<br>AAGNLLRLAGQLRRGYDSWGQGTQVTVSS |
| 54C01 | 21 | QVQLQESGGGLVQAGGSLRLSCAASGRTGSRY<br>AMGWFRQAPGKEREFVAAISWSGGSTYYADSV<br>KDRFTISRDNAKNTVYLQMHSLKPEDTAVYYC<br>ATRNRAGPHYSRGYTAGQEYDYWGQGTQVTVS<br>S |
| 54C04 | 22 | QVQLQESGGGLVQPGGSLRLSCAASGRIFSIN<br>AMGWYRQGPGKERELVVDMTSGGSINYADSVS<br>GRFTISRDNAKNTVYLQMNSLKPEDTAVYYCH<br>ANLRTAFWRNGNDYWGQGTQVTVSS |

TABLE 1-continued

VHH sequences

| Name | SEQ ID | VHH Amino acid sequence |
|---|---|---|
| 54C08 | 23 | QVQLQESGGGLVQPGGSLRLSCAASGSISSIN AMGWYRQAPGKQRELVASITSGGSTNYADSVK GRFTISRDNAKNTVNLQMNSLKPEDTAVYYCS AGPWYRRSWGRGTQVTVSS |
| 54C10 | 24 | QVQLQESGGGLVQPGESLRLSCAASASIFWVN DMGWYRQAPGKQRELVAQITRRGSTNYADSVK GRFTISRDNAKDEVYLQMNSLKPEDTAVYYCN ADLAVRGRYWGQGTQVTVSS |
| 54C11 | 25 | QVQLQESGGGLVQPGGSLRLSCAASGSFFPVN DMAWYRQALGNERELVANITRGGSTNYADSVK GRFTISRDNAKNTVYLQMNTLKPEDTAVYYCN VRIGFGWTAKAYWGQGTQVTVSS |
| 54D03 | 26 | QVQLQESGGGLVQPGGSLRLSCAASGGIFGIN AMRWYRQAPGKQRELVASISSGGNTNYSESVK GRFTISRDDANYTVYLQMNSLKPEDTAVYYCN FVRLWFPDYWGQGTQVTVSS |
| 54D06 | 27 | QVQLQESGGGLVQPGGSLRLSCAASGSTIRIN AMGWYRQAPGKQRELVATITRGGITNYADSVK GRFTISRDNAKFTVYLQMNSLKPEDTAVYYCN ARSWVGPEYWGQGTQVTVSS |
| 54D10 | 28 | QVQLQESGGGLVQPGGSLRLSCAASGMTYSIH AMGWYRQAPGKERELVAITSTSGTTDYTDSVK GRFTISRDGANNTVYLQMNSLKSEDTAVYYCH VKTRTWYNGKYDYWGQGTQVTVSS |
| 54E01 | 29 | QVQLQESGGGLVQPGGSLRLSCTASGSIFSIN PMGWYRQAPGKQRELVAAITSGGSTNYADYVK GRFTISRDNAKNVVYLQMNSLKPEDTAVYYCN GRSTLWRRDYWGQGTQVTVSS |
| 54E05 | 30 | QVQLQESGGGLVQPGGSLRLSCAASGSIFSIN TMGWYRQAPGKQRELVAAITNRGSTNYADFVK GRFTISRDNAKNTVYLQMNSLKPDDTAVYYCN AHRSWPRYDSWGQGTQVTVSS |
| 54E10 | 31 | QVQLQESGGGLVQPGGSLRLSCAASGSIFSFN AMGWYRQAPGKQRELVAAITRGGSTNYADSVK GRFTISRDNANNTVYLQMNSLKPEDTAVYYCN AESRIFRRYDWGPGTQVTVSS |
| 54F01 | 32 | QVQLQESGGGLVQPGGSLRLSCVTSGSIFGLN LMGWYRQAPGKQRELVATITRGGSTNYADSVK GRFTISRDNAKKTVYLQMNSLKPEDTAVYYCN VDRGWSSYWGQGTQVTVSS |
| 54F02 | 33 | QVQLQESGGGLVQPGGSLRLSCVTSGSIRSIN TMGWYRQAPGNERELVATITSGGTTNYADSVK NRFTISRDNAKNTVYLQMNSLKPEDTAVYYCN LHQRAWARSYVYWGQGTQVTVSS |
| 54G01 | 34 | QVQLQESGGGSVQPGGSLRLSCAASGSIFAVN AMGWYRQAPGHQRELVAIISSNSTSNYADSVK GRFTISRDNAKNTVYLQMNSLKPEDTAVYFCY AKRSWFSQEYWGQGTQVTVSS |
| 54G08 | 35 | QVQLQESGGGLVQPGGSLRLSCAASGSIFSFN LMGWYRQAPGKQRELVAAITSSSNTNYADSVK GRFTISRDNAKNTVYLQMNSLKPEDTAVYYCN AQYTITPWGIKKDYWGQGTQVTVSS |
| 54G09 | 36 | QVQLQESGGGLMQPGGSLRLSCTASGNIVNIR DMGWYRQVPGKQRELVATITSDQSTNYADSVK GRFTTTRDNAKKTVYLQMDSLKPEDTAGYYCN ARVRTVLRGWRDYWGQGTQVTVSS |
| 55B02 | 37 | QVQLQESGGGLVQPGESLRLSCVGSGSIFNIN SMNWYRQASGKQRELVADMRSDGSTNYADSVK GRFTISRDNARKTVYLQMNSLKPEDTAVYYCH ANSIFRSRDYWGQGTQVTVSS |
| 55B05 | 38 | QVQLQESGGGVVQAGDSLRLSCAASGRTFGGY TVAWFRQAPGKEREFVARISWSGIMAYYAESV KGRFTISRDNAKNTVYLQMNSLKPEDTAVYYC ASRSQIRSPWSSLDDYDRWGQGTQVTVSS |
| 55C05 | 39 | QVQLQESGGGLVQPGGSLRLSCVVSGSISSMK AMGWHRQAPGKERELVAQITRGDSTNYADSVK GRFTISRDNAKNTVYLQMNSLKPDDTGVYYCN ADRFFGRDYWGKGTQVTVSS |
| 55D08 | 40 | QVQLQESGGGLVQPGGSLRLSCAASRSILSIS AMGWYRQGPGKQREPVATITSAGSSNYSDSVK GRFTISRDNAKNTAYLQMNSLKPEDTAVYYCK TVYSRPLLGPLEVWGQGTQVTVSS |
| 55E02 | 41 | QVQLQESGGGLVQTGGSLRLSCVASGSMFSSN AMAWYRQAPGKQRELVARILSGGSTNYADSVK GRFTISRGNAKNTVYLQMNSLKPEDTAVYYCN AVRYLVNYWGQGTQVTVSS |
| 55E07 | 42 | QVQLQESGGGSVQVGDSLTLSCVASGRSLDIY GMGWFRQAPGKEREFVARITSGGSTYYADSVK GRFTLSRDNAKNTVYLQMNSLKPEDTAVYYCA AGVVVATSPKFYAYWGQGTQVTVSS |
| 55E09 | 43 | QVQLQESGGGLVQAGGSLRLSCAASKRIFSTY TMGWFRQAPGKEREFVAAIWSGGRTRYADSV KGRFTISRDNARNTVHLQMNSLEPEDTAVYYC YTRRLGTGYWGQGTQVTVSS |
| 55E10 | 44 | QVQLQESGGGLVQAGGSLRLSCAASGSTFSIQ TIGWYRQAPGKQRDRVATISSGGSTNYADSVK GRFTISRDNAKKTVYLQMNNLKPEDTAVYYCN LRYWFRDYWGQGTQVTVSS |
| 55F04 | 45 | QVQLQESGGGLVQPGGSLRLSCAASGSTFSIN VRGWYRQAPGKQRELVATITSDGSTNYADSVK GRFTISRDNAKNTAYLQMNSLKPEDTAVYYCN AVRLFRQYWGQGTQVTVSS |
| 55F09 | 46 | QVQLQESGGGLVQPGGSLRLSCAASGSIFRLN AMGWYRQAPGKQRELVAAITPGGGNTTYADSV KGRFTISRDNALNTIYLQMNSLKPEDTAVYYC NAGGSSRWYSSRYYPGGYWGQGTQVTVSS |
| 55F10 | 47 | QVQLQESGGGLVQAGGSLRLSCATSGGTFSRY AMGWFRQAPGKERELVATIRRSGSSTYYLDST KGRFTISRDNAKNTVYLQMNSLKLEDTAVYYC AADSSARALVGGPGNRWDYWGQGTQVTVSS |
| 55G02 | 48 | QVQLQESGGGLVQPGGSLRLSCAASGSIGSIN VMGWYRQYPGKQRELVAFITSGGITNYTDSVK GRFAISRDNAQNTVYLQMNSLTPEDTAVYYCH LKNAKNVRPGYWGQGTQVTVSS |
| 55G08 | 49 | QVQLQESGGGLVQPGGSLRLSCRASGGIFGIN AMRWYRQAPGKQRELVASISSGGTTDYVESVK GRFTISRDNATNTVDLQMSALKPEDTAVYYCN FVRFWFPDYWGQGTQVTVSS |
| 56A05 | 50 | QVQLQESGGGLVQAGGSLRLSCAASGITFMSN TMGWYRQAPGKQRELVASISSGGSTNYADSVK GRFTISRDNAKKTVYLQMNSLKPEDTAVYYCN ARRNVFISSWGQGTQVTVSS |
| 56A06 | 51 | QVQLQESGGGLVQPGGSLRLSCVASGSISVYG MGWYRQAPGKQRELVARITNIGTTNYADSVKG RFTISRDNAKNTVYLQMNSLQPEDTAVYYCNL RRLGRDYWGQGTQVTVSS |
| 56A09 | 52 | QVQLQESGGGLVQPGGSLRLSCAASRTALRLN SMGWYRQAPGSQRELVATITRGGTTNYADSVK GRFTISREIGNNTVYLQMNSLEPEDTAVYYCN ANFGILVGREYWGKGTQVTVSS |

TABLE 1-continued

VHH sequences

| Name | SEQ ID | VHH Amino acid sequence |
|---|---|---|
| 56C09 | 53 | QVQLQESGGGLVQAGGSLRLSCAVSGSIFSIL SMAWYRQTPGKQRELVANITSVGSTNYADSVK GRFTISRDIAKKTLYLQMNNLKPEDTAIYYCN TRMPFLGDSWGQGTQVTVSS |
| 56C12 | 54 | QVQLQESGGGLVQAGGSLRLSCAVSAFSFSNR AVSWYRQAPGKSREWVASISGIRITTYTNSVK GRFIISRDNAKKTVYLQMNDLRPEDTGVYRCY MNRYSGQGTQVTVSS |
| 56D06 | 55 | QVQLQESGGGSVQPGGSLRLSCAASGTVFFSI SAMGWYRQAPGKQRELVAGISRGGSTKYGDFV KGRFTISRDNGKKTIWLQMNNLQPEDTAIYYC RLTSITGTYLWGQGTQVTVSS |
| 56D07 | 56 | QVQLQESGGGLVQPGGSLRLSCAASGSIFSMK VMGWYRQGPGKLRELVAITSGGRTNYAESVK GRFTISRDNAKNTVSLQMNSLQPEDTAVYYCY YKTIRPYWGQGTQVTVSS |
| 56D10 | 57 | QVQLQESGGGLVQAGGSLRLSCAASGITFRIT TMGWYRQAPGKQRELVASSSSGGTTNYASSVK GRFTISRDNAKNTVYLQMNSLRPEDTAVYYCN ARKFITTPWSTDYWGQGTQVTVSS |
| 56E04 | 58 | QVQLQESGGGLVQPGDSLRLSCTPSGSIFNHK ATGWYRQAPGSQRELVAKITTGGTTNYADSVK GRFTISRDNAKNTVYLQMSSLKPEDTAVYYCN AERYFATTLWGQGTQVTVSS |
| 56E05 | 59 | QVQLQESGGGLVQAGGSLRLSCAASGITFSNN AGGWYRQAPGQQRELVARISSGGNTNYTDSVK GRFTISRDITKNTLSLQMNNLKPEDSAVYYCN AQRRVILGPRNYWGQGTQVTVSS |
| 56E08 | 60 | QVQLQESGGGLVQAGGSLRLSCAASGNIFRIN DMGWYRQAPGNQRELVATITSANITNYADSVK GRFTISRDNAKNTVYLQMNSLNPEDTAVYYCT AQAKKWRIGPWSDYWGQGTQVTVSS |
| 56F07 | 61 | QVQLQESGGGLVQPGGSLRLSCAASGRIFSIN DMAWYRQAPGKQRELVAIITNDDSTTYADSVK GRFTISRDNAKNTVYLQMNSLKPEDTAVYYCN ADINTAIWRRKYWGQGTQVTVSS |
| 56F11 | 62 | QVQLQESGGGLVQSGGSLRLSCVHSKTTFTRN AMGWYRQALGKERELVATITSGGTTNYADSVK GRFTISMDSAKNTVYLQMNSLKPEDTAVYYCN VNTRRIFGGTVREYWGQGTQVTVSS |
| 56G07 | 63 | QVQLQESGGGLVQPGGSLRLSCAVSGSRIFIH DMGWHRQAPGEPRELVATITPFGRRNYSEYVK GRFTVSRDIARNTMSLQMSNLKAEDTGMYYCN VRVNGVDYWGQGTQVTVSS |
| 56G08 | 64 | QVQLQESGGGLVQAGGSLRLSCAISGITFRRP FGISRMGWYRQAPGKERELVATLSRAGTSRYV DSVKGRFTISRDDAKNTLYLQMVSLNPEDTAV YYCYIAQLGTDYWGQGTQVTVSS |
| 56G10 | 65 | QVQLQESGGGLVQAGGSLRLSCVASGITLRMY QVGWYRQAPGKQRELVAEISSRGTTMYADSVK GRFTISRDGAKNIVYLQMNSLEPEDTAVYYCN ARAFAFGRNSWGQGTQVTVSS |
| 56H04 | 66 | QVQLQESGGGSVQAGGSLRLSCAVSGGTFSNK AMGWYRQSSGKQRALVARISTVGTAHYADSVK GRFTVSKDNAGNTLYLQMNSLKPEDTAVYYCN AQAGRLYLRNYWGQGTQVTVSS |
| 56H05 | 67 | QVQLQESGGGLVQPGESLRLSCVAAASTSITT FNTMAWYRQAPGKQRELVAQINNRDNTEYADS VKGRFIISRGNAKNTSNLQMNDLKSEDTGIYY CNAKRWSWSTGFWGQGTQVTVSS |
| 56H07 | 68 | QVQLQESGGGLVQAGGSLRLSCTASGLTFALG TMGWYRQAPGKQRELVASISTGSTNYADSVKG RFTISRDIIKNILYLQMNSLKPEDTAVYSCNA RLWWSNYWGQGTQVTVSS |
| 56H08 | 69 | QVQLQESGGGLVQAGGSLRLSCTASGRTSSVN PMGWYRQAPGKQRELVAVISSDGSTNYADSVK GRFTVSRDNAKNTLYLQMNSLKPEDTAVYYCN ANRRWSWGSEYWGQGTQVTVSS |
| 57A06 | 70 | QVQLQESGGGLVQAGGSLRLSCAASGITFTNN AGGWYRQAPGQQRELVARISSGGNTNYTDSVK GRFTISRDITKNTLSLQMNNLKPEDSAVYYCN AQRRVILGPRNYWGQGTQVTVSS |
| 57B01 | 71 | QVQLQESGGGLVQAGGSLRLSCEAPVSTFNIN AMAWYRQAPGKSRELVARISSGGSTNYADSVK GRFTISRDNAKNTVYLQMNSLKPEDTAVYICY VNRHWGWDYWGQGTQVTVSS |
| 57B07 | 72 | QVQLQESGGGLVQPGGTLRLSCVASGSFRSIN AMGWYRQAPGKQRELVATVDSGGYTNYADSVK GRFTISRDNAKNTVYLQMSSLTPEDTAVYYCY AGIYKWPWSVDARDYWGQGTQVTVSS |
| 57B11 | 73 | QVQLQESGGGLVQAGGSLRLSCAASGSSISMN SMGWYRQAPGKERERVALIRSSGGTYYADSVK GRFTISRDNAKNTVYLQMNNLKPEDTAVYYCQ ARRTWLSSESWGQGTQVTVSS |
| 57C07 | 74 | QVQLQESGGGLVQAGGSLRLSCAVSGSTFGIN TMGWYRQAPEKQRELVASIRGGMTNYADSVK GRFIISRDNAKNTVYLQMNSLKPEDTAVYCN AGIRSRWYGGPITTYWGQGTQVTVSS |
| 57C09 | 75 | QVQLQESGGGLVQAGGSLRLSCAASGSTGSIN AMGWYRQGPGKQRDLVASISSGGATNYADSVK GRFTISRDNSKNTVYLQMSSLKPEDTAVYYCN AKKSRWSWSIVHDYWGQGTQVTVSS |
| 57D02 | 76 | QVQLQESGGGSVQTGGSLTLSCTTSGSIFGRS DMGWYRQAPGKQRELVATITRRSRTNYAEFVK GRFTISRDSAKNLVTLQMNSLKPEDTNVYYCN ARWGAGGIFSTWGQGTQVTVSS |
| 57D09 | 77 | QVQLQESGGGLVQPGESLRLSCAASGSMSIDA MGWYRQAPGDQRELVASITTGGSTNYADSVKG RFTISRDNAKNTVWLQMNSLKPEDTAVYYCNA KVRLRWFRPPSDYWGQGTQVTVSS |
| 57D10 | 78 | QVQLQESGGGLVQPGGSLRLSCAASGRLLSIS TMGWYRRTPEDQREMVASITKDGTTNYADSVK GRLTISRDNAKNTVYLQMNSLKPDDTAVYVCN ARATTWVPYRRDAEFWGQGTQVTVSS |
| 57E07 | 79 | QVQLQESGGGLVQAGGSLRLSCAASGSIFGIN DMGWYRQAPGKQRDLVADITRSGSTHYVDSVK GRFTISRDNAKNTVYLQMNSLKPEDTAVYYCN ADSGSHWWNRRDYWGQGTQVTVSS |
| 57E11 | 80 | QVQLQESGGGLVQPGGSLKLSCAASGFTFSIN TMGWYRQAPGKQRELVARISRLRVTNYADSVK GRFTISRDNAKNTVYLQMNSLKPEDTAVYYCN AANWGLAGNEYWGQGTQVTVSS |
| 57G01 | 81 | QVQLQESGGGLVQAGGSLRPSCTASGSTLLIN SMGWYRQAPGKQRELVATISNSGTTNYVDAVK GRFAISRDNANHTVYLQMNSLEPEDTAVYYCN AQTFWRRNYWGQGTQVTVSS |
| 57G07 | 82 | QVQLQESGGGLVQAGGSLRLSCAVSGSTSRIN AMGWYRQAPGKKRESVATIRRGGNTKYADSVK GRFTISRDNANNTVYLQMNSLKPEDTAVYYCN AHSWLDYWGRGTQVTVSS |

TABLE 1-continued

VHH sequences

| Name | SEQ ID | VHH Amino acid sequence |
|---|---|---|
| 57G08 | 83 | QVQLQESGGGLVQAGGSLRLSCASRRRINGIT MGWYRQAPGKQRELVATIDIHNSTKYADSVKG RFIISRDNGKSMLYLQMNSLKPEDTAVYYCNR IPTFGRYWGQGTQVTVSS |
| 57H08 | 84 | QVQLQESGGGLVQAGGSLRLSCVASGSTFYTF STKNVGWYRQAPGKQRELVAQQRYDGSTNYAD SLQGRFTISRDNAKRTVYLQMNSLKPEDTAVY ICNVNRGFISYWGQGTQVTVSS |

In particular, the invention in some specific embodiments provides agrochemical compositions comprising at least one polypeptide that is directed against a pest target and that has at least 80%, preferably at least 85%, such as 90% or 95% or more sequence identity with at least one of the amino acid sequences of SEQ ID NO's: 1 to 84 (see Table 1), and nucleic acid sequences that encode such amino acid sequences.

Some particularly preferred polypeptide sequences as disclosed herein are those which can bind to and/or are directed against a pest and which have at least 90% amino acid identity with at least one of the amino acid sequences of SEQ ID NO's: 1 to 84 (see Table 1), in which for the purposes of determining the degree of amino acid identity, the amino acid residues that form the CDR sequences are disregarded.

In these polypeptides, the CDR sequences (see Table 2) are generally as further defined herein.

TABLE 2

CDR sequences

| Name | CDR1 sequence | SEQ ID | CDR2 sequence | SEQ ID | CDR3 sequence | SEQ ID |
|---|---|---|---|---|---|---|
| 40F07 | SYTMG | 85 | SIEGGGNTDYADSVKG | 169 | ARTWSIFRNY | 253 |
| 41D01 | RYGMG | 86 | SITRGGTTTYADSVKG | 170 | RSIWRDY | 254 |
| 41D06 | INAMR | 87 | SISSGGNTNYSESVKG | 171 | VRLWFPDY | 255 |
| 41G10 | INAMG | 88 | TITSGGTTNYADSVKG | 172 | EARRYFTRASQVY | 256 |
| 41H05 | INAMG | 89 | TITSGANTNYTDSVKG | 173 | VGRRWYGGYVEL | 257 |
| 42C11 | TYVMG | 90 | TITSSGKTNYAASVKG | 174 | DRWVLTRWSNY | 258 |
| 42C12 | ISSLG | 91 | SATSGGDTTYADSVKG | 175 | QRGVAWTRKEY | 259 |
| 50D03 | TYAMG | 92 | TITSSGKTNYAASVKG | 176 | DRWVLTRWSNY | 260 |
| 50D07 | IRDMG | 93 | TITSDQSTNYADSVKG | 177 | RVRTVLRGWRDY | 261 |
| 50E02 | INAMG | 94 | AITSDGSTNYADSVKG | 178 | RRRTFLKSSDY | 262 |
| 51B08 | SYAMG | 95 | GISSGGSTKYADSVRG | 179 | KYGRWTYTGRPEYDS | 263 |
| 51C06 | SDTMG | 96 | AITTGGNTNYADSVKG | 180 | RRRWSRDF | 264 |
| 51C08 | IKTMG | 97 | TISNGGSTNYADSVKG | 181 | RQQFIGAPYEY | 265 |
| 52A01 | LGTMG | 98 | SISTGSTNYADSVKG | 182 | RLLWSNY | 266 |
| 52B01 | INVMG | 99 | TISRGGSTNYADSVKG | 183 | AGWVGVTNY | 267 |
| 52G05 | ISAMG | 100 | SITRRGSTNYADSVKD | 184 | RRYYTRNDY | 268 |
| 53A01 | INTMG | 101 | SISSGGWTNYADSVKG | 185 | GAIGNW | 269 |
| 53F05 | LNAMG | 102 | SITTGGSTNYAEPVKG | 186 | ERRWGLPNY | 270 |
| 54A02 | RYGMG | 103 | ANRWSGGSTYYADSVRG | 187 | YAHITAWGMRNDYEYDY | 271 |
| 54B01 | RYTMG | 104 | GITWTGGSTDYADSVKG | 188 | GNLLRLAGQLRRGYDS | 272 |
| 54C01 | RYAMG | 105 | AISWSGGSTYYADSVKD | 189 | RNRAGPHYSRGYTAGQEYDY | 273 |
| 54C04 | INAMG | 106 | DMTSGGSINYADSVSG | 190 | NLRTAFWRNGNDY | 274 |
| 54C08 | INAMG | 107 | SITSGGSTNYADSVKG | 191 | GPWYRRS | 275 |
| 54C10 | VNDMG | 108 | QITRRGSTNYADSVKG | 192 | DLAVRGRY | 276 |
| 54C11 | VNDMA | 109 | NITRGGSTNYADSVKG | 193 | RIGFGWTAKAY | 277 |
| 54D03 | INAMR | 110 | SISSGGNTNYSESVKG | 194 | VRLWFPDY | 278 |
| 54D06 | INAMG | 111 | TITRGGITNYADSVKG | 195 | RSWVGPEY | 279 |

TABLE 2-continued

CDR sequences

| Name | CDR1 sequence | SEQ ID | CDR2 sequence | SEQ ID | CDR3 sequence | SEQ ID |
|---|---|---|---|---|---|---|
| 54D10 | IHAMG | 112 | ITSTSGTTDYTDSVKG | 196 | KTRTWYNGKYDY | 280 |
| 54E01 | INPMG | 113 | AITSGGSTNYADYVKG | 197 | RSTLWRRDY | 281 |
| 54E05 | INTMG | 114 | AITNRGSTNYADFVKG | 198 | HRSWPRYDS | 282 |
| 54E10 | FNAMG | 115 | AITRGGSTNYADSVKG | 199 | ESRIFRRYDY | 283 |
| 54F01 | LNLMG | 116 | TITRGGSTNYADSVKG | 200 | DRGWSSY | 284 |
| 54F02 | INTMG | 117 | TITSGGTTNYADSVKN | 201 | HQRAWARSYVY | 285 |
| 54G01 | VNAMG | 118 | IISSNSTSNYADSVKG | 202 | KRSWFSQEY | 286 |
| 54G08 | FNLMG | 119 | AITSSSNTNYADSVKG | 203 | QYTITPWGIKKDY | 287 |
| 54G09 | IRDMG | 120 | TITSDQSTNYADSVKG | 204 | RVRTVLRGWRDY | 288 |
| 55B02 | INSMN | 121 | DMRSDGSTNYADSVKG | 205 | NSIFRSRDY | 289 |
| 55B05 | GYTVA | 122 | RISWSGIMAYYAESVKG | 206 | RSQIRSPWSSLDDYDR | 290 |
| 55C05 | MKAMG | 123 | QITRGDSTNYADSVKG | 207 | DRFFGRDY | 291 |
| 55D08 | ISAMG | 124 | TITSAGSSNYSDSVKG | 208 | VYSRPLLGPLEV | 292 |
| 55E07 | IYGMG | 126 | RITSGGSTYYADSVKG | 210 | GVVVATSPKFYAY | 294 |
| 55E09 | TYTMG | 127 | AIIWSGGRTRYADSVKG | 211 | RRLGTGY | 295 |
| 55E10 | IQTIG | 128 | TISSGGSTNYADSVKG | 212 | RYWFRDY | 296 |
| 55F04 | INVRG | 129 | TITSDGSTNYADSVKG | 213 | VRLFRQY | 297 |
| 55F09 | LNAMG | 130 | AITPGGGNTTYADSVKG | 214 | GGSSRWYSSRYYPGGY | 298 |
| 55F10 | RYAMG | 131 | TIRRSGSSTYYLDSTKG | 215 | DSSARALVGGPGNRWDY | 299 |
| 55G02 | INVMG | 132 | FITSGGITNYTDSVKG | 216 | KNAKNVRPGY | 300 |
| 55G08 | INAMR | 133 | SISSGGTTDYVESVKG | 217 | VRFWFPDY | 301 |
| 56A05 | SNTMG | 134 | SISSGGSTNYADSVKG | 218 | RRNVFISS | 302 |
| 56A06 | VYGMG | 135 | RITNIGTTNYADSVKG | 219 | RRLGRDY | 303 |
| 56A09 | LNSMG | 136 | TITRGGTTNYADSVKG | 220 | NFGILVGREY | 304 |
| 56C09 | ILSMA | 137 | NITSVGSTNYADSVKG | 221 | RMPFLGDS | 305 |
| 56C12 | NRAVS | 138 | SISGIRITTYTNSVKG | 221 | NRY | |
| 56D06 | ISAMG | 139 | GISRGGSTKYGDFVKG | 223 | TSITGTYL | 306 |
| 56D07 | MKVMG | 140 | VITSGGRTNYAESVKG | 224 | KTIRPY | 307 |
| 56D10 | ITTMG | 141 | SSSSGGTTNYASSVKG | 225 | RKFITTPWSTDY | 308 |
| 56E04 | HKATG | 142 | KITTGGTTNYADSVKG | 226 | ERYFATTL | 309 |
| 56E05 | NNAGG | 143 | RISSGGNTNYTDSVKG | 227 | QRRVILGPRNY | 310 |
| 56E08 | INDMG | 144 | TITSANITNYADSVKG | 228 | QAKKWRIGPWSDY | 311 |
| 56F07 | INDMA | 145 | IITNDDSTTYADSVKG | 229 | DINTAIWRRKY | 312 |
| 56F11 | RNAMG | 146 | TITSGGTTNYADSVKG | 230 | NTRRIFGGTVREY | 313 |
| 56G07 | IHDMG | 147 | TITPFGRRNYSEYVKG | 231 | RVNGVDY | 314 |
| 56G08 | ISRMG | 148 | TLSRAGTSRYVDSVKG | 232 | AQLGTDY | 315 |
| 56G10 | MYQVG | 149 | EISSRGTTMYADSVKG | 233 | RAFAFGRNS | 316 |

TABLE 2-continued

CDR sequences

| Name | CDR1 sequence | SEQ ID | CDR2 sequence | SEQ ID | CDR3 sequence | SEQ ID |
|---|---|---|---|---|---|---|
| 56H04 | NKAMG | 150 | RISTVGTAHYADSVKG | 234 | QAGRLYLRNY | 317 |
| 56H05 | FNTMA | 151 | QINNRDNTEYADSVKG | 235 | KRWSWSTGF | 318 |
| 56H07 | LGTMG | 152 | SISTGSTNYADSVKG | 236 | RLWWSNY | 319 |
| 56H08 | VNPMG | 153 | VISSDGSTNYADSVKG | 237 | NRRWSWGSEY | 320 |
| 57A06 | NNAGG | 154 | RISSGGNTNYTDSVKG | 238 | QRRVILGPRNY | 321 |
| 57B01 | INAMA | 155 | RISSGGSTNYADSVKG | 239 | NRHWGWDY | 322 |
| 57B07 | INAMG | 156 | TVDSGGYTNYADSVKG | 240 | GIYKWPWSVDARDY | 323 |
| 57B11 | MNSMG | 157 | LIRSSGGTYYADSVKG | 241 | RRTWLSSES | 324 |
| 57C07 | INTMG | 158 | SISRGGMTNYADSVKG | 242 | GIRSRWYGGPITTY | 325 |
| 57C09 | INAMG | 159 | SISSGGATNYADSVKG | 243 | KKSRWSWSIVHDY | 326 |
| 57D02 | RSDMG | 160 | TITRRSRTNYAEFVKG | 244 | RWGAGGIFST | 327 |
| 57D09 | IDAMG | 161 | SITTGGSTNYADSVKG | 245 | KVRLRWFRPPSDY | 328 |
| 57D10 | ISTMG | 162 | SITKDGTTNYADSVKG | 246 | RATTWVPYRRDAEF | 329 |
| 57E07 | INDMG | 163 | DITRSGSTHYVDSVKG | 247 | DSGSHWWNRRDY | 330 |
| 57E11 | INTMG | 164 | RISRLRVTNYADSVKG | 248 | ANWGLAGNEY | 331 |
| 57G01 | INSMG | 165 | TISNSGTTNYVDAVKG | 249 | QTFWRRNY | 332 |
| 57G07 | INAMG | 166 | TIRRGGNTKYADSVKG | 250 | HSWLDYDY | 333 |
| 57G08 | GITMG | 167 | TIDIHNSTKYADSVKG | 251 | IPTFGRY | 334 |
| 57H08 | TKNVG | 168 | QQRYDGSTNYADSLQG | 252 | NRGFISY | 335 |

Again, such polypeptides may be derived in any suitable manner and from any suitable source, and may for example be naturally occurring $V_{HH}$ sequences (i.e. from a suitable species of Camelid) or synthetic or semi-synthetic heavy chain variable domains, including but not limited to "camelized" immunoglobulin sequences (and in particular camelized heavy chain variable domain sequences), as well as those that have been obtained by techniques such as affinity maturation (for example, starting from synthetic, random or naturally occurring immunoglobulin sequences), CDR grafting, veneering, combining fragments derived from different immunoglobulin sequences, PCR assembly using overlapping primers, and similar techniques for engineering immunoglobulin sequences well known to the skilled person; or any suitable combination of any of the foregoing as further described herein.

It is understood that the agrochemical compositions or the biological control compositions as disclosed herein are stable, both during storage and during utilization, meaning that the integrity of the agrochemical composition is maintained under storage and/or utilization conditions of the agrochemical composition, which may include elevated temperatures, freeze-thaw cycles, changes in pH or in ionic strength, UV-irradiation, presence of harmful chemicals and the like. More preferably, the polypeptide of between 80 and 200 amino acids, and the various sub-ranges described herein, remain stable in the agrochemical composition, meaning that the integrity and the pesticidal activity of the polypeptide is maintained under storage and/or utilization conditions of the agrochemical composition, which may include elevated temperatures, freeze-thaw cycles, changes in pH or in ionic strength, UV-irradiation, presence of harmful chemicals and the like. Most preferably, said polypeptide of between 80 and 200 amino acids, and the various sub-ranges described herein, remain stable in the agrochemical composition when the agrochemical composition is stored at ambient temperature for a period of two years or when the agrochemical composition is stored at 54° C. for a period of two weeks. Preferably, the agrochemical composition of the present invention retains at least about 70% activity, more preferably at least about 70% to 80% activity, most preferably about 80% to 90% activity or more. Optionally, the polypeptide may be comprised in a carrier, as defined, to protect the polypeptide from harmful effects caused by other components in the agrochemical composition or from harmful effects during storage or during application. Examples of suitable carriers include, but are not limited to alginates, gums, starch, β-cyclodextrins, celluloses, polyurea, polyurethane, polyester, microbial cells or clay.

The agrochemical composition may occur in any type of formulation, preferred formulations are powders, wettable powders, wettable granules, water dispersible granules, emulsions, emulsifiable concentrates, dusts, suspensions, suspension concentrates, suspoemulsions (mixtures of suspensions and emulsions), capsule suspensions, aqueous dispersions, oil dispersions, aerosols, pastes, foams, slurries or flowable concentrates.

The polypeptide of between 80 and 200 amino acids, and the various sub-ranges described herein before, may be the only active substance in the agrochemical or biological control composition according to the invention; however, it is also possible that the agrochemical composition comprises one or more additional agrochemicals, as defined, in addition to the polypeptide or amino acid sequence (or the at least one, at least two or at least three polypeptides or amino acid sequences as disclosed herein). Such additional agrochemicals or biological control compositions may have a different effect on plant pests as the polypeptide or amino acid sequence, they may have a synergistic effect with the polypeptide or amino acid sequence, or they may even modify the activity of the polypeptide or amino acid sequence on certain plants. Suitable additional agrochemicals can be herbicides, insecticides, fungicides, nematicides, acaricides, bactericides, viricides, plant growth regulators, safeners and the like and include, but are not limited to glyphosate, paraquat, metolachlor, acetochlor, mesotrione, 2,4-D, atrazine, glufosinate, sulfosate, fenoxaprop, pendimethalin, picloram, trifluralin, bromoxynil, clodinafop, fluroxypyr, nicosulfuron, bensulfuron, imazetapyr, dicamba, imidacloprid, thiamethoxam, fipronil, chlorpyrifos, deltamethrin, lambda-cyhalotrin, endosulfan, methamidophos, carbofuran, clothianidin, cypermethrin, abamectin, diflufenican, spinosad, indoxacarb, bifenthrin, tefluthrin, azoxystrobin, thiamethoxam, tebuconazole, mancozeb, cyazofamid, fluazinam, pyraclostrobin, epoxiconazole, chlorothalonil, copper fungicides, trifloxystrobin, prothioconazole, difenoconazole, carbendazim, propiconazole, thiophanate, sulphur, boscalid and other known agrochemicals or any suitable combination(s) thereof.

[Compositions Comprising Variants of Polypeptide Sequences]

In a certain aspects, the polypeptides comprised in the agrochemical compositions as disclosed herein may be optionally linked to one or more further groups, moieties, or residues via one or more linkers. These one or more further groups, moieties or residues can serve for binding to other targets of interest. It should be clear that such further groups, residues, moieties and/or binding sites may or may not provide further functionality to the polypeptides as disclosed herein (and/or to the composition in which it is present) and may or may not modify the properties of the polypeptides as disclosed herein. Such groups, residues, moieties or binding units may also for example be chemical groups which can be biologically active.

These groups, moieties or residues are, in particular embodiments, linked N- or C-terminally to the polypeptides in the compositions as disclosed herein.

In particular embodiments, the polypeptides in the agrochemical compositions as disclosed herein may also have been chemically modified. For example, such a modification may involve the introduction or linkage of one or more functional groups, residues or moieties into or onto the heavy chain variable domain. These groups, residues or moieties may confer one or more desired properties or functionalities to the polypeptides. Examples of such functional groups will be clear to the skilled person.

For example, the introduction or linkage of such functional groups to a polypeptide can result in an increase in the solubility and/or the stability of the polypeptide, in a reduction of the toxicity of the polypeptide, or in the elimination or attenuation of any undesirable side effects of the polypeptide, and/or in other advantageous properties.

In particular embodiments, the one or more groups, residues, moieties are linked to the polypeptide via one or more suitable linkers or spacers.

In further particular embodiments, two or more target-specific polypeptides in the agrochemical compositions disclosed herein may be linked to each other or may be interconnected. In particular embodiments, the two or more polypeptides are linked to each other via one or more suitable linkers or spacers. Suitable spacers or linkers for use in the coupling of different heavy polypeptides as disclosed herein will be clear to the skilled person and may generally be any linker or spacer used in the art to link peptides and/or proteins.

Some particularly suitable linkers or spacers include for example, but are not limited to, polypeptide linkers such as glycine linkers, serine linkers, mixed glycine/serine linkers, glycine- and serine-rich linkers or linkers composed of largely polar polypeptide fragments, or homo- or heterobifunctional chemical crosslinking compounds such as glutaraldehyde or, optionally PEG-spaced, maleimides or NHS esters.

For example, a polypeptide linker or spacer may be a suitable amino acid sequence having a length between 1 and 50 amino acids, such as between 1 and 30, and in particular between 1 and 10 amino acid residues. It should be clear that the length, the degree of flexibility and/or other properties of the linker(s) may have some influence on the properties of the polypeptides, including but not limited to the affinity, specificity or avidity for the pest target. It should be clear that when two or more linkers are used, these linkers may be the same or different. In the context and disclosure of the present invention, the person skilled in the art will be able to determine the optimal linkers for the purpose of coupling heavy chain variable domains as disclosed herein without any undue experimental burden.

[[Compositions Comprising Fragments of Polypeptide Sequences]

The present invention also encompasses parts, fragments, analogs, mutants, variants, and/or derivatives of the polypeptides comprised in the compositions as disclosed herein and/or polypeptides comprising or essentially consisting of one or more of such parts, fragments, analogs, mutants, variants, and/or derivatives, as long as these parts, fragments, analogs, mutants, variants, and/or derivatives are suitable for the purposes envisaged herein. Such parts, fragments, analogs, mutants, variants, and/or derivatives according to the invention are still capable of specifically binding to the pest target.

[Targets]

In particular embodiments, the polypeptides comprised in the compositions disclosed herein are obtained by affinity selection against a particular pest target. Obtaining suitable polypeptides by affinity selection against a particular pest target may for example be performed by screening a set, collection or library of cells that express polypeptides on their surface (e.g. bacteriophages) for binding against a pest target molecule, which molecule is known in the art to be a target for a pesticide; all of which may be performed in a manner known per se, essentially comprising the following non-limiting steps: a) obtaining an isolated solution or suspension of a pest target molecule, which molecule is known to be a target for a pesticide; b) bio-panning phages or other cells from a polypeptide library against said target molecule; c) isolating the phages or other cells binding to the target molecule; d) determining the nucleotide sequence encoding the polypeptide insert from individual binding phages or other cells; e) producing an amount of polypeptide according to this sequence using recombinant protein expression and f) determining the affinity of said polypeptide for said pest target and optionally g) testing the pesticidal activity of said polypeptide in a bio-assay for said pest. Various methods may be used to determine the affinity between the polypeptide and the pest target molecule, including for example, enzyme linked immunosorbent assays (ELISA) or Surface Plasmon Resonance (SPR) assays, which are common practice in the art, for example, as described in Sambrook et al. (2001), Molecular Cloning, A Laboratory Manual. Third Edition. Cold Spring Harbor Laboratory Press, Cold Spring Harbor, N.Y. The dissociation constant is commonly used to describe the affinity between a polypeptide and its pest target molecule. Typically, the dissociation constant of the binding between the polypeptide and its pest target molecule is lower than $10^{-5}$ M, more preferably, the dissociation constant is lower than $10^{-6}$ M, even more preferably, the dissociation constant is lower than $10^{-7}$ M, most preferably, the dissociation constant is lower than $10^{-8}$ M.

Pest target molecules as disclosed herein are molecules occurring in or on pest organisms and which, when bound and/or inhibited, kill or arrest, inhibit or reduce the growth or pesticidal activity of said pest organism. Such suitable target molecules are readily available from existing literature or patent databases for the skilled person and include, without limitation secreted parasitism proteins such as 16D10 as suitable pest target molecules for root knot nematodes (Huang et al (2006) PNAS 103: 14302-14306), the V-ATPase proton pump as suitable pest target molecule for coleopteran, hemipteran, dipteran insect species and nematodes (Knight A J and Behm C A (2011) Ex. Parasitol. September 19), the tetraspanin PLS1 as suitable fungal pest target molecule for *B. cinerea* and *M. grisea* (Gourgues et al (2002) Biochem. Biophys. Res. *Commun.* 297: 1197) or the proton-pumping-ATPase as antifungal target (Manavathu E K et al (1999) Antimicrob Agents and Chemotherapy, December p. 2950). It is understood that preferred pest target molecules are accessible in the extra-cellular space (as opposed to intracellular pest targets).

More particularly, a pest target to which the at least one polypeptide of the agrochemical compositions as disclosed herein bind, may be a plasma membrane component of a pest. A plasma membrane component of a pest as used herein may be any component comprised in or being part of (i.e. at least a part of which is associated with, present in, connected to or bound to) the plasma membrane phospholipid bilayer or any of the proteins embedded therein of a cell of the pest. In particular embodiments, a plasma membrane component of a pest may be a phospholipid, a glycoprotein, a carbohydrate or cholesterol.

In particular embodiments, the plasma membrane component of a pest to which the at least one polypeptide in the compositions disclosed herein specifically bind is not a protein.

Thus, in particular embodiments, the plasma membrane component of a pest to which the at least one polypeptide in the compositions disclosed herein specifically bind is a lipid, such as for instance a phospholipid, a carbohydrate or cholesterol.

According to further particular embodiments, the plasma membrane component of a pest to which the at least one polypeptide in the compositions disclosed herein specifically bind is a sphingolipid.

Sphingolipids constitute a distinctive group of membrane lipids characterized by a long-chain (monounsaturated), di-hydroxy amine structure (sphingosine). Sphingolipids are essential components of the plasma membrane of cells where they are typically found in the outer leaflet. They are membrane constituents of some bacterial groups, particularly anaerobes. These groups include *Bacteroides, Prevotella, Porphyromonas, Fusobacterium, Sphingomonas, Sphingobacterium, Bdellovibrio, Cystobacter, Mycoplasma, Flectobacillus*, and possibly *Acetobacter*. Fungi in which sphingolipids have been found comprise *Saccharomyces, Candida, Histoplasma, Phytophthora, Cryptococcus, Aspergillus, Neurospora, Schizosaccharomyces, Fusicoccum, Shizophyllum, Amanita, Hansenula, Lactarius, Lentinus, Penicillium, Clitocybe, Paracoccidioides, Agaricus, Sporothrix*, and oomycete plant pathogens.

The basic building block of fungal sphingolipids is sphinganine, which can be converted either to ceramide and finally to ceramide monohexosides (CMH; cerebrosides), or to phytoceramide and finally to ceramide dihexosides (CDH) or to glycoinositol phosphorylceramides (GIPCs). Non-limiting examples of sphinglolipids against which the at least one heavy chain variable antibody domains of the compositions as disclosed herein are directed include for instance 9-methyl 4,8-sphingadienine, glycosylceramides, glucosylceramide, monoglucosylceramides, oligoglucosylceramides, gangliosides, sulfatides, ceramides, sphingosine-1-phosphate, ceramide-1-phosphate, galactosylceramide, inositol-phosphorylceramide (IPC), mannosyl-inositol-phosphorylceramide (MIPC), galactosyl-inositol-phosphorylceramide, mannosyl-(inositol-phosphoryl)$_2$-ceramide (M(IP)$_2$C), dimannosyl-inositol-phosphorylceramide (M2IPC), galactosyl-dimannosyl-inositol-phosphorylceramide (GalM2IPC), mannosyl-di-inositol-diphosphorylceramide, di-inositol-diphosphorylceramide, trigalactosyl-glycosylceramide.

Non-limiting examples of sphingolipids against which the at least one polypeptide of the compositions as disclosed herein are directed include for instance glycosylceramides, glucosylceramide, sphingomyelin, monoglycosylceramides, oligoglycosylceramides, gangliosides, sulfatides, ceramides, sphingosine-1-phosphate and ceramide-1-phosphate.

In certain particular embodiments, the target to which the polypeptides in the agrochemical compositions of the present invention bind is not a cell wall component.

In certain specific embodiments, the target to which the polypeptides in the agrochemical compositions of the present invention bind is not chitin.

In a preferred embodiment, the plant pest(s) that is/are combated by the agrochemical composition or biological control composition as disclosed herein is a fungus, such as a plant pathogenic fungus, as defined before. Fungi can be highly detrimental for plants and can cause substantial harvest losses in crops. Plant pathogenic fungi include necrotrophic fungi and biotrophic fungi, and include *ascomycetes, basidiomycetes* and *oomycetes*.

Examples of plant pathogenic fungi are known in the art and include, but are not limited to, those selected from the group consisting of the Genera: *Alternaria; Ascochyta; Botrytis; Cercospora; Colletotrichum; Diplodia; Erysiphe; Fusarium; Leptosphaeria; Gaeumanomyces; Helminthosporium; Macrophomina; Nectria; Peronospora; Phoma; Phymatotrichum; Phytophthora; Plasmopara; Podosphaera; Puccinia; Puthium; Pyrenophora; Pyricularia; Pythium; Rhizoctonia; Scerotium; Sclerotinia; Septoria; Thielaviopsis; Uncinula; Venturia*; and *Verticillium*. Specific examples of plant fungi infections which may be combated with the agrochemical compositions of the invention include, *Erysiphe graminis* in cereals, *Erysiphe cichoracearum* and *Sphaerotheca fuliginea* in cucurbits,

*Podosphaera leucotricha* in apples, *Uncinula necator* in vines, *Puccinia* sp. in cereals, *Rhizoctonia* sp. in cotton, potatoes, rice and lawns, *Ustilago* sp. in cereals and sugarcane, *Venturia inaequalis* (scab) in apples, *Helminthosporium* sp. in cereals, *Septoria nodorum* in wheat, *Septoria tritici* in wheat, *Rhynchosporium secalis* on barley, *Botrytis cinerea* (gray mold) in strawberries, tomatoes and grapes, *Cercospora arachidicola* in groundnuts, *Peronospora tabacina* in tobacco, or other *Peronospora* in various crops, *Pseudocercosporella herpotrichoides* in wheat and barley, *Pyrenophera teres* in barley, *Pyricularia oryzae* in rice, *Phytophthora infestans* in potatoes and tomatoes, *Fusarium* sp. (such as *Fusarium oxysporum*) and *Verticillium* sp. in various plants, *Plasmopara viticola* in grapes, *Alternaria* sp. in fruit and vegetables, *Pseudoperonospora cubensis* in cucumbers, *Mycosphaerella fijiensis* in banana, *Ascochyta* sp. in chickpeas, *Leptosphaeria* sp. on canola, and *Colletotrichum* sp. in various crops. The compositions according to the invention are active against normally sensitive and resistant species and against all or some stages in the life cycle of the plant pathogenic fungus.

In particular embodiments, the agrochemical compositions as disclosed herein are directed against a plant pathogenic fungus from the genus chosen from the group comprising *Alternaria, Ascochyta, Botrytis, Cercospora, Colletotrichum, Diplodia, Erysiphe, Fusarium, Leptosphaeria, Gaeumanomyces, Helminthosporium, Macrophomina, Nectria, Penicillium, Peronospora, Phoma, Phymatotrichum, Phytophthora, Plasmopara, Podosphaera, Puccinia, Pyrenophora, Pyricularia, Pythium, Rhizoctonia, Scerotium, Sclerotinia, Septoria, Thielaviopsis, Uncinula, Venturia, Verticillium, Magnaporthe, Blumeria, Mycosphaerella, Ustilago, Melampsora, Phakospora, Monilinia, Mucor, Rhizopus,* and *Aspergillus*.

In certain particular embodiments, the compositions as disclosed herein at least comprise a polypeptide, which specifically binds to a target of a fungus from the fungal species *Botrytis, Fusarium* or *Penicillium*, such as a plasma membrane component of a fungus, in particular a sphingolipid of a fungus. In further particular embodiments, the fungal sphingolipid is a ceramide, such as in particular glucosylceramide.

In particular embodiments, the present invention provides agrochemical compositions comprising polypeptides that are specifically directed against a structural molecular component of the plasma cell membrane of a pest.

In particular embodiments, the present invention provides agrochemical compositions comprising polypeptides that are specifically directed against a structural molecular component of the plasma cell membrane of a pest, which is not a protein. Indeed, in certain embodiments, the inventors have surprisingly succeeded in identifying such polypeptides while it is generally described in the art that it is (technically) difficult to generate proteins or amino acid sequences having a unique and specific interaction with non-protein molecular structures.

Based on the present teaching, further non-limiting examples of suitable fungal pest target molecules can be envisaged by the person skilled in the art and comprise for example chitin synthase, β-1,3-glucan synthase, succinate dehydrogenase, fungal glycosylceramides, or the tetraspanin PLS1.

In yet another particular embodiment plant pests are plant pathogenic bacteria including, but not limited to, *Acidovorax avenae* subsp. *avenae* (causing bacterial brown stripe of rice), *Acidovorax avenae* subsp. *cattleyae* (causing bacterial brown spot of cattleya), *Acidovorax konjaci* Konnyaku (causing bacterial leaf blight), *Agrobacterium rhizogenes* (causing hairy root of melon), *Agrobacterium tumefaciens* (causing crown gall), *Burkholderia andropogonis* (causing bacterial spot of carnation), *Burkholderia caryophylli* (causing bacterial wilt of carnation), *Burkholderia cepacia* (causing bacterial brown spot of cymbidium), *Burkholderia gladioli* pv. *gladioli* (causing neck rot of *gladiolus*), *Burkholderia glumae* (causing bacterial grain rot of rice), *Burkholderia plantarii* (causing bacterial seedling blight of rice), *Clavibacter michiganensis* subsp. *michiganensis* (causing bacterial canker of tomato), *Clavibacter michiganensis* subsp. *sepedonicus* (causing ring rot of potato), *Clostridium* spp. (causing slimy rot of potato), Curtobacterium *flaccumfaciens* (causing bacterial canker of onion), *Erwinia amylovora* (causing fire blight of pear), *Erwinia ananas* (causing bacterial palea browning of rice), *Erwinia carotovora* subsp. *atroseptica* (causing black leg of potato), *Erwinia carotovora* subsp. *carotovora* (causing bacterial soft rot of vegetables), *Erwinia chrysanthemi* (causing bacterial seedling blight of taro), *Erwinia chrysanthemi* pv. *zeae* (causing bacterial foot rot of rice), *Erwinia herbicola* pv. *millettiae* (causing bacterial gall of *wisteria*), *Pseudomonas cichorii* (causing bacterial spot of *chrysanthemum*), *Pseudomonas corrugate* Pith (causing necrosis of tomato), *Pseudomonas fuscovaginae* (causing sheath brown rot of rice), *Pseudomonas marginalis* pv. *marginalis* (causing soft rot of cabbage) *Pseudomonas rubrisubalbicans* (causing mottled stripe of sugar cane), *Pseudomonas syringae* pv. *aptata* (causing bacterial blight of sugar beet), *Pseudomonas syringae* pv. *atropurpurea* (causing halo blight of ryegrass), *Pseudomonas syringae* pv. *castaneae* (causing bacterial canker of chestnut), *Pseudomonas syringae* pv. *glycinea* (causing bacterial blight of soybean), *Pseudomonas syringae* pv. *lachrymans* (causing bacterial spot of cucumber), *Pseudomonas syringae* pv. *maculicola* (causing bacterial black spot of cabbage), *Pseudomonas syringae* pv. *mori* (causing bacterial blight of mulberry), *Pseudomonas syringae* pv. *morsprunorum* (causing bacterial canker of plums), *Pseudomonas syringae* pv. *oryzae* (causing halo blight of rice), *Pseudomonas syringae* pv. *phaseolicola* (causing halo blight of kidney bean), *Pseudomonas syringae* pv. *pisi* (causing bacterial blight of garden pea), *Pseudomonas syringae* pv. *sesame* (causing bacterial spot of sesame), *Pseudomonas syringae* pv. *striafaciens* (causing bacterial stripe blight of oats), *Pseudomonas syringae* pv. *syringae* (causing bacterial brown spot of small red bead), *Pseudomonas syringae* pv. *tabaci* (causing wild fire of tobacco), *Pseudomonas syringae* pv. *theae* (causing bacterial shoot blight of tea), *Pseudomonas syringae* pv. tomato (causing bacterial leaf spot of tomato), *Pseudomonas viridiflava* (causing bacterial brown spot of kidney bean), *Ralstonia solanacearum* (causing bacterial wilt), *Rathayibacter rathayi* (causing bacterial head blight of orchardgrass), *Streptomyces* scabies (causing common scab of potato), *Streptomyces ipomoea* (causing soil rot of sweet potato), *Xanthomonas albilineans* (causing white streak of sugar cane), *Xanthomonas campestris* pv. *cerealis* (causing bacterial streak of rye), *Xanthomonas campestris* pv. *campestris* (causing black rot), *Xanthomonas campestris* pv. *citri* (causing canker of citrus), *Xanthomonas campestris* pv. *cucurbitae* (causing bacterial brown spot of cucumber), *Xanthomonas campestris* pv. glycines (causing bacterial pastule of soybean), *Xanthomonas campestris* pv. *incanae* (causing black rot of stock), *Xanthomonas campestris* pv. (causing angular leaf spot of cotton malvacearum), *Xanthomonas campestris* pv. (causing bacterial canker of mango), Mangiferaeindicae *Xanthomonas campestris* pv. *mellea* (causing wisconsin bacterial leaf spot of tobacco),

*Xanthomonas campestris* pv. (causing bacterial spot of great nigromaculans burdock), *Xanthomonas campestris* pv. *phaseoli* (causing bacterial pastule of kidney bean), *Xanthomonas campestris* pv. *pisi* (causing bacterial stem-rot of kidney bean), *Xanthomonas campestris* pv. *pruni* (causing bacterial shot hole of peach), *Xanthomonas campestris* pv. *raphani* (causing bacterial spot of Japanese radish), *Xanthomonas campestris* pv. *ricini* (causing bacterial spot of castor-oil plant), *Xanthomonas campestris* pv. *theicola* (causing canker of tea), *Xanthomonas campestris* pv. *translucens* (causing bacterial blight of orchardgrass), *Xanthomonas campestris* pv. *vesicatoria* (causing bacterial spot of tomato), *Xanthomonas oryzae* pv. *oryzae* (causing bacterial leaf blight of rice).

In yet another embodiment the agrochemical formulations of the invention can also be used to combat plant pests such as insects, arachnids, helminths, viruses, nematodes and molluscs encountered in agriculture, in horticulture, in forests, in gardens and in leisure facilities. The compositions according to the invention are active against normally sensitive and resistant species and against all or some stages of development. These plant pests include: pests from the phylum: Arthropoda, in particular from the class of the arachnids, for example *Acarus* spp., *Aceria sheldoni*, *Aculops* spp., *Aculus* spp., *Amblyomma* spp., *Amphitetranychus viennensis*, *Argas* spp., *Boophilus* spp., *Brevipalpus* spp., *Bryobia praetiosa*, *Centruroides* spp., *Chorioptes* spp., *Dermanyssus gallinae*, *Dermatophagoides pteronyssius*, *Dermatophagoides farinae*, *Dermacentor* spp., *Eotetranychus* spp., *Epitrimerus pyri*, *Eutetranychus* spp., *Eriophyes* spp., *Halotydeus destructor*, *Hemitarsonemus* spp., *Hyalomma* spp., *Ixodes* spp., *Latrodectus* spp., *Loxosceles* spp., *Metatetranychus* spp., *Nuphersa* spp., *Oligonychus* spp., *Ornithodorus* spp., *Ornithonyssus* spp., *Panonychus* spp., *Phyllocoptruta oleivora*, *Polyphagotarsonemus latus*, *Psoroptes* spp., *Rhipicephalus* spp., *Rhizoglyphus* spp., *Sarcoptes* spp., *Scorpio maurus*, *Stenotarsonemus* spp., *Tarsonemus* spp., *Tetranychus* spp., *Vaejovis* spp., *Vasates lycopersici*. Still other examples are from the order of the Anoplura (*Phthiraptera*), for example, *Damalinia* spp., *Haematopinus* spp., *Linognathus* spp., *Pediculus* spp., *Ptirus pubis*, *Trichodectes* spp. Still other examples are from the order of the Chilopoda, for example, *Geophilus* spp., *Scutigera* spp.

Still other examples are from the order of the Coleoptera, for example, *Acalymma vittatum*, *Acanthoscelides obtectus*, *Adoretus* spp., *Agelastica alni*, *Agriotes* spp., *Alphitobius diaperinus*, *Amphimallon solstitialis*, *Anobium punctatum*, *Anoplophora* spp., *Anthonomus* spp., *Anthrenus* spp., *Apion* spp., *Apogonia* spp., *Atomaria* spp., *Attagenus* spp., *Bruchidius obtectus*, *Bruchus* spp., *Cassida* spp., *Cerotoma trifurcata*, *Ceutorrhynchus* spp., *Chaetocnema* spp., *Cleonus mendicus*, *Conoderus* spp., *Cosmopolites* spp., *Costelytra zealandica*, *Ctenicera* spp., *Curculio* spp., *Cryptorhynchus lapathi*, *Cylindrocopturus* spp., *Dermestes* spp., *Diabrotica* spp., *Dichocrocis* spp., *Diloboderus* spp., *Epilachna* spp., *Epitrix* spp., *Faustinus* spp., *Gibbium psylloides*, *Hellula undalis*, *Heteronychus arator*, *Heteronyx* spp., *Hylamorpha elegans*, *Hylotrupes bajulus*, *Hypera postica*, *Hypothenemus* spp., *Lachnosterna consanguinea*, *Lema* spp., *Leptinotarsa decemlineata*, *Leucoptera* spp., *Lissorhoptrus oryzophilus*, *Lixus* spp., *Luperodes* spp., *Lyctus* spp., *Megascelis* spp., *Melanotus* spp., *Meligethes aeneus*, *Melolontha* spp., *Migdolus* spp., *Monochamus* spp., *Naupactus xanthographus*, *Niptus hololeucus*, *Oryctes rhinoceros*, *Oryzaephilus surinamensis*, *Oryzaphagus oryzae*, *Otiorrhynchus* spp., *Oxycetonia jucunda*, *Phaedon cochleariae*, *Phyllophaga* spp., *Phyllotreta* spp., *Popillia japonica*, *Premnotrypes* spp., *Prostephanus truncatus*, *Psylliodes* spp., *Ptinus* spp., *Rhizobius ventralis*, *Rhizopertha dominica*, *Sitophilus* spp., *Sphenophorus* spp., *Stegobium paniceum*, *Sternechus* spp., *Symphyletes* spp., *Tanymecus* spp., *Tenebrio molitor*, *Tribolium* spp., *Trogoderma* spp., *Tychius* spp., *Xylotrechus* spp., *Zabrus* spp.

Still other examples are from the order of the Collembola, for example, *Onychiurus armatus*. Still other examples are from the order of the Diplopoda, for example, *Blaniulus guttulatus*. Still other examples are from the order of the Diptera, for example, *Aedes* spp., *Agromyza* spp., *Anastrepha* spp., *Anopheles* spp., *Asphondylia* spp., *Bactrocera* spp., *Bibio hortulanus*, *Calliphora erythrocephala*, *Ceratitis capitata*, *Chironomus* spp., *Chrysomyia* spp., *Chrysops* spp., *Cochliomyia* spp., *Contarinia* spp., *Cordylobia anthropophaga*, *Culex* spp., *Culicoides* spp., *Culiseta* spp., *Cuterebra* spp., *Dacus oleae*, *Dasyneura* spp., *Delia* spp., *Dermatobia hominis*, *Drosophila* spp., *Echinocnemus* spp., *Fannia* spp., *Gasterophilus* spp., *Glossina* spp., *Haematopota* spp., *Hydrellia* spp., *Hylemyia* spp., *Hyppobosca* spp., *Hypoderma* spp., *Liriomyza* spp., *Lucilia* spp., *Lutzomia* spp., *Mansonia* spp., *Musca* spp., *Nezara* spp., *Oestrus* spp., *Oscinella frit*, *Pegomyia* spp., *Phlebotomus* spp., *Phorbia* spp., *Phormia* spp., *Prodiplosis* spp., *Psila rosae*, *Rhagoletis* spp., *Sarcophaga* spp., *Simulium* spp., *Stomoxys* spp., *Tabanus* spp., *Tannia* spp., *Tetanops* spp., *Tipula* spp.

Still other examples are from the order of the Heteroptera, for example, *Anasa tristis*, *Antestiopsis* spp., *Boisea* spp., *Blissus* spp., *Calocoris* spp., *Campylomma livida*, *Cavelerius* spp., *Cimex* spp., *Collaria* spp., *Creontiades dilutus*, *Dasynus piperis*, *Dichelops furcatus*, *Diconocoris hewetti*, *Dysdercus* spp., *Euschistus* spp., *Eurygaster* spp., *Heliopeltis* spp., *Horcias nobilellus*, *Leptocorisa* spp., *Leptoglossus phyllopus*, *Lygus* spp., *Macropes excavatus*, *Miridae*, *Monalonion atratum*, *Nezara* spp., *Oebalus* spp., *Pentomidae*, *Piesma quadrata*, *Piezodorus* spp., *Psallus* spp., *Pseudacysta persea*, *Rhodnius* spp., *Sahlbergella singularis*, *Scaptocoris castanea*, *Scotinophora* spp., *Stephanitis nashi*, *Tibraca* spp., *Triatoma* spp.

Still other examples are from the order of the Homoptera, for example, *Acyrthosipon* spp., *Acrogonia* spp., *Aeneolamia* spp., *Agonoscena* spp., *Aleurodes* spp., *Aleurolobus barodensis*, *Aleurothrixus* spp., *Amrasca* spp., *Anuraphis cardui*, *Aonidiella* spp., *Aphanostigma pin*, *Aphis* spp., *Arboridia apicalis*, *Aspidiella* spp., *Aspidiotus* spp., *Atanus* spp., *Aulacorthum solani*, *Bemisia* spp., *Brachycaudus helichrysii*, *Brachycolus* spp., *Brevicoryne brassicae*, *Calligypona marginata*, *Carneocephala fulgida*, *Ceratovacuna lanigera*, *Cercopidae*, *Ceroplastes* spp., *Chaetosiphon fragaefolii*, *Chionaspis tegalensis*, *Chlorita onukii*, *Chromaphis juglandicola*, *Chrysomphalus ficus*, *Cicadulina mbila*, *Coccomytilus halli*, *Coccus* spp., *Cryptomyzus ribis*, *Dalbulus* spp., *Dialeurodes* spp., *Diaphorina* spp., *Diaspis* spp., *Drosicha* spp., *Dysaphis* spp., *Dysmicoccus* spp., *Empoasca* spp., *Eriosoma* spp., *Erythroneura* spp., *Euscelis bilobatus*, *Ferrisia* spp., *Geococcus coffeae*, *Hieroglyphus* spp., *Homalodisca coagulata*, *Hyalopterus arundinis*, *lcerya* spp., *Idiocerus* spp., *Idioscopus* spp., *Laodelphax striatellus*, *Lecanium* spp., *Lepidosaphes* spp., *Lipaphis erysimi*, *Macrosiphum* spp., *Mahanarva* spp., *Melanaphis sacchari*, *Metcalfiella* spp., *Metopolophium dirhodum*, *Monellia costalis*, *Monelliopsis pecanis*, *Myzus* spp., *Nasonovia ribisnigri*, *Nephotettix* spp., *Nilaparvata lugens*, *Oncometopia* spp., *Orthezia praelonga*, *Parabemisia myricae*, *Paratrioza* spp., *Parlatoria* spp., *Pemphigus* spp., *Peregrinus maidis*, *Phenacoccus* spp., *Phloeomyzus passerinii*, *Phorodon humuli*, *Phylloxera* spp., *Pinnaspis aspidistrae*, *Planococcus* spp.,

*Protopulvinaria pyriformis, Pseudaulacaspis pentagona, Pseudococcus* spp., *Psylla* spp., *Pteromalus* spp., *Pyrilla* spp., *Quadraspidiotus* spp., *Quesada gigas, Rastrococcus* spp., *Rhopalosiphum* spp., *Saissetia* spp., *Scaphoides titanus, Schizaphis graminum, Selenaspidus articulatus, Sogata* spp., *Sogatella furcifera, Sogatodes* spp., *Stictocephala festina, Tenalaphara malayensis, Tinocallis caryaefoliae, Tomaspis* spp., *Toxoptera* spp., *Trialeurodes* spp., *Trioza* spp., *Typhlocyba* spp., *Unaspis* spp., *Viteus vitifolii, Zygina* spp.

Still other examples are from the order of the Hymenoptera, for example, *Acromyrmex* spp., *Athalia* spp., *Atta* spp., *Diprion* spp., *Hoplocampa* spp., *Lasius* spp., *Monomorium pharaonis, Solenopsis invicta, Tapinoma* spp., *Vespa* spp.

Still other examples are from the order of the Isopoda, for example, *Armadillidium vulgare, Oniscus asellus, Porcellio scaber.*

Still other examples are from the order of the Isoptera, for example, *Coptotermes* spp., *Cornitermes cumulans, Cryptotermes* spp., *Incisitermes* spp., *Microtermes obesi, Odontotermes* spp., *Reticulitermes* spp.

Still other examples are from the order of the Lepidoptera, for example, *Acronicta major, Adoxophyes* spp., *Aedia leucomelas, Agrotis* spp., *Alabama* spp., *Amyelois transitella, Anarsia* spp., *Anticarsia* spp., *Argyroploce* spp., *Barathra brassicae, Borbo cinnara, Bucculatrix thurberiella, Bupalus piniarius, Busseola* spp., *Cacoecia* spp., *Caloptilia theivora, Capua reticulana, Carpocapsa pomonella, Carposina niponensis, Chematobia brumata, Chilo* spp., *Choristoneura* spp., *Clysia ambiguella, Cnaphalocerus* spp., *Cnephasia* spp., *Conopomorpha* spp., *Conotrachelus* spp., *Copitarsia* spp., *Cydia* spp., *Dalaca noctuides, Diaphania* spp., *Diatraea saccharalis, Earias* spp., *Ecdytolopha aurantium, Elasmopalpus lignosellus, Eldana saccharina, Ephestia* spp., *Epinotia* spp., *Epiphyas postvittana, Etiella* spp., *Eulia* spp., *Eupoecilia ambiguella, Euproctis* spp., *Euxoa* spp., *Feltia* spp., *Galleria mellonella, Gracillaria* spp., *Grapholitha* spp., *Hedylepta* spp., *Helicoverpa* spp., *Heliothis* spp., *Hofmannophila pseudospretella, Homoeosoma* spp., *Homona* spp., *Hyponomeuta padella, Kakivoria flavofasciata, Laphygma* spp., *Laspeyresia molesta, Leucinodes orbonalis, Leucoptera* spp., *Lithocolletis* spp., *Lithophane antennata, Lobesia* spp., *Loxagrotis albicosta, Lymantria* spp., *Lyonetia* spp., *Malacosoma neustria, Maruca testulalis, Mamestra brassicae, Mocis* spp., *Mythimna separata, Nymphula* spp., *Oiketicus* spp., *Oria* spp., *Orthaga* spp., *Ostrinia* spp., *Oulema oryzae, Panolis flammea, Parnara* spp., *Pectinophora* spp., *Perileucoptera* spp., *Phthorimaea* spp., *Phyllocnistis citrella, Phyllonorycter* spp., *Pieris* spp., *Platynota stultana, Plodia interpunctella, Plusia* spp., *Plutella xylostella, Prays* spp., *Prodenia* spp., *Protoparce* spp., *Pseudaletia* spp., *Pseudoplusia includens, Pyrausta nubilalis, Rachiplusia nu, Schoenobius* spp., *Scirpophaga* spp., *Scotia segetum, Sesamia* spp., *Sparganothis* spp., *Spodoptera* spp., *Stathmopoda* spp., *Stomopteryx subsecivella, Synanthedon* spp., *Tecia solanivora, Thermesia gemmatalis, Tinea pellionella, Tineola bisselliella, Tortrix* spp., *Trichophaga tapetzella, Trichoplusia* spp., *Tuta absoluta, Virachola* spp.

Still other examples are from the order of the Orthoptera, for example, *Acheta domesticus, Blatta orientalis, Blattella germanica, Dichroplus* spp., *Gryllotalpa* spp., *Leucophaea maderae, Locusta* spp., *Melanoplus* spp., *Periplaneta* spp., *Pulex irritans, Schistocerca gregaria, Supella longipalpa.*

Still other examples are from the order of the Siphonaptera, for example, *Ceratophyllus* spp., *Ctenocephalides* spp., *Tunga penetrans, Xenopsylla cheopis.*

Still other examples are from the order of the Symphyla, for example, *Scutigerella* spp. Still other examples are from the order of the Thysanoptera, for example, *Anaphothrips obscurus, Baliothrips biformis, Drepanothris reuteri, Enneothrips flavens, Frankliniella* spp., *Heliothrips* spp., *Hercinothrips femoralis, Rhipiphorothrips cruentatus, Scirtothrips* spp., *Taeniothrips cardamoni, Thrips* spp.

Still other examples are from the order of the Zygentoma (=Thysanura), for example, *Lepisma saccharina, Thermobia domestica.* for example *Lepisma saccharina, Thermobia domestica.*

In another embodiment pests of the phylum Mollusca, in particular from the class of the Bivalvia, for example *Dreissena* spp. are also important plant pests.

In another embodiment pests of the class of the Gastropoda are important plant pests, for example, Anion spp., *Biomphalaria* spp., *Bulinus* spp., *Deroceras* spp., *Galba* spp., *Lymnaea* spp., *Oncomelania* spp., *Pomacea* spp., *Succinea* spp.

In yet another embodiment plant pests are from the phylum Nematoda are important plant pests, i.e. phytoparasitic nematodes, thus meaning plant parasitic nematodes that cause damage to plants. Plant nematodes encompass plant parasitic nematodes and nematodes living in the soil. Plant parasitic nematodes include, but are not limited to, ectoparasites such as *Xiphinema* spp., *Longidorus* spp., and *Trichodorus* spp.; semiparasites such as *Tylenchulus* spp.; migratory endoparasites such as *Pratylenchus* spp., *Radopholus* spp., and *Scutellonera.* spp.; sedentary parasites such as *Heterodera* spp., *Globodera* spp., and *Meloidogyne* spp., and stem and leaf endoparasites such as *Ditylenchus* spp., *Aphelenchoides* spp., and *Hirshmaniella* spp. In addition, harmful root parasitic soil nematodes are cyst-forming nematodes of the genera *Heterodera* or *Globodera*, and/or root knot nematodes of the genus *Meloidogyne*. Harmful species of these genera are for example *Meloidogyne incognata, Heterodera glycines* (soybean cyst nematode), *Globodera pallida* and *Globodera rostochiensis* (potato cyst nematode). Still other important genera of importance as plant pests comprise *Rotylenchulus* spp., *Paratriclodorus* spp., *Pratylenchus penetrans, Radolophus simuli, Ditylenchus dispaci, Tylenchulus semipenetrans, Xiphinema* spp., *Bursaphelenchus* spp., and the like. in particular *Aphelenchoides* spp., *Bursaphelenchus* spp., *Ditylenchus* spp., *Globodera* spp., *Heterodera* spp., *Longidorus* spp., *Meloidogyne* spp., *Pratylenchus* spp., *Radopholus similis, Trichodorus* spp., *Tylenchulus semipenetrans, Xiphinema* spp.

In yet another embodiment plant pests are viruses and the agrochemical formulations of the invention are directed to treating a viral infection or inhibiting viral infectivity in a plant, the plant virus is selected from an alfamovirus, an allexivirus, an alphacryptovirus, an anulavirus, an apscaviroid, an aureusvirus, an avenavirus, an aysunviroid, a badnavirus, a begomovirus, a benyvirus, a betacryptovirus, a betaflexiviridae, a bromovirus, a bymovirus, a capillovirus, a carlavirus, a carmovirus, a caulimovirus, a cavemovirus, a cheravirus, a closterovirus, a cocadviroid, a coleviroid, a comovirus, a crinivirus, a cucumovirus, a curtovirus, a cytorhabdovirus, a dianthovirus, an enamovirus, an umbravirus & B-type satellite virus, a fabavirus, a fijivirus, a furovirus, a hordeivirus, a hostuviroid, an idaeovirus, an ilarvirus, an ipomovirus, a luteovirus, a machlomovirus, a macluravirus, a marafivirus, a mastrevirus, a nanovirus, a necrovirus, a nepovirus, a nucleorhabdovirus, an oleavirus, an ophiovirus, an oryzavirus, a panicovirus, a pecluvirus, a petuvirus, a phytoreovirus, a polerovirus, a pomovirus, a pospiviroid, a potexvirus, a potyvirus, a reovirus, a rhabdovirus, a rymovirus, a sadwavirus, a SbCMV-like virus, a sequivirus, a sobemovirus, a tenuivirus, a TNsatV-like satellite virus, a tobamovirus, a topocuvirus, a tospovirus, a trichovirus, a tritimovirus, a tungrovirus, a tymovirus, an umbravirus, a varicosavirus, a vitivirus, or a waikavirus.

[Forms of Target Antigen]

It will be appreciated based on the disclosure herein that for agrochemical and biological control applications, the polypeptides of the compositions as disclosed herein will in principle be directed against or specifically bind to several different forms of the pest target. It is also expected that the polypeptides of the compositions as disclosed herein will bind to a number of naturally occurring or synthetic analogs, variants, mutants, alleles, parts and fragments of their pest target. More particularly, it is expected that the polypeptides of the compositions as disclosed herein will bind to at least to those analogs, variants, mutants, alleles, parts and fragments of the target that (still) contain the binding site, part or domain of the natural target to which those polypeptides bind.

[Formulations]

It is envisaged that the polypeptide content contained in the agrochemical or biological control composition as disclosed herein may vary within a wide range and it is generally up to the manufacturer to modify the concentration range of a particular polypeptide according to specific crop pest which is to be attenuated.

In particular embodiments, the present invention provides agrochemical compositions comprising at least one polypeptide, wherein said heavy chain variable domain is present in an amount effective to protect or treat a plant or a part of said plant from an infection or other biological interaction with said plant pathogen.

In a specific embodiment the concentration of the polypeptide contained in the agrochemical composition may be from 0.0001% to 50% by weight.

In particular embodiments, the present invention provides agrochemical compositions comprising at least one polypeptide, wherein the concentration of the at least one polypeptide in the agrochemical composition ranges from 0.001% to 50% by weight.

In yet another specific embodiment the concentration of the polypeptide contained in the agrochemical composition may be from 0.001% to 50% by weight. In yet another specific embodiment the concentration of the polypeptide contained in the agrochemical composition may be from 0.01% to 50% by weight. In yet another specific embodiment the concentration of the polypeptide contained in the agrochemical composition may be from 0.1% to 50% by weight.

In yet another specific embodiment the concentration of the polypeptide contained in the agrochemical composition may be from 1% to 50% by weight. In yet another specific embodiment the concentration of the polypeptide contained in the agrochemical composition may be from 10% to 50% by weight. In yet another specific embodiment the concentration of the polypeptide contained in the agrochemical composition may be from 0.0001% to 40% by weight. In yet another specific embodiment the concentration of the polypeptide contained in the agrochemical composition may be from 0.001% to 40% by weight. In yet another specific embodiment the concentration of the polypeptide contained in the agrochemical composition may be from 0.01% to 40% by weight. In yet another specific embodiment the concentration of the polypeptide contained in the agrochemical composition may be from 0.1% to 40% by weight. In yet another specific embodiment the concentration of the polypeptide contained in the agrochemical composition may be from 1% to 40% by weight. In yet another specific embodiment the concentration of the polypeptide contained in the agrochemical composition may be from 0.0001% to 30% by weight. In yet another specific embodiment the concentration of the polypeptide contained in the agrochemical composition may be from 0.001% to 30% by weight. In yet another specific embodiment the concentration of the polypeptide contained in the agrochemical composition may be from 0.01% to 30% by weight. In yet another specific embodiment the concentration of the polypeptide contained in the agrochemical composition may be from 0.1% to 30% by weight. In yet another specific embodiment the concentration of the polypeptide contained in the agrochemical composition may be from 1% to 30% by weight. In yet another specific embodiment the concentration of the polypeptide contained in the agrochemical composition may be from 0.0001% to 10% by weight. In yet another specific embodiment the concentration of the polypeptide contained in the agrochemical composition may be from 0.001% to 10% by weight. In yet another specific embodiment the concentration of the polypeptide contained in the agrochemical composition may be from 0.01% to 10% by weight. In yet another specific embodiment the concentration of the polypeptide contained in the agrochemical composition may be from 0.1% to 10% by weight. In yet another specific embodiment the concentration of the polypeptide contained in the agrochemical composition may be from 1% to 10% by weight. In yet another specific embodiment the concentration of the polypeptide contained in the agrochemical composition may be from 0.0001% to 1% by weight. In yet another specific embodiment the concentration of the polypeptide contained in the agrochemical composition may be from 0.001% to 1% by weight. In yet another specific embodiment the concentration of the polypeptide contained in the agrochemical composition may be from 0.01% to 1% by weight. In yet another specific embodiment the concentration of the polypeptide contained in the agrochemical composition may be from 0.1% to 1% by weight.

In particular embodiments, the agrochemical compositions disclosed herein comprise at least one polypeptide, which is formulated in an aqueous solution.

In further particular embodiments, the agrochemical compositions disclosed herein comprise at least one polypeptide and further comprise an agrochemically suitable carrier and/or one or more suitable adjuvants.

The compositions according to the invention may comprise, in addition to the anti-pest polypeptide described above, solid or liquid carriers which are acceptable in the pest treatment of plants and/or parts of plants and/or surfactants which are also acceptable in the pest treatment of plants and/or parts of plants. In particular, there may be used inert and customary carriers and customary surfactants. These compositions cover not only compositions ready to be applied to the plants and/or parts of plants to be treated by immersion or using a suitable device, but also the commercial concentrated compositions which have to be diluted before application to the plants and/or parts of plants.

These agrochemical compositions according to the invention may also contain any sort of other ingredients such as, for example, protective colloids, adhesives, thickeners, thixotropic agents, penetrating agents, stabilizers, sequestrants, texturing agents, flavouring agents, taste enhancers, sugars, sweeteners, colorants and the like. More generally, the active substances, i.e. the at least one heavy chain variable domain, may be combined with any solid or liquid additives corresponding to the usual formulation techniques.

These agrochemical compositions according to the invention may also contain any sort of other active ingredient such as, for example, other anti-bacterial or anti-fungal active ingredients.

The term "carrier", in the present disclosure, denotes a natural or synthetic organic or inorganic substance with which the anti-pest active substance is combined to facilitate its application to plants and/or one or more plant parts. This carrier is therefore generally inert and should be acceptable in the agri-sector. The carrier may be solid (clays, natural or synthetic silicates, silica, resins, waxes, solid fertilizers, and the like) or liquid (water, alcohols, in particular butanol, and the like).

The surfactant may be an emulsifying agent, a dispersing agent or a wetting agent of the ionic or nonionic type or a mixture of such surfactants. There may be mentioned, for example, salts of polyacrylic acids, salts of lignosulphonic acids, salts of phenolsulphonic or naphthalenesulphonic acids, polycondensates of ethylene oxide with fatty alcohols or with fatty acids or with fatty amines, substituted phenols (in particular alkylphenols or arylphenols), salts of esters of sulphosuccinic acids, derivatives of taurine (in particular alkyl taurates), phosphoric esters of polyoxyethylated phenols or alcohols, esters of fatty acids and polyols, sulphate, sulphonate and phosphate functional group-containing derivatives of the above compounds. The presence of at least one surfactant is generally essential when the inert carrier is not soluble in water and when the vector agent for application is water.

The agrochemical compositions as disclosed herein are themselves in fairly diverse, solid or liquid, forms.

As solid composition forms, there may be mentioned dustable powders (content of active substance which may be up to 100%) and granules, in particular those obtained by extrusion, by compacting, by impregnation of a granulated carrier, by granulation using a powder as starting material (the content of active substance in these granules being between 0.5 and 80% for these latter cases). Such solid compositions may be optionally used in the form of a liquid which is viscous to a greater or lesser degree, depending on the type of application desired, for example by diluting in water.

As liquid composition forms or forms intended to constitute liquid compositions during application, there may be mentioned solutions, in particular water-soluble concentrates, emulsions, suspension concentrates, wettable powders (or spraying powder), oils and waxes.

The suspension concentrates, which can be applied by spraying, are prepared so as to obtain a stable fluid product which does not form a deposit and they usually contain from 10 to 75% of active substance, from 0.5 to 15% of surfactants, from 0.1 to 10% of thixotropic agents, from 0 to 10% of appropriate additives, such as antifoams, corrosion inhibitors, stabilizers, penetrating agents and adhesives and, as carrier, water or an organic liquid in which the active substance is not or not very soluble: some organic solids or inorganic salts may be dissolved in the carrier to help prevent sedimentation or as antigels for water.

The agrochemical compositions as disclosed herein can be used as such, in form of their formulations or as the use forms prepared therefrom, such as aerosol dispenser, capsule suspension, cold fogging concentrate, hot fogging concentrate, encapsulated granule, fine granule, flowable concentrate for seed treatment, ready-to-use solutions, dustable powder, emulsifiable concentrate, emulsion oil in water, emulsion water in oil, macrogranule, macrogranule, oil dispersible powder, oil miscible flowable concentrate, oil miscible liquid, froths, paste, seed coated with a pesticide, suspension concentrate (flowable concentrate), suspensions-emulsions-concentrates, soluble concentrate, suspensions, soluble powder, granule, water soluble granules or tablets, water soluble powder for seed treatment, wettable powder, natural and synthetic materials impregnated with active compound, micro-encapsulation in polymeric materials and in jackets for seed, as well as ULV-cold and hot fogging formulations, gas (under pressure), gas generating product, plant rodlet, powder for dry seed treatment, solution for seed treatment, ultra low volume (ULV) liquid, ultra low volume (ULV) suspension, water dispersible granules or tablets, water dispersible powder for slurry treatment.

These formulations are prepared in a known manner by mixing the active compounds or active compound combinations with customary additives, such as, for example, customary extenders and also solvents or diluents, emulsifiers, dispersants, and/or bonding or fixing agent, wetting agents, water repellents, if appropriate siccatives and UV stabilisers, colorants, pigments, defoamers, preservatives, secondary thickeners, adhesives, gibberellins and water as well further processing auxiliaries.

These compositions include not only compositions which are ready to be applied to the plant or seed to be treated by means of a suitable device, such as a spraying or dusting device, but also concentrated commercial compositions which must be diluted before application to the crop.

[Methods of Plant Protection or Treatment]

In certain aspects, the present invention provides methods for protecting or treating a plant or a part of a plant from an infection or other biological interaction with a plant pathogen, at least comprising the step of applying directly or indirectly to the plant or to a part of the plant, an agrochemical composition as disclosed herein, under conditions effective to protect or treat the plant or a part of the plant against that infection or biological interaction with the plant pathogen.

In particular embodiments, these methods comprise applying directly or indirectly to the plant or to a part of the plant an agrochemical composition as disclosed herein at an application rate higher than 50 g of the agrochemical composition per hectare, such as but not limited to an application rate higher than 75 g of the agrochemical composition per hectare, such as an application rate higher than 100 g of the agrochemical composition per hectare, or in particular an application rate higher than 200 g of the agrochemical composition per hectare.

In particular embodiments, these methods comprise applying directly or indirectly to the plant or to a part of the plant an agrochemical composition as disclosed herein at an application rate between 50 g and 200 g of the agrochemical composition per hectare, such as but not limited to an application rate of between 50 g and 200 g of the agrochemical composition per hectare, in particular an application rate of between 75 g and 175 g of the agrochemical composition per hectare, such as between 75 g and 150 g of the agrochemical composition per hectare or between 75 g and 125 g per hectare.

In yet another embodiment, the invention provides methods for combating plant pests, which methods comprise applying an agrochemical or biological control composition according to the invention to a plant, such as a crop, or a part of a plant or a crop, at an application rate below 50 g of said polypeptide per hectare. In specific embodiments the application rate is below 45 g/ha, below 40 g/ha, below 35 g/ha, below 30 g/ha, below 25 g/ha, below 20 g/ha, below 15 g/ha, below 10 g/ha, below 5 g/ha, below 1 g/ha or even lower amounts of polypeptide/ha.

It is understood depending on the crop and the environmental pressure of the plant pests that the farmer can vary the application rate. These application rates variances are specified in the technical sheet delivered with the specific agrochemical composition.

In yet another embodiment, the invention provides the use of the agrochemical or biological control compositions of the invention for combating plant pests.

Applying an agrochemical or biological control composition according to the invention to a crop may be done using any suitable method for applying an agrochemical or biological control composition to a crop, including, but not limited to spraying (including high volume (HV), low volume (LV) and ultra low volume (ULV) spraying), brushing, dressing, dripping, coating, dipping, immersing, spreading, fogging, applying as small droplets, a mist or an aerosol.

Thus, in particular embodiments, the methods for protecting or treating a plant or a part of a plant from an infection or other biological interaction with a plant pathogen as disclosed herein, comprise applying the agrochemical composition directly or indirectly to the plant or to a part of the plant by spraying, atomizing, foaming, fogging, culturing in hydroculture, culturing in hydroponics, coating, submerging, and/or encrusting.

In certain particular embodiments, the present invention provides methods of inhibiting, preventing, reducing or controlling the growth of a plant pathogen, comprising at least the step of applying directly or indirectly to a plant or to a part of said plant, an agrochemical composition as disclosed herein.

In certain other embodiments, the present invention provides methods for of killing a plant pathogen, comprising at least the step of applying directly or indirectly to a plant or to a part of said plant, an agrochemical composition as disclosed herein.

Alternatively, the application rate of the agrochemical composition according to the invention, meaning the amount of the agrochemical composition that is applied to the crop, is such that less than 50 g, 45 g, 40 g, 35 g, 30 g, 25 g, 20 g, 20 g, 15 g, 10 g, 5 g, 1 g or even lower than 1 g of the polypeptide, comprised in the agrochemical or biological control composition according to the invention, is applied to the crop per hectare.

According to the methods as disclosed herein, the agrochemical or biological control composition can be applied once to a crop, or it can be applied two or more times after each other with an interval between every two applications. According to the method of the present invention, the agrochemical or biological control composition according to the invention can be applied alone or in mixture with other materials, preferably other agrochemical or biological control compositions, to the crop; alternatively, the agrochemical or biological control composition according to the invention can be applied separately to the crop with other materials, preferably other agrochemical or biological control compositions, applied at different times to the same crop. According to the method of the present invention, the agrochemical or biological control composition according to the invention may be applied to the crop prophylactically, or alternatively, may be applied once target pests have been identified on the particular crop to be treated.

The agrochemical compositions as disclosed herein can be applied directly to a plant, a crop or to one or more parts of the plant by the above mentioned methods, such as directly to the entire plant or directly to one or more parts of the plant, either in a pre-harvest or in a post-harvest stage. In certain further embodiments, the agrochemical compositions as disclosed herein can be applied directly to one or more parts of the plant by the above mentioned methods, such as directly to the stalks, leafs, tubers, stems, shoots, the seeds, the fruits, the roots, the flowers, grains, the buds etc.

The method of treatment as disclosed herein can also be used in the field of protecting storage goods against attack of plant pathogens. According to the present invention, the term "storage goods" is understood to denote natural substances of vegetable or animal origin and their processed forms, which have been taken from the natural life cycle and for which long-term protection is desired. Storage goods of vegetable origin, such as plants or parts thereof, for example stalks, leafs, tubers, seeds, fruits or grains, can be protected in the freshly harvested state or in processed form, such as pre-dried, moistened, comminuted, ground, pressed or roasted. Also falling under the definition of storage goods is timber, whether in the form of crude timber, such as construction timber, electricity pylons and barriers, or in the form of finished articles, such as furniture or objects made from wood. Storage goods of animal origin are hides, leather, furs, hairs and the like. The combinations according the present invention can prevent disadvantageous effects such as decay, discoloration or mold. Preferably "storage goods" is understood to denote natural substances of vegetable origin and their processed forms, more preferably fruits and their processed forms, such as pomes, stone fruits, soft fruits and citrus fruits and their processed forms.

The agrochemical compositions as disclosed herein can also be applied indirectly to a plant, a crop or to one or more parts of the plant by the above mentioned methods, such as indirectly to the entire plant or indirectly to one or more parts of the plant, either in a pre-harvest or in a post-harvest stage. Thus, in certain embodiments, the agrochemical compositions as disclosed herein can be applied indirectly to a plant, a crop or to one or more parts of the plant by the above mentioned methods, such as by applying the agrochemical composition to the surroundings or to the medium in which the plant or the one or more parts of the plant are growing or are stored, such as for instance but not limited to the air, the soil, the hydroponic culture, the hydroculture, or the liquid medium, such as for instance the aqueous liquid medium or water, in which the plant or the one or more parts of the plant are growing or are stored.

It thus should be generally understood in the context of this application that the treatment of plants and plant parts with the agrochemical compositions as disclosed herein is carried out directly or by action on their environment, habitat or storage area by means of the normal treatment methods, for example by watering (drenching), drip irrigation, spraying, vaporizing, atomizing, broadcasting, dusting, foaming, spreading-on, and as a powder. It is furthermore possible to apply the compositions by the ultra-low volume method, or to inject the active compound preparation or the active compound itself into the soil.

In particular embodiments, the methods for protecting or treating a plant or a part of a plant from an infection or other biological interaction with a plant pathogen as disclosed herein, comprise applying the agrochemical composition directly or indirectly to the plant or to a part of the plant either in a pre-harvest or in a post-harvest stage.

According to specific embodiments, the harvested produce is a fruit, flower, nut or vegetable, a fruit or vegetable with inedible peel, preferably selected from avocados, bananas, plantains, lemons, grapefruits, melons, oranges, pineapples, kiwi fruits, guavas, mandarins, mangoes and pumpkin, is preferred, more preferably bananas, oranges, lemons and peaches, in particular bananas. According to further specific embodiments, the harvested produce is a cut flower from ornamental plants, preferably selected from *Alstroemeria, Carnation, Chrysanthemum, Freesia, Gerbera, Gladiolus,* baby's breath (*Gypsophila* spec), *Helianthus, Hydrangea, Lilium, Lisianthus*, roses and summer flowers.

The plant species to which the agrochemical compositions as disclosed herein can be applied can for example be but are not limited to maize, soya bean, alfalfa, cotton, sunflower, *Brassica* oil seeds such as *Brassica napus* (e.g. canola, rape-seed), *Brassica rapa, B. juncea* (e.g. (field) mustard) and *Brassica carinata*, Arecaceae sp. (e.g. oilpalm, coconut), rice, wheat, sugar beet, sugar cane, oats, rye, barley, millet and sorghum, triticale, flax, nuts, grapes and vine and various fruit and vegetables from various botanic taxa, e.g. Rosaceae sp. (e.g. pome fruits such as apples and pears, but also stone fruits such as apricots, cherries, almonds, plums and peaches, and berry fruits such as strawberries, raspberries, red and black currant and gooseberry), *Ribesioidae* sp., *Juglandaceae* sp., *Betulaceae* sp., *Anacardiaceae* sp., *Fagaceae* sp., *Moraceae* sp., *Oleaceae* sp. (e.g. olive tree), *Actinidaceae* sp., *Lauraceae* sp. (e.g. avocado, cinnamon, camphor), *Musaceae* sp. (e.g. banana trees and plantations), *Rubiaceae* sp. (e.g. coffee), *Theaceae* sp. (e.g. tea), *Sterculiceae* sp., *Rutaceae* sp. (e.g. lemons, oranges, mandarins and grapefruit); *Solanaceae* sp. (e.g. tomatoes, potatoes, peppers, *capsicum*, aubergines, tobacco), *Liliaceae* sp., *Compositae* sp. (e.g. lettuce, artichokes and chicory—including root chicory, endive or common chicory), *Umbelliferae* sp. (e.g. carrots, parsley, celery and celeriac), *Cucurbitaceae* sp. (e.g. cucumbers—including gherkins, pumpkins, watermelons, calabashes and melons), *Alliaceae* sp. (e.g. leeks and onions), *Cruciferae* sp. (e.g. white cabbage, red cabbage, broccoli, cauliflower, Brussels sprouts, pak choi, kohlrabi, radishes, horseradish, cress and Chinese cabbage), *Leguminosae* sp. (e.g. peanuts, peas, lentils and beans—e.g. common beans and broad beans), *Chenopodiaceae* sp. (e.g. Swiss chard, fodder beet, spinach, beetroot), *Linaceae* sp. (e.g. hemp), *Cannabeacea* sp. (e.g. *cannabis*), *Malvaceae* sp. (e.g. okra, cocoa), Papaveraceae (e.g. poppy), Asparagaceae (e.g. asparagus); useful plants and ornamental plants in the garden and woods including turf, lawn, grass and *Stevia rebaudiana*; and in each case genetically modified types of these plants.

In a preferred embodiment of the treatment methods disclosed herein, the crop is selected from the group consisting of field crops, grasses, fruits and vegetables, lawns, trees and ornamental plants.

In certain aspects, the present invention thus also provides post-harvest treatment methods for protecting or treating a harvested plant or a harvested part of the plant from an infection or other biological interaction with a plant pathogen, at least comprising the step of applying directly or indirectly to the harvested plant or to a harvested part of the plant, an agrochemical composition as disclosed herein, under conditions effective to protect or treat the harvested plant or a harvested part of the plant against the infection or biological interaction with the plant pathogen. According to specific embodiments, the harvested produce is a fruit, flower, nut or vegetable, a fruit or vegetable with inedible peel, preferably selected from avocados, bananas, plantains, lemons, grapefruits, melons, oranges, pineapples, kiwi fruits, guavas, mandarins, mangoes and pumpkin, is preferred, more preferably bananas, oranges, lemons and peaches, in particular bananas. According to further specific embodiments, the harvested produce is a cut flower from ornamental plants, preferably selected from Alstroemeria, Carnation, *Chrysanthemum*, Freesia, *Gerbera, Gladiolus*, baby's breath (*Gypsophila* spec), *Helianthus, Hydrangea, Lilium, Lisianthus*, roses and summer flowers. According to further specific embodiments, the harvested produce is cut grass or wood.

Post-harvest disorders are e.g. lenticel spots, scorch, senescent breakdown, bitter pit, scald, water core, browning, vascular breakdown, $CO_2$ injury, $CO_2$ or $O_2$ deficiency, and softening. Fungal diseases may be caused for example by the following fungi: *Mycosphaerella* spp., *Mycosphaerella musae, Mycosphaerella* frag a ae, *Mycosphaerella citri; Mucor* spp., e.g. *Mucor piriformis; Monilinia* spp., e.g. *Monilinia fructigena, Monilinia laxa; Phomopsis* spp., *Phomopsis natalensis; Colletotrichum* spp., e.g. *Colletotrichum musae, Colletotrichum gloeosporioides, Colletotrichum coccodes; Verticillium* spp., e.g. *VerticiHium theobromae; Nigrospora* spp.; *Botrytis* spp., e.g. *Botrytis cinerea; Diplodia* spp., e.g. *Diplodia citri; Pezicula* spp.; *Alternaria* spp., e.g. *Alternaria citri, Alternaria alternata; Septoria* spp., e.g. *Septoria depressa; Venturia* spp., e.g. *Venturia inaequalis, Venturia pyrina; Rhizopus* spp., e.g. *Rhizopus stolonifer, Rhizopus oryzae; Glomerella* spp., e.g. *Glomerella cingulata; Sclerotinia* spp., e.g. *Sclerotinia fruiticola; Ceratocystis* spp., e.g. *Ceratocystis paradoxa; Fusarium* spp., e.g. *Fusarium semitectum, Fusarium moniliforme, Fusarium solani, Fusarium oxysporum; Cladosporium* spp., e.g. *Cladosporium fulvum, Cladosporium cladosporioides, Cladosporium cucumerinum, Cladosporium musae; Penicillium* spp., e.g. *Penicillium funiculosum, Penicillium expansum, Penicillium digitatum, Penicillium italicum; Phytophthora* spp., e.g. *Phytophthora citrophthora, Phytophthora fragariae, Phytophthora cactorum, Phytophthora parasitica; Phacydiopycnis* spp., e.g. *Phacydiopycnis malirum; Gloeosporium* spp., e.g. *Gloeosporium album, Gloeosporium perennans, Gloeosporium fructigenum, Gloeosporium singulata; Geotrichum* spp., e.g. *Geotrichum candidum; Phlyctaena* spp., e.g. *Phlyctaena vagabunda; Cylindrocarpon* spp., e.g. *Cylindrocarpon mail; Stemphyllium* spp., e.g. *Stemphyllium vesicaum; Thielaviopsis* spp., e.g. *Thielaviopsis paradoxy; Aspergillus* spp., e.g. *Aspergillus niger, Aspergillus carbonarius; Nectria* spp., e.g. *Nectria galligena; Cercospora* spp., e.g. *Cercospora angreci, Cercospora apii, Cercospora atrofiliformis, Cercospora musae, Cercospora zeae-maydis.*

In further aspects, the present invention provides uses of the agrochemical compositions as disclosed herein as an anti-pest agent, such as for instance a biostatic agent or a pesticidal agent, including but not limited to a fungistatic or a fungicidal agent.

In a particular embodiment, the plant pests combated by the method according to the present invention are plant pathogenic fungi, as defined before. Lesion number, lesion size, and extent of sporulation of fungal pathogens may all be decreased as a result of the application of the method according to the present invention.

[Medical Applications]

In certain other embodiments, the present invention provides methods for protecting or curing a human or animal from an infection by a pest and in particular a fungus, at least comprising the step of applying directly or indirectly to the human or animal or to a part of the human or animal, a composition comprising at least one polypeptide, which specifically binds to a pest, such as but not limited to a fungus, under conditions effective to protect or cure the human or animal from the pest.

Accordingly, the present invention provides polypeptides that specifically bind to a pest target or for use in a method for the prevention and/or treatment of at least one disease and/or disorder caused by a pest, such as for example a disease and/or disorder caused by a fungus.

In particular embodiments, the present invention also provides methods for the prevention and/or treatment of at least one disease and/or disorder caused by a pest, comprising administering to a subject in need thereof, a pharmaceutically active amount of one or more amino acid sequences, polypeptides and/or pharmaceutical compositions as disclosed herein. In particular, the pharmaceutically active amount may be an amount that is sufficient (to create a level of the amino acid sequence or polypeptide in circulation) to inhibit, prevent or decrease one or more biological activities or pathways of the pest bound thereby.

Therefore, in certain aspects the present invention provides compositions comprising at least one polypeptide, which specifically binds to a pest for use as an anti-pest agent in a subject, such as an animal or a human being, suffering from a disease and/or disorder caused by a pest (e.g. a fungus).

In specific embodiments, the anti-pest agent is a biostatic or a pesticidal agent. In specific embodiments, the anti-pest agent is a fungistatic or a fungicidal agent.

Also, in certain aspects, the present invention provides methods for the prevention and/or treatment of a disease and/or disorder caused by a pest, which methods comprise the steps of:

(a) providing an amino acid sequence, polypeptide or composition as disclosed herein, (b) administering the amino acid sequence, polypeptide or pharmaceutical composition to a patient suffering from the disease and/or disorder caused by a pest.

The efficacy of the polypeptides as disclosed herein, and of compositions comprising the same, can be tested using any suitable in vitro assay, cell-based assay, in vivo assay and/or animal model known per se, or any combination thereof, depending on the specific disease or disorder involved. Suitable assays and animal models will be clear to the skilled person as well as the assays and animal models used in the experimental part below and in the prior art cited herein. The skilled person will generally be able to select a suitable in vitro assay, cellular assay or animal model to test the amino acid sequences and polypeptides as disclosed herein for binding to a pest target or pest antigen or for their capacity to affect the activity of a pest target or pest antigen, and/or the biological mechanisms in which it is involved; as well as for their therapeutic and/or prophylactic effect in respect of one or more diseases and disorders that are associated with the pest antigen.

[Pharmaceutical Compositions]

In yet a further aspect, the present invention provides pharmaceutical compositions comprising one or more amino acid sequences, polypeptides and/or nucleic acid sequences as disclosed herein and optionally at least one pharmaceutically acceptable carrier (also referred to herein as pharmaceutical compositions of the invention). According to certain particular embodiments, the pharmaceutical compositions as disclosed herein may further optionally comprise at least one other pharmaceutically active compound.

The pharmaceutical compositions of the present invention can be used in the diagnosis, prevention and/or treatment of diseases and disorders associated with the pest, such as a fungus, of which the pest target is bound to the polypeptides disclosed herein.

In particular, the present invention provides pharmaceutical compositions comprising polypeptides that are suitable for prophylactic, therapeutic and/or diagnostic use in a warm-blooded animal, and in particular in a mammal, and more in particular in a human being.

The present invention also provides pharmaceutical compositions comprising amino acid sequences and polypeptides as disclosed herein that can be used for veterinary purposes in the prevention and/or treatment or diagnosis of one or more diseases, disorders or conditions associated with the pest, such as for instance a fungus, of which the pest target is bound to the polypeptides disclosed herein.

Generally, for pharmaceutical use, the polypeptides as disclosed herein may be formulated as a pharmaceutical preparation or compositions comprising at least one polypeptide as disclosed herein and at least one pharmaceutically acceptable carrier, diluent or excipient and/or adjuvant, and optionally one or more further pharmaceutically active polypeptides and/or compounds. Such a formulation may be suitable for oral, parenteral, topical administration or for administration by inhalation. Thus, the amino acid sequences, or polypeptides as disclosed herein and/or the compositions comprising the same can for example be administered orally, intraperitoneally (e.g. intravenously, subcutaneously, intramuscularly, transdermally, topically, by means of a suppository, by inhalation, again depending on the specific pharmaceutical formulation or composition to be used. The clinician will be able to select a suitable route of administration and a suitable pharmaceutical formulation or composition to be used in such administration.

The pharmaceutical compositions may also contain suitable binders, disintegrating agents, sweetening agents or flavoring agents. Tablets, pills, or capsules may be coated for instance with gelatin, wax or sugar and the like. In addition, the amino acid sequences and polypeptides as disclosed herein may be incorporated into sustained-release preparations and devices.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form must be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. Antibacterial and antifungal agents and the like can optionally be added.

Useful dosages of the amino acid sequences and polypeptides as disclosed herein can be determined by comparing their in vitro activity, and in vivo activity in animal models. Methods for the extrapolation of effective dosages in mice, and other animals, to humans are known to the skilled person.

The amount of the amino acid sequences and polypeptides as disclosed herein required for use in prophylaxis and/or treatment may vary not only with the particular amino acid sequence or polypeptide selected but also with the route of administration, the nature of the condition being treated and the age and condition of the patient and will be ultimately at the discretion of the attendant physician or clinician. Also the dosage of the amino acid sequences and polypeptides as disclosed herein may vary depending on the target cell, tumor, tissue, graft, or organ.

The amino acid sequences or polypeptides as disclosed herein and/or the compositions comprising the same are administered according to a regimen of treatment that is suitable for preventing and/or treating the disease or disorder to be prognosed, diagnosed, prevented or treated. The clinician will generally be able to determine a suitable treatment regimen. Generally, the treatment regimen will comprise the administration of one or more amino acid sequences or polypeptides as disclosed herein, or of one or more compositions comprising the same, in one or more pharmaceutically effective amounts or doses.

The desired dose may conveniently be presented in a single dose or as divided doses (which can again be sub-dosed) administered at appropriate intervals. An administration regimen could include long-term (i.e., at least two weeks, and for example several months or years) or daily treatment.

The amino acid sequences or polypeptides as disclosed herein will be administered in an amount which will be determined by the medical practitioner based inter alia on the severity of the condition and the patient to be treated. Typically, for each disease indication an optical dosage will be determined specifying the amount to be administered per kg body weight per day, either continuously (e.g. by infusion), as a single daily dose or as multiple divided doses during the day. The clinician will generally be able to determine a suitable daily dose, depending on the factors mentioned herein. It will also be clear that in specific cases, the clinician may choose to deviate from these amounts, for example on the basis of the factors cited above and his expert judgment.

In particular, the amino acid sequences or polypeptides as disclosed herein may be used in combination with other pharmaceutically active compounds or principles that are or can be used for the prevention and/or treatment of the diseases and disorders cited herein, as a result of which a synergistic effect may or may not be obtained. Examples of such compounds and principles, as well as routes, methods and pharmaceutical formulations or compositions for administering them will be clear to the clinician.

Compositions of the invention may be used in conjunction with known anti-fungals. Suitable anti-fungals include, but are not limited to, azoles (e.g. fluconazole, itraconazole), polyenes (e.g. amphotericin B), flucytosine, and squalene epoxidase inhibitors (e.g. terbinafine) [see also ref 57]. Compositions may also be used in conjunction with known antivirals e.g. HIV protease inhibitors, a 2',3'-dideoxynucleoside (e.g. DDC, DDI), 3'-azido-2',3'-dideoxynucleosides (AZT), 3'-fluoro-2',3'-dideoxynucleosides (FLT), 2',3'-didehydro-2',3'-dideoxynucleosides (e.g. D4C, D4T) and carbocyclic derivatives thereof (e.g. carbovir), 2'-fluoro-ara-2',3'-dideoxynucleosides, 1,3-dioxolane derivatives (e.g. 2',3'-dideoxyl-3'-thiacytidine), oxetanocin analogues and carbocyclic derivatives thereof (e.g. cyclobut-G) and the 9-(2-phosphonylmethoxyethyl)adenine (PMEA) and 9-(3-fluoro-2-phosphonylmethoxypropyl)adenine (FPMPA) derivatives, tetrahydro-irmidazo[4,5,1jk][1,4]-benzodiazepin-2(1H)one (TIBO), 1-[(2-hydroxyethoxy)-methyl]-6-(phenylthio)thymine (HEPT), dipyrido[3,2-b:2',3'-e]-[1,4] diazepin-6-one (nevirapine) and pyridin-2(1H)one derivatives, 3TC, etc.

The amino acid sequences, polypeptides and pharmaceutical compositions are particularly useful for treating infections in animals and humans of *Candida* species, such as *C. albicans*; *Cryptococcus* species, such as *C. neoformans*; *Enterococcus* species, such as *E. faecalis*; *Streptococcus* species, such as *Spneumoniae, S. mutans, S. agalactiae* and *S. pyogenes*; *Leishmania* species, such as *L. major* and *L. infantum*; *Acanthamoeba* species, such as *A. castellani*; *Aspergillus* species, such as *A. fumigatus* and *A. flavus*; *Pneumocystis* species, such as *P. carinii*; *Mycobacterium* species, such as *M. tuberculosis*; *Pseudomonas* species, such as *P. aeruginosa*; *Staphylococcus* species, such as *S. aureus*; *Salmonella* species, such as *S. typhimurium*; *Coccidioides* species such as *C. iminitis*; *Trichophyton* species such as *T. verrucosum*; *Blastomyces* species such as *B. dermatidis*; *Histoplasma* species such as *H. capsulatum*; *Paracoccidioides* species such as *P. brasiliensis*; *Pythiumn* species such as *P. insidiosum*; and *Escherichia* species, such as *E. coli*. The amino acid sequences, polypeptides and pharmaceutical compositions are particularly useful for treating diseases including, but not limited to: candidosis, aspergillosis, cryptococcosis, dermatomycoses, sporothrychosis and other subcutaneous mycoses, blastomycosis, histoplasmosis, coccidiomycosis, paracoccidiomycosis, pneumocystosis, thrush, tuberculosis, mycobacteriosis, respiratory infections, scarlet fever, pneumonia, impetigo, rheumatic fever, sepsis, septicaemia, cutaneous and visceral leishmaniasis, corneal acanthamoebiasis, keratitis, cystic fibrosis, typhoid fever, gastroenteritis and hemolytic-uremic syndrome. Anti *C. albicans* activity is particularly useful for treating infections in AIDS patients.

[Methods of Production and Manufacturing of the Polypeptides]

The invention further provides methods for preparing or generating the polypeptide sequences, as well as methods for producing nucleic acids encoding these and host cells, products and compositions comprising these polypeptide sequences. Some preferred but non-limiting examples of such methods will become clear from the further description herein.

As will be clear to the skilled person, one particularly useful method for preparing polypeptide sequences as disclosed herein generally comprises the steps of:

(a) expressing a nucleotide sequence encoding a polypeptide sequence as disclosed herein or a vector or genetic construct a nucleotide sequence encoding that polypeptide sequence and (b) optionally isolating and/or purifying the polypeptide sequence.

In particular embodiments envisaged herein, the pest-specific a polypeptide sequences can be obtained by methods which involve generating a random library of amino acid sequences and screening this library for an amino acid sequence capable of specifically binding to a pest target.

Accordingly, in particular embodiments, methods for preparing a polypeptide sequence as disclosed herein comprise the steps of a) providing a set, collection or library of amino acid sequences; and b) screening said set, collection or library of amino acid sequences sequences that can bind to and/or have affinity for the pest target.

and c) isolating the amino acid sequence(s) that can bind to and/or have affinity for the pest target.

In such a method, the set, collection or library of polypeptide sequences may be any suitable set, collection or library of amino acid sequences. For example, the set, collection or library of amino acid sequences may be a set, collection or library of immunoglobulin fragment sequences (as described herein), such as a naïve set, collection or library of immunoglobulin fragment sequences; a synthetic or semi-synthetic set, collection or library of immunoglobulin fragment sequences; and/or a set, collection or library of immunoglobulin fragment sequences that have been subjected to affinity maturation.

In particular embodiments of this method, the set, collection or library of amino acid sequences may be an immune set, collection or library of immunoglobulin fragment sequences, for example derived from a mammal that has been suitably immunized with a pest target or with a suitable antigenic determinant based thereon or derived therefrom, such as an antigenic part, fragment, region, domain, loop or other epitope thereof. In one particular aspect, said antigenic determinant may be an extracellular part, region, domain, loop or other extracellular epitope(s).

In the above methods, the set, collection or library of polypeptide sequences may be displayed on a phage, phagemid, ribosome or suitable micro-organism (such as yeast), such as to facilitate screening. Suitable methods, techniques and host organisms for displaying and screening (a set, collection or library of) amino acid sequences will be clear to the person skilled in the art, for example on the basis of the further disclosure herein. Reference is also made to the review by Hoogenboom in Nature Biotechnology, 23, 9, 1105-1116 (2005).

In other embodiments, the methods for generating the polypeptide sequences as disclosed herein comprises at least the steps of:
a) providing a collection or sample of cells expressing polypeptide sequences;
b) screening said collection or sample of cells for cells that express an amino acid sequence that can bind to and/or have affinity for a pest target;
and
c) either (i) isolating said amino acid sequence; or (ii) isolating from said cell a nucleic acid sequence that encodes said amino acid sequence, followed by expressing said amino acid sequence.

The collection or sample of cells may for example be a collection or sample of B-cells. Also, in this method, the sample of cells may be derived from a mammal that has been suitably immunized with a fungal target or with a suitable antigenic determinant based thereon or derived therefrom, such as an antigenic part, fragment, region, domain, loop or other epitope thereof. In one particular embodiment, the antigenic determinant may be an extracellular part, region, domain, loop or other extracellular epitope(s).

In other embodiments, the method for generating a polypeptide sequence directed against a pest target may comprise at least the steps of:
a) providing a set, collection or library of nucleic acid sequences encoding a polypeptide amino acid sequence;
b) screening said set, collection or library of nucleic acid sequences for nucleic acid sequences that encode an amino acid sequence that can bind to and/or has affinity for the pest target;
and
c) isolating said nucleic acid sequence, followed by expressing said amino acid sequence.

In the above methods, the set, collection or library of nucleic acid sequences encoding amino acid sequences may for example be a set, collection or library of nucleic acid sequences encoding a naïve set, collection or library of immunoglobulin fragment sequences; a set, collection or library of nucleic acid sequences encoding a synthetic or semi-synthetic set, collection or library of immunoglobulin fragment sequences; and/or a set, collection or library of nucleic acid sequences encoding a set, collection or library of immunoglobulin fragment sequences that have been subjected to affinity maturation.

In particular, in such a method, the set, collection or library of nucleic acid sequences encodes a set, collection or library of polypeptides (such as $V_H$ domains or $V_{HH}$ domains). For example, the set, collection or library of nucleic acid sequences may encode a set, collection or library of domain antibodies or single domain antibodies, or a set, collection or library of amino acid sequences that are capable of functioning as a domain antibody or single domain antibody. In specific embodiments, the set, collection or library of nucleotide sequences encodes a set, collection or library of $V_{HH}$ sequences.

In the above methods, the set, collection or library of nucleotide sequences may be displayed on a phage, phagemid, ribosome or suitable micro-organism (such as yeast), such as to facilitate screening. Suitable methods, techniques and host organisms for displaying and screening (a set, collection or library of) nucleotide sequences encoding amino acid sequences will be clear to the person skilled in the art, for example on the basis of the further disclosure herein. Reference is also made to the review by Hoogenboom in Nature Biotechnology, 23, 9, 1105-1116 (2005).

The invention also relates to polypeptide sequences that are obtainable or obtained by the above methods, or alternatively by a method that comprises one of the above methods and in addition at least the steps of determining the nucleotide sequence or amino acid sequence of said immunoglobulin sequence; and of expressing or synthesizing said amino acid sequence in a manner known per se, such as by expression in a suitable host cell or host organism or by chemical synthesis.

[Isolation of Polypeptide Sequences]

In some cases, the methods for producing the amino acid sequences binding specifically to a fungal target as envisaged herein may further comprise the step of isolating from the amino acid sequence library at least one polypeptide having detectable binding affinity for, or detectable in vitro effect on a pest target.

These methods may further comprise the step of amplifying a sequence encoding at least one polypeptide having detectable binding affinity for, or detectable in vitro effect on the activity of a pest target. For example, a phage clone displaying a particular amino acid sequence, obtained from a selection step of a method described herein, may be amplified by reinfection of a host bacteria and incubation in a growth medium.

In particular embodiments, these methods may encompass determining the sequence of the one or more amino acid sequences capable of binding to a pest target.

Where a polypeptide sequence, comprised in a set, collection or library of amino acid sequences, is displayed on a suitable cell or phage or particle, it is possible to isolate from said cell or phage or particle, the nucleotide sequence that encodes that amino acid sequence. In this way, the nucleotide sequence of the selected amino acid sequence library member(s) can be determined by a routine sequencing method.

In further particular embodiments, the methods for producing a polypeptide as envisaged herein comprise the step of expressing said nucleotide sequence(s) in a host organism under suitable conditions, so as to obtain the actual desired amino acid sequence. This step can be performed by methods known to the person skilled in the art.

In addition, the obtained polypeptide sequences having detectable binding affinity for, or detectable in vitro effect on the activity of a pest target, may be synthesized as soluble protein construct, optionally after their sequence has been identified.

For instance, the polypeptide sequences obtained, obtainable or selected by the above methods can be synthesized using recombinant or chemical synthesis methods known in the art. Also, the amino acid sequences obtained, obtainable or selected by the above methods can be produced by genetic engineering techniques. Thus, methods for synthesizing the polypeptide sequences obtained, obtainable or selected by the above methods may comprise transforming or infecting a host cell with a nucleic acid or a vector encoding an amino acid sequence having detectable binding affinity for, or detectable in vitro effect on the activity of a pest target. Accordingly, the amino acid sequences having detectable binding affinity for, or detectable in vitro effect on the activity of a pest target can be made by recombinant DNA methods. DNA encoding the amino acid sequences can be readily synthesized using conventional procedures. Once prepared, the DNA can be introduced into expression vectors, which can then be transformed or transfected into host cells such as E. coli or any suitable expression system, in order to obtain the expression of amino acid sequences in the recombinant host cells and/or in the medium in which these recombinant host cells reside.

It should be understood, as known by someone skilled in the art of protein expression and purification, that the polypeptide produced from an expression vector using a suitable expression system may be tagged (typically at the N-terminal or C-terminal end of the amino acid sequence) with e.g. a His-tag or other sequence tag for easy purification.

Transformation or transfection of nucleic acids or vectors into host cells may be accomplished by a variety of means known to the person skilled in the art including calcium phosphate-DNA co-precipitation, DEAE-dextran-mediated transfection, polybrene-mediated transfection, electroporation, microinjection, liposome fusion, lipofection, protoplast fusion, retroviral infection, and biolistics.

Suitable host cells for the expression of the desired polypeptide sequences may be any eukaryotic or prokaryotic cell (e.g., bacterial cells such as E. coli, yeast cells, mammalian cells, avian cells, amphibian cells, plant cells, fish cells, and insect cells), whether located in vitro or in vivo. For example, host cells may be located in a transgenic plant or animal.

Thus, the application also provides methods for the production of polypeptide sequences having detectable binding affinity for, or detectable in vitro effect on the activity of a pest target comprising transforming, transfecting or infecting a host cell with nucleic acid sequences or vectors encoding such amino acid sequences and expressing the amino acid sequences under suitable conditions.

In yet another embodiment, the invention further provides methods for the manufacture Or the production of which is equivalent wording) an agrochemical or biological control composition as disclosed herein.

In particular embodiments, the invention provides methods for producing an agrochemical composition as disclosed herein, at least comprising the steps of:
  obtaining at least one polypeptide, which specifically binds to a pest, and
  formulating the polypeptide or functional fragment thereof in an agrochemical composition.

In particular embodiments of these methods, the step of obtaining at least one polypeptide, which specifically binds to a pest comprises:
  (a) expressing a nucleotide sequence encoding a polypeptide, which specifically binds to a pest, and optionally
  (b) isolating and/or purifying the polypeptide.

In other particular embodiments of these methods, the step of obtaining at least one polypeptide, which specifically binds to a pest comprises:
a) providing a set, collection or library of polypeptide sequences;
b) screening said set, collection or library of polypeptide sequences for sequences that specifically bind to and/or have affinity for a pest, and optionally
c) isolating the polypeptide sequences that specifically bind to and/or have affinity for a pest.

The present application further discloses methods for the manufacture Or the production of which is equivalent wording) an agrochemical or biological control composition as disclosed herein, comprising formulating an amino acid sequence or polypeptide of between 80 and 200 amino acids, or other suitable sub-ranges as defined herein before, with pesticidal activity together with at least one customary agrochemical auxiliary agent.

Suitable manufacturing methods are known in the art and include, but are not limited to, high or low shear mixing, wet or dry milling, drip-casting, encapsulating, emulsifying, coating, encrusting, pilling, extrusion granulation, fluid bed granulation, co-extrusion, spray drying, spray chilling, atomization, addition or condensation polymerization, interfacial polymerization, in situ polymerization, coacervation, spray encapsulation, cooling melted dispersions, solvent evaporation, phase separation, solvent extraction, sol-gel polymerization, fluid bed coating, pan coating, melting, passive or active absorption or adsorption.

Specifically, the amino acid sequences or polypeptides of between 80 and 200 amino acids as disclosed herein, or other suitable sub-ranges as defined herein before, may be prepared by chemical synthesis.

It is further disclosed that the amino acid sequences or polypeptides of between 80 and 200 amino acids, or other suitable sub-ranges as defined herein before, may be prepared by recombinant microbial expression systems in vitro and isolated for further use. Such amino acid sequences or polypeptides may be either in crude cell lysates, suspensions, colloids, etc., or alternatively may be purified, refined, buffered and/or further processed before formulating together with customary agrochemical auxiliary agents.

Specifically recombinant methodologies generally involve inserting a DNA molecule expressing an amino acid sequence, protein or polypeptide of interest into an expression system to which the DNA molecule is heterologous (i.e. not normally present in the host). The heterologous DNA molecule is inserted into the expression system or vector in proper sense orientation and correct reading frame. The vector contains the necessary elements for the transcription and translation of the inserted protein-coding sequences. Transcription of DNA is dependent upon the presence of a promoter. Similarly, translation of mRNA in prokaryotes depends upon the presence of the proper prokaryotic signals which differ from those of eukaryotes. For a review on maximizing gene expression, see Roberts and Lauer, Methods in Enzymology 68:473 (1979. Regardless of the specific regulatory sequences employed, the DNA molecule is cloned into the vector using standard cloning procedures in the art, as described by Sambrook et al, Molecular Cloning: A Laboratory Manual, Cold Springs Laboratory, Cold Springs Harbor, N.Y. (1989). Once the isolated DNA molecule encoding the protein has been cloned into an expression system, it is ready to be incorporated into a host cell. Such incorporation can be carried out by the various forms of transformation, depending upon the vector/host cell system. Suitable host cells include, but are not limited to, bacteria, virus, yeast, mammalian cells, insect, plant, and the like. Optionally, the recombinant host cells can be host cells that express a native or recombinant, functional type III secretion system. This is described in detail in U.S. Pat. No. 6,596,509. As a consequence of expressing the functional type III secretion system, the cells will express the polypeptide and then secrete the protein into the culture medium. This can simplify isolation and purification of the polypeptide. The recombinant host cells can be grown in appropriate fermentation chambers, preferably under temperature and nutrient conditions that optimize growth of the host cells and the expression of the polypeptide. Persons of skill in the art are able to identify optimal conditions for particular host cells. After fermentation, for example the bacterial suspension may be diluted in, e.g. about 2 to 5 fold volume of a buffer to adjust the pH between about 5.5 to 10, more preferably to a pH of between about 7 to 9, and even more preferably to a pH of about 8.0. Suitable buffers are well-known in the art and may include, for example, potassium phosphate buffer or a Tris-EDTA buffer. The concentration of the buffer can be from about 0.001 mM to about 0.5 M. Following the pH adjustment, the (bacterial) suspension solution is heat treated to a temperature of about 60-130° C., preferably to a temperature of about 95-125° C. Heat treatment may be carried out for any suitable period of time. In one embodiment, heat treatment is carried out for a period of about five minutes up to about 30 minutes. The heated suspension solution is then cooled. A suitable cool down temperature is, without limitation, about 35-55° C., preferably about 45° C. Following cooling, bacterial cells in the bacterial suspension are lysed, if required, to liberate the polypeptide. Cell lysis may be carried out, e.g. by contacting the bacterial suspension with a lysozyme. The concentration of lysozyme may be anywhere from about 2 ppm to 100 ppm. Alternatively, cell lysis may involve non-chemical methods, such as high pressure or sonication, both of which are well known by persons of ordinary skill in the art. It may be desirable, after cell lysis, to incubate the bacterial suspension. Suitable incubation times may vary. For example, it may be desirable to incubate the bacterial suspension for a period of about 30-45 minutes at a temperature of about 40-42° C. After lysing, the desired polypeptide can be further extracted by removing the cell debris and the denatured proteins resulting from the previous heat treatment step. In one embodiment, the extract is centrifuged for about 10-20 minutes to remove some of the cell debris. Suitable centrifuge speeds may be from about 4,000 to 20,000 rpm and the spinning down time can be from about 10 minutes to 20 minutes. Further cell debris may then be removed by heat treating and centrifuging the supernatant to obtain a liquid extract that is substantially free of cellular debris by removing more than about 60%, 70%, 80%, 90%, or 95% of total solids. This subsequent heat treatment may be carried out at a temperature of about 60° C. for up to about two hours, at about 100° C. for about 10 minutes, or at about 121° C. with 15 psi of pressure for about 5 minutes. These temperatures and times may vary depending on other conditions. The method of making a stable liquid composition containing an amino acid sequence or polypeptide as disclosed herein further involves introducing into the liquid extract a biocidal agent and, optionally, one or both of a protease inhibitor and a non-ionic surfactant, thereby obtaining a liquid composition comprising the polypeptide. In one embodiment, a protease inhibitor is introduced into the liquid extract without a non-ionic surfactant. In another embodiment, a non-ionic surfactant is introduced into the liquid extract without a protease inhibitor. In a further embodiment, both a protease inhibitor and a non-ionic surfactant are introduced into the liquid extract. In yet another embodiment, neither a protease inhibitor nor a non-ionic surfactant are introduced into the liquid extract. Alternatively, the stability of the liquid composition as disclosed herein can be assessed using, e.g., HPLC analysis or other suitable procedures that can identify quantity of a specific protein or polypeptide. The stability of the amino acid sequences or polypeptides in a composition as disclosed herein can be determined by comparing the quantity of the protein in the aged liquid composition to that of a recently prepared liquid composition or to a prior quantitation performed on the same composition. The measurement of protein stability strongly correlates with a retention of its activity.

Customary agrochemical auxiliary agents are well-known in the art and include, but are not limited to aqueous or organic solvents, buffering agents, acidifiers, surfactants, wetting agents, spreading agents, tackifiers, stickers, carriers, fillers, thickeners, emulsifiers, dispersants, sequestering agents, anti-settling agents, coalescing agents, rheology modifiers, defoaming agents, photo-protectors, anti-freeze agents, biocides, penetrants, mineral or vegetable oils, pigments and drift control agents or any suitable combination thereof.

In yet another embodiment, the invention provides a polypeptide of between 80 and 200 amino acids or the sub-ranges disclosed herein before, obtained by affinity selection to a certain plant pest target, which is able to inhibit the growth and/or the activity of a plant pest at a minimum inhibitory concentration of about 0.00001 to 1 μM.

In particular embodiments of the methods as disclosed herein for protecting, preventing, curing or treating a plant from an infection by a fungus, the polypeptides or compositions as disclosed herein are directly or indirectly applied to the plant by spraying, atomizing, foaming, fogging, in hydroculture/hydroponics, coating, submerging, and/or encrusting.

[Nucleic Acid Sequences]

In a further aspect, the present invention provides nucleic acid sequences encoding the polypeptide sequences in the compositions as disclosed herein (or suitable fragments thereof).

These nucleic acid sequences can also be in the form of a vector or a genetic construct or polynucleotide. The nucleic acid sequences as disclosed herein may be synthetic or semi-synthetic sequences, nucleotide sequences that have been isolated from a library (and in particular, an expression library), nucleotide sequences that have been prepared by PCR using overlapping primers, or nucleotide sequences that have been prepared using techniques for DNA synthesis known per se.

[Constructs, Vectors, Host Cells]

The genetic constructs as disclosed herein may be DNA or RNA, and are preferably double-stranded DNA. The genetic constructs of the invention may also be in a form suitable for transformation of the intended host cell or host organism in a form suitable for integration into the genomic DNA of the intended host cell or in a form suitable for independent replication, maintenance and/or inheritance in the intended host organism. For instance, the genetic constructs of the invention may be in the form of a vector, such as for example a plasmid, cosmid, YAC, a viral vector or transposon. In particular, the vector may be an expression vector, i.e., a vector that can provide for expression in vitro and/or in vivo (e.g. in a suitable host cell, host organism and/or expression system).

Accordingly, in another further aspect, the present invention also provides vectors comprising one or more nucleic acid sequences of the invention.

In still a further aspect, the present invention provides hosts or host cells that express or are capable of expressing one or more amino acid sequences as disclosed herein. Suitable examples of hosts or host cells for expression of the amino acid sequences, polypeptides of the invention will be clear to the skilled person.

The application also discloses, polypeptides of between 80 and 200 amino acids or the sub-ranges discussed herein before, remain stable in an agrochemical or biological control composition, as defined, meaning that the integrity and the pesticidal activity, as defined, of the polypeptide is maintained under storage and/or utilization conditions of the agrochemical composition, which may include elevated temperatures, freeze-thaw cycles, changes in pH or in ionic strength, UV-irradiation, presence of harmful chemicals and the like. Most preferably, these polypeptides of between 80 and 200 amino acids remains stable in the agrochemical composition when the agrochemical composition is stored at ambient temperature for a period of two years or when the agrochemical composition is stored at 54° C. for a period of two weeks. Particularly, the polypeptides of between 80 and 200 amino acids comprised in an agrochemical composition retains at least about 70% activity, more particularly at least about 70% to 80% activity, most particularly about 80% to 90% activity, after having been stored in the agrochemical composition at ambient temperature for a period of two years or when the agrochemical composition containing the polypeptide is stored at 54° C. for a period of two weeks.

In yet another embodiment, for use in the methods disclosed herein, the application discloses nucleic acid sequences encoding a polypeptides of between 80 and 200 amino acids, wherein polypeptides are obtained by affinity selection to a specific plant pathogenic target, which polypeptide is able to inhibit the growth and/or the activity of a crop pest at a minimum inhibitory concentration of about 0.00001 to 1 µM.

Also disclosed are chimeric genes comprising the following operably linked DNA elements: a) a plant expressible promoter, b) a DNA region which when transcribed yields a mRNA molecule capable of being translated into a polypeptide and c) a 3' end region comprising transcription termination and polyadenylation signals functioning in cells of said plant.

A "chimeric gene" or "chimeric construct" is a recombinant nucleic acid sequence in which a promoter (e.g. a plant expressible promoter) or regulatory nucleic acid sequence is operatively linked to, or associated with, a nucleic acid sequence that codes for an mRNA, such that the regulatory nucleic acid sequence is able to regulate transcription or expression of the associated nucleic acid coding sequence when introduced into a cell such as a plant cell. The regulatory nucleic acid sequence of the chimeric gene is not normally operatively linked to the associated nucleic acid sequence as found in nature.

In the present invention, a "plant promoter" comprises regulatory elements, which mediate the expression of a coding sequence segment in plant cells. For expression in plants, the nucleic acid molecule must be linked operably to or comprise a suitable promoter which expresses the gene at the right point in time and with the required spatial expression pattern.

The term "operably linked" as used herein refers to a functional linkage between the promoter sequence and the gene of interest, such that the promoter sequence is able to initiate transcription of the gene of interest.

Plant expressible promoters comprise nucleic acid sequences which are able to direct the expression of a transgene in a plant. Examples of plant expressible promoters are constitutive promoters which are transcriptionally active during most, but not necessarily all, phases of growth and development and under most environmental conditions, in at least one cell, tissue or organ, other promoters are inducible promoters, other examples are tissue specific promoters, still other examples are abiotic stress inducible promoters.

The chimeric gene (or the expression cassette) when transformed in a plant expresses a nucleic acid which results in expression of a protein.

Also disclosed is a recombinant vector which comprises an expression cassette (or a chimeric gene) as herein described before.

The term "terminator" encompasses a control sequence which is a DNA sequence at the end of a transcriptional unit which signals 3' processing and polyadenylation of a primary transcript and termination of transcription. The terminator can be derived from the natural gene, from a variety of other plant genes, or from T-DNA. The terminator to be added may be derived from, for example, the nopaline synthase or octopine synthase genes, or alternatively from another plant gene, or less preferably from any other eukaryotic gene.

"Selectable marker", "selectable marker gene" or "reporter gene" includes any gene that confers a phenotype on a cell in which it is expressed to facilitate the identification and/or selection of cells that are transfected or transformed with a nucleic acid construct of the invention. These marker genes enable the identification of a successful transfer of the nucleic acid molecules via a series of different principles. Suitable markers may be selected from markers that confer antibiotic or herbicide resistance, that introduce a new metabolic trait or that allow visual selection. Examples of selectable marker genes include genes conferring resistance to antibiotics (such as nptII that phosphorylates neomycin and kanamycin, or hpt, phosphorylating hygromycin, or genes conferring resistance to, for example, bleomycin, streptomycin, tetracyclin, chloramphenicol, ampicillin, gentamycin, geneticin (G418), spectinomycin or blasticidin), to herbicides (for example bar which provides resistance to Basta®; aroA or gox providing resistance against glyphosate, or the genes conferring resistance to, for example, imidazolinone, phosphinothricin or sulfonylurea), or genes that provide a metabolic trait (such as manA that allows plants to use mannose as sole carbon source or xylose isomerase for the utilisation of xylose, or antinutritive markers such as the resistance to 2-deoxyglucose). Expression of visual marker genes results in the formation of colour (for example β-glucuronidase, GUS or β-galactosidase with its coloured substrates, for example X-Gal), luminescence (such as the luciferin/luciferase system) or fluorescence (Green Fluorescent Protein, GFP, and derivatives thereof). This list represents only a small number of possible markers. The skilled worker is familiar with such markers. Different markers are preferred, depending on the organism and the selection method.

It is known that upon stable or transient integration of nucleic acids into plant cells, only a minority of the cells takes up the foreign DNA and, if desired, integrates it into its genome, depending on the expression vector used and the transfection technique used. To identify and select these integrants, a gene coding for a selectable marker (such as the ones described above) is usually introduced into the host cells together with the gene of interest. These markers can for example be used in mutants in which these genes are not functional by, for example, deletion by conventional methods. Furthermore, nucleic acid molecules encoding a selectable marker can be introduced into a host cell on the same vector that comprises the sequence encoding the polypeptides of the invention or used in the methods of the invention, or else in a separate vector. Cells which have been stably transfected with the introduced nucleic acid can be identified for example by selection (for example, cells which have integrated the selectable marker survive whereas the other cells die).

Since the marker genes, particularly genes for resistance to antibiotics and herbicides, are no longer required or are undesired in the transgenic host cell once the nucleic acids have been introduced successfully, the process according to the invention for introducing the nucleic acids advantageously employs techniques which enable the removal or excision of these marker genes. One such a method is what is known as co-transformation. The co-transformation method employs two vectors simultaneously for the transformation, one vector bearing the nucleic acid according to the invention and a second bearing the marker gene(s). A large proportion of transformants receives or, in the case of plants, comprises (up to 40% or more of the transformants), both vectors. In case of transformation with Agrobacteria, the transformants usually receive only a part of the vector, i.e. the sequence flanked by the T-DNA, which usually represents the expression cassette. The marker genes can subsequently be removed from the transformed plant by performing crosses. In another method, marker genes integrated into a transposon are used for the transformation together with desired nucleic acid (known as the Ac/Ds technology). The transformants can be crossed with a transposase source or the transformants are transformed with a nucleic acid construct conferring expression of a transposase, transiently or stable. In some cases (approx. 10%), the transposon jumps out of the genome of the host cell once transformation has taken place successfully and is lost. In a further number of cases, the transposon jumps to a different location. In these cases the marker gene must be eliminated by performing crosses. In microbiology, techniques were developed which make possible, or facilitate, the detection of such events. A further advantageous method relies on what is known as recombination systems; whose advantage is that elimination by crossing can be dispensed with. The best-known system of this type is what is known as the Cre/lox system. Cre1 is a recombinase that removes the sequences located between the loxP sequences. If the marker gene is integrated between the loxP sequences, it is removed once transformation has taken place successfully, by expression of the recombinase. Further recombination systems are the HIN/HIX, FLP/FRT and REP/STB system (Tribble et al., J. Biol. Chem., 275, 2000: 22255-22267; Velmurugan et al., J. Cell Biol., 149, 2000: 553-566). A site-specific integration into the plant genome of the nucleic acid sequences according to the invention is possible.

For the purposes of the invention, "transgenic", "transgene" or "recombinant" means with regard to, for example, a nucleic acid sequence, an expression cassette, gene construct or a vector comprising the nucleic acid sequence or an organism transformed with the nucleic acid sequences, expression cassettes or vectors according to the invention.

A transgenic plant for the purposes of the invention is thus understood as meaning, as above, that the nucleic acids used in the method of the invention are not present in, or originating from, the genome of said plant, or are present in the genome of said plant but not at their natural locus in the genome of said plant, it being possible for the nucleic acids to be expressed homologously or heterologously. However, as mentioned, transgenic also means that, while the nucleic acids according to the invention or used in the inventive method are at their natural position in the genome of a plant, the sequence has been modified with regard to the natural sequence, and/or that the regulatory sequences of the natural sequences have been modified. Transgenic is preferably understood as meaning the expression of the nucleic acids according to the invention at an unnatural locus in the genome, i.e. homologous or, heterologous expression of the nucleic acids takes place. Preferred transgenic plants are mentioned herein.

The term "expression" or "gene expression" means the transcription of a specific gene or specific genes or specific genetic construct. The term "expression" or "gene expression" in particular means the transcription of a gene or genes or genetic construct into structural RNA (rRNA, tRNA) or mRNA with or without subsequent translation of the latter into a protein. The process includes transcription of DNA and processing of the resulting mRNA product.

The term "increased expression" or "overexpression" as used herein means any form of expression that is additional to the original wild-type expression level. For the purposes of this invention, the original wild-type expression level might also be zero, i.e. absence of expression or immeasurable expression.

Methods for increasing expression of genes or gene products are well documented in the art and include, for example, overexpression driven by appropriate promoters (as described herein before), the use of transcription enhancers or translation enhancers. Isolated nucleic acids which serve as promoter or enhancer elements may be introduced in an appropriate position (typically upstream) of a non-heterologous form of a polynucleotide so as to upregulate expression of a nucleic acid encoding the polypeptide of interest. If polypeptide expression is desired, it is generally desirable to include a polyadenylation region at the 3'-end of a polynucleotide coding region. The polyadenylation region can be derived from the natural gene, from a variety of other plant genes, or from T-DNA. The 3' end sequence to be added may be derived from, for example, the nopaline synthase or octopine synthase genes, or alternatively from another plant gene, or less preferably from any other eukaryotic gene.

An intron sequence may also be added to the 5' untranslated region (UTR) or the coding sequence of the partial coding sequence to increase the amount of the mature message that accumulates in the cytosol. Inclusion of a spliceable intron in the transcription unit in both plant and animal expression constructs has been shown to increase gene expression at both the mRNA and protein levels up to 1000-fold (Buchman and Berg (1988) Mol. Cell biol. 8: 4395-4405; Callis et al. (1987) Genes Dev 1:1 183-1200). Such intron enhancement of gene expression is typically greatest when placed near the 5' end of the transcription unit. Use of the maize introns Adh1-S intron 1, 2, and 6, the Bronze-1 intron are known in the art. For general information see: The Maize Handbook, Chapter 116, Freeling and Walbot, Eds., Springer, N.Y. (1994).

The term "introduction" or "transformation" as referred to herein encompass the transfer of an exogenous polynucleotide or chimeric gene (or expression cassette) into a host cell, irrespective of the method used for transfer. Plant tissue capable of subsequent clonal propagation, whether by organogenesis or embryogenesis, may be transformed with a genetic construct of the present invention and a whole plant regenerated there from. The particular tissue chosen will vary depending on the clonal propagation systems available for, and best suited to, the particular species being transformed. Exemplary tissue targets include leaf disks, pollen, embryos, cotyledons, hypocotyls, megagametophytes, callus tissue, existing meristematic tissue (e.g., apical meristem, axillary buds, and root meristems), and induced meristem tissue (e.g., cotyledon meristem and hypocotyl meristem). The polynucleotide may be transiently or stably introduced into a host cell and may be maintained non-integrated, for example, as a plasmid. Alternatively, it may be integrated into the host genome. The resulting transformed plant cell may then be used to regenerate a transformed plant in a manner known to persons skilled in the art.

The transfer of foreign genes into the genome of a plant is called transformation. Transformation of plant species is now a fairly routine technique. Advantageously, any of several transformation methods may be used to introduce the gene of interest into a suitable ancestor cell. The methods described for the transformation and regeneration of plants from plant tissues or plant cells may be utilized for transient or for stable transformation. Transformation methods include the use of liposomes, electroporation, chemicals that increase free DNA uptake, injection of the DNA directly into the plant, particle gun bombardment, transformation using viruses or pollen and microprojection. Methods may be selected from the calcium/polyethylene glycol method for protoplasts (Krens, F. A. et al., (1982) Nature 296, 72-74; Negrutiu I et al. (1987) Plant Mol Biol 8: 363-373); electroporation of protoplasts (Shillito R. D. et al. (1985) Bio/Technol 3, 1099-1 102); microinjection into plant material (Crossway A et al., (1986) Mol. Gen Genet 202: 179-185); DNA or RNA-coated particle bombardment (Klein T M et al., (1987) Nature 327: 70) infection with (non-integrative) viruses and the like. Transgenic plants, including transgenic crop plants, are preferably produced via *Agrobacterium*-mediated transformation. An advantageous transformation method is the transformation in planta. To this end, it is possible, for example, to allow the agrobacteria to act on plant seeds or to inoculate the plant meristem with agrobacteria. It has proved particularly expedient in accordance with the invention to allow a suspension of transformed agrobacteria to act on the intact plant or at least on the flower primordia. The plant is subsequently grown on until the seeds of the treated plant are obtained (Clough and Bent, Plant J. (1998) 16, 735-743). Methods for *Agrobacterium*-mediated transformation of rice include well known methods for rice transformation, such as those described in any of the following: European patent application EP1198985, Aldemita and Hodges (Planta 199: 612-617, 1996); Chan et al. (Plant Mol Biol 22 (3): 491-506, 1993), Hiei et al. (Plant J 6 (2): 271-282, 1994), which disclosures are incorporated by reference herein as if fully set forth. In the case of corn transformation, the preferred method is as described in either Ishida et al. (Nat. Biotechnol 14(6): 745-50, 1996) or Frame et al. (Plant Physiol 129(1): 13-22, 2002), which disclosures are incorporated by reference herein as if fully set forth. Said methods are further described by way of example in B. Jenes et al., Techniques for Gene Transfer, in: Transgenic Plants, Vol. 1, Engineering and Utilization, eds. S. D. Kung and R. Wu, Academic Press (1993) 128-143 and in Potrykus Annu. Rev. Plant Physiol. Plant Molec. Biol. 42 (1991) 205-225). The nucleic acids or the construct to be expressed is preferably cloned into a vector, which is suitable for transforming *Agrobacterium tumefaciens*, for example pBin19 (Bevan et al (1984) *Nucl. Acids Res.* 12-8711). Agrobacteria transformed by such a vector can then be used in known manner for the transformation of plants, such as plants used as a model, like *Arabidopsis* (*Arabidopsis thaliana* is within the scope of the present invention not considered as a crop plant), or crop plants such as, by way of example, tobacco plants, for example by immersing bruised leaves or chopped leaves in an agrobacterial solution and then culturing them in suitable media. The transformation of plants by means of *Agrobacterium tumefaciens* is described, for example, by Hofgen and Willmitzer in Nucl. Acid Res. (1988) 16, 9877 or is known inter alia from F. F. White, Vectors for Gene Transfer in Higher Plants; in Transgenic Plants, Vol. 1, Engineering and Utilization, eds. S. D. Kung and R. Wu, Academic Press, 1993, pp. 15-38.

In addition to the transformation of somatic cells, which then have to be regenerated into intact plants, it is also possible to transform the cells of plant meristems and in particular those cells which develop into gametes. In this case, the transformed gametes follow the natural plant development, giving rise to transgenic plants. Thus, for example, seeds of *Arabidopsis* are treated with agrobacteria and seeds are obtained from the developing plants of which a certain proportion is transformed and thus transgenic [Feldman, K A and Marks M D (1987). Mol Gen Genet 208:1-9; Feldmann K (1992). In: C Koncz, N-H Chua and J Shell, eds, Methods in *Arabidopsis* Research. Word Scientific, Singapore, pp. 274-289]. Alternative methods are based on the repeated removal of the inflorescences and incubation of the excision site in the center of the rosette with transformed agrobacteria, whereby transformed seeds can likewise be obtained at a later point in time (Chang (1994). Plant J. 5: 551-558; Katavic (1994). Mol Gen Genet, 245: 363-370). However, an especially effective method is the vacuum infiltration method with its modifications such as the "floral dip" method. In the case of vacuum infiltration of *Arabidopsis*, intact plants under reduced pressure are treated with an agrobacterial suspension [Bechthold, N (1993). CR Acad Sci Paris Life Sci, 316: 1 194-1 199], while in the case of the "floral dip" method the developing floral tissue is incubated briefly with a surfactant-treated agrobacterial suspension [Clough, S J and Bent A F (1998) The Plant J. 16, 735-743]. A certain proportion of transgenic seeds are harvested in both cases, and these seeds can be distinguished from non-transgenic seeds by growing under the above-described selective conditions. In addition the stable transformation of plastids is of advantages because plastids are inherited maternally is most crops reducing or eliminating the risk of transgene flow through pollen. The transformation of the chloroplast genome is generally achieved by a process which has been schematically displayed in Klaus et al., 2004 [Nature Biotechnology 22 (2), 225-229]. Briefly the sequences to be transformed are cloned together with a selectable marker gene between flanking sequences homologous to the chloroplast genome. These homologous flanking sequences direct site specific integration into the plastome. Plastidal transformation has been described for many different plant species and an overview is given in Bock (2001) Transgenic plastids in basic research and plant biotechnology. J Mol Biol. 2001 Sep. 21; 312 (3):425-38 or Maliga, P (2003) Progress towards commercialization of plastid transformation technology. Trends Biotechnol. 21, 20-28. Further biotechnological progress has recently been reported in form of marker free plastid transformants, which can be produced by a transient co-integrated maker gene (Klaus et al., 2004, Nature Biotechnology 22(2), 225-229).

The genetically modified plant cells can be regenerated via all methods with which the skilled worker is familiar. Suitable methods can be found in the abovementioned publications by S. D. Kung and R. Wu, Potrykus or Hofgen and Willmitzer.

Generally after transformation, plant cells or cell groupings are selected for the presence of one or more markers which are encoded by plant-expressible genes co-transferred with the gene of interest, following which the transformed material is regenerated into a whole plant. To select transformed plants, the plant material obtained in the transformation is, as a rule, subjected to selective conditions so that transformed plants can be distinguished from untransformed plants. For example, the seeds obtained in the above-described manner can be planted and, after an initial growing period, subjected to a suitable selection by spraying. A further possibility consists in growing the seeds, if appropriate after sterilization, on agar plates using a suitable selection agent so that only the transformed seeds can grow into plants. Alternatively, the transformed plants are screened for the presence of a selectable marker such as the ones described above. Following DNA transfer and regeneration, putatively transformed plants may also be evaluated, for instance using Southern analysis, for the presence of the gene of interest, copy number and/or genomic organisation. Alternatively or additionally, expression levels of the newly introduced DNA may be monitored using Northern and/or Western analysis, both techniques being well known to persons having ordinary skill in the art.

The generated transformed plants may be propagated by a variety of means, such as by clonal propagation or classical breeding techniques. For example, a first generation (or T1) transformed plant may be selfed and homozygous second-generation (or T2) transformants selected, and the T2 plants may then further be propagated through classical breeding techniques. The generated transformed organisms may take a variety of forms. For example, they may be chimeras of transformed cells and non-transformed cells; clonal transformants (e.g., all cells transformed to contain the expression cassette); grafts of transformed and untransformed tissues (e.g., in plants, a transformed rootstock grafted to an untransformed scion).

The following non-limiting Examples describe methods and means according to the invention. Unless stated otherwise in the Examples, all techniques are carried out according to protocols standard in the art. The following examples are included to illustrate embodiments of the invention. Those of skill in the art should, in light of the present disclosure, appreciate that many changes can be made in the specific embodiments which are disclosed and still obtain a like or similar result without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

Thus, the Figures, Sequence Listing and the Experimental Part/Examples are only given to further illustrate the invention and should not be interpreted or construed as limiting the scope of the invention and/or of the appended claims in any way, unless explicitly indicated otherwise herein.

The above disclosure will now be further described by means of the following non-limiting Examples and Figures, in which the figures show:

FIG. 1: Binding of VHH as crude VHH-containing periplasmic extracts to coated fungal GlcCer from *Pleurotus citrinopileatus*. Anti-GlcCer VHH bind to fungal GlcCer, no binding is observed for unrelated VHH.

Figure 2:
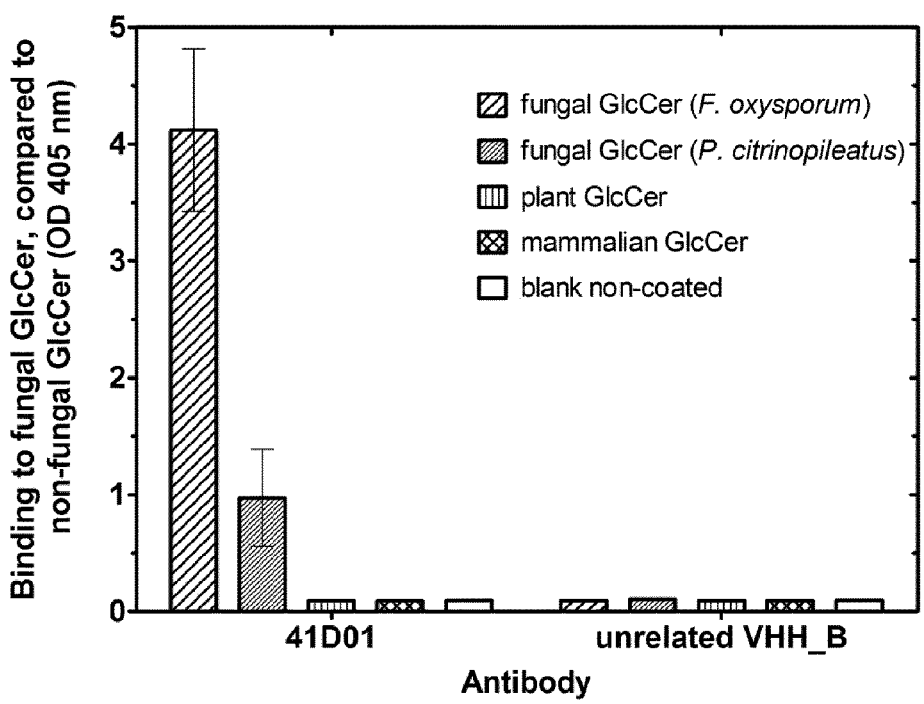

FIG. 2: Binding specificity of VHH 41D01. Binding of purified VHH 41D01 at 0.1 µg/ml to coated fungal GlcCer from *Fusarium oxysporum* or *Pleurotus citrinopileatus*, and non-fungal GlcCer from plant (soy), or mammal (pork). Bars represent average OD 405 nm values, error bars represent standard errors of the mean of n=6. Anti-GlcCer VHH 41 D01 specifically binds fungal GlcCer and not plant or mammalian GlcCer.

Figure 3A:
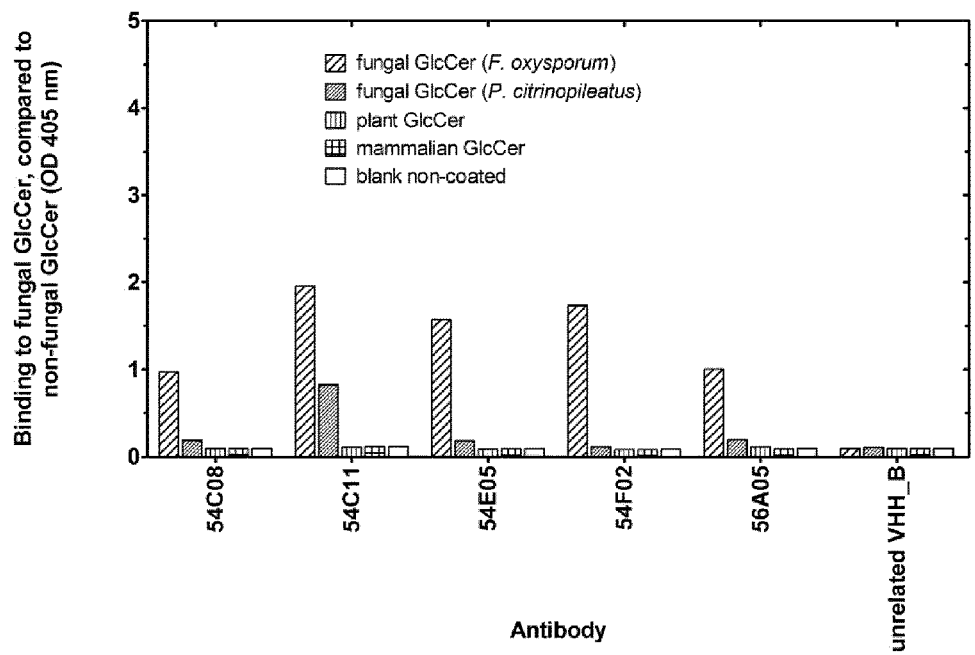

FIG. 3A: Binding specificity of VHH. Binding of purified VHH at 1 µg/ml to coated fungal GlcCer from *Fusarium oxysporum* or *Pleurotus citrinopileatus*. Different anti-GlcCer VHH specifically bind to different fungal GlcCer.

Figure 3B:
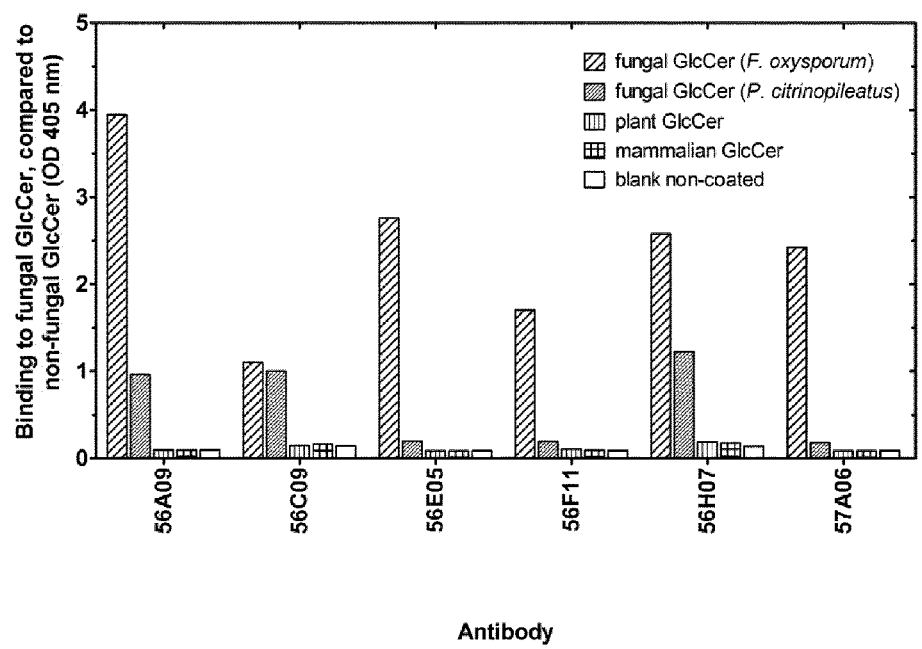

FIG. 3B: Binding specificity of VHH. Binding of purified VHH at 1 µg/ml to coated non-fungal GlcCer from plant (soy). Different anti-GlcCer VHH do not bind plant GlcCer.

Figure 3C:
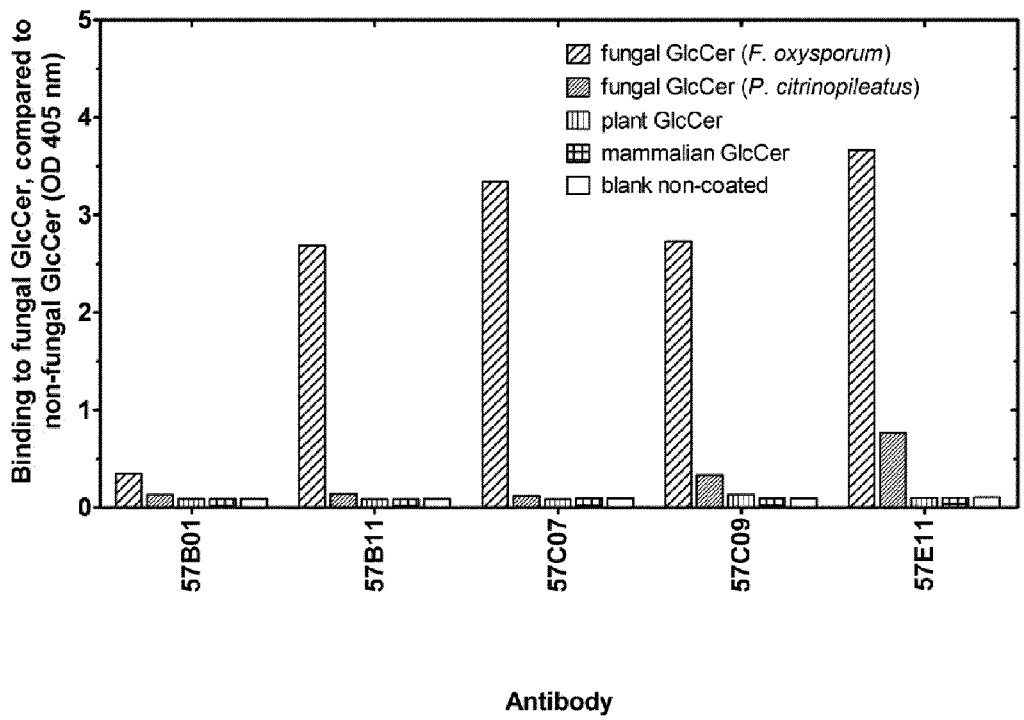

FIG. 3C: Binding specificity of VHH. Binding of purified VHH at 1 µg/ml to coated non-fungal mammalian GlcCer (pork). Different anti-GlcCer VHH do not bind mammalian GlcCer.

Figure 4:
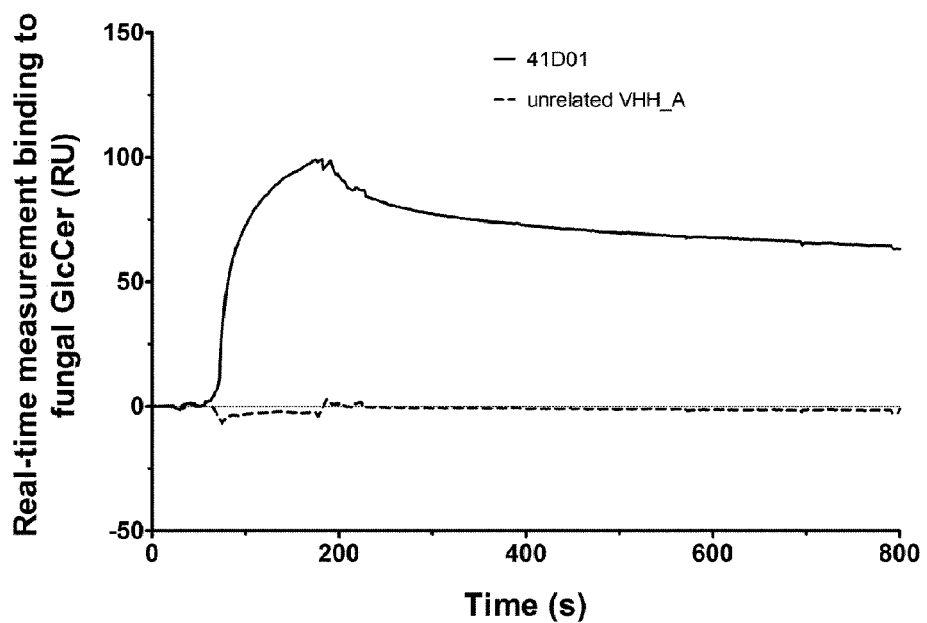

FIG. 4: Real-time measurement of the antibody-antigen interaction between VHH 41 D01 and fungal GlcCer. VHH 41 D01 binds fungal GlcCer. A slow dissociation of GlcCer from VHH 41 D01 is observed. Unrelated VHH_A does not bind fungal GlcCer.

Figure 5:
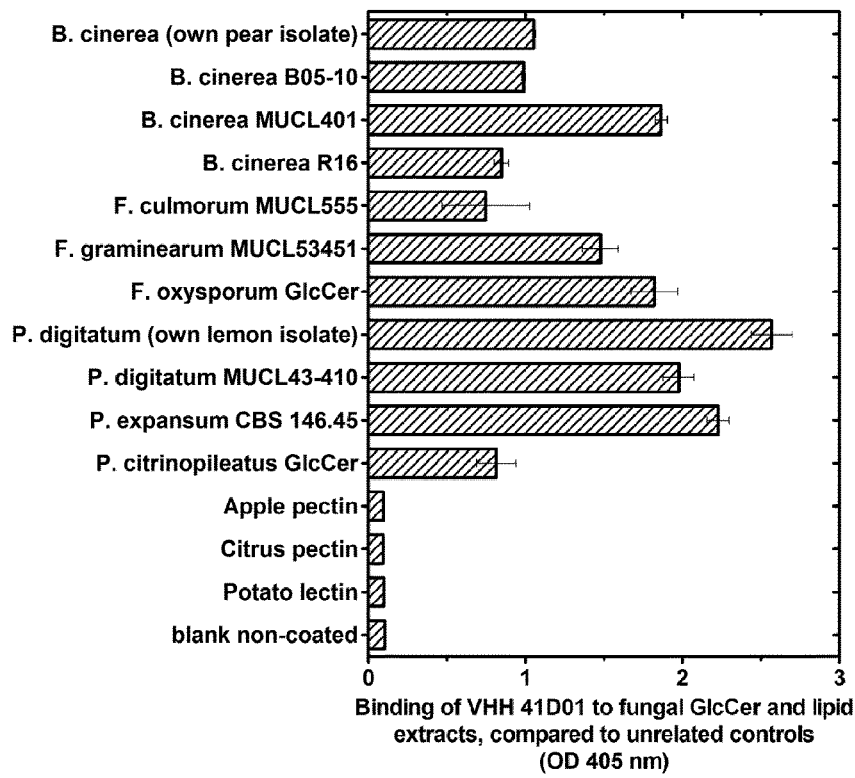
Figure 5:
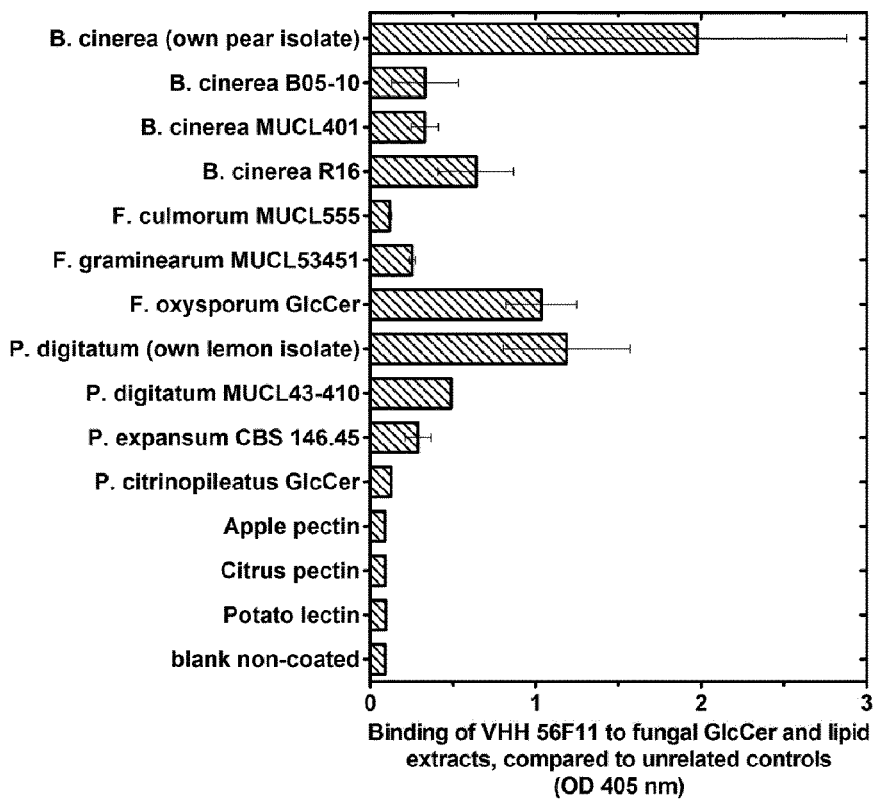

FIG. 5: Cross-reactivity and specificity of VHH 41 D01 and VHH 56F11. Binding of purified VHH 41 D01 at 0.1 µg/ml and VHH 56F11 at 1 µg/ml to coated fungal lipid extracts, GlcCer from *Pleurotus citrinopileatus*, and unrelated compounds: apple pectin, citrus pectin, or potato lectin. Bars represent average OD 405 nm values, error bars represent standard errors of the mean of n=2. Anti-GlcCer VHH 41 D01 and VHH 56F11 specifically bind each of the fungal lipid extracts tested. Anti-GlcCer VHH 41D01 and VHH 56F11 do not show binding to unrelated coated compounds or non-coated wells.

Figure 6:
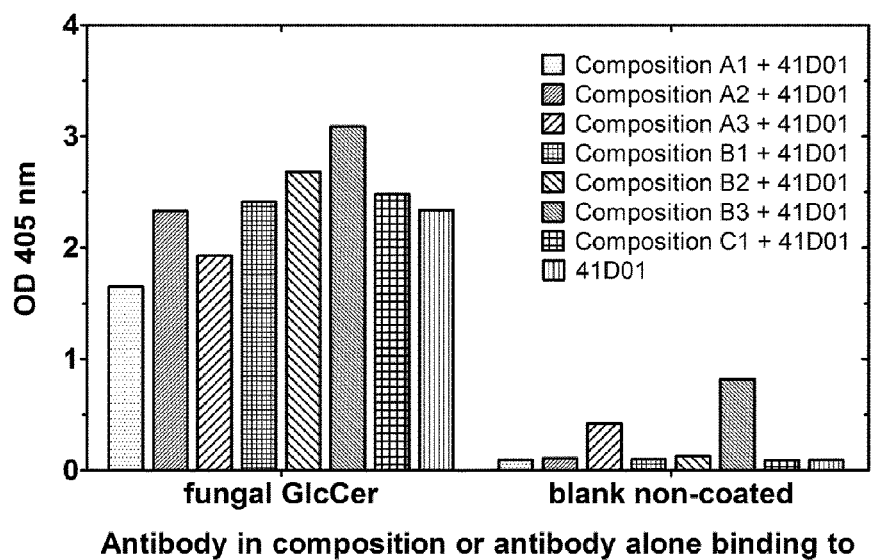

FIG. 6: Binding of VHH 41D01 in different compositions to fungal GlcCer from *Fusarium oxysporum*. Aqueous compositions containing anti-GlcCer VHH 41D01 at 0.1 µg/ml and protease inhibitors and/or non-ionic surfactant and/or preservative were tested for binding to fungal GlcCer. GlcCer-specific VHH 41D01 binds to fungal GlcCer in all compositions tested without adverse effects of any of the additives.

Figure 7A:
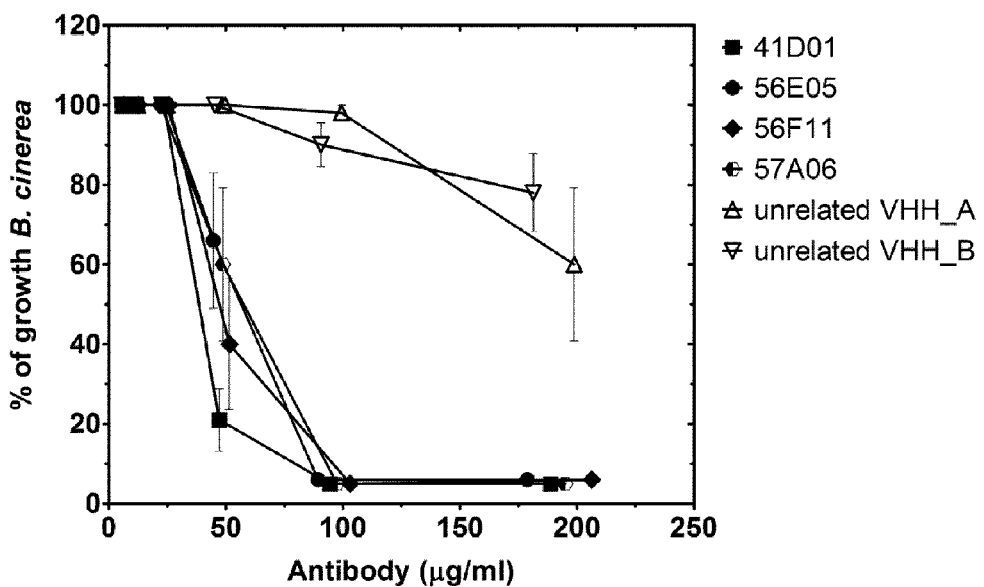

FIG. 7A: Visual scoring of fungal growth. Serial dilution of VHH (anti-GlcCer VHH's 41D01, 56E05, 56F11, and 57A06 as well as unrelated VHH_A or unrelated VHH_B) were inoculated with *Botrytis cinerea* spores (1 E+05/ml) and incubated at room temperature. Effect on fungal growth of anti-GlcCer VHH's 41D01, 56E05, 56F11, and 57A06, unrelated VHH_A or unrelated VHH_B was quantified based on a set of photographic standards. Bars represent average % of growth, error bars represent standard errors of the mean of at least 3 replicas.

Figures 7B, 7C:
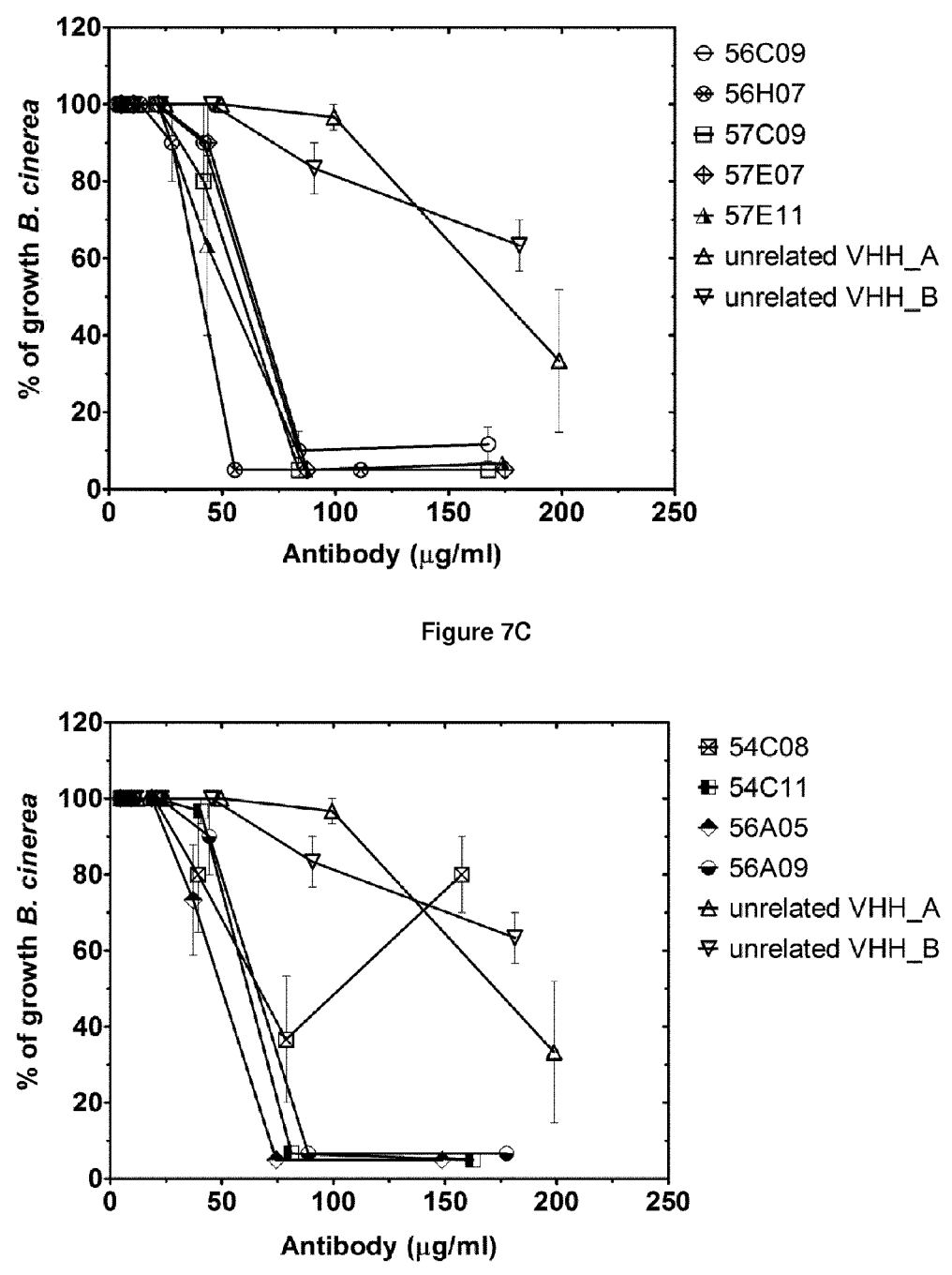

FIG. 7B: Visual scoring of fungal growth. Serial dilution of VHH (anti-GlcCer VHH's 56C09, 56H07, 57C09, 57E07, 57E11 as well as unrelated VHH_A or unrelated VHH_B) were inoculated with *Botrytis cinerea* spores (1E+05/ml) and incubated at room temperature. Effect on fungal growth of anti-GlcCer VHH's 56C09, 56H07, 57C09, 57E07, 57E11, unrelated VHH_A or unrelated VHH_B was quantified based on a set of photographic standards. Bars represent average % of growth, error bars represent standard errors of the mean of at least 3 replicas.

FIG. 7C: Visual scoring of fungal growth. Serial dilution of VHH (anti-GlcCer VHH's 54C08, 54C11, 56A05, 56A09 as well as unrelated VHH_A or unrelated VHH_B) were inoculated with *Botrytis cinerea* spores (1 E+05/ml) and incubated at room temperature. Effect on fungal growth of anti-GlcCer VHH's 54C08, 54C11, 56A05, 56A09, unrelated VHH_A or unrelated VHH_B was quantified based on a set of photographic standards. Bars represent average % of growth, error bars represent standard errors of the mean of at least 3 replicas.

Figure 8A:
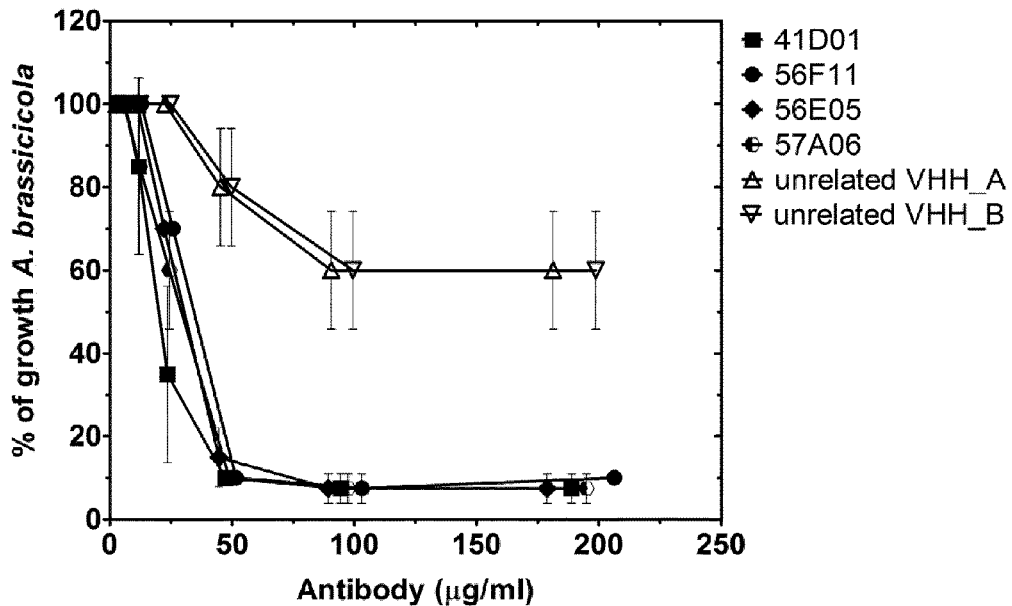

FIG. 8A: Visual scoring of fungal growth of different fungal species. Two-fold serial dilutions of VHH (anti-GlcCer VHH or unrelated VHH) are incubated with spores (1E+05/ml) of *Alternaria brassicicola* at room temperature. Effect on fungal growth of VHH and control compounds was based on a set of photographic standards. Bars represent average % growth, error bars represent standard errors of the mean of n=2.

Figure 8B:
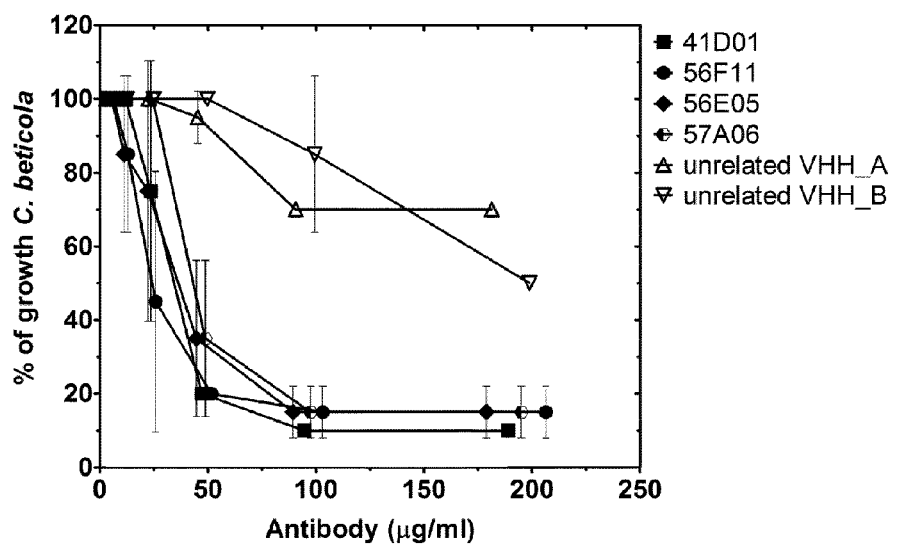

FIG. 8B: Visual scoring of fungal growth of different fungal species. Two-fold serial dilutions of VHH (anti-GlcCer VHH or unrelated VHH) are incubated with spores (1E+05/ml) of *Cercospora beticola* at room temperature. Effect on fungal growth of VHH and control compounds was based on a set of photographic standards. Bars represent average % growth, error bars represent standard errors of the mean of n=2.

Figure 8C:
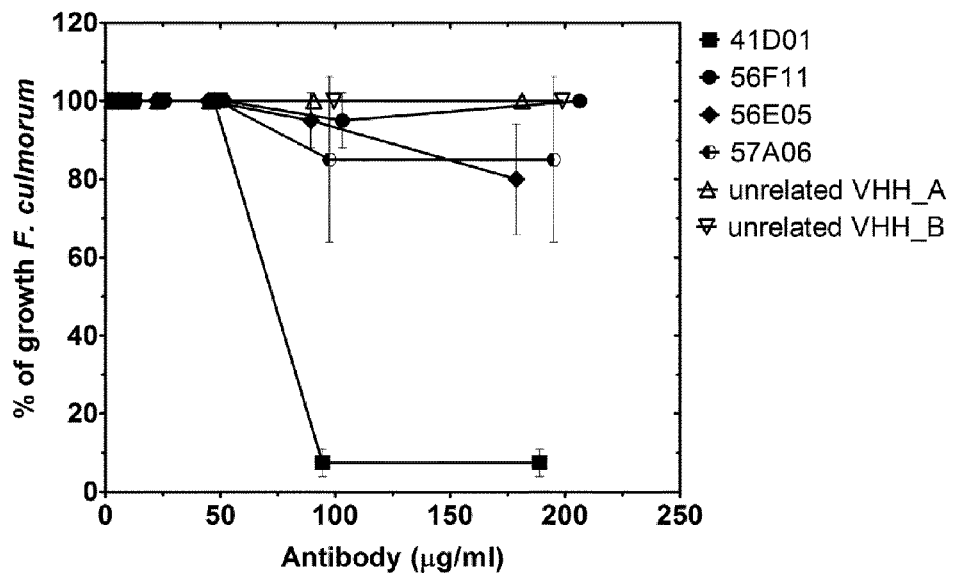

FIG. 8C: Visual scoring of fungal growth of different fungal species. Two-fold serial dilutions of VHH (anti-GlcCer VHH or unrelated VHH) are incubated with spores (1 E+05/ml) of *Fusarium culmorum* at room temperature. Effect on fungal growth of VHH and control compounds was based on a set of photographic standards. Bars represent average % growth, error bars represent standard errors of the mean of n=2.

Figure 8D:
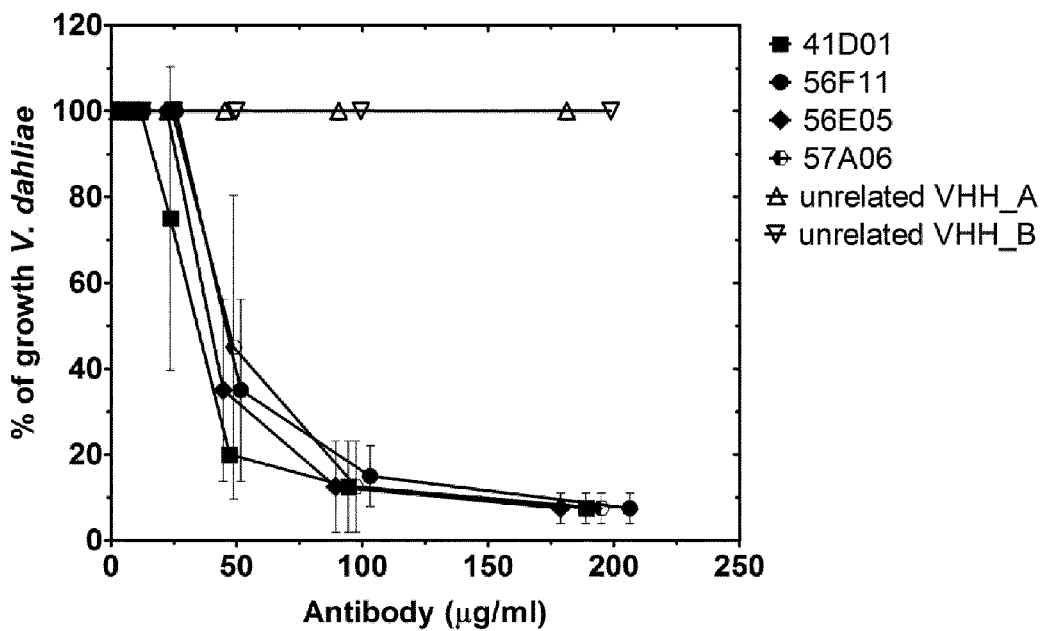

FIG. 8D: Visual scoring of fungal growth of different fungal species. Two-fold serial dilutions of VHH (anti-GlcCer VHH or unrelated VHH) are incubated with spores (1E+05/ml) of *Verticillium dahliae* at room temperature. Effect on fungal growth of VHH and control compounds was based on a set of photographic standards. Bars represent average % growth, error bars represent standard errors of the mean of n=2.

Figure 9:
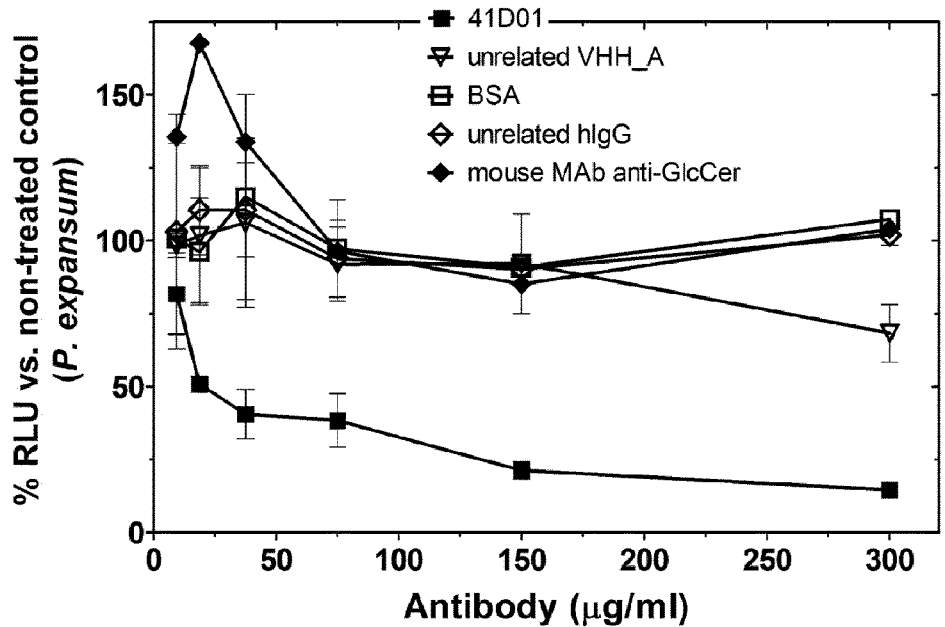

FIG. 9: In-vitro antifungal assay using *Penicillium expansum*. Two-fold serial dilutions of VHH were inoculated with *P. expansum* spores (1 E+03/ml) at room temperature. Anti-GlcCer VHH 41D01, unrelated VHH_A, BSA, unrelated hIgG, anti-GlcCer mouse monoclonal antibody and water were tested. Luminescence (RLU) was measured after 24 h incubation. % RLU of treated spores are expressed versus untreated spores. Values represent average % RLU, error bars represent standard errors of the mean of n=4.

Figure 10:
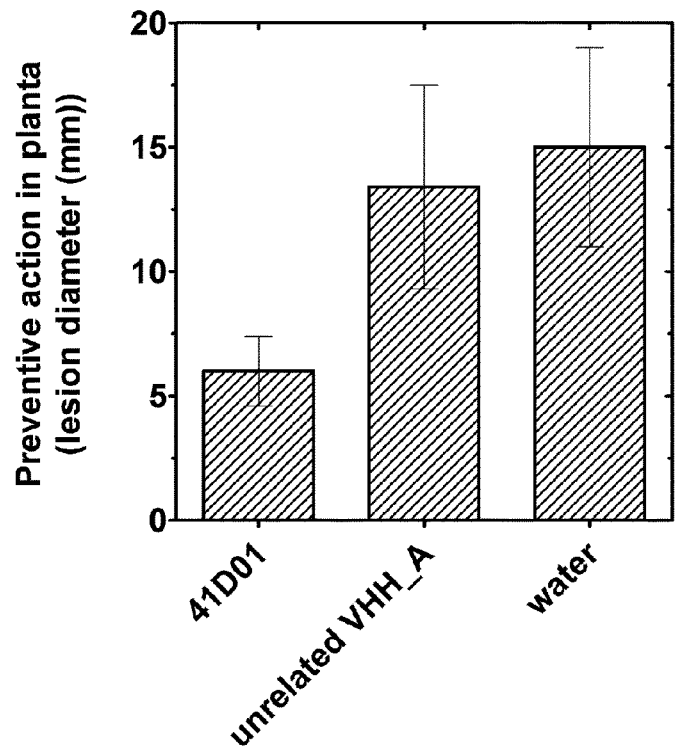

FIG. 10: Disease severity was measured on tomato leaves preventively treated with anti-GclCer VHH 41D01, unrelated VHH_A, or water, and inoculated with *Botrytis cinerea* spores (6E+06 spores/ml). Bars represent average lesion diameter (mm) scored at 6 days post infection, error bars represent standard errors of the mean of n=5.

Figure 11:
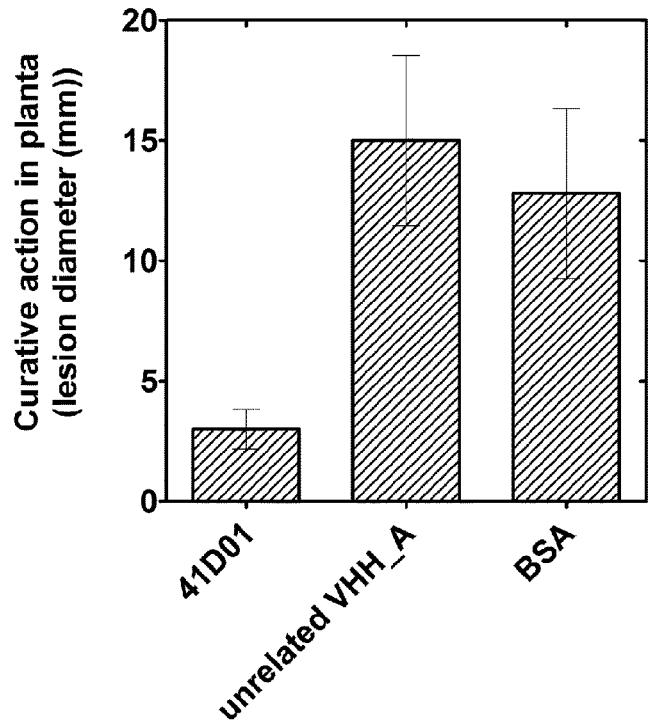

FIG. 11: Disease severity was measured on tomato leaves curatively treated with anti-GclCer VHH 41D01, unrelated VHH_A, or BSA, and inoculated with *Botrytis cinerea* spores (6E+06 spores/ml). Bars represent average lesion diameter (mm) scored at 5 days post infection, error bars represent standard errors of the mean of n=5.

Figure 12:
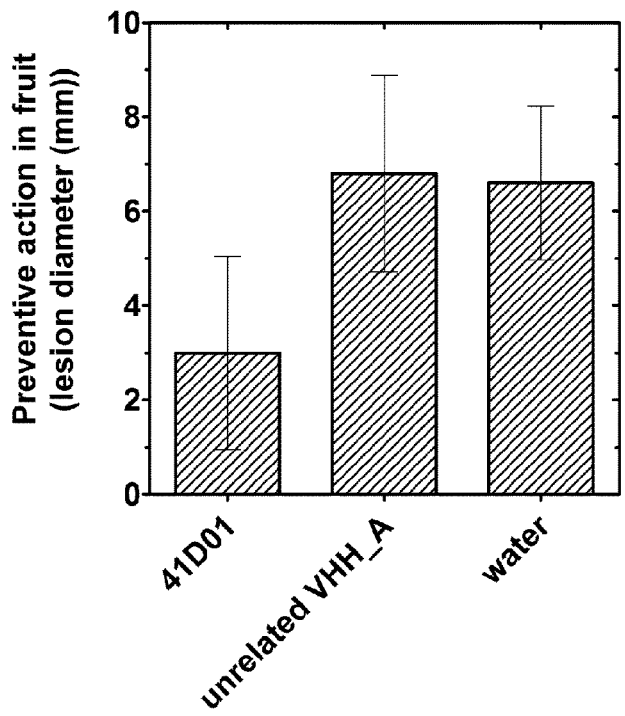

FIG. 12: Disease severity was measured on pears preventively treated with anti-GclCer VHH 41D01, unrelated VHH_A, or water, and inoculated with *Botrytis cinerea* spores (1E+04 spores/ml). Bars represent average lesion diameter (mm) scored at 4 days post infection, error bars represent standard errors of the mean of n=5

EXAMPLES AND MATERIALS AND METHODS

Example 1

Isolation of Nucleic Acid Sequences Encoding Peptides with Affinity for Fungal Glucosylceramide Animal Immunizations:

VHH's were generated from llamas immunized with fungal glucosylceramide (GlcCer). Llamas were immunized according to standard protocols with 6 boosts of thin Layer Chromatography (TLC)-purified (99%) glucosylceramide (GlcCer) from *Pleurotus citrinopileatus* (Nacalai Tesque). Purified GlcCer was dissolved in a water:methanol:chloroform mixture and spotted on a TLC silica glass plate. Silica with adsorbed GlcCer was scraped from the plate and suspended in phosphate buffer. The suspension was sonicated, mixed with Freund incomplete adjuvant, and used for subcutaneous injections. VHH were also generated from llamas immunized with native germinated fungal or oomycete spores. Llamas were immunized according to standard protocols with 6 boosts of native germinated spores of *Botrytis cinerea* or *Phytophthora infestans* by subcutaneous injections. All llamas remained healthy throughout the immunization process and blood samples were taken before and after immunizations.

Library Construction:

A phage library of antibodies is a phage population in which each individual phage exposes a unique antigen-binding antibody domain on its surface as a part of a chimeric pIII protein. Peripheral blood mononuclear cells were prepared from blood samples of the immunized llamas using Ficoll-Hypaque according to the manufacturer's instructions. Total RNA was extracted from these cells and used as starting material for RT-PCR to amplify VHH encoding gene fragments. These fragments were cloned into phagemid vector pASF20. pASF20 is an expression vector that is derived from pUC119 which contains the lacZ promotor, a synthetic leader sequence, a multiple cloning site, a coliphage pIII protein coding sequence, a resistance gene for ampicillin, and an M13 phage origin for single strand production. In frame with the VHH conding sequence, the vector codes for a C-terminal (His)6 peptide tag and c-myc peptide tag. Phage were prepared according to standard methods (Phage Display of Peptides and Proteins: A Laboratory Manual; Brian K. Kay, Jill Winter, Dr. John McCafferty). 4 libraries each with a clonal diversity equal to or greater than 1 E+08 were obtained and phage were produced ensuring presentation of the antibody diversity.

VHH Selections by Phage Display:

Phage expressing antigen-binding antibody domains specific for a particular antigen were isolated by selecting the phage in the library for binding to the antigen. Fungal GlcCer were immobilized on polystyrene Maxisorp multi-well plates by dissolving fungal GlcCer in a water:methanol:

chloroform mixture or methanol at different concentrations, adding dissolved fungal GlcCer to wells of the multiwell plate, and allowing to dry overnight at room temperature. Wells with coated fungal GlcCer were washed and blocked with 1% fish gelatin in preparation of VHH selections by phage display. VHH library phage were allowed to bind for two hours at room temperature to wells of 96-well plate coated with fungal GlcCer. To specifically select for phage binding to fungal GlcCer phage were pre-incubated with 1% fish gelatin and/or BSA and/or skimmed milk and/or plant GlcCer and/or mammalian GlcCer. Non-bound phage were removed by extensive washing and bound phage were eluted by competitive elution with RsAFP2 (Osborn et al., 1995) or with trypsin. One to three consecutive rounds of selection were performed, and the titers of phage from fungal GlcCer-coated wells were compared to titers of phage from blank wells and non-target pathogen sphingolipids for enrichment and specificity, respectively. Enrichments were observed in first and subsequent rounds of selection, and phage populations after one or more selection rounds already showed specificity for fungal GlcCer in ELISA (not shown). Individual clones were picked from first, second and/or third round selections for further characterization by sequence analysis and primary binding assays.

VHH Characterization by Sequencing and Binding Assays:

The diversity of the obtained antibody or antibody domain population can be rapidly determined using high-throughput DNA sequencing and allows precise quantification of clonal diversity. Antibody or antibody domain binding and specificity of binding to an antigen can be analyzed in assays for binding to that antigen and compared to related and unrelated controls. Each antibody or antibody domain can bind to a specific antigen and possibly to antigenic variants of that antigen. Specificity is the degree to which the binding of an antibody or antibody domain discriminates between antigenic variants. From individual VHH clones that were picked from first, second or third round phage display selections the DNA was amplified in a colony PCR and PCR products were sequenced by Sanger-sequencing. After sequence analysis and based on sequence diversity, VHH were selected for further characterization. To check for species specificity, fungal and non-fungal GlcCer from target and non-target species were used in binding assays. Primary binding assays to identify which clones were functionally selected from the libraries were performed with TLC-purified (99%) GlcCer or GlcCer-enriched Glycosphingolipids (GSL) fractions from *A. brassicicola, B. cinerea, C. beticola, F. culmorum, F. graminearum, F. oxysporum, P. citrinopileatus P. digitatum, P. expansum,* or *V. dahlia* (prepared as described in Ternes et al., 2011 JBC 286:11401-14). GlcCer from soybean and porcine GlcCer were purchased from Avanti Polar Lipids. VHH were produced in 96-well deep-well plates and the binding profile of diluted crude VHH-containing periplasmic extracts was assessed in ELISA format. In the same way, binding assays were performed with purified VHH.

From the primary binding assays 130 VHH-containing periplasmic extracts showed to bind fungal GlcCer with higher OD 405 nm values than the unrelated VHH_A, unrelated VHH_B and blank. OD 405 nm values demonstrating the specific binding of several of these fungal GlcCer binding VHH's are shown in FIG. 1. Sequence analysis revealed 84 unique sequences from the identified set of anti-GlcCer VHH.

Further Characterization by Differential Binding Screens:

For further characterization, VHH belonging to the abovementioned lead panel were produced in *E. coli* in culture flasks according to standard procedures. Hexahistidine-tagged VHH were purified from the periplasmic extract with TALON metal affinity resin (Clontech), according to the manufacturer's instructions. Purified VHH were concentrated and dialyzed to PBS. VHH were also purified using automated purification systems using a combination of immobilized Nickel IMAC and desalting columns. VHH of the lead panel that scored positively in primary binding assays, were subsequently tested for their specificity towards GlcCer or cell wall fractions from different fungal phytopathogens.

As demonstrated in FIGS. 2, 3A, 3B and 3C, GlcCer-specific VHH showed specific binding to fungal GlcCer (*Pleurotus citrinopileatus, Fusarium oxysporum*) and not to other non-fungal GlcCer or blank non-coated well.

Surface Plasmon Resonance:

Binding of VHH to fungal GlcCer was characterised by surface plasmon resonance in a Biacore 3000 instrument. Anti-GlcCer VHH 41 D01 or unrelated VHH_A were covalently bound to CM5 sensor chips surface via amine coupling until an increase of 1000 response units was reached. Remaining reactive groups were inactivated. A range of concentrations of in solution *Fusarium oxysporum* GlcCer prepared according to Salio et al., 2013 PNAS 110, E4753-E4761 was injected for 2 minutes at a flow rate of 30 µl/min to allow for binding to chip-bound VHH. Running buffer without GlcCer was injected over the chip at the same flow rate to allow spontaneous dissociation of bound fungal GlcCer for 10 minutes. A Koff-value was calculated from the sensorgrams obtained for the different fungal GlcCer concentrations with 1:1 Langmuir dissociation global fitting model.

For anti-GlcCer VHH a slow off-rate of 4.86*1 E-4/s was calculated. As shown in FIG. 4, an unrelated VHH did not bind fungal GlcCer.

Plant (soy), mammalian (pork) and fungal (*Fusarim oxysporum*) GlcCer in solution were sequentially injected for 2 minutes at a flow rate of 30 µl/min to allow for binding to chip-bound VHH (anti-GlcCer VHH 41D01 or unrelated VHH_A). Running buffer without GlcCer was injected over the chip between each injection at the same flow rate to allow spontaneous dissociation of bound GlcCer.

No plant or mammalian GlcCer binding to anti-GlcCer VHH 41 D01 or unrelated VHH_A was observed. Specific binding of fungal GlcCer was observed for anti-GlcCer VHH 41 D01 and not for unrelated VHH_A.

Differential Binding to Different Fungal Lipid Extracts:

The binding of anti-GlcCer VHH compositions to different fungal lipid extracts compared to unrelated compounds.

Fungal extracts were prepared according to Rodrigues et al. 2000 Infection and Immunity 68 (12): 7049-60. Briefly, mycelium from *Botrytis cinerea* B05-10, *Botrytis cinerea* MUCL401, *Botrytis cinerea* R16, *Botrytis cinerea* (own pear isolate), *Fusarium culmorum* MUCL555, *Fusarium graminearum* MUCL53451, *Penicillium digitatum* MUCL43-410, *Penicillium digitatum* (own lemon isolate) or *Penicillium expansum* CBS 146.45 were harvested from fungi grown in agar plates and lipids were extracted with chloroform/methanol 2:1 (vol/vol) and 1:2 (vol/vol); crude lipid extract was partitioned according to Folch et al. 1957. Journal of Biological Chemistry 226 (1): 497-509. Fungal lipid extracts were recovered from Folch's lower phase. Binding of anti-GlcCer VHH 41D01 (0.1 µg/ml) and anti-GlcCer VHH 56F11 (1 µg/ml) was evaluated to wells coated with the extracted fungal lipids (each in 1/20 dilution), purified *Fusarium oxysporum* GlcCer, purified *Pleurotus citrinopileatus* GlcCer and unrelated compounds: apple pectin (Apple pectin high esterified 70-75%, Sigma, cat#: 76282), citrus pectin (Citrus pectin low esterified 20-34%, Sigma, cat#P9311) or potato lectin (*Solanum Tuberosum* Lectin, Vector labs, cat#: L-1160) or a blank non-coated well. Binding was measured after consecutive incubation with enzyme-conjugated detection antibodies adding substrate and measuring absorbance at 405 nm. Bars represent average OD 405 nm values, error bars represent standard errors of the mean of n=2.

As shown in FIG. 5, anti-GlcCer VHH 41 D01 and 56F11 specifically recognized all the fungi lipid extracts tested. Anti-GlcCer VHH 41D01 and 56F11 did not show binding to unrelated coated compounds or non-coated wells. The binding of the anti-GlcCer VHH compositions to a wide array of fungal lipids extracts potentiates a variety of applications for the anti-GlcCer VHH compositions as disclosed herein against different fungi.

Binding of Anti-GlcCer VHH to Fungal GlcCer in Different Aqueous Compositions:

Aqueous compositions containing anti-GlcCer VHH 41 D01 and/or protease inhibitors and/or non-ionic surfactants and/or preservatives were prepared. Composition A1 (protease inhibitors: 0.06 µg/ml aprotinin (Roche, cat#: 10236624001), 0.5 µg/ml leupeptin (Roche, cat#: 11017101001), 24 µg/ml 4-benzenesulfonyl fluoride hydrochloride (Sigma, A8456), 1 mM EDTA (Carl-Roth, cat#8040.1) and non-ionic surfactant: 0.00001% Polysorbate 20 (Tween$^{20}$, Sigma, cat#P2287); Composition A2 (protease inhibitors: 1 µg/ml aprotinin, 2.5 µg/ml leupeptin, 100 µg/ml 4-benzenesulfonyl fluoride hydrochloride, 1 mM EDTA and non-ionic surfactant: 0.05% Polysorbate 20); Composition A3 (protease inhibitors: 2 µg/ml aprotinin, 5 µg/ml leupeptin, 240 µg/ml 4-benzenesulfonyl fluoride hydrochloride, 1 mM EDTA and non-ionic surfactant: 5% Polysorbate 20), Composition B1 (non-ionic surfactant: 0.0001%% Polysorbate 20), Composition B2 (non-ionic surfactant: 0.05% Polysorbate 20), Composition B3 (non-ionic surfactant: 5% Polysorbate 20) and Composition C1 (preservative: 0.05% sodium benzoate (Sigma, cat#B3420)). Binding of anti-GlcCer VHH (at 0.1 µg/ml) to fungal GlcCer in different aqueous compositions was tested in ELISA with coated GlcCer from *F. oxysporum* and compared to blank non-coated wells. Binding was measured after consecutive incubation with enzyme-conjugated detection antibodies, adding substrate and measuring absorbance at 405 nm.

In FIG. 6, values of GlcCer-specific VHH 41 D01 in the different compositions were compared with 41 D01 in solution without other additives. It is shown in FIG. 6 that GlcCer-specific VHH 41 D01 was capable of specifically binding to fungal GlcCer in all tested compositions.

Example 2

In Vitro Evaluation of the Antifungal Activity of Anti-GlcCer VHH Compositions

In Vitro Evaluation of the Antifuncial Activity of VHH:

The antifungal activity of the anti-GlcCer-VHH was tested using antifungal assays in liquid media and on agar plates as described in Thevissen et al., 2011, Bioorg. Med. Chem. Lett. 21(12): 3686-92; Francois et al., 2009, J. Biol. Chem. 284(47): 32680-5; Aerts et al., 2009, FEBS Lett. 583(15): 25143-6. The minimal inhibitory concentration (MIC) was determined for the VHH on in vitro growth of *Botrytis cinerea* and *Phytophthora infestans*.

An in vitro assay to test fungal growth in liquid media in 96-well plate format can also be used to directly screen different VHH that are generated against integral fungal material and selected against molecular antigens, different from GlcCer, for antifungal activity. This screening is performed on crude VHH-containing periplasmic extracts of *E. coli* cells in which the VHH are produced, or with purified VHH.

In Vitro Evaluation of the Antifuncial Activity of Anti-GlcCer VHH Compositions Against Different Plant Pathogenic Fungi:

The antifungal activity of anti-GlcCer VHH compositions was assessed in vitro against a number of plant pathogenic fungi and compared with the antifungal activity of unrelated VHH.

Two-fold dilutions of the aqueous VHH compositions in water (starting at 1.5 mg VHH/ml) were prepared in 96-well microtiter plates. To 20 µl of these dilutions and to 20 µl of water as a control, 80 µl of fungal spores suspension (1 E+05 spores/ml in half strength potato dextrose broth (PDB)) were added. The fungal test strains were *Alternaria brassicicola* MUCL20297, *Botrytis cinerea* R16, *Cercospora beticola* (own sugar beet isolate), *Fusarium culmorum* MUCL555 and *Verticillium dahliae* MUCL6963. The test plates were incubated for 72 h at room temperature in the dark and the antifungal activity of the test compounds was scored microscopically and quantified based on photographic standards, whereby a score of 0 or 100 referred to no or maximal fungal growth, respectively. All tests were performed in at least 2 replicas.

The results of the antifungal activity assays, shown in FIGS. 7A, 7B, 7C, 8A, 8B, 8C and 8D indicated a clear difference between the growth inhibition pattern, expressed as the % fungal growth in function of VHH concentration (µg/ml), of the anti-GlcCer VHH (including 41D01, 56F11, 56E05 or 57A06) and the unrelated VHH (VHH_A and VHH_B). This difference was clear irrespective of the species of the test fungus. Generally, at a test concentration of 100 µg/ml, all the anti-GlcCer VHH didn't allow more than 20% fungal growth, whereas at 100 µg/ml the unrelated VHH showed very weak or no antifungal activity (80% or more fungal growth). From all the different tested anti-GlcCer VHH, 41D01 showed the most prominent antifungal activity, for several test strains, even at test concentrations lower than 50 µg/ml fungal growth was less than 20%.

The results show the antifungal potency of anti-GlcCer VHH compared to unrelated VHH. Moreover, the results reveal a broad-spectrum of antifungal activity of anti-GlcCer VHH compositions towards at least 5 different fungal plant pathogens and indicate that the spectrum of antifungal activity of the selected anti-GlcCer VHH can be broadened to other plant pathogenic fungi.

In Vitro Evaluation of the Antifungal Activity of Anti-GlcCer VHH Compositions Against *Penicillium expansum* Using Luminescence:

The in vitro antifungal activity of anti-GlcCer VHH 41D01 composition was assessed against the plant pathogen fungus *Penicillium expansum* CBS 146.45 and compared with the antifungal activity of unrelated VHH_A, a mouse monoclonal anti-GlcCer antibody (mouse MAb anti-GlcCer), human immunoglobulin G (hIgG) or bovine serum albumin (BSA) as controls using luminescence as read-out.

Two-fold serial dilutions of all the test compositions in water (starting at 1.5 mg/ml) were prepared in 96-well microtiter plates. To 20 µl of these dilutions and to 20 µl of water as a control, 80 µl of fungal spores suspension (1 E+03 spores/ml in 4-fold PDB) were added. The test plates were incubated for 24 h at room temperature in the dark and the spore viability was determined at 24 post inoculation (hpi) using luminescence according to the supplier's instructions (BacTiter Glo; Promega). The relative light units (RLU) were determined (Tecan luminometer) and the RLU measured for anti-GlcCer VHH 41D01, unrelated VHH_A, hIgG, mouse MAb anti-GlcCer or BSA treated fungal spores were expressed versus the RLU determined for the untreated fungal spores as % RLU. Four replicas were included in the test (n=4).

As shown in FIG. 9, the % RLU determined upon anti-GlcCer VHH 41D01 composition treatment differed clearly from the % RLU recorded upon unrelated VHH_A, mouse MAb anti-GlcCer, hIgG or BSA treatments. Particularly, the effect of 41 D01 treatment on fungal spores, expressed as % RLU versus non-treated control was less than 25% at 300 µg/ml or 150 µg/ml of 41 D01, and less than 50% at 75 µg/ml, 37.5 µg/ml and 19 µg/ml. In contrast, the effect of all the other test compositions, expressed as % RLU versus non-treated control was generally 100% for all the tested concentrations.

These results show that the specific anti-GlcCer VHH 41 D01 composition had a clear antifungal effect on the plant pathogenic fungus *Penicillium expansum* down to 19 µg/ml and is outperforming non-related VHH_A, mouse MAb anti-GlcCer, hIgG, or BSA. As such, anti-GlcCer VHH compositions can be used to protect plants against plant pathogenic fungi.

Example 3

Formulation of VHH into Agricultural Formulations

Anti-GlcCer VHH were produced as recombinant proteins in a suitable *E. coli* production strain. Anti-GlcCer VHH were purified from the media and/or the periplasm and/or the *E. coli* cells were killed and lysed at the end of the fermentation process. Anti-GlcCer VHH can also be produced as recombinant proteins in *Pichia pastoris*, or *Saccharomyces cerevisiae* and secreted into the fermentation media. Anti-GlcCer VHH are then purified from media components and cell constituents by diafiltration.

The resulting protein solution is diluted in a suitable buffer, such as phosphate buffered saline, to adjust the pH to about 7. Optionally a biocidal agent, such as sodium azide in a concentration of about 0.0001% to 0.1% and a non-ionic detergent, such as Tween20 in a concentration of about 0.0001% to 5%, is added to the buffered protein solution.

Alternatively, the resulting protein solution is admixed with a suitable wetting and dispersing agent in the presence of a customary filler material before being spray dried into wettable granules.

Example 4

Evaluation of Antifungal Activity of VHH on Crops

The efficacy of the VHH with potent in vitro antifungal activity against *B. cinerea* and *P. infestans* is further evaluated in planta via disease bio-assays on (i) detached leaves from tomato and potato plants and (ii) on greenhouse-grown tomato and potato plants.

Detached leaf disease assays are performed by using the model pathosystems tomato-*B. cinerea* and potato-*P. infestans*. Greenhouse-grown tomato and potato plants are sprayed in a spraying cabinet with an aqueous VHH solution in a volume equivalent to 300 liter per ha and with an application rate below 50 g VHH per hectare. After spraying, the spray deposit is allowed to dry on the plants and composite leaves are subsequently detached from the plants and placed on water agar-plates. The leaves on the water-agar-plates are drop-inoculated at different time points with a spore suspension of *B. cinerea* or *P. infestans* ($5 \times 10^5$ spores/ml). Disease development is monitored visually and/or digitally via measuring lesion diameter and image analysis software, respectively (Assess, Lamari 2002, St. Paul, Minn., USA: APS Press).

Example 5

In Planta Evaluation of the Antifungal Activity of Anti-GlcCer VHH Composition to Protect Crops Against Fungal Infection Efficacy of Anti-GlcCer VHH Compositions on Tomato Leaves Inoculated with *Botrytis cinerea*: Preventive Treatment:

The effect of a preventive treatment with anti-GlcCer VHH compositions on the disease severity of *Botryts. cinerea* B05-10 inoculated tomato leaves was evaluated and compared with the effects of unrelated VHH, water or a formulated commercial chemical fungicide.

Detached leaves from greenhouse grown tomato plants were treated with 10 µl of an aqueous VHH composition (anti-GlcCer or an unrelated VHH at 5 mg/ml), and, water and Scala (1 mg pyrimethanil/ml, as recommended by the manufacturer) as controls. Upon drying of the applied compositions, 10 µl drops of a *Botrytis cinerea* spores suspension (6 E+06 spores/ml in 4-fold diluted PDB) were applied on the treated surfaces. Treated and inoculated leaves were incubated at high relative humidity and at room temperature in small plant propagators. Disease severity was scored measuring the bidirectional diameter at 6 days post inoculation (dpi).

As shown in FIG. 10, preventive treatment with the anti-GlcCer VHH composition resulted in an average lesion diameter of 6 mm (+/−1.4 mm), whereas treatment with an unrelated VHH or water showed an average lesion diameter of 13.4 mm (+/−4 mm) or 15 mm (+/−4 mm), respectively. In the control treatment with a formulated commercial chemical fungicide, tomato leaves were effectively protected against *Botrytis cinerea* infection (without a visible lesion).

As also shown in FIG. 10, preventive treatment of tomato leaves with the application of the anti-GlcCer VHH composition clearly resulted in a 2-fold reduction of disease severity compared with the treatment with an unrelated VHH or water. Therefore, the specific anti-GlcCer VHH, yet applied as an unformulated aqueous composition at 5 mg/ml, showed the potency of specific anti-GlcCer VHH to be used as antifungal compounds to protect crops against fungal pathogens in agricultural applications.

Efficacy of Anti-GlcCer VHH Compositions on Tomato Leaves Inoculated with *Botrytis cinerea*: Curative Treatment:

The effect of a curative treatment with anti-GlcCer VHH compositions on the disease severity of *Botrytis cinerea* B05-10 inoculated tomato leaves was evaluated and compared with the effect of unrelated VHH, bovine serum albumin (BSA) or a formulated commercial chemical fungicide.

Detached leaves from greenhouse-grown tomato plants were inoculated with 10 µl drops of a *Botrytis cinerea* spores suspension ((6 E+06 spores/ml) in 4-fold diluted potato dextrose broth). One hour after inoculation, the inoculated spots on the leaves were treated with 10 µl of an aqueous VHH composition (anti-GlcCer and unrelated VHH at 1.6 mg/ml), and, BSA at 1.6 mg/ml and Scala (1 mg pyrimethanil/ml, as recommended by the manufacturer) as controls. Inoculated and treated leaves were incubated at high relative humidity and at room temperature in small plant propagators. Disease severity was scored measuring the bidirectional diameter at 5 dpi.

As shown in FIG. 11, curative treatment with the anti-GlcCer VHH composition resulted in an average lesion diameter of 3 mm (+/−0.8 mm), whereas treatment with an unrelated VHH or BSA showed an average lesion diameter of 15 mm (+/−3.5 mm) or 13 mm (+/−3.5 mm), respectively. In the control treatment with a formulated commercial chemical fungicide, tomato leaves were effectively protected against *Botrytis cinerea* infection (without a visible lesion).

As also shown in FIG. 11, curative treatment of tomato leaves with the application of the anti-GlcCer VHH composition clearly resulted in a 4-fold reduction of disease severity compared with the treatment of unrelated VHH or BSA. Therefore, the specific anti-GlcCer VHH, yet applied as an unformulated aqueous composition at 1.6 mg/ml, showed the potency of specific anti-GlcCer VHH to be used as antifungal compounds to protect crops against fungal pathogens in agricultural applications.

Efficacy of Anti-GlcCer VHH Compositions on Pears Inoculated with *Botrytis cinerea*: Preventive Treatment:

The effect of a preventive treatment with anti-GlcCer VHH compositions on the disease severity of *Botrytis cinerea* (own isolate from pears) inoculated pears was evaluated and compared with the effect of unrelated VHH, water, or a formulated commercial chemical fungicide.

Pears (variety Williams) from biological agriculture, previously confirmed as untreated, were treated with 10 µl of aqueous VHH compositions (containing anti-GlcCer VHH or an unrelated VHH at 5 mg/ml), and, water and Scala (1 mg pyrimethanil/ml, as recommended by the manufacturer) as controls. Upon drying of the applied solutions, 10 µl drops of a *Botrytis cinerea* spores suspension (1 E+04 spores/ml in water) were applied on the treated surfaces. Treated and inoculated pears were incubated at high relative humidity and at room temperature in small containers. Disease severity was scored measuring the bidirectional diameter at 4 dpi.

As shown in FIG. 12, preventive treatment with the anti-GlcCer VHH composition resulted in an average lesion diameter of 3 mm (+/−2 mm), whereas treatment with an unrelated VHH or water showed an average lesion diameter of 9.6 mm (+/−0.8 mm) or 6.6 mm (+/−1.6 mm), respectively. In the control preventive treatment with a formulated commercial chemical fungicide pears were effectively protected against *Botrytis cinerea* infection (without a visible lesion).

As also shown in FIG. 12, preventive treatment of pears with the application of the anti-GlcCer VHH composition clearly resulted in an at least 2-fold reduction of disease severity compared with the treatment of an unrelated VHH or water. Therefore, the specific anti-GlcCer VHH, yet applied as an unformulated aqueous solution at 5 mg/ml, showed the potency of specific anti-GlcCer VHH to be used as an antifungal compounds to protect crops against fungal pathogens in agricultural applications.

Anti-GlcCer VHH Composition to Protect Plant Seeds Against Fungal Infection:

The effect of an anti-GlcCer VHH composition on the protection of plant seeds against pathogenic fungi can be evaluated as follows. Surface-sterile plant seeds, treated with an anti-GlcCer VHH, an unrelated VHH, water or a formulated commercial chemical fungicide are put on top of a potato dextrose agar plate containing 1 E+03 spores/ml of the test fungus *Fusarium graminearum*. Test plates are incubated at room temperature and the fungal growth inhibition zones (mm) surrounding the seeds can be measured allowing comparing the effect of the different treatments.

Anti-GlcCer VHH Composition to Protect Plant Roots Against Fungal Infection in Hydroponics:

The effect of an anti-GlcCer VHH composition on the protection of plant roots against pathogenic fungi and on plant health in general can be evaluated as follows. Tomato plants are grown with their roots in a mineral nutrient solution or on inert media such as perlite supplemented or drenched, respectively with an anti-GlcCer VHH composition, an unrelated VHH, water or a formulated commercial chemical fungicide. *Verticillium dahliae* (1 E+03 spores/ml) can be used to inoculate the plant roots and the effect of the different treatments is scored at harvest measuring disease severity on the plants based on an arbitrary scale of diseases classes: 0=no symptoms, 1=slight yellowing of leaf, stunting, or wilting, 2=moderate yellowing of leaf, stunting, or wilting, 3=severe yellowing of leaf, stunting, or wilting, and 4=leaf death (as described by Fakhro et al., 2010).

Anti-GlcCer VHH Composition to Protect Plant Flowers Against Fungal Infection:

The effect of an anti-GlcCer VHH composition on the protection of plant flowers against pathogenic fungi can be evaluated using cereals or *Arabidopsis thaliana* and *Fusarium culmorum* or *Fusarium graminearum* as test fungi (as described by Urban et al., 2002). In short, flowering plants are spray-inoculated with 1 E+05 spores/ml) of *Fusarium culmorum* or *Fusarium graminearum* followed by a treatment with an anti-GlcCer VHH composition, an unrelated VHH, water or a formulated commercial chemical fungicide (curative treatment) or vice versa (preventive treatment). Plants are incubated and the disease scoring is performed as described by Urban et al. (2002) and allows quantifying the effect of the different treatments.

The invention claimed is:

1. An antifungal composition comprising at least one polypeptide that specifically binds to a glucosylceramide of a fungal pest, wherein the at least one polypeptide is a heavy chain variable domain of a heavy chain antibody ($V_{HH}$) or a functional fragment thereof, or wherein the at least one polypeptide is an alphabody or a functional fragment thereof.

2. The composition of claim 1, which further comprises an agrochemically or pharmaceutically suitable carrier and/or one or more suitable adjuvants.

3. The composition of claim 1, wherein said pest is a pathogenic fungus.

4. An anti-pest composition comprising the composition of claim 1.

5. A fungicidal and/or fungistatic agent comprising:
the composition of claim 1.

6. The composition of claim 3, wherein the pathogenic fungus is a plant pathogenic fungus selected from the group consisting of *Alternaria, Ascochyta, Botrytis, Cercospora, Colletotrichum, Diplodia, Erysiphe, Fusarium, Leptosphaeria, Gaeumanomyces, Helminthosporium, Macrophomina, Nectria, Penicillium, Peronospora, Phoma, Phymatotrichum, Phytophthora, Plasmopara, Podosphaera, Puccinia, Pyrenophora, Pyricularia, Pythium, Rhizoctonia, Scerotium, Sclerotinia, Septoria, Thielaviopsis, Uncinula, Venturia, Verticillium, Magnaporthe, Blumeria, Mycosphaerella, Ustilago, Melampsora, Phakospora, Monilinia, Mucor, Rhizopus,* and *Aspergillus*; or
a human or animal pathogenic fungus selected from the group consisting of selected from the group consisting of *Candida* species, *Candida albicans, Cryptococcus* species, *Cryptococcus neoformans, Aspergillus* species, *Aspergillus fumigatus, Aspergillus flavus, Pneumocystis* species, *Pneumocystis carinii, Coccidioides* species, *Coccidioides iminitis, Trichophyton* species, *Trichophyton verrucosum, Blastomyces* species, *Blastomyces dermatidis, Histoplasma* species, *Histoplasma capsulatum, Paracoccidioides* species, *Paracoccidioides brasiliensis; Pythium* species, and *Pythium insidiosumi.*

7. The composition of claim 2, wherein the polypeptide is from 0.0001% to 50% by weight of the composition.

\* \* \* \* \*